US008748412B2

(12) United States Patent
Liao et al.

(10) Patent No.: US 8,748,412 B2
(45) Date of Patent: Jun. 10, 2014

(54) PHENYLALANINE DERIVATIVES AND THEIR USE AS NON-PEPTIDE GLP-1 RECEPTOR MODULATORS

(75) Inventors: Jiayu Liao, Carlsbad, CA (US); Yufeng Hong, San Diego, CA (US); Yong Wang, San Diego, CA (US); Thomas W. Von Geldern, Richmond, IL (US); Kanyin E. Zhang, San Diego, CA (US)

(73) Assignee: Argusina Bioscience Inc., George Town, Grand Cayman (KY)

( * ) Notice: Subject to any disclaimer, the term of this patent is extended or adjusted under 35 U.S.C. 154(b) by 0 days.

(21) Appl. No.: 13/019,851

(22) Filed: Feb. 2, 2011

(65) Prior Publication Data

US 2012/0004198 A1 Jan. 5, 2012

(51) Int. Cl.
*A61K 31/635* (2006.01)
*A61K 31/341* (2006.01)
*A61K 31/27* (2006.01)
*A61K 31/4245* (2006.01)
*A61K 31/4439* (2006.01)
*A61K 31/506* (2006.01)
*A61K 31/454* (2006.01)
*A61K 31/5377* (2006.01)
*A61K 31/551* (2006.01)
*C07C 271/28* (2006.01)
*C07D 271/06* (2006.01)
*C07D 413/12* (2006.01)
*C07D 413/14* (2006.01)
*C07D 307/68* (2006.01)

(52) U.S. Cl.
USPC ........... 514/158; 514/471; 514/483; 514/364; 514/340; 514/275; 514/326; 514/236.2; 514/218; 549/487; 548/131; 546/269.1; 546/209; 544/324; 544/138; 540/575; 560/25

(58) Field of Classification Search
USPC ......... 514/158, 471, 483, 364, 340, 275, 326, 514/236.2, 218; 549/487; 560/25; 548/131; 546/269.1, 209; 544/324, 138; 540/575; 435/375
See application file for complete search history.

(56) References Cited

U.S. PATENT DOCUMENTS

| 4,004,008 A | 1/1977 | Makovec et al. |
| 6,191,171 B1 * | 2/2001 | DeLaszlo et al. ............. 514/617 |

FOREIGN PATENT DOCUMENTS

| CN | 1281430 | 1/2001 |
| CN | 1208323 C | 6/2005 |
| CN | 1917881 | 2/2007 |
| EP | 1167357 | 1/2002 |
| WO | WO 99/10312 | 3/1999 |
| WO | WO 00/37429 | 6/2000 |
| WO | WO 00/59889 | 10/2000 |
| WO | WO 03/070709 | 8/2003 |

OTHER PUBLICATIONS

Vippagunta et al., Crystalline solids, 2001, Advanced Drug Delivery Reviews, 48, pp. 3 and 18.*
International Search Report and Written Opinion for International Application No. PCT/CN2010/000141, mailed Nov. 11, 2010.
International Search Report and Written Opinion for International Application No. PCT/US2011/023482, mailed Jun. 15, 2011.
Knudsen, L. B. et al., "Small-molecule agonists for the glucagon-like peptide 1 receptor," PNAS, 104(3):937-942 (2007).
Underwood, C. R. et al., "Crystal structure of glucagon-like peptide-1 in complex with the extracellular domain of the glucagon-like peptide-1 receptor," The Journal of Biological Chemistry, 285(1):723-730 (2010).
Supplementary European Search Report for European Application No. 11740300, mailed May 14, 2013.
Office Action and Search Report for Chinese Application No. 201180017470.3, dated Oct. 12, 2013.

* cited by examiner

*Primary Examiner* — Kristin Vajda
(74) *Attorney, Agent, or Firm* — Cooley LLP

(57) ABSTRACT

Provided herein are non-peptide GLP-1 receptor modulator compounds, for example, of Formula I, pharmaceutical compositions comprising such compounds, and processes of preparation thereof. Also provided are methods of their use for the treatment of a metabolic disorder.

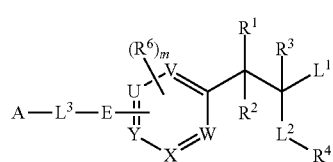

(I)

54 Claims, No Drawings

US 8,748,412 B2

PHENYLALANINE DERIVATIVES AND THEIR USE AS NON-PEPTIDE GLP-1 RECEPTOR MODULATORS

CROSS-REFERENCE TO RELATED APPLICATION

This application claims the benefit of International Application No. PCT/CN2010/000141, filed Feb. 2, 2010 and entitled "PHENYLALANINE DERIVATIVES AND THEIR USE AS NON-PEPTIDE GLP-1 RECEPTOR MODULATORS", the contents of which are hereby incorporated by references in their entireties for all purposes.

FIELD OF THE INVENTION

The present invention relates to compounds that modulate the activity of GLP-1 receptor, compositions comprising these compounds, processes of preparing these compounds, and the therapeutic use of these compounds.

BACKGROUND

Diabetes is a growing epidemic that is estimated to affect over 300 million people by the year 2025 pending an effective pharmaceutical cure. Type 2 diabetes accounts for 90-95% of all cases. Complications resulting from sustained elevated plasma glucose levels include cardiovascular disease, nephropathy, neuropathy, and retinopathy. Current treatments for diabetes are associated with a variety of deleterious side effects, including hypoglycemia and weight gain. In addition, current treatments for type 2 diabetes do not cure the disease but simply prolong the time until patients require insulin therapy.

Glucagon-like peptide-1 (GLP-1) is a 30 amino acid hormone secreted from gut endocrine cells in response to nutrient ingestion. GLP-1 travels through the circulation and binds to the GLP-1 receptor on the pancreas, resulting in an increase in insulin secretion. In addition, it has been shown that GLP-I reduces gastric emptying which decreases the amount of glucose that is released into the circulation. These actions combine to lower blood glucose levels. Thus, the mechanism of biological activity of GLP-1 suggests that it could be an attractive therapeutic for the treatment of type 2 diabetes. GLP-I also has the potential to treat obesity. Several studies have shown that GLP-1 administered either peripherally or intracerebroventricularly (ICV) decreases food intake in animal models. A study in humans shows that delivering GLP-1 continuously for five days in obese, diabetic patients resulted in a reduction in food intake and a reduction in body weight. However, GLP-I is not being developed as a therapeutic because of its exceptionally short half-life ($T_{1/2}$~1-2 min) (Holst, *Gastroenterology* 1994, 107, 1848-1855). It is rapidly degraded by dipeptidyl protease (DPP-IV), thus reducing the length of the peptide by 2 amino acids at the N-terminus and inactivating it.

Accordingly, there is a need for GLP-1 receptor modulators for the treatment of various metabolic diseases, such as diabetes, obesity, and metabolic syndrome.

SUMMARY OF THE DISCLOSURE

In one embodiment, the present invention provides a compound of Formula (I):

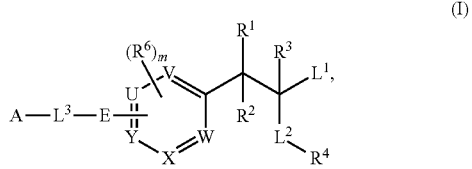

or a pharmaceutically acceptable salt, solvate, or prodrug thereof;
wherein:
A is $C_{3-8}$ carbocyclyl, $C_{6-14}$ aryl, $C_{7-15}$ aralkyl, heteroaryl, or heterocyclyl;

E is a bond, $C_{2-6}$ alkenylene, $C_{2-6}$ alkynylene, arylene, heteroarylene, carbocyclylene, hetcrocyclylene; with the proviso that E is not 4-oxo-imidazolidinylene;

$L^3$ is a bond, —C(O)—, —C(O)O—, —OC(O)—, —C(O)NR$^{1a}$—, —NR$^{1a}$C(O)—, —O—, —OC(O)O—, —OC(O)NR$^{1a}$—, —NR$^{1a}$C(O)O—, —OS(O)—, —S(O)O—, —OS(O)$_2$—, —S(O)$_2$O—, —OS(O)NR$^{1a}$—, —NR$^{1a}$S(O)O—, —OS(O)$_2$NR$^{1a}$—NR$^{1a}$S(O)$_2$O—, —NR$^{1a}$—, —NR$^{1a}$C(O)NR$^{1d}$—, —NR$^{1a}$S(O)NR$^{1d}$, —NR$^{1a}$S(O)$_2$NR$^{1d}$—, —S—, —S(O)—, —S(O)$_2$—, —S(O)NR$^{1a}$—, —NR$^{1a}$S(O)—, —S(O)$_2$NR$^{1a}$—, or —NR$^{1a}$S(O)$_2$—; with the provisos that (a) E and $L^3$ are not both a bond at the same time; and (b) when $L^3$-E together is —O—, $R^6$ is not iodo or benzoxy;

m is an integer of 0, 1, 2, 3, or 4;

$L^1$ is a carboxylate bioisostere selected from the group consisting of —CH$_2$OH, —CONH$_2$, —CO$_2$H, —P(O)(OH)$_2$, —P(OH)$_2$, tetrazolyl, or 3-hydroxyisoxazolyl;

$L^2$ is —CH$_2$N(R$^5$)—, —N(R$^5$)CH$_2$—, —N(R$^5$)—, —O—, —S—, —C(O)NR$^5$—, —NR$^5$C(O)—, —CH$_2$C(O)NR$^5$—, —NR$^5$C(O)CH$_2$—, —CH=CH—C(O)NR$^5$—, —NR$^5$C(O)—CH=CH—, —C≡C—C(O)NR$^5$—, —NR$^5$C(O)—C≡C—, —S(O)NR$^5$—, —NR$^5$S(O)—, —S(O)$_2$NR$^5$—, —NR$^5$S(O)$_2$—, —NR$^5$C(O)NR$^{5a}$—, —NR$^5$S(O)$_2$NR$^{5a}$—, —CH$_2$NR$^5$S(O)$_2$NR$^{5a}$—, —NR$^5$S(O)$_2$NR$^{5a}$CH$_2$—, —NR$^5$C(O)-alkylene, —NR$^5$S(O)-alkylene, —NR$^5$S(O)$_2$-alkylene, —NR$^5$C(O)-alkenylene, —NR$^5$S(O)-alkenylene, or —NR$^5$S(O)$_2$-alkenylene; or alternatively; or alternatively, $L^2$ and V or W, together with other atoms to which they are attached, form 5- to 8-membered optionally substituted carbocyclyl or heterocyclyl; or alternatively, V or W and the carbon atom which is attached to $R^3$, $L^1$, and $L^2$, together with other atoms to which they are attached, form 5- to 8-membered optionally substituted carbocyclyl or heterocyclyl;

U, V, W, X, and Y are each independently C, CH, or N; and U, V, W, X, and Y, together with the carbon atom to which V and W are attached, form an aromatic 6-membered ring; with the proviso that at most 3 of U, V, W, X, and Y are N or NH;

$R^1$, $R^2$, and $R^3$ are selected from (i), (ii), (iii), and (iv):

(i) $R^1$, $R^2$, and $R^3$ are each independently (a) hydrogen, halo, or cyano; (b) $C_{1-6}$ alkyl, $C_{2-6}$ alkenyl, $C_{2-6}$ alkynyl, $C_{3-8}$ carbocyclyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

(ii) $R^1$ or $R^2$ forms a double bond with $R^3$; and the other of $R^1$ and $R^2$ is selected as in (i);

(iii) two of $R^1$, $R^2$, and $R^3$ are joined together to form $C_{3-8}$ carbocyclyl, or 3- to 8-membered heterocyclyl; and the third is selected as in (i); and (iv) $R^3$ and V or W, together with the other atoms to which are attached, form $C_{5-8}$ carbocyclyl, or 5- to 8-membered heterocyclyl; and $R^1$ and $R^2$ are selected as in (i);

$R^4$ is $C_{1-6}$ alkyl, $C_{2-6}$ alkenyl, $C_{2-6}$ alkynyl, $C_{3-7}$ carbocyclyl, $C_{6-14}$ aryl, $C_{7-15}$ aralkyl, heteroaryl, or heterocyclyl; or alternatively, $R^4$ and $R^5$ together with the N atom to which they are attached form heterocyclyl;

$R^5$ and $R^{5a}$ are each independently hydrogen, $C_{1-6}$ alkyl, —C(O)—$C_{1-6}$ alkyl; $C_{2-6}$ alkenyl, $C_{2-6}$ alkynyl, $C_{3-7}$ carbocyclyl, $C_{6-14}$ aryl, $C_{7-15}$ aralkyl, heteroaryl, or heterocyclyl; or alternatively, $R^4$ and $R^5$ are joined together to form heterocyclyl;

$R^6$ is cyano, halo, azido, nitro, $C_{1-6}$ alkyl, $C_{2-6}$ alkenyl, $C_{2-6}$ alkynyl, $C_{3-7}$ carbocyclyl, $C_{6-14}$ aryl, $C_{7-15}$ aralkyl, heteroaryl, heterocyclyl, —C(O)$R^{1a}$, —C(O)O$R^{1a}$, —C(O)N$R^{1b}R^{1c}$, —C(N$R^{1a}$)N$R^{1b}R^{1c}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

when U, V, W, X, and Y are each independently C or CH; $R^1$, $R^2$, and $R^3$ are hydrogen; $L^1$ is —CONH$_2$ or —CO$_2$H; $L^2$ is —N$R^5$C(O)—; and $R^4$ is -heteroaryl-aryl; then A-$L^3$-E- is cyano group;

each $R^{1a}$, $R^{1b}$, $R^{1c}$, and $R^{1d}$ is independently hydrogen, $C_{1-6}$ alkyl, $C_{2-6}$ alkenyl, $C_{2-6}$ alkynyl, $C_{3-7}$ carbocyclyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl;

wherein each alkyl, alkenyl, alkenylene, alkynyl, alkynylene, carbocyclyl, carbocyclylene, aryl, arylene, aralkyl, heteroaryl, heteroarylene, heterocyclyl, and heterocyclylene, in $R^1$, $R^2$, $R^3$, $R^4$, $R^5$, $R^{5a}$, $R^6$, $R^{1a}$, $R^{1b}$, $R^{1c}$, $R^{1d}$, A, and E is optionally substituted with one or more substituents Q, where each Q is independently selected from (a) cyano, halo, azido, and nitro;

(b) $C_{1-6}$ alkyl, $C_{2-6}$ alkenyl, $C_{2-6}$ alkynyl, $C_{3-7}$ carbocyclyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(=N$R^a$)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —S$R^a$, —S(O)$R^a$, —S(O)$_2R^a$, —S(O)N$R^bR^c$, and —S(O)$_2$N$R^bR^c$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-7}$ carbocyclyl, $C_{6-14}$ aryl, $C_{7-15}$ aralkyl, heteroaryl, or heterocyclyl, each optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$; and wherein each $Q^a$ is independently selected from the group consisting of (a) cyano, halo, and nitro; (b) $C_{1-6}$ alkyl, $C_{2-6}$ alkenyl, $C_{2-6}$ alkynyl, $C_{3-7}$ carbocyclyl, $C_{6-14}$ aryl, $C_{7-15}$ aralkyl, heteroaryl, and heterocyclyl; and (c) —C(O)$R^e$, —C(O)O$R^e$, —C(O)N$R^fR^g$, —C(N$R^e$)N$R^fR^g$, —O$R^e$, —OC(O)$R^e$, —OC(O)O$R^e$, —OC(O)N$R^fR^g$, —OC(=N$R^e$)N$R^fR^g$, —OS(O)$R^e$, —OS(O)$_2R^e$, —OS(O)N$R^fR^g$, —OS(O)$_2$N$R^fR^g$, —N$R^fR^g$, —N$R^e$C(O)$R^h$, —N$R^e$C(O)O$R^f$, —N$R^e$C(O)N$R^fR^g$, —N$R^e$C(=N$R^h$)N$R^fR^g$, —N$R^e$S(O)$R^h$, —N$R^e$S(O)$_2R^h$, —N$R^e$S(O)N$R^fR^g$, —N$R^e$S(O)$_2$N$R^fR^g$, —S$R^e$, —S(O)$R^e$, —S(O)$_2R^e$, —S(O)N$R^fR^g$, and —S(O)$_2$N$R^fR^g$; wherein each $R^e$, $R^f$, $R^g$, and $R^h$ is independently (i) hydrogen; (ii) $C_{1-6}$ alkyl, $C_{2-6}$ alkenyl, $C_{2-6}$ alkynyl, $C_{3-7}$ carbocyclyl, $C_{6-14}$ aryl, $C_{7-15}$ aralkyl, heteroaryl, or heterocyclyl; or (iii) $R^f$ and $R^g$ together with the N atom to which they are attached form heterocyclyl.

In another embodiment, the present invention provides a pharmaceutical composition comprising a compound of the present invention, and one or more pharmaceutically acceptable carriers.

In another embodiment, the present invention provides a method of modulating the activity of glucagon-like peptide-1 (GLP-1) receptor comprising contacting an effective amount of a compound of the present invention with a cell containing GLP-1 receptor.

In another embodiment, the present invention provides a method of treating a condition, disease, and/or a disorder associated with GLP-1, or one or more symptoms thereof, in a subject comprising administering to the subject an effective amount of a compound of the present invention.

DETAILED DESCRIPTIONS

Compounds of the present invention exert biological activities that include, but are not limited to, modulating the activity of GLP-1 receptor as demonstrated by the data herein. Such compounds therefore can be utilized in multiple applications by, a person of ordinary skill in the art. For example, compounds described herein can be used, for example, for treating any condition or disease related to the activity of GLP-1 receptor.

Definitions

To facilitate understanding of the disclosure set forth herein, a number of terms are defined below. Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs.

The terms "a" and "an" do not denote a limitation of quantity, but rather denote the presence of at least one of the referenced item. The terms "a" and "an" are used interchangeable with "one or more" or "at least one". The term "or" or "and/or" is used as a function word to indicate that two words or expressions are to be taken together or individually. The terms "comprising", "having", "including", and "containing" are to be construed as open-ended terms (i.e., meaning "including, but not limited to"). The endpoints of all ranges directed to the same component or property are inclusive and independently combinable.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "compound(s) of the invention", "these compounds", "such compound(s)", "the compound(s)", and "the present compound(s)" refer to compounds encompassed by structural formulae disclosed herein, e.g., Formula (I'), (I), (II), (III), (IV), (V), (VI), (VII), (VIII), (IX), (X), (XI), (XII), (XV) or any subgenus thereof, including any specific compounds, i.e., species, within these formulae or any subgenus thereof whose structure is disclosed herein. Compounds may be identified either by their chemical structure and/or chemical name. When the chemical structure and chemical name conflict, the chemical structure is determinative of the identity of the compound. Furthermore, the present compounds can modulate, i.e., inhibit or enhance, the biological activity of a GLP-1 receptor, and thereby is also referred to herein as a "modulator(s)" or "GLP-1 receptor modulator(s)". Compounds of Formula (I'), (I), (II), (III), (IV), (V), (VI), (VII), (VIII), (IX), (X), (XI), (XII), (XV), or any subgenus thereof, including any species within these formulae or any subgenus thereof, are exemplary "modulators".

The compounds described herein may contain one or more chiral centers and/or double bonds and therefore, may exist as stereoisomers, such as double-bond isomers (i.e., geometric isomers such as E and Z), enantiomers or diastereomers. The invention includes each of the isolated stereoisomeric forms (such as the enantiomerically pure isomers, the E and Z isomers, and etc.) as well as mixtures of stereoisomers in varying degrees of chiral purity or percentage of E and Z, including racemic mixtures, mixtures of diastereomers, and mixtures of E and Z isomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The invention includes each of the isolated stereoisomeric forms as well as mixtures of stereoisomers in varying degrees of chiral purity, including racemic mixtures. It also encompasses the various diastereomers. Other structures may appear to depict a specific isomer, but that is merely for convenience, and is not intended to limit the invention to the depicted olefin isomer. When the chemical name does not specify the isomeric form of the compound, it denotes any one of the possible isomeric forms or a mixtures of those isomeric forms of the compound.

In certain embodiments, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of one enantiomer and about 5% or less of the other enantiomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S. The phrase "a single enantiomer, a mixture of enantiomers, a mixture of diastereomers, or an isotopic variant thereof; or a pharmaceutically acceptable salt, solvate, or prodrug thereof" has the same meaning as the phrase "a single enantiomer, a mixture of enantiomers, a mixture of diastereomers, or an isotopic variant of the compound referenced therein; or a pharmaceutically acceptable salt, solvate, or prodrug of the compound referenced therein, or a single enantiomer, a mixture of enantiomers, a mixture of diastereomers, or an isotopic variant of the compound referenced therein."

The compounds may also exist in several tautomeric forms, and the depiction herein of one tautomer is for convenience only, and is also understood to encompass other tautomers of the form shown. Accordingly, the chemical structures depicted herein encompass all possible tautomeric forms of the illustrated compounds. The term "tautomer" as used herein refers to isomers that change into one another with great ease so that they can exist together in equilibrium. For example, ketone and enol are two tautomeric forms of one compound. In another example, a substituted 1,2,4-triazole derivative may exist in at least three tautomeric forms as shown below:

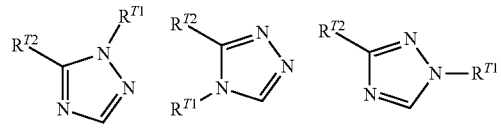

$R^{T1}$ is H or optionally substituted alkyl.
$R^{T2}$ is an optionally substituted aryl.

The term "isotopic variant" refers to a compound that contains an unnatural proportion of an isotope at one or more of the atoms that constitute such compounds. In certain embodiments, an "isotopic variant" of a compound contains unnatural proportions of one or more isotopes, including, but not limited to, hydrogen ($^{1}$H), deuterium ($^{2}$H), tritium ($^{3}$H), carbon-11 ($^{11}$C), carbon-12 ($^{12}$C), carbon-13 ($^{11c}$), carbon-14 ($^{14}$C), nitrogen-13 ($^{13}$N), nitrogen-14 ($^{14}$N), nitrogen-15 ($^{15}$N), oxygen-14 ($^{14}$O), oxygen-15 ($^{15}$O), oxygen-16 ($^{16}$O), oxygen-17 ($^{17}$O), oxygen-18 ($^{18}$O), fluorine-17 ($^{17}$F), fluorine-18 ($^{18}$F), phosphorus-31 ($^{31}$P), phosphorus-32 ($^{32}$P), phosphorus-33 ($^{33}$P), sulfur-32 ($^{32}$S), sulfur-33 ($^{33}$S), sulfur-34 ($^{34}$S), sulfur-35 ($^{35}$S), sulfur-36 ($^{36}$S), chlorine-35 ($^{35}$Cl), chlorine-36 ($^{36}$Cl), chlorine-37 ($^{37}$Cl), bromine-79 ($^{79}$Br), bromine-81 ($^{8}$Br), iodine-123 ($^{123}$I), iodine-125 ($^{125}$I), iodine-127 ($^{127}$I), iodine-129 ($^{129}$I), and iodine-131 ($^{131}$I). In certain embodiments, an "isotopic variant" of a compound is in a stable form, that is, non-radioactive. In certain embodiments, an "isotopic variant" of a compound contains unnatural proportions of one or more isotopes, including, but not limited to, hydrogen ($^{1}$H), deuterium ($^{2}$H), carbon-12 ($^{12}$C), carbon-13 ($^{11c}$), nitrogen-14 ($^{14}$N), nitrogen-15 ($^{15}$N), oxygen-16 ($^{16}$O), oxygen-17 ($^{17}$O), oxygen-18 ($^{18}$O), fluorine-17 ($^{17}$F), phosphorus-31 ($^{31}$P), sulfur-32 ($^{32}$S), sulfur-33 ($^{33}$S), sulfur-34 ($^{34}$S), sulfur-36 ($^{36}$S), chlorine-35 ($^{35}$Cl), chlorine-37 ($^{37}$Cl), bromine-79 ($^{79}$Br), bromine-81 ($^{81}$Br), and iodine- 127 ($^{127}$I). In certain embodiments, an "isotopic variant" of a compound is in an unstable form, that is, radioactive. In certain embodiments, an "isotopic variant" of a compound contains unnatural proportions of one or more isotopes, including, but not limited to, tritium ($^3$H), carbon-11 ($^{11}$C), carbon-14 ($^{14}$C), nitrogen-13 ($^{13}$N), oxygen-14 ($^{14}$O), oxygen-15 ($^{15}$O), fluorine-18 ($^{18}$F), phosphorus-32 ($^{32}$P), phosphorus-33 ($^{33}$P), sulfur-35 ($^{35}$S), chlorine-36 ($^{36}$Cl), iodine-123 ($^{123}$I), iodine-125 ($^{125}$I), iodine-129 ($^{129}$I), and iodine-131 ($^{131}$I). It will be understood that, in a compound as provided herein, any hydrogen can be $^2$H, for example, or any carbon can be $^{11c}$, as example, or any nitrogen can be $^{15}$N, as example, and any oxygen can be $^{18}$O, where feasible according to the judgment of one of skill. In certain embodiments, an "isotopic variant" of a compound contains unnatural proportions of deuterium.

The descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocyclyl or heteroaryl is attached to the remainder of the molecule via a ring heteroatom in compliance with principles of chemical bonding known to those skilled in the art thereby avoiding inherently unstable compounds.

The compounds of the invention often have ionizable groups so as to be capable of preparation as salts. In that case, wherever reference is made to the compound, it is understood in the art that a pharmaceutically acceptable salt may also be used. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases are well-known in the art, such as hydrochloric, sulphuric, hydrobromic, acetic, lactic, citric, or tartaric acids for forming acid addition salts, and potassium hydroxide, sodium hydroxide, ammonium hydroxide, caffeine, various amines, and the like for forming basic salts. Methods for preparation of the appropriate salts are well-established in the art. In some cases, the compounds may contain both an acidic and a basic functional group, in which case they may have two ionized groups and yet have no net charge. Standard methods for the preparation of pharmaceutically acceptable salts and their formulations are well known in the art, and are disclosed in various references, including for example, "*Remington: The Science and Practice of Pharmacy*", A. Gennaro, ed., 20th edition, Lippincott, Williams & Wilkins, Philadelphia, Pa.

"Solvate", as used herein, means a compound formed by solvation (the combination of solvent molecules with molecules or ions of the solute), or an aggregate that consists of a solute ion or molecule, i.e., a compound of the invention, with one or more solvent molecules. When water is the solvent, the corresponding solvate is "hydrate". Examples of hydrate include, but are not limited to, hemihydrate, monohydrate, dihydrate, trihydrate, hexahydrate, etc. It should be understood by one of ordinary skill in the art that the pharmaceutically acceptable salt, and/or prodrug of the present compound may also exist in a solvate form. The solvate is typically formed via hydration which is either part of the preparation of the present compound or through natural absorption of moisture by the anhydrous compound of the present invention.

The term "ester" means any ester of a present compound in which any of the —COOH functions of the molecule is replaced by a —COOR function, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl and substituted derivatives thereof. The hydrolysable esters of the present compounds are the compounds whose carboxyls are present in the form of hydrolysable ester groups. That is, these esters are pharmaceutically acceptable and can be hydrolyzed to the corresponding carboxyl acid in vivo. These esters may be conventional ones, including lower alkanoyloxyalkyl esters, e.g. pivaloyloxymethyl and 1-pivaloyloxyethyl esters; lower alkoxycarbonylalkyl esters, e.g., methoxycarbonyloxymethyl, 1-ethoxycarbonyloxyethyl, and 1-isopropylcarbonyloxyethyl esters; lower alkoxymethyl esters, e.g., methoxymethyl esters, lactonyl esters, benzofuran keto esters, thiobenzofuran keto esters; lower alkanoylaminomethyl esters, e.g., acetylaminomethyl esters. Other esters can also be used, such as benzyl esters and cyano methyl esters. Other examples of these esters include: (2,2-dimethyl-1-oxypropyloxy)methyl esters; (1RS)-1-acetoxyethyl esters, 2-[(2-methylpropyloxy)carbonyl]-2-pentenyl esters, 1-[[(1-methylethoxy)carbonyl]-oxy]ethyl esters; isopropyloxycarbonyloxyethyl esters, (5-methyl-2-oxo-1,3-dioxole-4-yl)methyl esters, 1-[[(cyclohexyloxy)carbonyl] oxy]ethyl esters; 3,3-dimethyl-2-oxobutyl esters. It is obvious to those skilled in the art that hydrolysable esters of the compounds of the present invention can be formed at free carboxyls of said compounds by using conventional methods. Representative esters include pivaloyloxymethyl esters, isopropyloxycarbonyloxyethyl esters and (5-methyl-2-oxo-1,3-dioxole-4-yl)methyl esters.

The term "prodrug" refers to a precursor of a pharmaceutically active compound wherein the precursor itself may or may not be pharmaceutically active but, upon administration, will be converted, either metabolically or otherwise, into the pharmaceutically active compound or drug of interest. For example, prodrug can be an ester, ether, or amide form of a pharmaceutically active compound. Various types of prodrug have been prepared and disclosed for a variety of pharmaceuticals. See, for example, Bundgaard, H. and Moss, J., J. Pharm. Sci. 78: 122-126 (1989). Thus, one of ordinary skill in the art knows how to prepare these prodrugs with commonly employed techniques of organic synthesis.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, 2$^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

As used herein, "pharmaceutically acceptable" means suitable for use in contact with the tissues of humans and animals without undue toxicity, irritation, allergic response, and the like, commensurate with a reasonable benefit/risk ratio, and effective for their intended use within the scope of sound medical judgment.

"Excipient" or "carrier" refers to a diluent, adjuvant, or vehicle with which a compound is administered. The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, Remington: The Science and Practice of Pharmacy, 21st ed.; Lippincott Williams & Wilkins: Philadelphia, Pa., 2005; Handbook of Pharmaceutical Excipients, 6th ed.; Rowe et al., Eds.; The Pharmaceutical Press and the American Pharmaceutical Association: 2009; Handbook of Pharmaceutical Additives, 3rd ed.; Ash and Ash Eds.; Gower Publishing Company: 2007; Pharmaceutical Preformulation and Formulation, 2nd ed.; Gibson Ed.; CRC Press LLC: Boca Raton, Fla., 2009.

An "effective amount" or "therapeutically effective amount" is the quantity of the present compound in which a beneficial outcome is achieved when the compound is administered to a patient or alternatively, the quantity of compound that possesses a desired activity in vivo or in vitro. In the case of proliferative disorders, a beneficial clinical outcome includes reduction in the extent or severity of the symptoms associated with the disease or disorder and/or an increase in the longevity and/or quality of life of the patient compared with the absence of the treatment. For example, for a subject with cancer, a "beneficial clinical outcome" includes a reduction in tumor mass, a reduction in the rate of tumor growth, a reduction in metastasis, a reduction in the severity of the symptoms associated with the cancer and/or an increase in the longevity of the subject compared with the absence of the treatment. The precise amount of compound administered to a subject will depend on the type and severity of the disease or condition and on the characteristics of the patient, such as general health, age, sex, body weight and tolerance to drugs. It will also depend on the degree, severity and type of proliferative disorder. The skilled artisan will be able to determine appropriate dosages depending on these and other factors.

As used herein, the terms "alkyl," "alkenyl" and "alkynyl" include straight-chain, branched-chain and cyclic monovalent hydrocarbyl radicals, and combinations of these, which contain only C and H when they are unsubstituted, and "alkyl" refers to such a saturated monovalent hydrocarbon radical, "alkenyl" refers to such a monovalent hydrocarbon radical, which contains one or more, in one embodiment, one to five, in another embodiment, one, carbon-carbon double bond(s), and "alkynyl" refers to a linear or branched monovalent hydrocarbon radical, which contains one or more, in one embodiment, one to five, in another embodiment, one, carbon-carbon triple bond(s). The total number of carbon atoms in each such group is sometimes described herein, e.g., when the group can contain up to ten carbon atoms it can be represented as 1-10C or as C1-C10 or C1-10 (or $C_1$-$C_{10}$ or $C_{1-10}$). When heteroatoms (N, O and S typically) are allowed to replace carbon atoms as in heteroalkyl groups, for example, the numbers describing the group, though still written as e.g. C1-C6, represent the sum of the number of carbon atoms in the group plus the number of such heteroatoms that are included as replacements for carbon atoms in the backbone of the ring or chain being described. Where a ring is included, it is understood that the group contains at least three carbon atoms as a 3-membered ring is the smallest size for a ring. Alkyl, alkenyl and alkynyl groups are often optionally substituted to the extent that such substitution makes sense chemically.

The alkyl may optionally be substituted with one or more substituents Q as described herein. For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms).

The alkenyl may be optionally substituted with one or more substituents Q as described herein. The term "alkenyl" embraces radicals having a "cis" or "trans" configuration or a mixture thereof, or alternatively, a "Z" or "E" configuration or a mixture thereof, as appreciated by those of ordinary skill in the art. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

The alkynyl may be optionally substituted with one or more substituents Q as described herein. For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkynyl groups include, but are not limited to, ethynyl (—C≡CH), propynyl (including all isomeric forms, e.g., 1-propynyl (—C≡CCH$_3$) and propargyl (—CH$_2$C≡CH)), butynyl (including all isomeric forms, e.g., 1-butyn-1-yl and 2-butyn-1-yl), pentynyl (including all isomeric forms, e.g., 1-pentyn-1-yl and 1-methyl-2-butyn-1-yl), and hexynyl (including all isomeric forms, e.g., 1-hexyn-1-yl).

The terms "cycloalkyl" "cycloalkenyl" and "cycloalkynyl" are included by "alkyl," "alkenyl" and "alkynyl" as referring to these monovalent hydrocarbyl radicals when they are cyclic. The term "cycloalkyl" refers to a cyclic monovalent hydrocarbon radical, which may be optionally substituted with one or more substituents Q as described herein. In one embodiment, cycloalkyl groups may be saturated or unsaturated but non-aromatic, and/or bridged, and/or non-bridged, and/or fused bicyclic groups. In certain embodiments, the cycloalkyl has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclopentenyl, cyclohexyl, cyclohexenyl, cyclohexadienyl, cycloheptyl, cycloheptenyl, bicyclo[2.1.1]hexyl, bicyclo[2.2.1]heptyl, decalinyl, and adamantyl.

The term "optionally substituted" is intended to mean that a group or substituent, such as an alkyl, alkenyl, alkenylene, alkynyl, alkynylene, cycloalkyl, aryl, aralkyl, heteroaryl, tetrazolyl, heteroarylene, heteroaryl-alkyl, heterocyclyl, heterocyclylene, and heterocyclyl-alkyl group, may be substituted with one or more substituents Q, each of which is independently selected from, e.g., (a) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (b) halo, cyano (—CN), nitro (—$NO_2$), —C(O)$R^a$, —C(O)O$R^a$, —C(O)N$R^b R^c$, —C(N$R^a$)N$R^b R^c$, —O$R^a$, —OC(O)$R^a$, —OC(O)O$R^a$, —OC(O)N$R^b R^c$, —OC(=N$R^a$)N$R^b R^c$, —OS(O)$R^a$, —OS(O)$_2 R^a$, —OS(O)N$R^b R^c$, —OS(O)$_2$N$R^b R^c$, —N$R^b R^c$, —N$R^a$C(O)$R^d$, —N$R^a$C(O)O$R^d$, —N$R^a$C(O)N$R^b R^c$, —N$R^a$C(=N$R^d$)N$R^b R^c$, —N$R^a$S(O)$R^d$, —N$R^a$S(O)$_2 R^d$, —N$R^a$S(O)N$R^b R^c$, —N$R^a$S(O)$_2$N$R^b R^c$, —S$R^a$, —S(O)$R^a$, —S(O)$_2 R^a$, —S(O)N$R^b R^c$, and —S(O)$_2$N$R^b R^c$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^a$; or (iii) $R^b$ and $R^c$ together with the N atom to which they are attached form heteroaryl or heterocyclyl, optionally substituted with one or more, in one embodiment, one, two, three, or four, substituents $Q^a$. As used herein, all groups that can be substituted are "optionally substituted," unless otherwise specified.

In one embodiment, each $Q^a$ is independently selected from the group consisting of (a) cyano, halo, and nitro; and (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^f R^g$, —C(N$R^e$)N$R^f R^g$, —O$R^e$, —OC(O)$R^e$, —OC(O)O$R^e$, —OC(O)N$R^f R^g$, —OC(=N$R^e$)N$R^f R^g$, —OS(O)$R^e$, —OS(O)$_2 R^e$, —OS(O)N$R^f R^g$, —OS(O)$_2$N$R^f R^g$, —N$R^f R^g$, —N$R^e$C(O)$R^h$, —N$R^e$C(O)O$R^h$, —N$R^e$C(O)N$R^f R^g$, —N$R^e$C(=N$R^h$)N$R^f R^g$, —N$R^e$S(O)$R^h$, —N$R^e$S(O)$_2 R^h$, —N$R^e$S(O)N$R^f R^g$, —N$R^e$S(O)$_2$N$R^f R^g$, —S$R^e$, —S(O)$R^e$, —S(O)$_2 R^e$, —S(O)N$R^f R^g$, and —S(O)$_2$N$R^f R^g$; wherein each $R^e$, $R^f$, $R^g$, and $R^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) $R^f$ and $R^g$ together with the N atom to which they are attached form heteroaryl or heterocyclyl.

"Acetylene" substituents are 2-10C alkynyl groups that contain at least one carbon-carbon triple bond and are optionally substituted with the groups described herein as suitable for alkyl groups; in some embodiments, the alkynyl groups are of the formula —C≡C—$R^a$, wherein $R^a$ is H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-12 heteroarylalkyl.

Each $R^a$ group is optionally substituted with one or more substituents selected from halo, =O, =N—CN, =N—OR', =NR', OR', NR'$_{12}$, SR', $SO_2$R', $SO_2$NR'$_2$, NR'$SO_2$R', NR'CONR'$_2$, NR'CSNR'$_2$, NR'C(=NR')NR'$_2$, NR'COOR', NR'COR', CN, COOR', CONR'$_2$, OOCR', COR', and $NO_2$, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, CN, C1-C4 alkyl, C2-C4 heteroalkyl, C1-C6 acyl, C1-C6 heteroacyl, C1-C4 alkoxy, C1-C4 alkylamino, di(C1-C4 alkyl)amino, hydroxy, amino, and =O; and wherein two R' can be linked to form a 3-7 membered ring optionally containing up to three heteroatoms selected from N, O and S. In some embodiments, $R^a$ of —C≡C—$R^a$ is H or Me.

"Heteroalkyl", "heteroalkenyl", and "heteroalkynyl" and the like are defined similarly to the corresponding hydrocarbyl (alkyl, alkenyl and alkynyl) groups, but the 'hetero' terms refer to groups that contain 1-3 O, S or N heteroatoms or combinations thereof within the backbone residue; thus at least one carbon atom of a corresponding alkyl, alkenyl, or alkynyl group is replaced by one of the specified heteroatoms to form, respectively, a heteroalkyl, heteroalkenyl, or heteroalkynyl group. The typical and preferred sizes for heteroforms of alkyl, alkenyl and alkynyl groups are generally the same as for the corresponding hydrocarbyl groups, and the substituents that may be present on the heteroforms are the same as those described above for the hydrocarbyl groups. For reasons of chemical stability, it is also understood that, unless otherwise specified, such groups do not include more than two contiguous heteroatoms except where an oxo group is present on N or S as in a nitro or sulfonyl group.

Similarly, "heterocyclyl" may be used to describe a non-aromatic cyclic group that contains at least one heteroatom (typically selected from N, O and S) as a ring member and that is connected to the molecule via a ring atom, which may be C (carbon-linked) or N (nitrogen-linked); and "heterocyclylalkyl" may be used to describe such a group that is connected to another molecule through a linker. The heterocyclyl can be fully saturated or partially saturated, but non-aromatic. The sizes and substituents that are suitable for the cycloalkyl, cycloalkylalkyl, heterocyclyl, and heterocyclylalkyl groups are the same as those described above for alkyl groups. The heterocyclyl groups typically contain 1, 2 or 3 heteroatoms, selected from N, O and S as ring members; and the N or S can be substituted with the groups commonly found on these atoms in heterocyclic systems. As used herein, these terms also include rings that contain a double bond or two, as long as the ring that is attached is not aromatic. The substituted cycloalkyl and heterocyclyl groups also include cycloalkyl or heterocyclic rings fused to an aromatic ring or heteroaromatic ring, provided the point of attachment of the group is to the cycloalkyl or heterocyclyl ring rather than to the aromatic/heteroaromatic ring.

Like alkyl groups, the cycloalkyl and heterocyclyl groups described herein can be substituted to the extent permitted by their valence and stability considerations, which are well understood by those of skill in the art. Substituents for the cycloalkyl and heterocyclyl rings or ring systems include those described herein as suitable for placement on alkyl groups.

As used herein, "acyl" encompasses groups comprising an alkyl, alkenyl, alkynyl, aryl or arylalkyl radical attached at one of the two available valence positions of a carbonyl carbon atom, and heteroacyl refers to the corresponding groups wherein at least one carbon other than the carbonyl carbon has been replaced by a heteroatom chosen from N, O and S. Thus heteroacyl includes, for example, —C(=O)OR and —C(=O)NR$_2$ as well as —C(=O)-heteroaryl.

Acyl and heteroacyl groups are bonded to any group or molecule to which they are attached through the open valence of the carbonyl carbon atom. Typically, they are C1-C8 acyl groups, which include formyl, acetyl, pivaloyl, and benzoyl, and C2-C8 heteroacyl groups, which include methoxyacetyl, ethoxycarbonyl, and 4-pyridinoyl. The hydrocarbyl groups, aryl groups, and heteroforms of such groups that comprise an acyl or heteroacyl group can be substituted with the substituents described herein as generally suitable substituents for each of the corresponding component of the acyl or heteroacyl group.

The term "aryl" refers to a monovalent monocyclic aromatic group and/or monovalent polycyclic aromatic group that contain at least one aromatic carbon ring. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In certain embodiments, aryl may be optionally substituted with one or more substituents Q as described herein.

Similarly, "heteroaromatic" and "heteroaryl" refer to such monocyclic or fused bicyclic ring systems which contain as ring members one or more heteroatoms selected from O, S and N. The inclusion of a heteroatom permits aromaticity in 5-membered rings as well as 6-membered rings. Typical heteroaromatic systems include monocyclic C5-C6 aromatic groups such as pyridyl, pyrimidyl, pyrazinyl, thienyl, furanyl, pyrrolyl, pyrazolyl, thiazolyl, oxazolyl, triazolyl, triazinyl, tetrazolyl, tetrazinyl, and imidazolyl and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms and up to four heteroatoms selected from N, O and S. Frequently, the monocyclic heteroaryls contain 5-6 ring members and up to three such heteroatoms, and the bicyclic heteroaryls contain 8-10 ring members and up to four such heteroatoms. The number and placement of heteroatoms in such rings is in accordance with the well-known limitations of aromaticity and stability, where stability requires the heteroaromatic group to be stable enough to be exposed to water without rapid degradation.

Aryl and heteroaryl moieties may be substituted with a variety of substituents including C1-C8 alkyl, C2-C8 alkenyl, C2-C8 alkynyl, C5-C12 aryl, C1-C8 acyl, and heteroforms of these, each of which can itself be further substituted; other substituents for aryl and heteroaryl moieties include halo, OR, $NR_2$, SR, $SO_2R$, $SO_2NR_2$, $NRSO_2R$, $NRCONR_2$, $NRCSNR_2$, NRC(=NR)$NR_2$, NRCOOR, NRCOR, CN, C≡CR, COOR, $CONR_2$, OOCR, COR, and $NO_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C3-C8 heterocyclyl, C4-C10 heterocyclylalkyl, C6-C10 aryl, C5-C10 heteroaryl, C7-C12 arylalkyl, or C6-C12 heteroarylalkyl, and each R is optionally substituted as described above for alkyl groups. The substituent groups on an aryl or heteroaryl group may of course be further substituted with the groups described herein as suitable for each type of such substituents or for each component of the substituent. Thus, for example, an arylalkyl substituent may be substituted on the aryl portion with substituents described herein as typical for aryl groups, and it may be further substituted on the alkyl portion with substituents described herein as typical or suitable for alkyl groups. Where a substituent group contains two R groups on the same or adjacent atoms (e.g., —$NR_2$, or —NR—C(O)R), the two R groups can optionally be taken together with the atom(s) in the substituent group to which the are attached to form a ring having 5-8 ring members, which can be substituted as allowed for the R itself, and can contain an additional heteroatom (N, O or S) as a ring member.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is C1-C8 alkyl or a hetero form thereof. These linkers may also include a carbonyl group, thus making them able to provide substituents as an acyl or heteroacyl moiety. An aryl or heteroaryl ring in an arylalkyl or heteroarylalkyl group may be substituted with the same substituents described above for aryl groups. Preferably, an arylalkyl group includes a phenyl ring optionally substituted with the groups defined above for aryl groups and a C1-C4 alkylene that is unsubstituted or is substituted with one or two C1-C4 alkyl groups or heteroalkyl groups, where the alkyl or heteroalkyl groups can optionally cyclize to form a ring such as cyclopropane, dioxolane, or oxacyclopentane. Similarly, a heteroarylalkyl group preferably includes a C5-C6 monocyclic heteroaryl group that is optionally substituted with the groups described above as substituents typical on aryl groups and a C1-C4 alkylene that is unsubstituted or is substituted with one or two C1-C4 alkyl groups or heteroalkyl groups, or it includes an optionally substituted phenyl ring or C5-C6 monocyclic heteroaryl and a C1-C4 heteroalkylene that is unsubstituted or is substituted with one or two C1-C4 alkyl or heteroalkyl groups, where the alkyl or heteroalkyl groups can optionally cyclize to form a ring such as cyclopropane, dioxolane, or oxacyclopentane.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenylethyl is a C8-arylalkyl.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. Thus, for example, C7-heteroarylalkyl would include pyridylmethyl, phenoxy, and N-pyrrolylmethoxy.

"Alkylene", "alkenylene", or "alkynylene", as used herein, each refers to a divalent hydrocarbyl group of alkyl, alkenyl, or alkynyl; because it is divalent, it can link two other groups together. For example, "alkylene" refers to —$(CH_2)_n$—, "alkenylene" refers to —$(CH=CH)_n$—, and "alkynylene" refers to —$(C\equiv C)_n$—, where n is an integer, and preferably n is 1 to 8, though where specified, an alkylene or alkenylene can also be substituted by other groups, and can be of other lengths, and the open valences need not be at opposite ends of a chain. Thus —CH(Me)- and —C(Me)$_2$- may also be referred to as alkylenes, as can a cyclic group such as cyclopropan-1,1-diyl. Where an alkylene or alkenylene group is substituted, the substituents include those typically present on alkyl or alkenyl groups as described herein. Similarly, "arylene", "heteroarylene", "carbocyclylene", or "heterocyclylene" refers to the corresponding divalent "aryl", heteroaryl", "carbocyclyl", or "heterocyclyl".

In general, any alkyl, alkenyl, alkynyl, acyl, or aryl or arylalkyl group or any heteroform of one of these groups that is contained in a substituent may itself optionally be substituted by additional substituents. The nature of these substituents is similar to those recited with regard to the primary substituents themselves if the substituents are not otherwise described. Thus, where an embodiment of, for example, $R^x$ is alkyl, this alkyl may optionally be substituted by the remaining substituents listed as embodiments for $R^x$ where this makes chemical sense, and where this does not undermine the size limit provided for the alkyl per se; e.g., alkyl substituted by alkyl or by alkenyl would simply extend the upper limit of carbon atoms for these embodiments, and is not included. However, alkyl substituted by aryl, amino, alkoxy, =O, and the like would be included within the scope of the invention, and the atoms of these substituent groups are not counted in the number used to describe the alkyl, alkenyl, etc. group that is being described. Where no number of substituents is specified, each such alkyl, alkenyl, alkynyl, acyl, or aryl group may be substituted with a number of substituents according to its available valences; in particular, any of these groups may be substituted with fluorine atoms at any or all of its available valences, for example.

"Heteroform" as used herein refers to a derivative of a group such as an alkyl, aryl, or acyl, wherein at least one carbon atom of the designated carbocyclic group has been replaced by a heteroatom selected from N, O and S. Thus the heteroforms of alkyl, alkenyl, alkynyl, acyl, aryl, and arylalkyl are heteroalkyl, heteroalkenyl, heteroalkynyl, heteroacyl, heteroaryl, and heteroarylalkyl, respectively. It is understood that no more than two N, O or S atoms are ordinarily connected sequentially, except where an oxo group is attached to N or S to form a nitro or sulfonyl group.

"Halo", "halogen", or "halide", as used herein includes fluoro, chloro, bromo and iodo. Fluoro and chloro are often preferred.

"Amino" as used herein refers to NH$_2$, but where an amino is described as "substituted" or "optionally substituted", the term includes NR'R" wherein each R' and R" is independently H, or is an alkyl, alkenyl, alkynyl, acyl, aryl, or arylalkyl group or a heteroform of one of these groups, and each of the alkyl, alkenyl, alkynyl, acyl, aryl, or arylalkyl groups or heteroforms of one of these groups is optionally substituted with the substituents described herein as suitable for the corresponding group. The term also includes forms wherein R' and R" are taken together with the N to which they are attached to form a 3-8 membered ring which may be saturated, unsaturated or aromatic and which contains 1-3 heteroatoms independently selected from N, O and S as ring members, and which is optionally substituted with the substituents described as suitable for alkyl groups or, if NR'R" is an aromatic group, it is optionally substituted with the substituents described as typical for heteroaryl groups.

As used herein, the term "carbocycle", "carbocyclyl", or "carbocyclic" refers to a cyclic ring containing only carbon atoms in the ring, whereas the term "heterocycle", "heterocyclyl", or "heterocyclic" refers to a ring comprising a heteroatom. The carbocyclyl or heterocyclyl can be fully saturated or partially saturated, but non-aromatic. For example, the carbocyclyl encompasses cycloalkyl. The carbocyclic and heterocyclic structures encompass compounds having monocyclic, bicyclic or multiple ring systems; and such systems may mix aromatic, heterocyclic, and carbocyclic rings. Mixed ring systems are described according to the ring that is attached to the rest of the compound being described; for example, 1,2,3,4-tetrahydronaphth-1-yl would be encompassed by an optionally substituted cycloalkyl or carbocyclic group, while the group 1,2,3,4-tetrahydronaphth-6-yl would be included within optionally substituted aromatic groups.

As used herein, the term "heteroatom" refers to any atom that is not carbon or hydrogen, such as nitrogen, oxygen or sulfur. When it is part of the backbone or skeleton of a chain or ring, a heteroatom must be at least divalent, and will typically be selected from N, O, P, and S.

Illustrative examples of heterocycles and heteroaryls include but are not limited to tetrahydrofuran, 1,3-dioxolane, 2,3-dihydrofuran, pyran, tetrahydropyran, benzofuran, isobenzofuran, 1,3-dihydro-isobenzofuran, isoxazole, 4,5-dihydroisoxazole, piperidine, pyrrolidine, pyrrolidin-2-one, pyrrole, pyridine, pyrimidine, octahydro-pyrrolo[3,4 b]pyridine, piperazine, pyrazine, morpholine, thiomorpholine, imidazole, imidazolidine 2,4-dione, 1,3-dihydrobenzimidazol-2-one, indole, thiazole, benzothiazole, thiadiazole, thiophene, tetrahydro thiophene 1,1-dioxide, diazepine, triazole, guanidine, diazabicyclo[2.2.1]heptane, 2,5-diazabicyclo[2.2.1]heptane, 2,3,4,4a,9,9a-hexahydro-1H-β-carboline, oxirane, oxetane, tetrahydropyran, dioxane, lactones, aziridine, azetidine, piperidine, lactams, and may also encompass heteroaryls. Other illustrative examples of heteroaryls include but are not limited to furan, pyrrole, pyridine, pyrimidine, imidazole, benzimidazole and triazole.

The term "heteroaryl" refers to a monovalent monocyclic aromatic group or monovalent polycyclic aromatic group that contain at least one aromatic ring, wherein at least one aromatic ring contains one or more heteroatoms independently selected from O, S, and N in the ring. Heteroaryl groups are bonded to the rest of a molecule through the aromatic ring. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, heteroaryl may also be optionally substituted with one or more substituents Q as described herein.

The term "heteroarylene" refers to a divalent monocyclic aromatic group or divalent polycyclic aromatic group that contain at least one aromatic ring, wherein at least one aromatic ring contains one or more heteroatoms independently selected from O, S, and N in the ring. Each ring of a heteroarylene group can contain one or two O atoms, one or two S atoms, and/or one to four N atoms, provided that the total number of heteroatoms in each ring is four or less and each ring contains at least one carbon atom. In certain embodiments, the heteroarylene has from 5 to 20, from 5 to 15, or from 5 to 10 ring atoms. Examples of monocyclic heteroarylene groups include, but are not limited to, furanylene, imidazolylene, isothiazolylene, isoxazolylene, oxadiazolylene, oxadiazolylene, oxazolylene, pyrazinylene, pyrazolylene, pyridazinylene, pyridylene, pyrimidinylene, pyrrolylene, thiadiazolylene, thiazolylene, thienylene, tetrazolylene, triazinylene, and triazolylene. Examples of bicyclic heteroarylene groups include, but are not limited to, benzofuranylene, benzimidazolylene, benzoisoxazolylene, benzopyranylene, benzothiadiazolylene, benzothiazolylene, benzothienylene, benzotriazolylene, benzoxazolylene, furopyridylene, imidazopyridinylene, imidazothiazolylene, indolizinylene, indolylene, indazolylene, isobenzofuranylene, isobenzothienylene, isoindolylene, isoquinolinylene, isothiazolylene, naphthyridinylene, oxazolopyridinylene, phthalazinylene, pteridinylene, purinylene, pyridopyridylene, pyrrolopyridylene, quinolinylene, quinoxalinylene, quinazolinylene, thiadiazolopyrimidylene, and thienopyridylene. Examples of tricyclic heteroarylene groups include, but are not limited to, acridinylene, benzindolylene, carbazolylene, dibenzofuranylene, perimidinylene, phenanthrolinylene, phenanthridinylene, phenarsazinylene, phenazinylene, phenothiazinylene, phenoxazinylene, and xanthenylene. In certain embodiments, heteroarylene may also be optionally substituted with one or more substituents Q as described herein.

The term "heterocyclyl" or "heterocyclic" refers to a monovalent monocyclic non-aromatic ring system or monovalent polycyclic ring system that contains at least one non-aromatic ring, wherein one or more of the non-aromatic ring atoms are heteroatoms independently selected from O, S, and N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. Heterocyclyl groups are bonded to the rest of a molecule through the non-aromatic ring. In certain embodiments, the heterocyclyl is a monocyclic, bicyclic, tricyclic, or tetracyclic ring system, which may be fused or bridged, and in which nitrogen or sulfur atoms may be optionally oxidized, nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic groups include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, heterocyclic may also be optionally substituted with one or more substituents Q as described herein.

The term "heterocyclylene" refers to a divalent monocyclic non-aromatic ring system or divalent polycyclic ring system that contains at least one non-aromatic ring, wherein one or more of the non-aromatic ring atoms are heteroatoms independently selected from O, S, and N; and the remaining ring atoms are carbon atoms. In certain embodiments, the heterocyclylene group has from 3 to 20, from 3 to 15, from 3 to 10, from 3 to 8, from 4 to 7, or from 5 to 6 ring atoms. In certain embodiments, the heterocyclylene is a monocyclic, bicyclic, tricyclic, or tetracyclic ring system, which may be fused or bridged, and in which nitrogen or sulfur atoms may be optionally oxidized, nitrogen atoms may be optionally quaternized, and some rings may be partially or fully saturated, or aromatic. The heterocyclylene may be attached to the main structure at any heteroatom or carbon atom which results in the creation of a stable compound. Examples of such heterocyclylene groups include, but are not limited to, azepinylene, benzodioxanylene, benzodioxolylene, benzofuranonylene, benzopyranonylene, benzopyranylene, benzotetrahydrofuranylene, benzotetrahydrothienylene, benzothiopyranylene, benzoxazinylene, β-carbolinylene, chromanylene, chromonylene, cinnolinylene, coumarinylene, decahydroisoquinolinylene, dihydrobenzisothiazinylene, dihydrobenzisoxazinylene, dihydrofurylene, dihydroisoindolylene, dihydropyranylene, dihydropyrazolylene, dihydropyrazinylene, dihydropyridinylene, dihydropyrimidinylene, dihydropyrrolylene, dioxolanylene, 1,4-dithianylene, furanonylene, imidazolidinylene, imidazolinylene, indolinylene, isobenzotetrahydrofuranylene, isobenzotetrahydrothienylene, isochromanylene, isocoumarinylene, isoindolinylene, isothiazolidinylene, isoxazolidinylene, morpholinylene, octahydroindolylene, octahydroisoindolylene, oxazolidinonylene, oxazolidinylene, oxiranylene, piperazinylene, piperidinylene, 4-piperidonylene, pyrazolidinylene, pyrazolinylene, pyrrolidinylene, pyrrolinylene, quinuclidinylene, tetrahydrofurylene, tetrahydroisoquinolinylene, tetrahydropyranylene, tetrahydrothienylene, thiamorpholinylene, thiazolidinylene, tetrahydroquinolinylene, and 1,3,5-trithianylene. In certain embodiments, heterocyclic may also be optionally substituted with one or more substituents Q as described herein.

The term "subject" or "patient" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject, in one embodiment, a human.

The terms "treat," "treating," and "treatment" are meant to include alleviating, abrogating, or preventing a disorder, disease, or condition, and/or one or more of the symptoms associated with the disorder, disease, or condition; or alleviating, eradicating, or preventing the cause(s) of the disorder, disease, or condition itself. The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

Embodiments of the Compounds

The compounds of the present invention can modulate the activity of GLP-1 receptor, for example, the compounds may act as agonists or sensitizers of GLP-1 receptor or may have dual activities, i.e., as both agonists and sensitizers of GLP-1 receptor.

In one embodiment, the present invention provides a compound of Formula (I'):

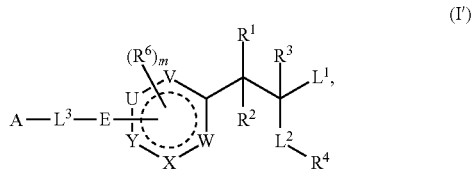

or a pharmaceutically acceptable salt, solvate, or prodrug thereof;
wherein:
A is $C_{3-8}$ carbocyclyl, $C_{6-14}$ aryl, $C_{7-15}$ aralkyl, heteroaryl, or heterocyclyl;
E is a bond, $C_{2-6}$ alkenylene, $C_{2-6}$ alkynylene, arylene, heteroarylene, carbocyclylene, heterocyclylene; with the proviso that E is not 4-oxo-imidazolidinylene;
$L^3$ is a bond, —C(O)—, —C(O)O—, —OC(O)—, —C(O)NR$^{1a}$—, —NR$^{1a}$C(O)—, —O—, —OC(O)O—, —OC(O)NR$^{1a}$—, —NR$^{1a}$C(O)O—, —OS(O)—, —S(O)O—, —OS(O)$_2$—, —S(O)$_2$O—, —OS(O)NR$^{1a}$—, —NR$^{1a}$S(O)O—, —OS(O)$_2$NR$^{1a}$—, —NR$^{1a}$S(O)$_2$O—, —NR$^{1a}$—, —NR$^{1a}$C(O)NR$^{1d}$—, —NR$^{1a}$S(O)NR$^{1d}$—, —NR$^{1a}$S(O)$_2$NR$^{1d}$—, —S—, —S(O)—, —S(O)$_2$—, —S(O)NR$^{1a}$—, —NR$^{1a}$S(O)—, —S(O)$_2$NR$^{1a}$—, or —NR$^{1a}$S(O)$_2$—; with the provisos that (a) E and $L^3$ are not both a bond at the same time; and (b) when $L^3$-E together is —O—, $R^6$ is not iodo or benzoxy;
m is an integer of 0, 1, 2, 3, or 4;
$L^1$ is a carboxylate bioisostere;
$L^2$ is —CH$_2$N(R$^5$)—, —N(R$^5$)CH$_2$—, —N(R$^5$)—, —O—, —S—, —C(O)NR$^5$—, —NR$^5$C(O)—, —CH$_2$C(O)NR$^5$—, —NR$^5$C(O)CH$_2$—, —CH=CH—C(O)NR$^5$—, —NR$^5$C(O)—CH=CH—, —C≡C—C(O)NR$^5$—, —NR$^5$C(O)—C≡C—, —S(O)NR$^5$—, —NR$^5$S(O)—, —S(O)$_2$NR$^5$—, —NR$^5$S(O)$_2$—, —NR$^5$C(O)NR$^{5a}$—, —NR$^5$S(O)$_2$NR$^{5a}$—, —CH$_2$NR$^5$S(O)$_2$NR$^{5a}$—, —NR$^5$S(O)$_2$NR$^{5a}$CH$_2$—, —NR$^5$C(O)-alkylene, —NR$^5$S(O)-alkylene, —NR$^5$S(O)$_2$-alkylene, —NR$^5$C(O)-alkenylene, —NR$^5$S(O)-alkenylene, or —NR$^5$S(O)$_2$-alkenylene; or alternatively; or alternatively, $L^2$ and V or W, together with other atoms to which they are attached, form 5- to 8-membered optionally substituted carbocyclyl or heterocyclyl; or alternatively, V or W and the carbon atom which is attached to $R^3$, $L^1$, and $L^2$, together with other atoms to which they are attached, form 5- to 8-membered optionally substituted carbocyclyl or heterocyclyl;
U, V, W, X, and Y are each independently C, CH, CH$_2$, N, or NH; and U, V, W, X, and Y, together with the carbon atom to which V and W are attached, form a 6-membered ring that is fully saturated, partially saturated, or unsaturated; with the proviso that at most 3 of U, V, W, X, and Y are N or NH;
$R^1$, $R^2$, and $R^3$ are selected from (i), (ii), (iii), and (iv):
(i), $R^1$, $R^2$, and $R^3$ are each independently (a) hydrogen, halo, or cyano; (b) $C_{1-6}$ alkyl, $C_{2-6}$ alkenyl, $C_{2-6}$ alkynyl, $C_{3-8}$ carbocyclyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^a$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;
(ii) $R^1$ or $R^2$ forms a double bond with $R^3$; and the other of $R^1$ and $R^2$ is selected as in (i);
(iii) two of $R^1$, $R^2$, and $R^3$ are joined together to form $C_{3-8}$ carbocyclyl, or 3- to 8-membered heterocyclyl; and the third is selected as in (i); and
(iv) $R^3$ and V or W, together with the other atoms to which are attached, form $C_{5-8}$ carbocyclyl, or 5- to 8-membered heterocyclyl; and $R^1$ and $R^2$ are selected as in (i);
$R^4$ is $C_{1-6}$ alkyl, $C_{2-6}$ alkenyl, $C_{2-6}$ alkynyl, $C_{3-7}$ carbocyclyl, $C_{6-14}$ aryl, $C_{7-15}$ aralkyl, heteroaryl, or heterocyclyl; or alternatively, $R^4$ and $R^5$ together with the N atom to which they are attached form heterocyclyl;
$R^5$ and $R^{5a}$ are each independently hydrogen, $C_{1-6}$ alkyl, —C(O)—$C_{1-6}$ alkyl; $C_{2-6}$ alkenyl, $C_{2-6}$ alkynyl, $C_{3-7}$ carbocyclyl, $C_{6-14}$ aryl, $C_{7-15}$ aralkyl, heteroaryl, or heterocyclyl; or alternatively, $R^4$ and $R^5$ are joined together to form heterocyclyl;
$R^6$ is cyano, halo, azido, nitro, $C_{1-6}$ alkyl, $C_{2-6}$ alkenyl, $C_{2-6}$ alkynyl, $C_{3-7}$ carbocyclyl, $C_{6-14}$ aryl, $C_{7-15}$ aralkyl, heteroaryl, heterocyclyl, —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;
each $R^{1a}$, $R^{1b}$, $R^{1c}$, and $R^{1d}$ is independently hydrogen, $C_{1-6}$ alkyl, $C_{2-6}$ alkenyl, $C_{2-6}$ alkynyl, $C_{3-7}$ carbocyclyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl;
wherein each alkyl, alkenyl, alkenylene, alkynyl, alkynylene, carbocyclyl, carbocyclylene, aryl, arylene, aralkyl, heteroaryl, heteroarylene, heterocyclyl, and heterocyclylene, in $R^1$, $R^2$, $R^3$, $R^4$, $R^5$, $R^{5a}$, $R^6$, $R^{1a}$, $R^{1b}$, $R^{1c}$, $R^{1d}$, A, and E is optionally substituted with one or more substituents Q, where each Q is independently selected from
(a) cyano, halo, azido, and nitro;
(b) $C_{1-6}$ alkyl, $C_{2-6}$ alkenyl, $C_{2-6}$ alkynyl, $C_{3-7}$ carbocyclyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and
(c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O) R$^d$, —NR$^a$C(O)OR$^d$, —NR$^a$C(O)NR$^b$R$^c$, —NR$^a$C(=NR$^d$) NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)

$NR^bR^c$, and $-S(O)_2NR^bR^c$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-7}$ carbocyclyl, $C_{6-14}$ aryl, $C_{7-15}$ aralkyl, heteroaryl, or heterocyclyl, each optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$; and wherein each $Q^a$ is independently selected from the group consisting of (a) cyano, halo, and nitro; (b) $C_{1-6}$ alkyl, $C_{2-6}$ alkenyl, $C_{2-6}$ alkynyl, $C_{3-7}$ carbocyclyl, $C_{6-14}$ aryl, $C_{7-15}$ aralkyl, heteroaryl, and heterocyclyl; and (c) $-C(O)R^e$, $-C(O)OR^e$, $-C(O)NR^fR^g$, $-C(NR^e)NR^fR^g$, $-OR^e$, $-OC(O)R^e$, $-OC(O)OR^e$, $-OC(O)NR^fR^g$, $-OC(=NR^e)NR^fR^g$, $-OS(O)R^e$, $-OS(O)_2R^e$, $-OS(O)NR^fR^g$, $-OS(O)_2NR^fR^g$, $-NR^fR^g$, $-NR^eC(O)R^h$, $-NR^eC(O)OR^f$, $-NR^eC(O)NR^fR^g$, $-NR^eC(=NR^h)NR^fR^g$, $-NR^eS(O)R^h$, $-NR^eS(O)_2R^h$, $-NR^eS(O)NR^fR^g$, $-NR^eS(O)_2NR^fR^g$, $-SR^e$, $-S(O)R^e$, $-S(O)_2R^e$, $-S(O)NR^fR^g$, and $-S(O)_2NR^fR^g$; wherein each $R^e$, $R^f$, $R^g$, and $R^h$ is independently (i) hydrogen; (ii) $C_{1-6}$ alkyl, $C_{2-6}$ alkenyl, $C_{2-6}$ alkynyl, $C_{3-7}$ carbocyclyl, $C_{6-14}$ aryl, $C_{7-15}$ aralkyl, heteroaryl, or heterocyclyl; or (iii) $R^f$ and $R^g$ together with the N atom to which they are attached form heterocyclyl.

In one embodiment of Formula (I'), the compounds have structural Formula (I):

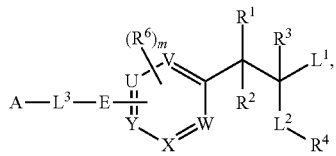

(I)

wherein, U, V, W, X, and Y are each independently C, CH, or N; and U, V, W, X, and Y, together with the carbon atom to which V and W are attached, form an aromatic 6-membered ring. A, $L^3$, $R^6$, E, m, Y, U, V, W, X, $R^1$, $R^2$, $R^3$, $L^1$, $L^2$, and $R^4$ are the same as defined in Formula (I').

The compounds of Formula (I) or (I'), or any of the subgenus thereof, include agonists, sensitizers, and the dual action compounds (both agonists ans sensitizers). In one embodiment, the dual action compounds have agonist activity level of A, B, or C and sensitizer activity level of A, B, or C at concentration of 2, 5, or 10 µM. In another embodiment, the dual action compounds have agonist activity level of A or B, and sensitizer activity level of A or B at concentration of 2, 5, or 10 µM. The protocols for determining the agonist or sensitizer activity are described herein in Examples below in this application. Certain specific embodiments of the dual action compounds include exemplary Compounds 228 to 327 in Table 3A.

In one embodiment of Formula (I), the carboxylate bioisostere is selected from the group consisting of $-CH_2OH$,

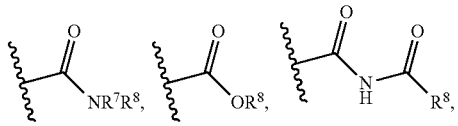

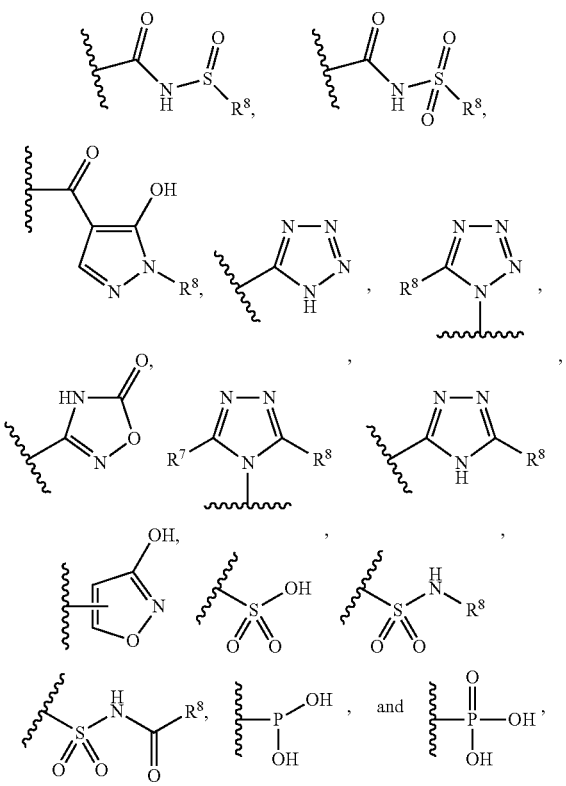

wherein each $R^7$ and $R^8$ is independently hydrogen or an optionally substituted member selected from the group consisting of alkyl, alkenyl, heteroalkyl, carbocyclyl, and heterocyclyl.

In another embodiment of Formula (I), the carboxylate bioisostere is $-CH_2OH$, $-CONH_2$, $-CO_2H$, $-P(O)(OH)_2$, $-P(OH)_2$, tetrazolyl, or 3-hydroxyisoxazolyl.

In one embodiment of the present invention, the compounds of Formula (I) has the structure of Formula (Ia) or (Ib):

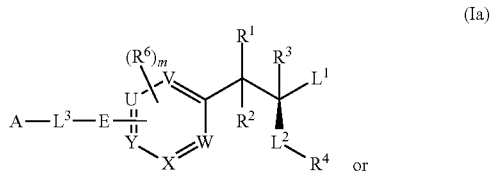

(Ia)

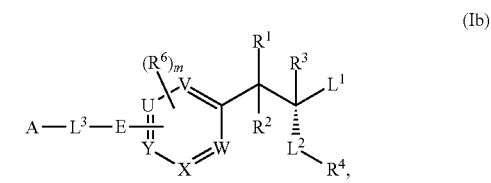

(Ib)

wherein A, $L^3$, $R^6$, E, m, Y, U, V, W, X, $R^1$, $R^2$, $R^3$, $L^1$, $L^2$, and $R^4$ are the same as defined in Formula (I).

In one embodiment of the present invention, the compounds of Formula (I) has the structure of Formula (II) or (III):

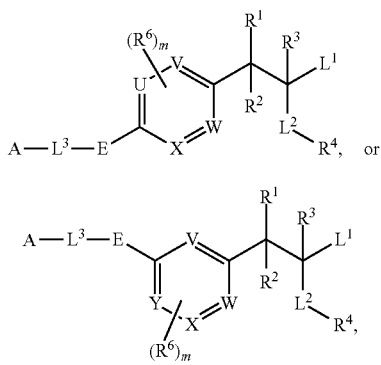
(II)

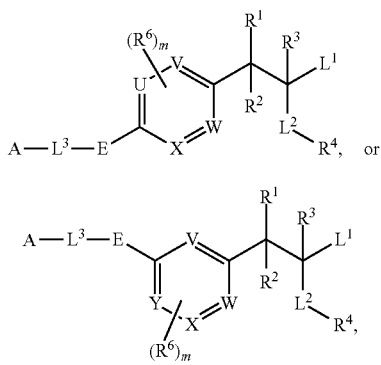
(III)

wherein A, $L^3$, $R^6$, E, m, Y, U, V, W, X, $R^1$, $R^2$, $R^3$, $L^1$, $L^2$, and $R^4$ are the same as defined in Formula (I).

In one embodiment of the present invention, the compounds of Formula (II) or (III) has the structure of Formula (IIa), (IIb), (IIIa), or (IIIb):

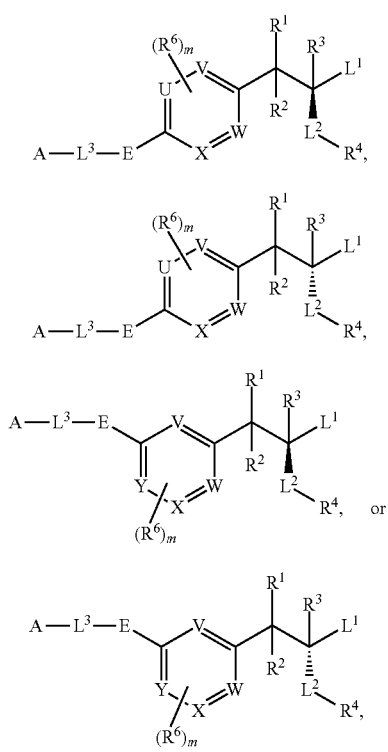
(IIa)

(IIb)

(IIIa)

(IIIb)

wherein A, $L^3$, $R^6$, E, m, Y, U, V, W, X, $R^1$, $R^2$, $R^3$, $L^1$, $L^2$, and $R^4$ are the same as defined in Formula (I).

In one embodiment of the present invention, the compounds of Formula (I) has the structure of Formula (IV):

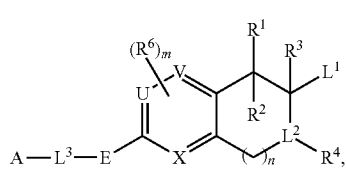
(IV)

wherein, A, $L^3$, $R^6$, E, $R^1$, $R^2$, $R^3$, $L^1$, $L^2$, and $R^4$ are the same as defined in Formula (I); m is zero, 1, 2, or 3; n is zero, 1, 2, or 3; when n is zero, $L^2$ is directly attached to the carbon atom adjacent to X to form a 5-membered ring; and U, V, and X in (IIc) are independently CH or N.

In one embodiment of the present invention, the compounds of Formula (IV) has the structure Formula (IVa) or (IVb):

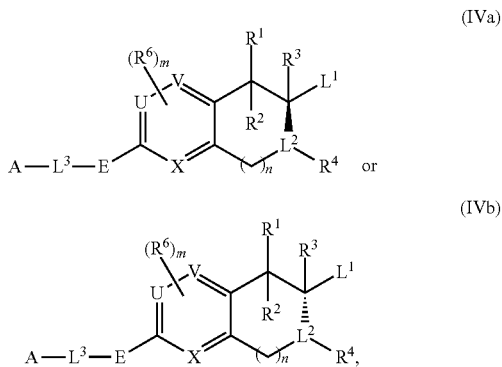
(IVa)

(IVb)

wherein A, $L^3$, $R^6$, E, m, Y, U, V, W, X, $R^1$, $R^2$, $R^3$, $L^1$, $L^2$, and $R^4$ are the same as defined in Formula (IV).

In one embodiment of the present invention, the compounds of Formula (I) has the structure of Formula (V):

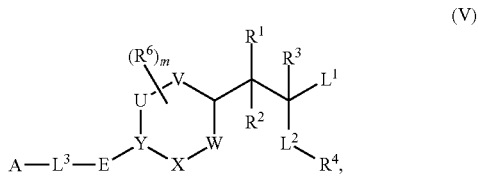
(V)

wherein,

A, $L^3$, $R^6$, E, $R^1$, $R^2$, $R^3$, $L^1$, and $R^4$ are the same as defined in Formula (I); m is zero, 1, 2, or 3; U, V, W, X, Y in (IId) are independently N, NH, CH, or $CH_2$; $L^2$ in (IId) is —$CH_2$N($R^5$)—, —N($R^5$)$CH_2$—, —N($R^5$)—, —O—, —S—, —C(O)NR$^5$—, —NR$^5$C(O)—, —$CH_2$C(O)NR$^5$—, —NR$^5$C(O)$CH_2$—, —CH=CH—C(O)NR$^5$—, —NR$^5$C(O)CH=CH—, —S(O)NR$^5$—, —NR$^5$S(O)—, —S(O)$_2$NR$^5$—, —NR$^5$S(O)$_2$—, —NR$^5$C(O)NR$^{5a}$—, —NR$^5$S(O)$_2$NR$^{5a}$—, —$CH_2$NR$^5$S(O)$_2$NR$^{5a}$—, or —NR$^5$S(O)$_2$NR$^a$$CH_2$—; and $R^5$ and $R^{5a}$ are the same as defined in Formula (I).

In one embodiment of the present invention, the compounds of Formula (V) has the structure Formula (Va) or (Vb):

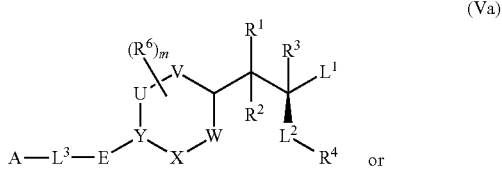
(Va)

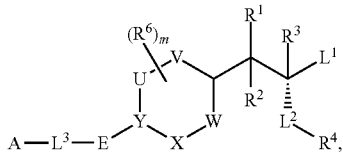

(Vb)

wherein A, L³, R⁶, E, m, Y, U, V, W, X, R¹, R², R³, L¹, L², and R⁴ are the same as defined in Formula (V).

In one embodiment of Formula (I'), (I), or any subgenus thereof, -L³-E- is $C_{2-6}$ alkenylene, $C_{2-6}$ alkynylene, arylene, carbocyclylene, heteroarylene, heterocyclylene, —NR$^{1a}$C(O)-arylene-, —NR$^{1a}$C(O)-heteroarylene-, —NR$^{1a}$C(O)-heterocyclylene-, —C(O)-arylene-, —C(O)-heteroarylene-, —C(O)-heterocyclylene-, —C(O)—, —C(O)O—, —OC(O)—, —C(O)NR$^{1a}$—, —NR$^{1a}$C(O)—, —O—, —OC(O)O—, —OC(O)NR$^{1a}$—, —NR$^{1a}$C(O)O—, —OS(O)—, —S(O)O—, —OS(O)₂—, —S(O)₂O—, —OS(O)NR$^{1a}$—, —NR$^{1a}$(O)O—, —OS(O)₂NR$^{1a}$—, —NR$^{1a}$S(O)₂O—, —NR$^{1a}$—, —NR$^{1a}$C(O)NR$^{1d}$—, —NR$^{1a}$S(O)NR$^{1d}$—, —NR$^{1a}$S(O)₂NR$^{1d}$—, —S—, —S(O)—, —S(O)₂—, —S(O)NR$^{1a}$—, —NR$^{1a}$S(O)—, —S(O)₂NR$^{1a}$—, or —NR$^{1a}$S(O)₂—.

In another embodiment of Formula (I'), (I), or any subgenus thereof, -L³-E- has the structure of:

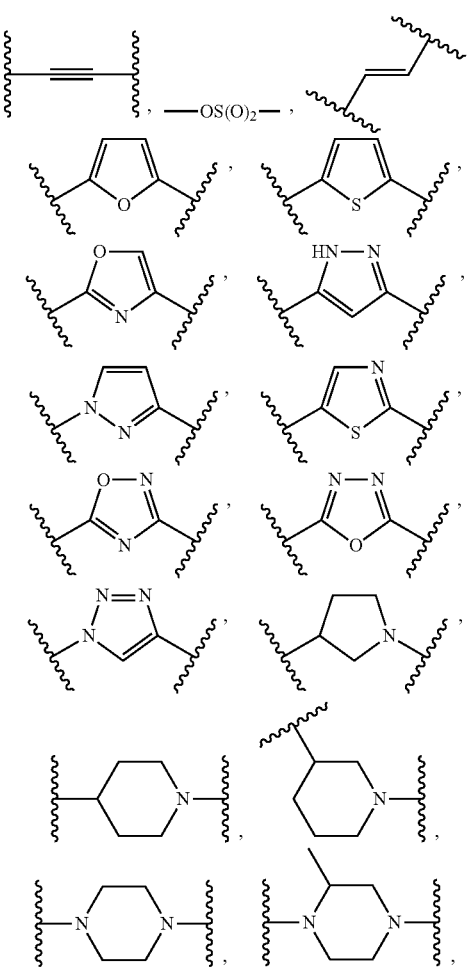

In one embodiment of Formula (I'), (I), or any subgenus thereof, E is a 5-membered heteroarylene or 6-membered heterocyclylene; and L³ is a bond or —C(O)—, —C(O)O—, —OC(O)—, —C(O)NR$^{1a}$—, —NR$^{1a}$C(O)—, —OC(O)O—, —NR$^{1a}$C(O)NR$^{1d}$—, —OC(O)NR$^{1a}$—, —NR$^{1a}$C(O)O—, —OS(O)—, —S(O)O—, —OS(O)₂—, —S(O)₂O—, —S(O)₂NR$^{1a}$—, or —NR$^{1a}$S(O)₂—.

In one embodiment of Formula (I'), (I), or any subgenus thereof, A is $C_{3-8}$ carbocyclyl or $C_{6-14}$ aryl, optionally substituted with one or more substituents Q, where each Q is independently selected from (a) cyano, halo, azido, and nitro; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)₂R$^a$, —OS(O)NR$^b$R$^c$, —OS(O)₂NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)₂R$^d$, —NR$^a$S(O)NR$^b$R$^c$, —NR$^a$S(O)₂NR$^b$R$^c$, —SR$^a$, —S(O)R$^a$, —S(O)₂R$^a$, —S(O)NR$^b$R$^c$, and —S(O)₂NR$^b$R$^c$, wherein each R$^a$, R$^b$, R$^c$, and R$^d$ is independently (i) hydrogen; (ii) $C_{1-6}$ alkyl, $C_{2-6}$ alkenyl, $C_{2-6}$ alkynyl, $C_{3-7}$ carbocyclyl, $C_{6-14}$ aryl, $C_{7-15}$ aralkyl, heteroaryl, or heterocyclyl, each optionally substituted with one or more, in one embodiment, one, two, three, or four, substituents Q$^a$; or (iii) R$^b$ and R$^c$ together with the N atom to which they are attached form heterocyclyl, optionally substituted with one or more, in one embodiment, one, two, three, or four, substituents Q$^a$.

In one embodiment of Formula (I'), (I), or any subgenus thereof, R¹ and R² are both hydrogen.

In one embodiment of Formula (I'), (I), or any subgenus thereof, R³ is hydrogen or $C_{1-6}$ alkyl.

In one embodiment of Formula (I'), (I), or any subgenus thereof, -L²-R⁴ is selected from the group consisting of —NR⁵S(O)₂—C₁₋₆ alkyl, —NR⁵C(O)CH₂—C₃₋₇ carbocyclyl, —NR⁵C(O)CH₂—C₆₋₁₄ aryl, —NR⁵C(O)CH₂-heteroaryl, —NR⁵C(O)CH₂-heterocyclyl, —N(R⁵)—C₃₋₇ carbocyclyl, —N(R⁵)—C₆₋₁₄ aryl, —N(R⁵)-heteroaryl, —N(R⁵)-heterocyclyl, —NR⁵C(O)—CH═CH—C₃₋₇ carbocyclyl, —NR⁵C(O)—CH═CH—C₆₋₁₄ aryl, —NR⁵C(O)—CH═CH-heteroaryl, —NR⁵C(O)—CH═CH-heterocyclyl, NR⁵C(O)—C≡C—C₃₋₇ carbocyclyl, NR⁵C(O)—C≡C—C₆₋₁₄ aryl, —NR⁵C(O)—C≡C-heteroaryl, —NR⁵C(O)—C≡C-heterocyclyl, —CH₂N(R⁵)—C₃₋₈ carbocyclyl, —CH₂N(R⁵)—C₆₋₁₄ aryl, —CH₂N(R⁵)-heteroaryl, —CH₂N(R⁵)-heterocyclyl, —NR⁵C(O)—C₃₋₇ carbocyclyl, —NR⁵S(O)₂—C₃₋₇ carbocyclyl, —NR⁵C(O)NR⁵ᵃ—C₃₋₇ carbocyclyl, —NR⁵S(O)₂NRᵃ—C₃₋₇ carbocyclyl, —NR⁵C(O)—C₆₋₁₄ aryl, —NR⁵S(O)₂—C₆₋₁₄ aryl, —NR⁵C(O)NR⁵ᵃ—C₆₋₁₄ aryl, —NR⁵S(O)₂NR⁵ᵃ—C₆₋₁₄ aryl, —NR⁵C(O)-heteroaryl, —NR⁵S(O)₂-heteroaryl, —NR⁵C(O)NR⁵ᵃ-heteroaryl, —NR⁵S(O)₂NR⁵ᵃ-heteroaryl, —NR⁵C(O)-heterocyclyl, —NR⁵S(O)₂-heterocyclyl, —NR⁵C(O)NR⁵ᵃ-heterocyclyl, and —NR⁵S(O)₂NR⁵ᵃ-heterocyclyl, where each of the C₁₋₆ alkyl, C₃₋₇ carbocyclyl, C₆₋₁₄ aryl, heteroaryl, heterocyclyl is optionally substituted with one or more substituents Q.

In one embodiment of Formula (I'), (I), or any subgenus thereof, R⁵ and R⁵ᵃ are each independently hydrogen, C₁₋₆ alkyl, or —C(O)—C₁₋₆ alkyl, where each C₁₋₆ alkyl is optionally substituted with one or more substituents Q.

In one embodiment of Formula (I'), (I), or any subgenus thereof, the 6-membered ring formed by U, V, W, X, and Y is phenyl, pyridine, pyrimidine, or piperidine.

In one embodiment of Formula (I'), (I), or any subgenus thereof, m is 1 or 2; and R⁶ is (i) cyano or halo; or (ii) C₁₋₆ alkyl, optionally substituted with one or more substituents Q.

In one embodiment of Formula (I), the present compounds have the structure of Formula (VI):

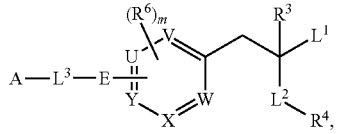

(VI)

wherein:
R³ is hydrogen or C₁₋₆ alkyl;
A is C₃₋₈-carbocyclyl, C₆₋₁₄ aryl, C₇₋₁₅ aralkyl, heteroaryl, or heterocyclyl;
-L³-E- is C₂₋₆ alkenylene, C₂₋₆ alkynylene, arylene, carbocyclylene, heteroarylene, heterocyclylene, —NR¹ᵃC(O)-arylene-, —NR¹ᵃC(O)-heteroarylene-, —NR¹ᵃC(O)-heterocyclylene-, —NR¹ᵃS(O)₂-arylene-, —NR¹ᵃS(O)₂-heteroarylene-, —NR¹ᵃS(O)₂-heterocyclylene-, —C(O)—, —C(O)O—, —OC(O)—, —C(O)NR¹ᵃ—, or —NR¹ᵃC(O)—;
U, V, W, X, and Y, together with the carbon atom to which V and W are attached, form a fully saturated or unsaturated 6-membered ring;
L¹ is —CH₂OH, —CONH₂, —CO₂H, —P(O)(OH)₂, —P(OH)₂, tetrazolyl, or 3-hydroxyisoxazolyl;
L² is —NR⁵C(O)—, —NR⁵S(O)—, —NR⁵S(O)₂—, or —NR⁵S(O)₂NR⁵ᵃ—, —NR⁵C(O)-alkylene, —NR⁵S(O)-alkylene, —NR⁵S(O)₂-alkylene, —NR⁵C(O)-alkenylene, —NR⁵S(O)-alkenylene, or —NR⁵S(O)₂-alkenylene; or alternatively, L² and V or W, together with other atoms to which they are attached, form 5- to 8-membered optionally substituted carbocyclyl or heterocyclyl;

R⁴ is C₁₋₆ alkyl, C₃₋₇ carbocyclyl, C₆₋₁₄ aryl, C₇₋₁₅ aralkyl, heteroaryl, or heterocyclyl;
R⁶ and m are the same as defined in claim 1; and
when U, V, W, X, and Y are each independently C or CH; R¹, R², and R³ are hydrogen; L¹ is —CONH₂ or —CO₂H; L² is —NR⁵C(O)—; and R⁴ is -heteroaryl-aryl; then A-L³-E- is cyano group;
when A is aryl, heteroaryl, carbocyclyl, or heterocyclyl; -L³-E- is heteroaryl, —NR⁵C(O)-heteroaryl, or —NR⁵C(O)-heterocyclyl; and -L²- is —NR⁵C(O)— or —NR⁵S(O)₂—; then R⁴ is substituted aryl or substituted heteroaryl wherein the substituent is optionally substituted aryl or optionally substituted heteroaryl;
wherein each alkyl, alkenyl, alkenylene, alkynyl, alkynylene, carbocyclyl, aryl, arylene, aralkyl, heteroaryl, heteroarylene, heterocyclyl, and heterocyclylene, in R³, R⁵, R⁵ᵃ, R⁶, R¹ᵃ, R¹ᵇ, R¹ᶜ, R¹ᵈ, A, and E, is optionally substituted with one or more substituents Q as defined in claim 1;
wherein each alkyl, alkenyl, alkenylene, alkynyl, alkynylene, carbocyclyl, aryl, arylene, aralkyl, heteroaryl, heteroarylene, heterocyclyl, and heterocyclylene in R⁴ is optionally substituted with one or more substituents Q, where each Q is independently selected from (a), (b), and (c) as follows:
(a) cyano, halo, azido, and nitro;
(b) C₁₋₆ alkyl, C₂₋₆ alkenyl, and C₂₋₆ alkynyl, each of which is optionally substituted with one or more, in one embodiment, one, two, three, or four, substituents Qᵃ; and
(c) —C(O)Rᵃ, —C(O)ORᵃ, —C(O)NRᵇRᶜ, —C(NRᵃ)NRᵇRᶜ, —ORᵃ, —OC(O)Rᵃ, —OC(O)ORᵃ, —OC(O)NRᵇRᶜ, —OC(═NRᵃ)NRᵇRᶜ, —OS(O)Rᵃ, —OS(O)₂Rᵃ, —OS(O)NRᵇRᶜ, —OS(O)₂NRᵇRᶜ, —NRᵇRᶜ, —NRᵃC(O)Rᵈ, —NRᵃC(O)ORᵈ, —NRᵃC(O)NRᵇRᶜ, —NRᵃC(═NRᵈ)NRᵇRᶜ, —NRᵃS(O)Rᵈ, —NRᵃS(O)₂Rᵈ, —NRᵃS(O)NRᵇRᶜ, —NRᵃS(O)₂NRᵇRᶜ, —SRᵃ, —S(O)Rᵃ, —S(O)₂Rᵃ, —S(O)NRᵇRᶜ, and —S(O)₂NRᵇRᶜ, wherein each Rᵃ, Rᵇ, Rᶜ, and Rᵈ is independently (i) hydrogen; (ii) C₁₋₆ alkyl, C₂₋₆ alkenyl, C₂₋₆ alkynyl, C₃₋₇ carbocyclyl, C₆₋₁₄ aryl, C₇₋₁₅ aralkyl, heteroaryl, or heterocyclyl, each optionally substituted with one or more, in one embodiment, one, two, three, or four, substituents Qᵃ; or (iii) Rᵇ and Rᶜ together with the N atom to which they are attached form heterocyclyl, optionally substituted with one or more substituents Qᵃ;
when -L³-E- is —C(O)—, then A is a C₆₋₁₄ aryl substituted with a C₆₋₁₄ aryl which is optionally substituted with one or more substituents Qᵃ;
when -L³-E- is —NR¹ᵃC(O)-heteroarylene- or —NR¹ᵃC(O)-heterocyclylene-, then A is a C₆₋₁₄ aryl or heteroaryl substituted with a C₆₋₁₄ aryl which is optionally substituted with one or more substituents Qᵃ.

In one embodiment of Formula (VI), the compound has the structure of Formula (VIa) or (VIb):

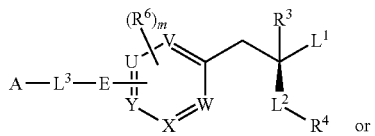

(VIa)

or

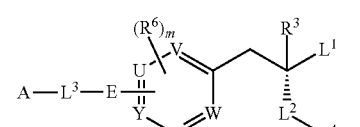

(VIb)

wherein A, L³, R⁶, E, m, Y, U, V, W, X, R³, L¹, L², and R⁴ are the same as defined in Formula (VI).

In one embodiment of Formula (VI) or any subgenus thereof, -L³-E- has the structure of:

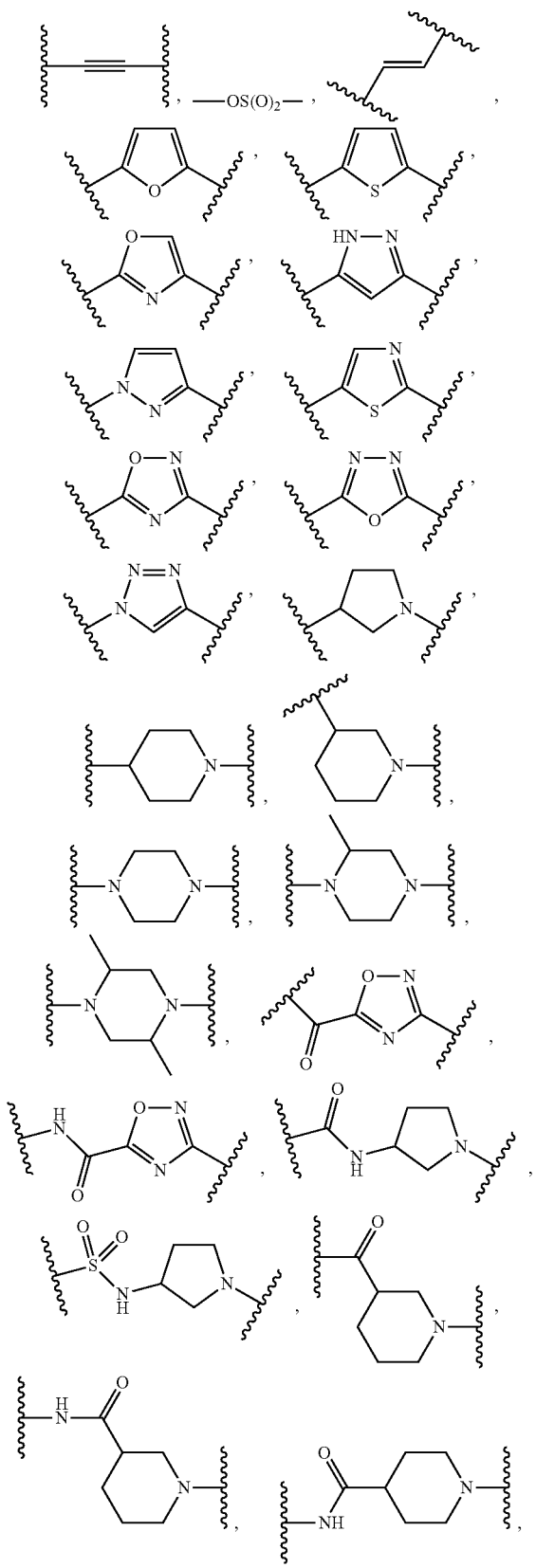

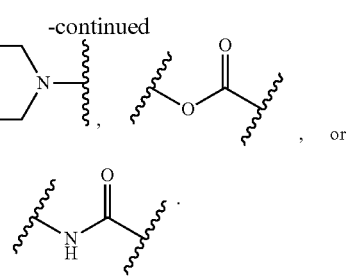

In one embodiment of Formula (VI), the compounds have the structure of Formula (VII) or (VIII):

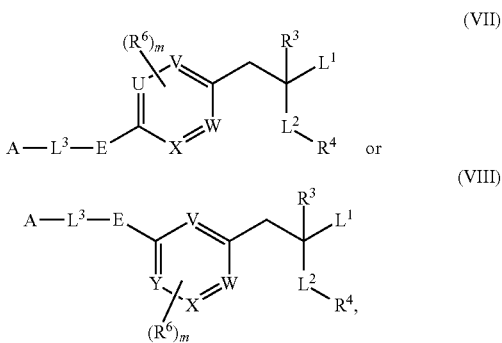

wherein A, L³, R⁶, E, m, Y, U, V, W, X, R³, L¹, L², and R⁴ are the same as defined in Formula (VI).

In one embodiment of Formula (VII) or (VIII), the compounds have the structure of Formula (VIIa), (VIIb), (VIIIa), or (VIIIb):

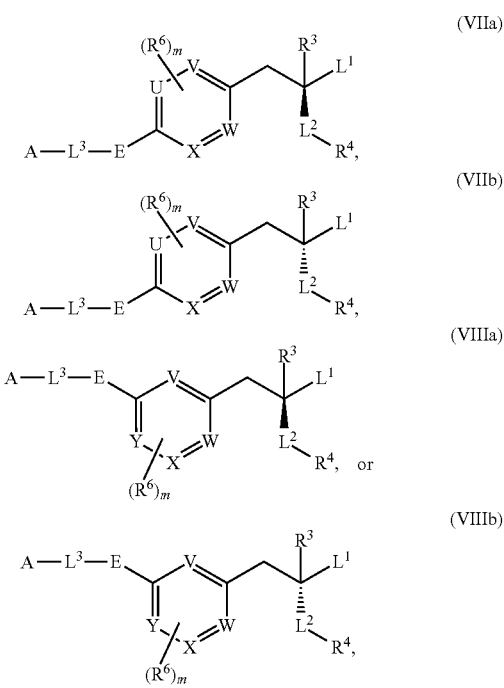

wherein A, L³, R⁶, E, m, Y, U, V, W, X, R³, L¹, L², and R⁴ are the same as defined in Formula (VI).

In one embodiment of Formula (VI) or any subgenus thereof, Y, U, V, W, and X are independently CH or $CH_2$.

In one embodiment of Formula (VI) or any subgenus thereof, $A-L^3-E-$ is selected from the group consisting of carbocyclyl-C≡C—, aryl-C≡C—, heteroaryl-C≡C—, heterocyclyl-C≡C—, carbocyclyl-heteroarylene-, aryl-heteroarylene-, heteroaryl-heteroarylene-, heterocyclyl-heteroarylene-, aryl-C(O)O—, heteroaryl-C(O)O—, aryl-S(O)$_2$O—, heteroaryl-S(O)$_2$O—, aryl-C(O)—, aryl-$NR^{1a}$C(O)-heteroarylene-, heteroaryl-$NR^{1a}$C(O)-heteroarylene-, aryl-$NR^{1a}$C(O)-heteroarylene-, or heteroaryl-$NR^{1a}$C(O)-heterocyclylene-.

In one embodiment of Formula (VI) or any subgenus thereof, $L^2$ is —$NR^5$C(O)—, —$NR^5$S(O)—, —$NR^5$S(O)$_2$—, or —$NR^5$S(O)$_2NR^a$—; and $R^4$ is $C_{1-6}$ alkyl, $C_{3-7}$ carbocyclyl, $C_{6-14}$ aryl, heteroaryl, or heterocyclyl.

In one embodiment of Formula (VI) or any subgenus thereof, the compound has the structure of Formula (IX):

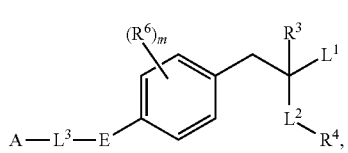

(IX)

wherein $A-L^3-E-$ is selected from the group consisting of carbocyclyl-C≡C—, aryl-C≡C—, heteroaryl-C≡C—, heterocyclyl-C≡C—, carbocyclyl-heteroarylene-, aryl-heteroarylene-, heteroaryl-heteroarylene-, heterocyclyl-heteroarylene-, aryl-C(O)O—, heteroaryl-C(O)O—, aryl-S(O)$_2$O—, heteroaryl-S(O)$_2$O—, aryl-C(O)—, aryl-$NR^{1a}$C(O)-heteroarylene-, heteroaryl-$NR^{1a}$C(O)-heterocyclylene-, aryl-$NR^{1a}$C(O)-heteroarylene-, or heteroaryl-$NR^{1a}$C(O)-heterocyclylene-; $L^2$ is —$NR^5$C(O)—, —$NR^5$C(O)$CH_2$—, —$NR^5$S(O)—, —$NR^5$S(O)$_2$—, or —$NR^5$S(O)$_2NR^{5a}$—; and $R^4$ is $C_{1-6}$ alkyl, $C_{3-7}$ carbocyclyl, $C_{6-14}$ aryl, heteroaryl, or heterocyclyl.

In one embodiment of Formula (IX), the compound has the structure of Formula (IXa) or (IXb):

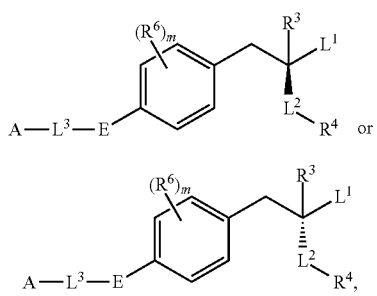

(IXa)

(IXb)

wherein A, $L^3$, $R^6$, E, m, $R^3$, $L^1$, $L^2$, and $R^4$ are the same as defined in Formula (IX).

In one embodiment of Formula (VI), the compound has the structure of Formula (X):

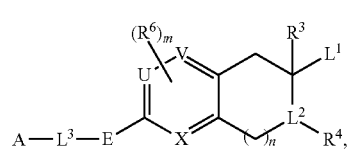

(X)

wherein A, $L^3$, $R^6$, E, $R^3$, $L^1$, $L^2$, and $R^4$ are the same as defined in Formula (VI); m is zero, 1, 2, or 3; n is zero, 1, 2, or 3; U, V, and X are independently CH or N.

In one embodiment of Formula (VI), the compound has the structure of Formula (XI):

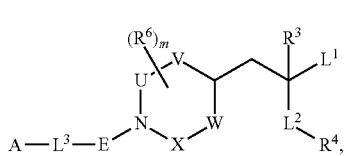

(XI)

wherein A, $L^3$, $R^6$, E, $R^3$, $L^1$, $L^2$, and $R^4$ are the same as defined in Formula (VI); m is zero, 1, 2, or 3; U, V, W, X in are independently CH or $CH_2$.

The compounds of Formula (VI) have sensitizer activity as shown in the exemplary data described herein below in this application. In one embodiment of Formula (VI) and any subgenus thereof, the compound has no agonist activity. By "no agonist activity", it is meant agonist activity level below D when tested at concentrations 5, 10, or 20 μM using the bioassay protocols described herein in the Examples below in this application. In certain specific embodiments, the sensitizer compounds include exemplary Compounds 163 to 227 in Table 2A below.

In one embodiment of Formula (I), the compound has the structure of Formula (XII):

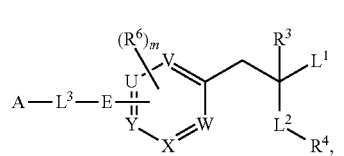

(XII)

wherein:

$R^3$ is hydrogen or $C_{1-6}$ alkyl;

A is $C_{3-8}$ carbocyclyl, $C_{6-14}$ aryl, $C_{7-15}$ aralkyl, heteroaryl, or heterocyclyl;

$-L^3-E-$ is $C_{2-6}$ alkenylene, $C_{2-6}$ alkynylene, arylene, carbocyclylene, heteroarylene, heterocyclylene, —C(O)-heteroarylene, —C(O)O—, —OC(O)—, —C(O)$NR^{1a}$—, or —$NR^{1a}$C(O)—;

U, V, W, X, and Y are independently CH, $CH_2$, or N;

$L^1$ is —$CH_2$OH, —$CONH_2$, —$CO_2$H, —P(O)(OH)$_2$, —P(OH)$_2$, tetrazolyl, or 3-hydroxyisoxazolyl;

$L^2$ is —N($R^5$)$CH_2$—, —N($R^5$)—, —O—, —S—, —$NR^5$C(O)—, —$CH_2NR^5$C(O)—, —$NR^5$C(O)$CH_2$—, —$NR^5$C(O)—CH=CH—, —$NR^5$C(O)—C≡C—, —$NR^5$S(O)—, —$NR^5$S(O)$_2$—, or —$NR^5$C(O)$NR^{5a}$—; or alternatively, $L^2$ and V or W, together with other atoms to which they are attached, form 5- to 8-membered optionally substituted carbocyclyl or heterocyclyl; or alternatively, V or W and the carbon atom which is attached to $R^3$, $L^1$, and $L^2$, together with other atoms to which they are attached, form 5- to 8-membered optionally substituted carbocyclyl or heterocyclyl;

$R^6$ and m are the same as defined in claim 1;

$R^4$ is —$R^{4a}$—$R^q$ or —$R^{4b}$;

$R^{4a}$ is $C_{3-7}$ carbocyclylene, $C_{6-14}$ arylene, heteroarylene, or heterocyclylene;

$R^q$ is $C_{3-7}$ carbocyclyl, $C_{6-14}$ aryl, $C_{7-15}$ aralkyl, heteroaryl, heteroarylalkyl, or heterocyclyl;

$R^{4b}$ is $C_{3-7}$ carbocyclyl, $C_{6-14}$ aryl, heteroaryl, or heterocyclyl;

wherein each alkyl, alkenylene, alkynylene, carbocyclyl, aryl, aralkyl, heteroaryl, heterocyclyl, arylene, carbocyclylene, heteroarylene, and heterocyclylene in $R^3$, $R^6$, $R^q$, A, and -L³-E- is optionally substituted with one or more substitutents Q as defined in claim 1;

wherein each carbocyclylene, arylene, heteroarylene, and heterocyclylene in $R^{4a}$ and each carbocyclyl, aryl, heteroaryl, and heterocyclyl in $R^{4b}$ is optionally substituted with one or more substitutents Q, where each Q is independently selected from:

(a) cyano, halo, azido, and nitro;

(b) $C_{1-6}$ alkyl, $C_{2-6}$ alkenyl, and $C_{2-6}$ alkynyl, each of which is optionally substituted with one or more, in one embodiment, one, two, three, or four, substituents $Q^a$; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) $C_{1-6}$ alkyl, $C_{2-6}$ alkenyl, $C_{2-6}$ alkynyl, $C_{3-7}$ carbocyclyl, $C_{6-14}$ aryl, $C_{7-15}$ aralkyl, heteroaryl, or heterocyclyl, each optionally substituted with one or more, in one embodiment, one, two, three, or four, substituents $Q^a$; or (iii) R$^b$ and R$^c$ together with the N atom to which they are attached form heterocyclyl, optionally substituted with one or more substituents $Q^a$.

In one embodiment of Formula (XII), when -L³-E- is $C_{2-6}$ alkenylene, $C_{2-6}$ alkynylene, —C(O)NR$^{1a}$—, or —NR$^{1a}$C(O)—; then R$^4$ is —R$^{4a}$—R$^q$.

In one embodiment of Formula (XII), the compound has the structure of Formula (XIIa) or (XIIb):

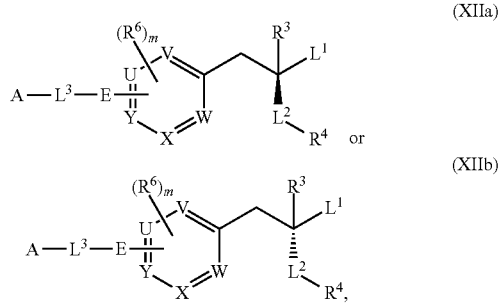

wherein A, L³, R⁶, E, m, Y, U, V, W, X, R³, L¹, L², and R⁴ are the same as defined in Formula (XII).

In one embodiment of Formula (XII), the compound has the structure of Formula (XIII) or (XIV):

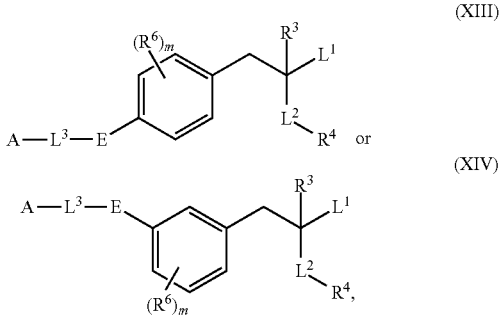

wherein A, L³, R⁶, E, m, R³, L¹, L², and R⁴ are the same as defined in Formula (XII).

In one embodiment of Formula (XIII) or (XIV), the compound has the structure of Formula (XIIIa), (XIIIb), (XIVa), or (XIVb):

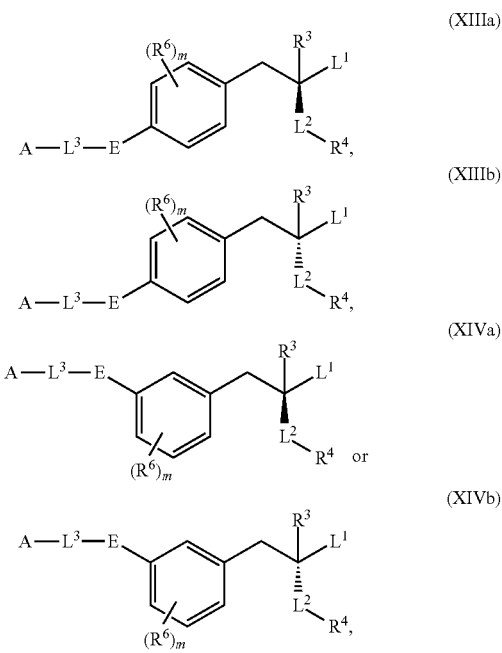

wherein A, L³, R⁶, E, m, R³, L¹, L², and R⁴ are the same as defined in Formula (XII).

In one embodiment of Formula (XII) and any subgenus thereof, A-L³-E- is aryl-$C_{2-6}$ alkenylene, aryl-$C_{2-6}$ alkynylene, aryl-heteroarylene-, aryl-C(O)O—, aryl-OC(O)—, aryl-C(O)NR$^{1a}$—, aryl-NR$^{1a}$C(O)—, or heterocyclylene-C(O)-heteroarylene-.

In one embodiment of Formula (XII) and any subgenus thereof, m is 1 or 2; and R⁶ is (i) cyano or halo; or (ii) $C_{1-6}$ alkyl, optionally substituted with one or more substituents Q.

In one embodiment of Formula (XII) and any subgenus thereof, A-L³-E- is aryl-$C_{2-6}$ alkenylene, aryl-$C_{2-6}$ alkynylene, aryl-heteroarylene-, aryl-C(O)O—, aryl-OC(O)—, aryl-C(O)NR$^{1a}$—, aryl-NR$^{1a}$C(O)—, or heterocyclylene-C(O)-heteroarylene-; L² is —N(R⁵)CH$_2$—, —N(R⁵)—, —O—, —S—, —NR⁵C(O)—, —CH$_2$NR⁵C(O)—, —NR⁵C(O)CH$_2$—, —NR⁵C(O)—CH=CH—, —NR⁵C(O)—C≡C—, —NR⁵S(O)—, —NR⁵S(O)$_2$—, or —NR⁵C(O)NR$^{5a}$—; and R⁴ is —R$^{4a}$—R$^q$.

In one embodiment of Formula (XII), the compounds have the structure of Formula (XV):

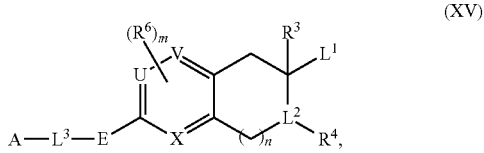

wherein, -L³-E- is arylene, heteroarylene, —C(O)O—, —OC(O)—, —C(O)NR$^{1a}$—, or —NR$^{1a}$C(O)—; A is aryl or heteroaryl; U, V, and X are independently C or CH; n is zero, 1, or 2; and L² is —NR⁵C(O)— or —NR⁵S(O)$_2$—.

In one embodiment of Formula (XII) and any subgenus thereof, the compound has no sensitizer activity.

The compounds of Formula (XII) have agonist activity as shown in the exemplary data described herein below in this application. In one embodiment of Formula (XII) and any subgenus thereof, the compound has no sensitizer activity. By "no sensitizer activity", it is meant sensitizer activity level below D when tested at concentrations 5, 10, or 20 µM using the bioassay protocols described herein below in this application. In certain specific embodiments, the agonist compounds include exemplary Compounds 1 to 162 as described in Table 1A below.

The compound provided herein may also be provided as a prodrug, which is a functional derivative of the compound, for example, of Formula I and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See, Harper, *Progress in Drug Research* 1962, 4, 221-294; Morozowich et al. in *Design of Biopharmaceutical Properties through Prodrugs and Analogs*; Roche Ed., APHA Acad. Pharm. Sci.: 1977; Gangwar et al., *Des. Biopharm. Prop. Prodrugs Analogs,* 1977, 409-421; Bundgaard, *Arch. Pharm. Chem.* 1979, 86, 1-39; Farquhar et al., *J. Pharm. Sci.* 1983, 72, 324-325; Wernuth in *Drug Design: Fact or Fantasy*; Jolles et al. Eds.; Academic Press: London, 1984; pp 47-72; *Design of Prodrugs*; Bundgaard et al. Eds.; Elsevier: 1985; Fleisher et al., *Methods Enzymol.* 1985, 112, 360-381; Stella et al., *Drugs* 1985, 29, 455-473; *Bioreversible Carriers in Drug Design, Theory and Application*; Roche Ed.; APHA Acad. Pharm. Sci.: 1987; Bundgaard, *Controlled Drug Delivery* 1987, 17, 179-96; Waller et al., *Br. J. Clin. Pharmac.* 1989, 28, 497-507; Balant et al., *Eur. J. Drug Metab. Pharmacokinet.* 1990, 15, 143-53; Freeman et al., *J. Chem. Soc., Chem. Commun.* 1991, 875-877; Bundgaard, *Adv. Drug Delivery Rev.* 1992, 8, 1-38; Nathwani and Wood, *Drugs* 1993, 45, 866-94; Friis and Bundgaard, *Eur. J. Pharm. Sci.* 1996, 4, 49-59; Fleisher et al., *Adv. Drug Delivery Rev.* 1996, 19, 115-130; Sinhababu and Thakker, *Adv. Drug Delivery Rev.* 1996, 19, 241-273; Taylor, *Adv. Drug Delivery Rev.* 1996, 19, 131-148; Gaignault et al., *Pract. Med. Chem.* 1996, 671-696; Browne, *Clin. Neuropharmacol.* 1997, 20, 1-12; Valentino and Borchardt, *Drug Discovery Today* 1997, 2, 148-155; Pauletti et al., *Adv. Drug. Delivery Rev.* 1997, 27, 235-256; Mizen et al., *Pharm. Biotech.* 1998, 11, 345-365; Wiebe and Knaus, *Adv. Drug Delivery Rev.* 1999, 39, 63-80; Tan et al., *Adv. Drug Delivery Rev.* 1999, 39, 117-151; Balimane and Sinko, *Adv. Drug Delivery Rev.* 1999, 39, 183-209; Wang et al., *Curr. Pharm. Design* 1999, 5, 265-287; Han et al., *AAPS Pharmsci.* 2000, 2, 1-11; Asgharnejad in *Transport Processes in Pharmaceutical Systems*; Amidon et al., Eds.; Marcell Dekker: 2000; pp 185-218; Sinha et al., *Pharm. Res.* 2001, 18, 557-564; Anand et al., *Expert Opin. Biol. Ther.* 2002, 2, 607-620; Rao, *Resonace* 2003, 19-27; Sloan et al., *Med. Res. Rev.* 2003, 23, 763-793; Patterson et al., *Curr. Pharm. Des.* 2003, 9, 2131-2154; Hu, *IDrugs* 2004, 7, 736-742; Robinson et al., *Proc. Natl. Acad. Sci. U.S.A.* 2004, 101, 14527-14532; Erion et al., *J. Pharmacol. Exp. Ther.* 2005, 312, 554-560; Fang et al., *Curr. Drug Discov. Technol.* 2006, 3, 211-224; Stanczak et al., *Pharmacol. Rep.* 2006, 58, 599-613; Sloan et al., *Pharm. Res.* 2006, 23, 2729-2747; Stella et al., *Adv. Drug Deliv. Rev.* 2007, 59, 677-694; Gomes et al., *Molecules* 2007, 12, 2484-2506; Krafz et al., *ChemMedChem* 2008, 3, 20-53; Rautio et al., *AAPS J.* 2008, 10, 92-102; Rautio et al., *Nat. Rev. Drug. Discov.* 2008, 7, 255-270; Pavan et al., *Molecules,* 2008, 13, 1035-1065; Sandros et al., *Molecules* 2008, 13, 1156-1178; Singh et al., *Curr. Med. Chem.* 2008, 15, 1802-1826; Onishi et al., *Molecules,* 2008, 13, 2136-2155; Huttunen et al., *Curr. Med. Chem.* 2008, 15, 2346-2365; and Serafin et al., *Mini Rev. Med. Chem.* 2009, 9, 481-497.

Utilities of the Compounds:

In another aspect, the present invention provides a method of modulating the activity of glucagon-like peptide-1 (GLP-1) receptor. The method comprises contacting an effective amount of a compound of the present invention with a cell containing GLP-1 receptor. The method may be conducted in vitro or in vivo.

In one embodiment, provided herein is a method to treat a condition or disease associated with GLP-1 receptor. The method comprises administering to a subject in need of such treatment an effective amount of a compound of the present invention.

In one embodiment, provided herein is a method for treating or preventing a metabolic disorder in a subject, which comprises administering to the subject a therapeutically effective amount of a compound disclosed herein, e.g., a compound of Formula I, including a single enantiomer, a mixture of enantiomers, a mixture of diastereomers, or an isotopic variant thereof; or a pharmaceutically acceptable salt, solvate, or prodrug thereof.

In another embodiment, provided herein is a method for treating, preventing, or ameliorating one or more symptoms of a metabolic disorder in a subject, comprising administering to the subject a therapeutically effective amount of a compound disclosed herein, e.g., a compound of Formula I, including a single enantiomer, a mixture of enantiomers, a mixture of diastereomers, or an isotopic variant thereof; or a pharmaceutically acceptable salt, solvate, or prodrug thereof.

In certain embodiments, the metabolic disorder is Type 1 diabetes or obesity.

In yet another embodiment, provided herein is a method for treating or preventing diabetes in a subject, which comprises administering to the subject a therapeutically effective amount of a compound disclosed herein, e.g., a compound of Formula I, including a single enantiomer, a mixture of enantiomers, a mixture of diastereomers, or an isotopic variant thereof; or a pharmaceutically acceptable salt, solvate, or prodrug thereof.

In yet another embodiment, provided herein is a method for treating, preventing, or ameliorating one or more symptoms of diabetes in a subject, comprising administering to the subject a therapeutically effective amount of a compound disclosed herein, e.g., a compound of Formula I, including a single enantiomer, a mixture of enantiomers, a mixture of diastereomers, or an isotopic variant thereof; or a pharmaceutically acceptable salt, solvate, or prodrug thereof.

In yet another embodiment, provided herein is a method for increasing insulin secretion in a subject, comprising administering to the subject a therapeutically effective amount of a compound disclosed herein, e.g., a compound of Formula I, including a single enantiomer, a mixture of enantiomers, a mixture of diastereomers, or an isotopic variant thereof; or a pharmaceutically acceptable salt, solvate, or prodrug thereof.

In yet another embodiment, provided herein is a method for reducing gastric motility in a subject, comprising administering to the subject a therapeutically effective amount of a compound disclosed herein, e.g., a compound of Formula I, including a single enantiomer, a mixture of enantiomers, a mixture of diastereomers, or an isotopic variant thereof; or a pharmaceutically acceptable salt, solvate, or prodrug thereof.

In yet another embodiment, provided herein is a method for delaying gastric emptying in a subject, comprising administering to the subject a therapeutically effective amount of a compound disclosed herein, e.g., a compound of Formula I, including a single enantiomer, a mixture of enantiomers, a mixture of diastereomers, or an isotopic variant thereof; or a pharmaceutically acceptable salt, solvate, or prodrug thereof.

In yet another embodiment, provided herein is a method for lowering plasma glucagon levels in a subject, comprising administering to the subject a therapeutically effective amount of a compound disclosed herein, e.g., a compound of Formula I, including a single enantiomer, a mixture of enantiomers, a mixture of diastereomers, or an isotopic variant thereof; or a pharmaceutically acceptable salt, solvate, or prodrug thereof.

In yet another embodiment, provided herein is a method for suppressing prandial glucagon secretion in a subject, comprising administering to the subject a therapeutically effective amount of a compound disclosed herein, e.g., a compound of Formula I, including a single enantiomer, a mixture of enantiomers, a mixture of diastereomers, or an isotopic variant thereof; or a pharmaceutically acceptable salt, solvate, or prodrug thereof.

In yet another embodiment, provided herein is a method for reducing food intake in in a subject, comprising administering to the subject a therapeutically effective amount of a compound disclosed herein, e.g., a compound of Formula I, including a single enantiomer, a mixture of enantiomers, a mixture of diastereomers, or an isotopic variant thereof; or a pharmaceutically acceptable salt, solvate, or prodrug thereof.

In yet another embodiment, provided herein is a method for reducing appetite in a subject, comprising administering to the subject a therapeutically effective amount of a compound disclosed herein, e.g., a compound of Formula I, including a single enantiomer, a mixture of enantiomers, a mixture of diastereomers, or an isotopic variant thereof; or a pharmaceutically acceptable salt, solvate, or prodrug thereof.

In yet another embodiment, provided herein is a method for treating or preventing obesity in a subject, which comprises administering to the subject a therapeutically effective amount of a compound disclosed herein, e.g., a compound of Formula I, including a single enantiomer, a mixture of enantiomers, a mixture of diastereomers, or an isotopic variant thereof; or a pharmaceutically acceptable salt, solvate, or prodrug thereof.

In yet another embodiment, provided herein is a method for treating or preventing hyperlipidemia in a subject, which comprises administering to the subject a therapeutically effective amount of a compound disclosed herein, e.g., a compound of Formula I, including a single enantiomer, a mixture of enantiomers, a mixture of diastereomers, or an isotopic variant thereof; or a pharmaceutically acceptable salt, solvate, or prodrug thereof.

In still another embodiment, provided herein is a method for treating or preventing a cardiovascular disease in a subject, which comprises administering to the subject a therapeutically effective amount of a compound disclosed herein, e.g., a compound of Formula I, including a single enantiomer, a mixture of enantiomers, a mixture of diastereomers, or an isotopic variant thereof; or a pharmaceutically acceptable salt, solvate, or prodrug thereof.

In one embodiment, the subject is a mammal. In another embodiment, the subject is a human. Depending on the disease to be treated and the subject's condition, the compounds or compositions provided herein may be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical (e.g., transdermal or local) routes of administration, and may be formulated, alone or together, in suitable dosage unit with pharmaceutically acceptable carriers, adjuvants and vehicles appropriate for each route of administration. Also provided is administration of the compounds or compositions provided herein in a depot formulation, in which the active ingredient is released over a predefined time period.

In the treatment, prevention, or amelioration of one or more symptoms of the conditions, disorders, or diseases described herein, an appropriate dosage level generally is about 0.001 to 100 mg per kg patient body weight per day (mg/kg per day), about 0.01 to about 75 mg/kg per day, about 0.1 to about 50 mg/kg per day, about 0.5 to about 25 mg/kg per day, or about 1 to about 20 mg/kg per day, which may be administered in single or multiple doses. Within this range the dosage may be 0.005 to 0.05, 0.05 to 0.5, or 0.5 to 5.0, 1 to 15, 1 to 20, or 1 to 50 mg/kg per day. In certain embodiments, the dosage level is about 0.001 to 100 mg/kg per day. In certain embodiments, the dosage level is about 0.01 to about 75 mg/kg per day. In certain embodiments, the dosage level is about 0.1 to about 50 mg/kg per day. In certain embodiments, the dosage level is about 0.5 to about 25 mg/kg per day. In certain embodiments, the dosage level is about 1 to about 20 mg/kg per day.

For oral administration, the pharmaceutical compositions can be provided in the form of tablets containing 1.0 to 1,000 mg of the active ingredient, particularly about 1, about 5, about 10, about 15, about 20, about 25, about 50, about 75, about 100, about 150, about 200, about 250, about 300, about 400, about 500, about 600, about 750, about 800, about 900, and about 1,000 mg of the active ingredient for the symptomatic adjustment of the dosage to the patient to be treated. The compositions may be administered on a regimen of 1 to 4 times per day, including once, twice, three times, and four times per day. In certain embodiments, the compositions may be administered with a regimen of 1-3 tablets per treatment.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

In certain embodiments, the compounds provided herein are non-peptide GLP-1 agonists. In certain embodiments, the compounds provided herein are non-peptide GLP-1 partial agonists. In certain embodiments, the compounds provided herein are non-peptide GLP-1 sensitizers. In certain embodiments, the compounds provided herein are selective agonists of GLP-1 receptor over GLP-2 or glucagon receptor.

In certain embodiments, the compounds provided herein activate a GLP-1 receptor. In certain embodiments, the compounds provided herein activate a GLP-1 receptor without competing with a GLP-1. In certain embodiments, the compounds provided herein activate a GLP-1 receptor without competing with a native GLP-1. In certain embodiments, the compounds provided herein activate a GLP-1 receptor without competing with a GLP-1 in a competition binding assay. In certain embodiments, the compounds provided herein activate a GLP-1 receptor without competing with a native GLP-1 in a competition binding assay.

In certain embodiments, the compounds provided herein activate a human GLP-1 receptor. In certain embodiments, the compounds provided herein activate a human GLP-1 receptor without competing with a human GLP-1. In certain embodiments, the compounds provided herein activate a human GLP-1 receptor without competing with a native human GLP-1. In certain embodiments, the compounds provided herein activate a human GLP-1 receptor without competing with a human GLP-1 in a competition binding assay. In certain embodiments, the compounds provided herein activate a human GLP-1 receptor without competing with a native human GLP-1 in a competition binding assay.

Compositions and Routes of Administration:

In another aspect, the invention provides pharmaceutical compositions (i.e., formulations). The pharmaceutical compositions can comprise a compound of any of Formula (I'), (I), (II), (III), (IV), (V), (VI), (VII), (VIII), (IX), (X), (XI), (XII), (XV), or any subgenus thereof, including any species within these formulae or any subgenus thereof which is admixed with at least one pharmaceutically acceptable excipient or carrier. Frequently, the composition comprises at least two pharmaceutically acceptable excipients or carriers.

While the compositions and methods of the present invention will typically be used in therapy for human patients, they may also be used in veterinary medicine to treat similar or identical diseases. The compositions may, for example, be used to treat mammals, including, but not limited to, primates and domesticated mammals. The compositions of the present invention include geometric and optical isomers of one or more of the compounds, wherein each compound is a racemic mixture of isomers or one or more purified isomers.

Pharmaceutical compositions suitable for use in the present invention include compositions wherein the active ingredients are contained in an effective amount to achieve the intended purpose. Determination of the effective amounts is well within the capability of those skilled in the art, especially in light of the detailed disclosure provided herein.

Suitable excipients are well known to those skilled in the art, and non-limiting examples of suitable excipients are provided herein. Whether a particular excipient is suitable for incorporation into a pharmaceutical composition or dosage form depends on a variety of factors well known in the art, including, but not limited to, the method of administration. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided herein are pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient. In one embodiment, lactose-free compositions comprise an active ingredient provided herein, a binder/filler, and a lubricant. In another embodiment, lactose-free dosage forms comprise an active ingredient, microcrystalline cellulose, pre-gelatinized starch, and magnesium stearate.

The compound provided herein may be administered alone, or in combination with one or more other compounds provided herein. The pharmaceutical compositions that comprise a compound provided herein, e.g., a compound of Formula I, including a single enantiomer, a racemic mixture, a mixture of diastereomers, or an isotopic variant thereof; or a pharmaceutically acceptable salt, solvate, or prodrug thereof, can be formulated in various dosage forms for oral, parenteral, and topical administration. The pharmaceutical compositions can also be formulated as modified release dosage forms, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Delivery Technology*, 2nd ed.; Rathbone et al., Eds.; Marcel Dekker, Inc.: New York, N.Y., 2008).

In one embodiment, the pharmaceutical compositions are provided in a dosage form for oral administration, which comprise a compound provided herein, e.g., a compound of Formula I, including a single enantiomer, a racemic mixture, a mixture of diastereomers, or an isotopic variant thereof; or a pharmaceutically acceptable salt, solvate, or prodrug thereof; and one or more pharmaceutically acceptable excipients or carriers.

In another embodiment, the pharmaceutical compositions are provided in a dosage form for parenteral administration, which comprise a compound provided herein, e.g., a compound of Formula I, including a single enantiomer, a racemic mixture, a mixture of diastereomers, or an isotopic variant thereof; or a pharmaceutically acceptable salt, solvate, or prodrug thereof; and one or more pharmaceutically acceptable excipients or carriers.

In yet another embodiment, the pharmaceutical compositions are provided in a dosage form for topical administration, which comprise a compound provided herein, e.g., a compound of Formula I, including a single enantiomer, a racemic mixture, a mixture of diastereomers, or an isotopic variant thereof; or a pharmaceutically acceptable salt, solvate, or prodrug thereof; and one or more pharmaceutically acceptable excipients or carriers.

The pharmaceutical compositions provided herein can be provided in a unit-dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. For example, a 100 mg unit dose contains about 100 mg of an active ingredient in a packaged tablet or capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

In certain embodiments, pharmaceutical compositions provided herein are formulated as capsules, each of which comprises 100 mg of a compound provided herein (an active ingredient), e.g., a compound of Formula I, as an active ingredient, including a single enantiomer, a racemic mixture, a mixture of diastereomers, or an isotopic variant thereof; or a pharmaceutically acceptable salt, solvate, or prodrug thereof; 150 mg of lactose, 50 mg of cellulose, and 6 mg of magnesium stearate. In certain embodiments, the capsules are prepared by filling standard two-piece hard gelatin capsules each with a powdered active ingredient (100 mg), lactose (150 mg), cellulose (50 mg), and magnesium stearate (6 mg).

In certain embodiments, pharmaceutical compositions provided herein are formulated as soft gelatin capsules, each of which comprises 100 mg of a compound provided herein (an active ingredient), e.g., a compound of Formula I, as an active ingredient, including a single enantiomer, a racemic mixture, a mixture of diastereomers, or an isotopic variant thereof; or a pharmaceutically acceptable salt, solvate, or prodrug thereof; and a digestible oil, in one embodiment, soybean oil, cottonseed oil or olive oil. In certain embodiments, the soft gelatin capsules are prepared by injecting a mixture of an active ingredient in a digestiable oil into gelatin to form soft gelatin capsules each containing 100 milligrams of the active ingredient.

In certain embodiments, pharmaceutical compositions provided herein are formulated as tablets, each of which comprises 100 mg of a compound provided herein (an active ingredient), e.g., a compound of Formula I, as an active ingredient, including a single enantiomer, a racemic mixture, a mixture of diastereomers, or an isotopic variant thereof; or a pharmaceutically acceptable salt, solvate, or prodrug thereof; 0.2 mg of colloidal silicon dioxide, 5 mg of magnesium stearate, 275 mg of microcrystalline cellulose, 11 mg of starch, and 98.8 mg of lactose. The tablets can be prepared by any method known to one of skill in the art.

In certain embodiments, pharmaceutical compositions provided herein are formulated as injectables, which comprise 11.5% by weight of a compound provided herein (an active ingredient), e.g., a compound of Formula I, as an active ingredient, including a single enantiomer, a racemic mixture, a mixture of diastereomers, or an isotopic variant thereof; or a pharmaceutically acceptable salt, solvate, or prodrug thereof; in 10% by volume of propylene glycol. In certain embodiments, the injectables are prepared by stirring 1.5% by weight of active ingredient in 10% by volume propylene glycol.

In certain embodiments, pharmaceutical compositions provided herein are formulated as suspection for oral administration, each 5 mL of which comprises 100 mg of a finely divided compound provided herein (an active ingredient), e.g., a compound of Formula I, as an active ingredient, including a single enantiomer, a racemic mixture, a mixture of diastereomers, or an isotopic variant thereof; or a pharmaceutically acceptable salt, solvate, or prodrug thereof; 100 mg of sodium carboxymethyl cellulose, 5 mg of sodium benzoate, 1.0 g of sorbitol solution USP, and 0.025 mL of vanillin.

A. Oral Administration

The pharmaceutical compositions provided herein for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, dragees, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The amount of a binder or filler in the pharmaceutical compositions provided herein varies upon the type of formulation, and is readily discernible to those of ordinary skill in the art. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include, but are not limited to, colloidal silicon dioxide, CAB-O-SIL® (Cabot Co. of Boston, Mass.), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin; acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic add, sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve a plurality of functions, even within the same formulation.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl)acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration can be also provided in the forms of liposomes, micelles, microspheres, or nanosystems. Micellar dosage forms can be prepared as described in U.S. Pat. No. 6,350,458.

The pharmaceutical compositions provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein for oral administration can be formulated as immediate or modified release dosage forms, including delayed-, sustained, pulsed-, controlled, targeted-, and programmed-release forms.

B. Parenteral Administration

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

When the pharmaceutical compositions provided herein are formulated for multiple dosage administration, the multiple dosage parenteral formulations must contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein for parenteral administration can be formulated as immediate or modified release dosage forms, including delayed-, sustained, pulsed-, controlled, targeted-, and programmed-release forms.

The pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulation of the pharmaceutical compositions provided herein can also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions can also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream base can be oil-in-water or water-in-oil. Suitable cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include, but are not limited to, crosslinked acrylic acid polymers, such as carbomers, carboxypolyalkylenes, and CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, and hydrogels, such as polyvinyl alcohol, hydroxyethyl methacrylate, and polyacrylic acid. Combinations of the various vehicles can also be used. Rectal and vaginal suppositories may be prepared by compressing or molding. The typical weight of a rectal and vaginal suppository is about 2 to about 3 g.

The pharmaceutical compositions provided herein can be administered ophthalmically in the forms of solutions, suspensions, ointments, emulsions, gel-forming solutions, powders for solutions, gels, ocular inserts, and implants.

The pharmaceutical compositions provided herein can be administered intranasally or by inhalation to the respiratory tract. The pharmaceutical compositions can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions can also be provided as a dry powder for insufflation, alone or in combination with an inert carrier such as lactose or phospholipids; and nasal drops. For intranasal use, the powder can comprise a bioadhesive agent, including chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of the active ingredient provided herein; a propellant as solvent; and/or a surfactant, such as sorbitan trioleate, oleic acid, or an oligolactic acid.

The pharmaceutical compositions provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters, and cartridges for use in an inhaler or insufflator can be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients or carriers include, but are not limited to, dextran, glucose, maltose, sorbitol, xylitol, fructose, sucrose, and trehalose. The pharmaceutical compositions provided herein for inhaled/intranasal administration can further comprise a suitable flavor, such as menthol and levomenthol; and/or sweeteners, such as saccharin and saccharin sodium.

The pharmaceutical compositions provided herein for topical administration can be formulated to be immediate release or modified release, including delayed-, sustained-, pulsed-, controlled-, targeted, and programmed release.

D. Modified Release

The pharmaceutical compositions provided herein can be formulated as a modified release dosage form. As used herein, the term "modified release" refers to a dosage form in which the rate or place of release of the active ingredient(s) is different from that of an immediate dosage form when administered by the same route. Modified release dosage forms include, but are not limited to, delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphorism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,958,458; 5,972,891; 5,980,945; 5,993,855; 6,045,830; 6,087,324; 6,113,943; 6,197,350; 6,248,363; 6,264,970; 6,267,981; 6,270,798; 6,375,987; 6,376,461; 6,419,961; 6,589,548; 6,613,358; 6,623,756; 6,699,500; 6,793,936; 6,827,947; 6,902,742; 6,958,161; 7,255,876; 7,416,738; 7,427,414; 7,485,322; Bussemer et al., *Crit. Rev. Ther. Drug Carrier Syst.* 2001, 18, 433-458; *Modified-Release Drug Delivery Technology*, 2nd ed.; Rathbone et al., Eds.; Marcel Dekker AG: 2005; Maroni et al., *Expert. Opin. Drug Deliv.* 2005, 2, 855-871; Shi et al., *Expert Opin. Drug Deliv.* 2005, 2, 1039-1058; *Polymers in Drug Delivery*; Ijeoma et al., Eds.; CRC Press LLC: Boca Raton, Fla., 2006; Badawy et al., *J. Pharm. Sci.* 2007, 9, 948-959; *Modified-Release Drug Delivery Technology*, supra; Conway, *Recent Pat. Drug Deliv. Formul.* 2008, 2, 1-8; Gazzaniga et al., *Eur. J. Pharm. Biopharm.* 2008, 68, 11-18; Nagarwal et al., *Curr. Drug Deliv.* 2008, 5, 282-289; Gallardo et al., *Pharm. Dev. Technol.* 2008, 13, 413-423; Chrzanowski, *AAPS PharmSciTech.* 2008, 9, 635-638; Chrzanowski, *AAPS PharmSciTech.* 2008, 9, 639-645; Kalantzi et al., *Recent Pat. Drug Deliv. Formul.* 2009, 3, 49-63; Saigal et al., *Recent Pat. Drug Deliv. Formul.* 2009, 3, 64-70; and Roy et al., *J. Control Release* 2009, 134, 74-80.

1. Matrix Controlled Release Devices

The pharmaceutical compositions provided herein in a modified release dosage form can be fabricated using a matrix controlled release device known to those skilled in the art. See, Takada et al. in *Encyclopedia of Controlled Drug Delivery*; Mathiowitz Ed.; Wiley: 1999; Vol 2.

In certain embodiments, the pharmaceutical compositions provided herein in a modified release dosage form is formulated using an erodible matrix device, which is water-swellable, erodible, or soluble polymers, including, but not limited to, synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethyl hydroxyethyl cellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methyl methacrylate, ethyl methacrylate, ethylacrylate, (2-dimethylaminoethyl)methacrylate, and (trimethylaminoethyl)methacrylate chloride.

In certain embodiments, the pharmaceutical compositions provided herein are formulated with a non-erodible matrix device. The active ingredient(s) is dissolved or dispersed in an inert matrix and is released primarily by diffusion through the inert matrix once administered. Materials suitable for use as a non-erodible matrix device include, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubbers, epichlorohydrin rubbers, ethylene/vinyl alcohol copolymer, ethylene/vinyl acetate/vinyl alcohol terpolymer, ethylene/vinyloxyethanol copolymer, polyvinyl chloride, plasticized nylon, plasticized polyethylene terephthalate, natural rubber, silicone rubbers, polydimethylsiloxanes, and silicone carbonate copolymers; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form can be prepared by methods known to those skilled in the art, including direct compression, dry or wet granulation followed by compression, and melt-granulation followed by compression.

2. Osmotic Controlled Release Devices

The pharmaceutical compositions provided herein in a modified release dosage form can be fabricated using an osmotic controlled release device, including, but not limited to, one-chamber system, two-chamber system, asymmetric membrane technology (AMT), and extruding core system (ECS). In general, such devices have at least two components: (a) a core which contains an active ingredient; and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents is water-swellable hydrophilic polymers, which are also referred to as "osmopolymers" and "hydrogels." Suitable water-swellable hydrophilic polymers as osmotic agents include, but are not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates can be employed to influence how rapidly the active ingredient(s) is initially delivered from the dosage form. For example, amorphous sugars, such as MANNOGEM™ EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly (acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form can further comprise additional conventional excipients or carriers as described herein to promote performance or processing of the formulation.

The osmotic controlled-release dosage forms can be prepared according to conventional methods and techniques known to those skilled in the art. See, *Remington: The Science and Practice of Pharmacy*, supra; Santus and Baker, *J. Controlled Release* 1995, 35, 1-21; Verma et al., *Drug Develop-*

*ment and Industrial Pharmacy* 2000, 26, 695-708; and Verma et al., *J. Controlled Release* 2002, 79, 7-27.

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and International Pat. Appl. Publ. No. WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxylethyl cellulose, and other pharmaceutically acceptable excipients or carriers.

3. Multiparticulate Controlled Release Devices

The pharmaceutical compositions provided herein in a modified release dosage form can be fabricated as a multiparticulate controlled release device; which comprises a multiplicity of particles, granules, or pellets, ranging from about 10 μm to about 3 mm, about 50 μm to about 2.5 mm, or from about 100 μm to about 1 mm in diameter. Such multiparticulates can be made by the processes known to those skilled in the art, including wet- and dry-granulation, extrusion/spheronization, roller-compaction, melt-congealing, and by spray-coating seed cores. See, for example, *Multiparticulate Oral Drug Delivery*; Ghebre-Sellassie Ed.; Marcel Dekker: 1994; and *Pharmaceutical Pelletization Technology*; Ghebre-Sellassie Ed.; Marcel Dekker: 1989.

Other excipients or carriers as described herein can be blended with the pharmaceutical compositions to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

4. Targeted Delivery

The pharmaceutical compositions provided herein can also be formulated to be targeted to a particular tissue, receptor, or other area of the body of the subject to be treated, including liposome-, resealed erythrocyte-, and antibody-based delivery systems. Examples include, but are not limited to, those disclosed in U.S. Pat. Nos. 5,709,874; 5,759,542; 5,840,674; 5,900,252; 5,972,366; 5,985,307; 6,004,534; 6,039,975; 6,048,736; 6,060,082; 6,071,495; 6,120,751; 6,131,570; 6,139,865; 6,253,872; 6,271,359; 6,274,552; 6,316,652; and 7,169,410.

Therapeutic Combinations

Compounds of the invention may be used alone or in combination with another therapeutic agent, i.e., an additional therapeutic agent. The invention provides methods to treat related conditions or diseases by administering to a subject in need of such treatment a therapeutically effective amount of a therapeutic agent useful for treating said disorder and administering to the same subject a therapeutically effective amount of a modulator of the present invention, i.e., a compound of the invention. The therapeutic agent and the modulator may be "co-administered", i.e, administered together, either as separate pharmaceutical compositions or admixed in a single pharmaceutical composition. By "administered together", the therapeutic agent and the modulator may also be administered separately, including at different times and with different frequencies. The modulator may be administered by any known route, such as orally, intravenously, intramuscularly, nasally, and the like; and the therapeutic agent may also be administered by any conventional route. In many embodiments, at least one and optionally both of the modulator and the therapeutic agent may be administered orally.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a subject with a disease or disorder. A first therapy (e.g., a prophylactic or therapeutic agent such as a compound provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

As used herein, the term "synergistic" includes a combination of a compound provided herein and another therapy (e.g., a prophylactic or therapeutic agent) which has been or is currently being used to prevent, treat, or manage a condition, disorder, or disease, which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject with a condition, disorder, or disease. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention, treatment, or management of a condition, disorder, or disease). In addition, a synergistic effect can result in improved efficacy of agents in the prevention, treatment, or management of a condition, disorder, or disease. Finally, a synergistic effect of a combination of therapies (e.g., a combination of prophylactic or therapeutic agents) may avoid or reduce adverse or unwanted side effects associated with the use of either therapy alone.

The compound provided herein can be administered in combination or alternation with another therapeutic agent, such as an anti-diabetic agent, hypolipidemic agents, anti-obesity or appetite-regulating agents, anti-hypertensive agents, HDL-increasing agents, cholesterol absorption modulators, thrombin inhibitors, aldosterone inhibitors, inhibitors of platelet aggregation, estrogen, testosterone, selective estrogen receptor modulators, selective androgen receptor modulators, chemotherapeutic agents, and/or 5-HT$_3$ or 5-HT$_4$ receptor modulators. In combination therapy, effective dosages of two or more agents are administered together, whereas in alternation or sequential-step therapy, an effective dosage of each agent is administered serially or sequentially. The dosages given will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

Suitable examples of anti-diabetic agents include, but are not limited to, insulin, including insulin derivatives and mimetics; insulin secretagogues, including sulfonylureas (e.g., glipizide, glyburide or amaryl); insulinotropic sulfonylurea receptor ligands, including meglitinides (e.g., nateglinide or repaglinide); insulin sensitisers, including protein tyrosine phosphatase-1B (PTP-1B) inhibitors (e.g., PTP-112); GSK3 (glycogen synthase kinase-3) inhibitors, including SB-517955, SB-4195052, SB-216763, N,N-57-05441 or N,N-57-05445; RXR ligands, including GW-0791 or AGN-194204; sodium-dependent glucose cotransporter inhibitors, including T-1095; glycogen phosphorylase A inhibitors, including BAY R3401; biguanides, including metformin; alpha-glucosidase inhibitors, including acarbose; GLP-1 (glucagon like peptide-1), including GLP-1 analogues and mimetics (e.g., exendin-4, exenatide (BYTTA™), or liraglutide); DPPIV (dipeptidyl peptidase IV) inhibitors, including DPP728, LAF237 (vildagliptin), MK-0431, saxagliptin or GSK23A; AGE breakers; and thiazolidone derivatives, including glitazone, pioglitazone, rosiglitazone or (R)-1-{4-[5-methyl-2-(4-trifluoromethyl-phenylyoxazol-4-yl-methoxy]-benzen-esulfonyl}-2,3-dihydro-1H-indole-2-carboxylic acid or a non-glitazone type PPAR-agonist (e.g., GI-262570).

Suitable examples of anti-obesity/appetite-regulating agents include, but are not limited to, phentermine, leptin, bromocriptine, dexamphetamine, amphetamine, fenfluramine, dexfenfluramine, sibutramine, dexfenfluramine, mazindol, phentermine, phendimetrazine, diethylpropion, fluoxetine, bupropion, topiramate, diethylpropion, benzphetamine, phenylpropanolamine, ecopipam, ephedrine, and pseudoephedrine and cannabinoid receptor antagonists.

Preparations and Examples

The compounds of the present invention can be synthesized using methods, techniques, and materials known to those of skill in the art, such as described, for example, in March, ADVANCED ORGANIC CHEMISTRY 4.sup.th Ed., (Wiley 1992); Carey and Sundberg, ADVANCED ORGANIC CHEMISTRY 3.sup.rd Ed., Vols. A and B (Plenum 1992), and Green and Wuts, PROTECTIVE GROUPS IN ORGANIC SYNTHESIS 2.sup.nd Ed. (Wiley 1991). Starting materials useful for preparing compounds of the invention and intermediates thereof are commercially available from sources, such as Aldrich Chemical Co. (Milwaukee, Wis.), Sigma Chemical Co. (St. Louis, Mo.), Maybridge (Cornwall, England), Asinex (Winston-Salem, N.C.), ChemBridge (San Diego, Calif.), ChemDiv (San Diego, Calif.), SPECS (Delft, The Netherlands), Timtec (Newark, Del.), or alternatively can be prepared by well-known synthetic methods (see, e.g., Harrison et al., "Compendium of Synthetic Organic Methods", Vols. 1-8 (John Wiley and Sons, 1971-1996); "Beilstein Handbook of Organic Chemistry," Beilstein Institute of Organic Chemistry, Frankfurt, Germany; Feiser et al., "Reagents for Organic Synthesis," Volumes 1-21, Wiley Interscience; Trost et al., "Comprehensive Organic Synthesis," Pergamon Press, 1991; "Theilheimer's Synthetic Methods of Organic Chemistry," Volumes 1-45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," 3d Edition, John Wiley & Sons, 1995). Other methods for synthesis of the present compounds and/or starting materials thereof are either described in the art or will be readily apparent to the skilled artisan. Alternatives to the reagents and/or protecting groups may be found in the references provided above and in other compendiums well known to one skilled in the art.

Preparation of the present compounds may include one or more steps of protection and deprotection (e.g., the formation and removal of acetal groups). Guidance for selecting suitable protecting groups can be found, for example, in Greene & Wuts, "Protective Groups in Organic Synthesis," Wiley Interscience, 1999. In addition, the preparation may include various purifications, such as column chromatography, flash chromatography, thin-layer chromatography (TLC), recrystallization, distillation, high-pressure liquid chromatography (HPLC) and the like. Also, various techniques well known in the chemical arts for the identification and quantification of chemical reaction products, such as proton and carbon-13 nuclear magnetic resonance ($^1$H and $^{13}$C NMR), infrared and ultraviolet spectroscopy (IR and UV), X-ray crystallography, elemental analysis (EA), HPLC and mass spectroscopy (MS) can be used as well. The preparation may also involve any other methods of protection and deprotection, purification and identification and quantification that are well known in the chemical arts.

The compounds provided herein can be prepared, isolated, or obtained by any method known to one of ordinary skill in the art or according to the examples described herein. For an example, a compound of Formula I can be prepared as shown in Scheme I.

Compound I-1 is brominated with a bromination reagent (e.g., NBS), optionally in the presence of radical initiator (e.g., AIBN or BPO) to yield bromo compound I-2. Compound I-2 is coupled with N-benzylidene I-3, where group L1 is protected with a suitable protection group PG, optionally in the presence of a base (e.g., sodium hydroxide or potassium hydroxide) and/or a phase-transfer catalyst (e.g., tetrabutylammonium bromide) to form compound I-4. When L1 is —COOH, suitable PG groups include, but are not limited to, methyl, ethyl, t-butyl, or benzyl, and thus L1-PG is —COOCH3, —COOEt, —COO-tBu, or —COOBn, respectively. Deprotection under acidic conditions such as HCl/THF yields compound I-5. Groups R4 and/or R5 are then introduced to form compound I-6 via appropriate chemistry, including, but not limited to, amino alkylation, reductive amination, acylation, sulfonation, urea formation, or carbamate formation.

To form a 1,2,4-oxadiazole derivative, compound I-6 is treated with NH2OH to form N-acyloxyamidine I-7. Compound I-7 is then treated with an activated derivative of carboxylic acid A-COOH, optionally in the presence of a suitable base to give N-ayloxyamidine I-8. The carboxylic acid A-COOH in this reaction can be activated with a reagent such as N,N'-dicyclohexylcarbodiimide, 1-(3-dimethylaminopropyl)-3-ethylcarbodiimide, 1,1'-carbonyldiimidazole, or bis (2-oxo-3-oxazolidinyl)phosphinic chloride, optionally in the presence of a suitable base, such as triethylamine, N,N-diisopropylethylamine, or sodium bicarbonate. Alternatively, an acid chloride, acid anhydride, or acyl imidazole can also be employed. N-Ayloxyamidine I-8 is cyclized via dehydrogation to form 1,2,4-oxadiazole 1-9, optionally in the presence of a base, such as pyridine, N,N-diisopropylethylamine or tetrabutylammonium fluoride. However, N-Ayloxyamidine I-8 needs not be purified or separated in some embodiments. In certain embodiments, the acylation and cyclization is carried out in a single continuous step, that is, 1,2,4-oxadiazole I-9 is formed from compound I-7 in a single step. Oxadiazole I-9 can also be made according to the methods described in Clapp, "1,2,3- and 1,2,4-Oxadiazoles" in Comprehensive Heterocyclic Chemistry, Vol. 6, Potts Ed.; Pergamon Press: 1984; pp. 366-391. Protecting group PG of compound I-9 is then removed to form compound I-10, which can be accomplished under basic, acidic, or reductive conditions depending on the chemical structures of L1 and PG. For example, when L1 is —COOH, the deprotection is achieved using aqueous lithium, sodium, or potassium hydroxide.

Scheme I

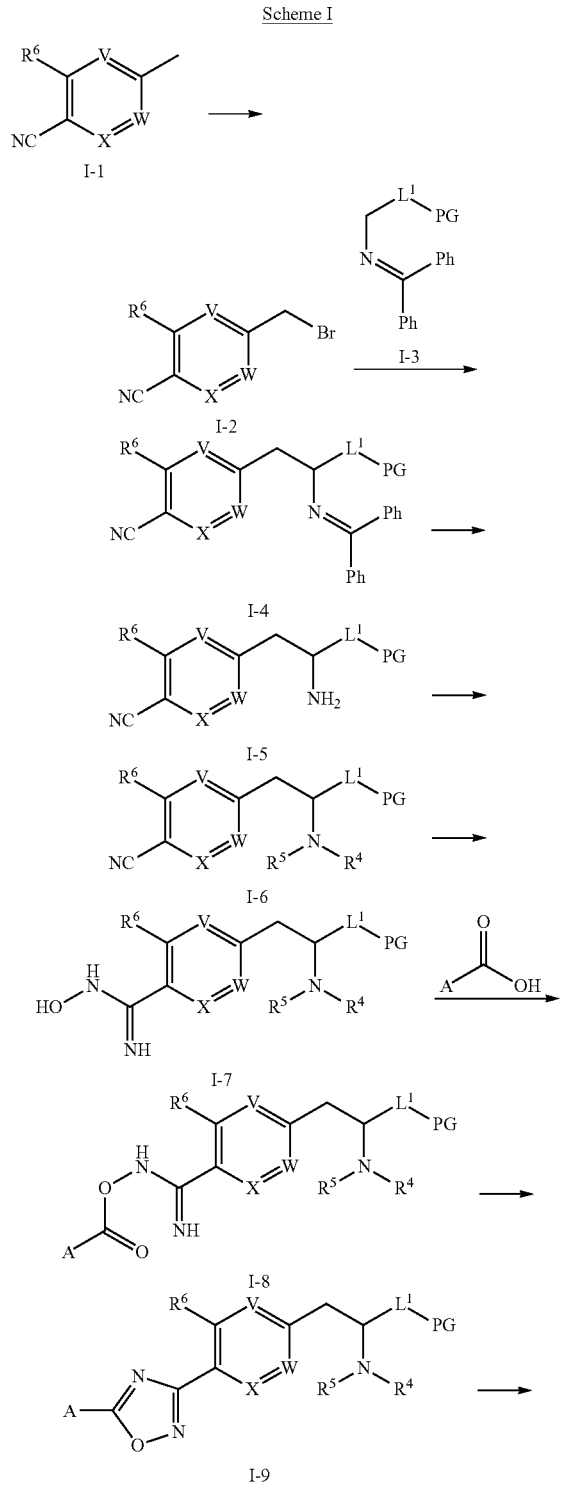

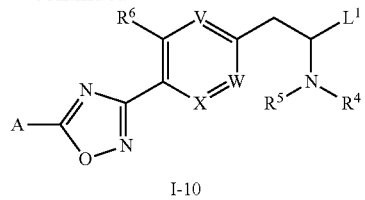

The compounds provided herein can be converted into another analogous compound by standard chemical manipulations. These chemical manipulations are known to those skilled in the art and include, but are not limited to (a) removal of a protecting group (Greene and Wuts, Protective Groups in Organic Synthesis, 2nd Ed.; John Wiley and Sons: New York, 1991); (b) displacement of a leaving group (e.g., halide, mesylate, or tosylate) with a primary or secondary amine, thiol, or alcohol to form a secondary or tertiary amine, thioether, or ether, respectively; (c) treatment of primary and secondary amines with an isocyanate, acid chloride (or other activated carboxylic acid derivative), alkylaryl chloroformate, or sulfonyl chloride to provide the corresponding urea, amide, carbamate, or sulfonamide; and (d) reductive amination of a primary or secondary amine using an aldehyde.

The enantiomers of the title compound can be prepared by preparative Chiral HPLC or through asymmetric synthesis. For an example of stereoselective synthesis, a compound of Formula II-8 can be prepared as shown in Scheme II. Compound II-1 is treated with NH2OH to form N-acyloxyamidine II-2. Compound II-2 is then treated with an activated derivative of carboxylic acid A-COOH, optionally in the presence of a suitable base, and cyclized via dehydrogation to form 1,2, 4-oxadiazole derivative II-3, as described in Scheme 1. Compound II-3 is then coupled with 3-iodo-α-amino acid derivative II-4, under standard Negishi coupling conditions known to the person skill in the art to form the phenyl alanine derivative II-5. The reaction is usually carried out in a suitable solvent (such as DMF) at ambient temperature (60° C.) in the presence of a catalytic amount (5%) of palladium catalyst (such as palladium acetate) and a phosphine ligand (10%, such as $P(Otol)_3$). Deprotection of PG2 under acidic or basic conditions such as morpholine/DMF yields compound II-6. Groups R4 and/or R5 are then introduced to form compound II-7 via appropriate chemistry, including, but not limited to, amino alkylation, reductive amination, acylation, sulfonation, urea formation, or carbamate formation. Finally Removal of protecting group PG1 was carried out under basic conditions similar to what described in Scheme 1.

Scheme II

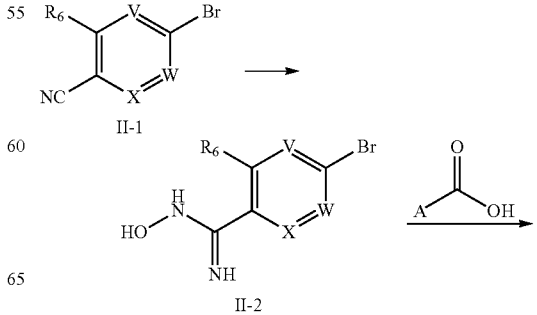

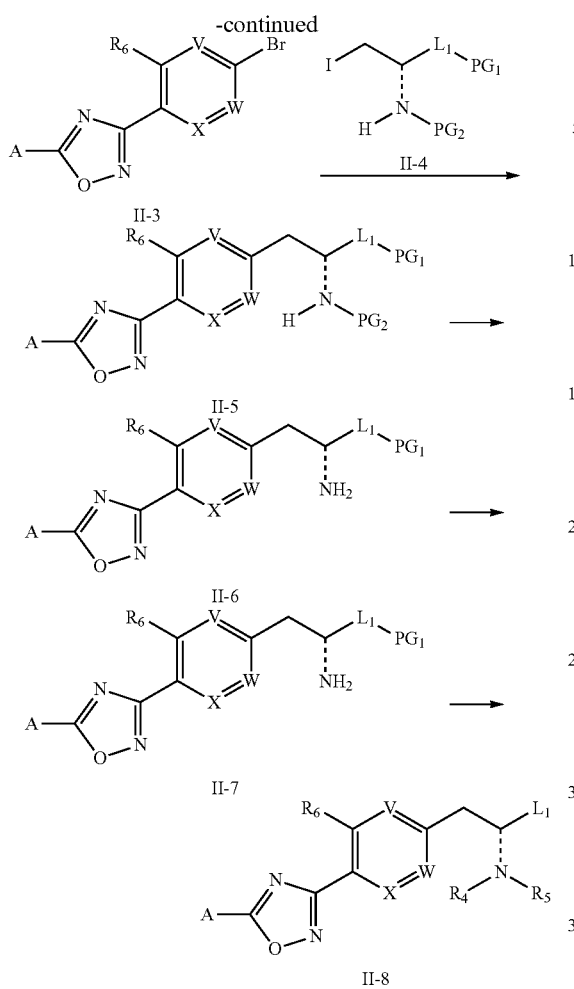

acid); BOP (benzotriazole-1-yl-oxy-tris-(dimethylamino)-phosphonium hexafluorophosphate); HATU (2-(7-aza-1H-benzotriazole-1-yl)-1,1,3,3-tetramethyluronium hexafluorophosphate); TBTU (O-(benzotriazol-1-yl)-N,N,N',N'-tetramethyluronium tetrafluoroborate); DIPC (1,3-diisopropylcarbodiimide); BINAP (2,2'-bis(diphenylphosphino)-1,1'-binaphthyl); BPO (benzoyl peroxide); EDCI (3-ethyl-1(N,N-dimethyl)aminopropylcarbodiimide); HOBt (hydroxybenzotriazole); Pd2(dba)3 (tris(dibenzylideneacetone)dipalladium(0)); NBS (N-bromosuccinimide); and TBAB (tetra-n-butylammonium bromide).

For all of the following examples, standard work-up and purification methods known to those skilled in the art can be utilized. Unless otherwise indicated, all temperatures are expressed in ° C. (degrees Centigrade). All reactions conducted at room temperature unless otherwise noted. Synthetic methodologies herein are intended to exemplify the applicable chemistry through the use of specific examples and are not indicative of the scope of the disclosure.

Method A

Example 1

3-{4-[5-(4-tert-Butoxycarbonylamino-phenyl)-[1,2,4]oxadiazol-3-yl]-3-fluoro-phenyl}-2-[(5-p-tolyl-furan-2-carbonyl)-amino]-propionic acid 6

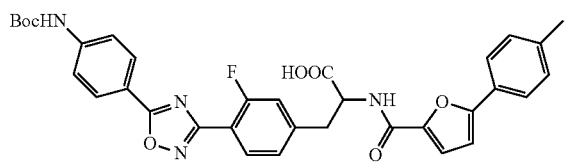 [SMILES: Cc1ccc(-c2ccc(C(=O)NC(Cc3ccc(-c4noc(-c5ccc(NC(=O)OC(C)(C)C)cc5)n4)c(F)c3)C(=O)O)o2)cc1]

The disclosure will be further understood by the following non-limiting examples.

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); µL (microliters); L (liter); mM (millimolar); M (micromolar); Hz (Hertz); MHz (megahertz); mmol (millimoles); eq. (equivalent); hr or hrs (hours); min (minutes); MS (mass spectrometry); NMR (nuclear magnetic resonance); ESI (electrospray ionization); HPLC (high-performance liquid chromatography or high pressure liquid chromatography); TLC (thin layer chromatography); Ac (acetyl); and AcO (acetate); Bn (benzyl); nBu (butyl); tBu (tert-butyl); Boc (tert-butoxylcarbony); Et (ethyl); Fmoc (9H-fluoren-9-ylmethoxycarbonyl); Me (methyl); Ph (phenyl); Pr (propyl); iPr (isopropyl); ACN (acetonitrile); CDCl3 (deuterated chloroform); DCM (dichloromethane); DMF (N,N-dimethylformamide); DME (dimethyl ether); DMSO (dimethylsulfoxide); DMSO-d6 (deuterated dimethylsulfoxide); EtOAc (ethyl acetate); Et2o (diethyl ether); EtOH (ethanol); MeOH (methanol); PE (petroleum ether); THF (tetrahydrofuran); DIPEA (N,N-diisopropylethylamine); TEA or Et3N (triethylamine); AcOH (acetic acid); TFA (trifluoroacetic Step A. 4-Bromomethyl-2-fluoro-benzonitrile. To a solution of 2-fluoro-4-methylbenzonitrile (135.0 g, 1.0 mol) and BPO (13.5 g, 0.06 mol) in CHCl3 (800 mL) was added NBS (178.0 g, 1 mol) in three portions. The mixture was stirred for 4 hrs at reflux. After cooling to room temperature, the solution was poured to a saturated aqueous NaHCO3 and extracted with CH2Cl2 (3×300 mL). The combined organic layer was washed with brine, dried over anhydrous Na2SO4, and concentrated under reduced pressure to give the title compound (232 g) as a yellow viscous liquid, which was used directly in the next step without further purification.

Step B. 2-Amino-3-(4-cyano-3-fluoro-phenyl)-propionic acid ethyl ester. In a 1.0 L flask, a mixture of ethyl 2-(diphenylmethyleneamino)acetate (267 g, 1.0 mol) and the catalyst Bu4NBr (32 g, 0.1 mol) in CH3CN (1000 mL) was treated sequentially with 4-(bromomethyl)-2-fluorobenzonitrile (232 g) and K2CO3 (276 g, 2 mol). The mixture was then stirred for 24 hrs at room temperature. The mixture was filtered and concentrated to give ethyl 3-(4-cyano-3-fluorophenyl)-2-(diphenylmethyleneamino)propanoate (400 g, 100% yield) as a yellow oil. The crude was treated with 2M HCl (600 mL) in THF (400 mL) overnight, and then extracted with EtOAc (3×200 mL). The water phase was basified with a saturated Na2CO3 to pH 10 and extracted with EtOAc (3×200 mL). The combined organic layer was washed with brine, dried over anhydrous Na2SO4, and concentrated under reduced pressure to yield the title compound (153 g, yield 65% for the last three steps). The crude was not further purified and used straightly in next step.

Step C. 3-(4-Cyano-3-fluoro-phenyl)-2-(9H-fluoren-9-yl-methoxycarbonyl-amino)-propionic acid ethyl ester. Fmoc-Cl (185 g, 0.72 mol) in 1,4-dioxane (300 mL) was added slowly dropwise to a solution of ethyl 2-amino-3-(4-cyano-3-fluorophenyl)propanoate (153 g, 0.65 mol) and 10% NaHCO3 aqueous solution (600 mL) in 1,4-dioxane (300 mL) for 30 min at 0° C. The resulting solution was stirred overnight at room temperature. The solution was then concentrated and extracted with EtOAc (3×300 mL). The combined organic layer was washed with brine, dried over anhydrous Na2SO4, and concentrated under reduced pressure to give the title compound (304 g, 100% yield) as a yellow viscous liquid. The crude was used directly in the next step without further purification.

Step D. 2-(9H-Fluoren-9-ylmethoxycarbonylamino)-3-[3-fluoro-4-(N-hydroxycarbamimidoyl)phenyl]propionic acid ethyl ester. To a suspension of (9H-fluoren-9-yl)methyl 1-(ethoxycarbonyl)-2-(4-cyano-3-fluorophenyl)ethylcarbamate (304 g) and NaHCO3 (214 g, 2.56 mol) in dry ethanol (4000 mL) was added hydroxylamine hydrochloride (180 g, 2.56 mol). The mixture was stirred for 8 hrs at reflux. The mixture was then filtered at 78° C. and the solid was discarded. The solution was concentrated and the crude was purified by column chromatography (PE/EtOAc, 3/1) to give the title compound as a light yellow solid.

Step E. 3-{4-[5-(4-tert-Butoxycarbonylamino-phenyl)-[1,2,4]oxadiazol-3-yl]-3-fluoro-phenyl}-2-(9H-fluoren-9-yl-methoxycarbonylamino)-propionic acid ethyl ester. At 0° C., oxalyl chloride (4.27 mL, 48.8 mol) was added dropwise slowly to a solution of tert-butyl 4-carboxylic acid phenylcarbamate (11.6 g, 48.8 mol) and DMF (10.2 mL) for 30 min. The result solution was stirred for 2 hrs and then concentrated to give acyl chloride. The residue was dissolved in toluene (50 mL) and the solution was added dropwise to a solution of (9H-fluoren-9-yl)methyl 1-(ethoxycarbonyl)-2-((Z)-4-amidino-3-fluorophenyl)-ethylcarbamate (15 g, 30.4 mol) and pyridine (15 mL) in THF-toluene (125 mL, 1:4 (v/v)). The mixture was stirred at reflux overnight. The mixture was then concentrated and extracted with EtOAc (3×100 mL). The combined organic layer was washed sequentially with 2N HCl (1×100 mL) and brine, dried over anhydrous Na2SO4, and concentrated under reduced pressure. The crude was purified by column chromatography (PE/EtOAc, 6/1 to 2/1) to give the title compound (8.25 g, 39% yield) as a light yellow solid. 1H NMR (400 MHz, DMSO-d6): δ 9.91 (s, 1H), 8.08 (d, J=8.4 Hz, 2H), 7.99 (t, J=8.0 Hz, 1H), 7.92 (d, J=8.8 Hz, 1H), 7.86 (d, J=7.2 Hz, 2H), 7.73 (d, J=8.8 Hz, 2H), 7.62 (d, J=7.2 Hz, 2H), 7.28-7.41 (m, 6H), 4.31-4.40 (m, 1H), 4.09-4.27 (m, 3H), 4.10 (q, J=7.2 Hz, 2H), 2.85-3.17 (m, 2H), 1.50 (s, 9H), 1.14 (t, J=6.8 Hz, 3H); EI-MS (m/z): 693 (M+H)+.

Step F. 2-Amino-3-{4-[5-(4-tert-butoxycarbonylamino-phenyl)-[1,2,4]oxadiazol-3-yl]-3-fluorophenyl}propionic acid ethyl ester. To a stirring solution of 3-{4-[5-(4-tert-butoxycarbonylamino-phenyl)-[1,2,4]oxadiazol-3-yl]-3-fluorophenyl}-2-(9H-fluoren-9-ylmethoxycarbonylamino)propionic acid ethyl ester (8.25 g, 12 mol) in DMF (10 mL) was added morpholine (30 mL). The solution was stirred for 2 hrs at room temperature. The solution was then concentrated and extracted with EtOAc (3×100 mL). The combined organic layers were washed sequentially with brine and dried over anhydrous Na2SO4, and concentrated under reduced pressure. The crude was purified by column chromatography (PE/EtOAc, 2/1) to give the title compound (4.1 g, 72.7% yield) as a light yellow solid. 1H-NMR (400 MHz, DMSO-d6): δ 9.91 (s, 1H), 8.08 (d, J=8.8 Hz, 2H), 7.99 (t, J=8.0 Hz, 1H), 7.32 (d, J=8.8 Hz, 1H), 7.27 (d, J=8.0 Hz, 1H), 4.02-4.08 (m, 2H), 3.63 (t, J=6.8 Hz, 1H), 2.85-2.99 (m, 2H), 1.50 (s, 9H), 1.13 (t, J=6.8 Hz, 3H); EI-MS (m/z): 469 (M−H)−.

Step G. 3-{4-[5-(4-tert-Butoxycarbonylamino-phenyl)-[1,2,4]oxadiazol-3-yl]-3-fluorophenyl}-2-[(5-p-tolyl-furan-2-carbonyl)amino]-propionic acid ethyl ester. EDCI (0.038 g, 0.2 mmol) and HOBt (0.033 g, 0.2 mmol) were added to a solution of 5-p-tolyl-furan-2-carboxylic acid (0.041 g, 0.2 mmol) in dry CH2Cl2 (5 mL). After the mixture was stirred for 0.5 hr, 2-amino-3-({4-[5-(4-tert-butoxycarbonylamino-phenyl)-[1,2,4]oxadiazol-3-yl]-3-fluorophenyl}-propionic acid ethyl ester (0.094 g, 0.2 mmol) was added and the mixture was stirred for another 5 hrs at room temperature. The mixture was partitioned between EtOAc and water. The combined organic layers were washed with brine, dried over anhydrous Na2SO4, and concentrated under reduced pressure to give the crude product, which was used for next step without further purification.

Step H. 3-{4-[5-(4-tert-Butoxycarbonylamino-phenyl)-[1,2,4]oxadiazol-3-yl]-3-fluoro-phenyl}-2-[(5-p-tolyl-furan-2-carbonyl)-amino]-propionic acid A441. To a solution of 3-{4-[5-(4-tert-butoxycarbonylamino-phenyl)-[1,2,4]oxadiazol-3-yl]-3-fluorophenyl}-2-[(5-p-tolyl-furan-2-carbonyl)amino]-propionic acid ethyl ester in CH3OH (2 mL) was added 1N NaOH aqueous solution at 0° C. The mixture was stirred for 5 hrs at room temperature. The mixture was acidified with AcOH and concentrated under reduced pressure. The residue was purified by HPLC to give the title compound (0.064 g, 51.2% yield for the last two steps) as a white solid.

Method A1

Example 2

3-{4-[5-(4-tert-Butoxycarbonylamino-phenyl)-[1,2,4]oxadiazol-3-yl]-3-fluoro-phenyl}-2-[(6-p-tolyl-pyridine-2-carbonyl)-amino]-propionic acid 32

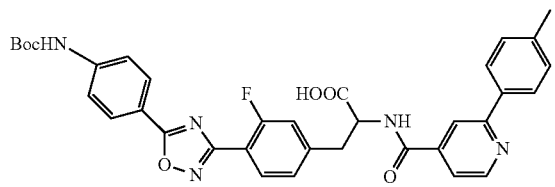 [SMILES: Cc1ccc(-c2cc(C(=O)NC(Cc3ccc(-c4noc(-c5ccc(NC(=O)OC(C)(C)C)cc5)n4)c(F)c3)C(=O)O)ccn2)cc1]

Step A. 6-p-Tolyl-pyridine-2-carboxylic acid. A mixture of 6-bromo-pyridine-2-carboxylic acid (202 mg, 1 mmol), 4-methylphenylboronic acid (163 mg, 1.2 mmol), and Pd(PPh3)4 (25 mg) in saturated aq. NaHCO3 solution (3 mL) and DME (3 mL) was irradiated in a microwave on a Biotage Smith Synthesizer at 100° C. for 2 hrs. TLC showed the reaction was completed. The mixture was filtered and washed with water (2×50 mL) and ether (2×50 mL). The organic and aqueous layers were separated. The pH of the aqueous portion was adjusted to about 1 with 1 N aq. HCl solution. The aqueous layer was then extracted with ethyl acetate (3×60 mL). The combined organic layer was dried over anhydrous sodium sulfate and filtered. The solvent was evaporated to give the title compound (191 mg, 90% yield).

Step B. 3-{4-[5-(4-tert-Butoxycarbonylamino-phenyl)-[1,2,4]oxadiazol-3-yl]-3-fluorophenyl}-2-[(6-p-tolyl-pyridine-2-carbonyl)-amino]-propionic acid ethyl ester. A mixture of 6-p-tolyl-pyridine-2-carboxylic acid (47 mg, 0.1 mmol), 2-amino-3-{4-[5-(4-tert-butoxycarbonylamino-phenyl)-[1, 2,4]oxadiazol-3-yl]-3-fluorophenyl}propionic acid ethyl ester (30 mg), HATU (46 mg, 0.12 mmol), and Et3N (15 mg, 0.15 mmol) in dichloromethane (5 mL) was stirred at room temperature overnight. TLC showed the reaction was completed. Saturated aqueous NaHCO3 (20 mL) was added to the mixture, and organic and aqueous layers were separated. The aqueous portion was extracted with dichloromethane (2×50 mL). The combined organic layers were washed sequentially with aq. HCl (1N, 2×50 mL) and brine (50 mL), dried over anhydrous sodium sulfate, and filtered. The solvent was evaporated to give the title compound (53 mg, 80% yield).

Step C. 3-{4-[5-(4-tert-Butoxycarbonylamino-phenyl)-[1,2,4]oxadiazol-3-yl]-3-fluorophenyl}-2-[(6-p-tolyl-pyridine-2-carbonyl)-amino]-propionic acid A437. A solution of 3-{4-[5-(4-tert-butoxycarbonylamino-phenyl)-[1,2,4]oxadiazol-3-yl]-3-fluorophenyl}-2-[(6-p-tolyl-pyridine-2-carbonyl)-amino]propionic acid ethyl ester (53 mg) and aq. LiOH solution (2N, 1 mL) in THF (3 mL) was stirred at room temperature 3 hrs. TLC showed the reaction was completed. The solution was concentrated and the pH of the mixture was adjusted to about 2 with 1 N aq. HCl solution. The aqueous layer was extracted with ethyl acetate (3×20 mL). The combined organic layers were dried over anhydrous sodium sulfate and filtered. The solvent was evaporated to give a crude product, which was purified by preparative HPLC to afford the title compound (27.7 mg, 43% yield) as a white solid. 1H NMR (400 MHz, DMSO-d6): δ 1.49 (s, 9H), 2.33 (s, 3H), 3.10-3.25 (m, 2H), 4.83-4.88 (m, 1H), 7.32 (d, 2H), 7.38 (d, 1H), 7.43 (d, 1H), 7.70 (d, 2H), 7.90 (d, 1H), 7.89-8.14 (m, 7H), 8.86 (d, 1H), 9.89 (s, 1H); (ESI) m/z: 636 (M−H)−

Method A2

Example 3

3-{4-[5-(4-tert-Butoxycarbonylamino-phenyl)-[1,2,4]oxadiazol-3-yl]-3-fluoro-phenyl}-2-[(5-m-tolyl-furan-2-carbonyl)-amino]-propionic acid

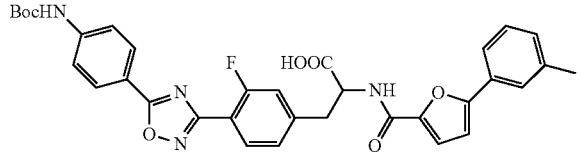 [SMILES: Cc1cccc(-c2ccc(C(=O)NC(Cc3ccc(-c4noc(-c5ccc(NC(=O)OC(C)(C)C)cc5)n4)c(F)c3)C(=O)O)o2)c1]

Step A. 5-m-Tolylfuran-2-carboxylic acid. To a solution of 3-methylphenylboronic acid (0.136 g, 2 mmol), methyl 5-bromofuran-2-carboxylate (0.408 g, 2 mmol), and Na2CO3 (0.424 g, 4 mmol) in propan-2-ol (5 mL) was added Pd(PPh3)2Cl2 (0.07 g) under Nitrogen. The reaction mixture was stirred at reflux for 5 hrs, and then concentrated under reduced pressure. The residue was extracted with EtOAc (2×5 mL). The combined organic layers were washed with brine and concentrated. The crude was purified on a flash column chromatograph (PE/EtOAc, 20/1) to give a colorless oil. The oil was treated with 1N NaOH (0.5 mL) in methanol (2 mL) for 0.5-1 hr at room temperature. The solution was then concentrated, acidified with 5N HCl to pH 2-3, and filtered to afford 5-m-tolylfuran-2-carboxylic acid (0.279 g, 69.1% yield for the last two step) as a grey solid.

Step B. 3-{4-[5-(4-tert-Butoxycarbonylamino-phenyl)-[1,2,4]oxadiazol-3-yl]-3-fluorophenyl}-2-[(5-m-tolyl-furan-2-carbonyl)-amino]-propionic acid A442. The title compound was prepared using the procedure as described for compound A441, substituting 5-m-tolylfuran-2-carboxylic acid for 5-p-tolylfuran-2-carboxylic acid.

Method A3

Example 4

3-{4-[5-(4-tert-Butoxycarbonylamino-phenyl)-[1,2,4]oxadiazol-3-yl]-3-fluorophenyl}-2-[3-(4-methyl-piperidin-1-yl)-benzoylamino]-propionic acid

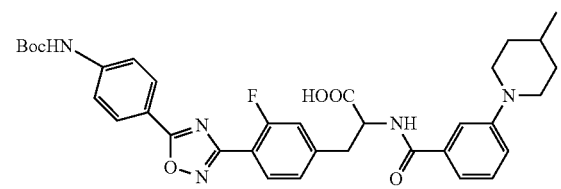 [SMILES: CC1CCN(c2cccc(C(=O)NC(Cc3ccc(-c4noc(-c5ccc(NC(=O)OC(C)(C)C)cc5)n4)c(F)c3)C(=O)O)c2)CC1]

Step A. 3-(4-Methyl-piperidin-1-yl)-benzoic acid ethyl ester. A mixture of 3-bromo-benzoic acid ethyl ester (229 mg, 1 mmol), 4-methylpiperidine (120 mg, 1.2 mmol), Pd2(dba)3 (25 mg), BINAP (25 mg), and tBuONa (130 mg) in toluene (6 mL) was heated at 90° C. overnight. After the reaction was completed as indicated by TLC, the mixture was filtered and the filtrate was concentrated in vacuo. Ethyl acetate (50 mL) and aq. HCl (1N, mL) were then added. The aqueous portion was extracted with ethyl acetate (2×50 mL). The combined organic layers were washed with brine (50 mL), dried over anhydrous sodium sulfate, and filtered, concentrated, and purified by chromatography to give the title compound (76 mg, 31%).

Step B. 3-(4-Methyl-piperidin-1-yl)-benzoic acid. A solution of 3-(4-methyl-piperidin-1-yl)-benzoic acid methyl ester (76 mg), aq. LiOH solution (2N, 1 mL) in THF (3 mL) was stirred at room temperature 3 hrs. After the reaction was completed as indicated by TLC, the solution was concentrated and adjusted to about pH 2 with 1N aq. HCl solution. The aqueous layer was extracted with ethyl acetate (3×20 mL). The combined organic layers were dried over anhydrous sodium sulfate, filtered, and concentrated to yield the title compound (57 mg, 85%).

Step C. 3-{4-[5-(4-tert-Butoxycarbonylamino-phenyl)-[1,2,4]oxadiazol-3-yl]-3-fluoro-phenyl}-2-[3-(4-methyl-piperidin-1-yl)-benzoylamino]-propionic acid. The title compound was prepared following the procedure as described in Example 1, substituting 4-diethylamino-benzoic acid for 5-p-tolylfuran-2-carboxylic acid.

Method A4

Example 5

3-{4-[5-(4-tert-Butoxycarbonylamino-phenyl-[1,2,4]oxadiazol-3-yl]-3-fluorophenyl}-2-{[1-(4-tert-butylphenyl)-1H-[1,2,3]triazole-4-carbonyl]-amino}-propionic acid 183

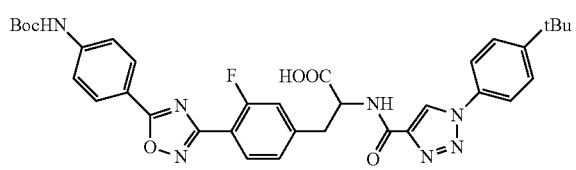 [SMILES: CC(C)(C)OC(=O)Nc1ccc(-c2nc(-c3ccc(CC(NC(=O)c4cn(-c5ccc(C(C)(C)C)cc5)nn4)C(=O)O)cc3F)no2)cc1]

Step A. 1-(4-tert-Butylphenyl)-1H-1,2,3-triazole-4-carboxylic acid. To a stirring solution of 1-tert-butyl-4-azidobenzene (2.0 g, 11.4 mmol) and methyl but-3-ynoate (1.44 g, 17.1 mmol) in diisopropylethylamine (2.2 g, 17.1 mmol) in THF (10 mL) was added CuI (0.1 g) at room temperature. The resulting mixture was stirred for 2 hrs. After the reaction was complete as indicated with LC-MS, the mixture was concentrated and extracted with EtOAc (100 mL). The combined organic layers were concentrated under reduced pressure. The residue was treated with LiOH (2N, 3 mL) in THF (20 mL) for 1 hr, acidified with 1N HCl, and extracted with EtOAc (100 mL). The combined organic layers were washed with brine, dried over anhydrous Na2SO4, and concentrated under reduced pressure to give the title compound (2.1 g, 75% yield for the last two steps) as a grey solid, which was used directly in the next step without further purification.

Step B. 3-{4-[5-(4-tert-Butoxycarbonylamino-phenyl)-[1,2,4]oxadiazol-3-yl]-3-fluoro-phenyl}-2-{[1-(4-tert-butyl-phenyl)-1H-[1,2,3]triazole-4-carbonyl]-amino}-propionic acid. The title compound was prepared using the procedure as described in Example 1, substituting 1-(4-tert-butylphenyl)-1H-1,2,3-triazole-4-carboxylic acid for 5-p-tolylfuran-2-carboxylic acid. 1H-NMR (400 MHz, CD3OD): δ 8.81 (s, 1H), 8.27 (s, 1H), 8.08 (d, J=8.8 Hz, 2H), 8.03 (t, J=8 Hz, 1H), 7.75 (d, J=8.8 Hz, 2H), 7.60-7.75 (m, 4H), 7.26 (t, J=9.6 Hz, 2H), 4.96-4.98 (m, 1H), 3.45-3.51 (m, 1H), 3.25-3.30 (m, 1H), 1.50 (s, 9H), 1.36 (s, 9H). EI-MS (m/z): 668 (M–H)–.

Method A5

Example 6

3-(4-(5-(4-((tert-butoxcarbonyl)amino)phenyl)-1,2,4-oxadiazol-3-yl)-3-fluorophenyl)-2-(1-(3-fluoro-4-methylphenyl)-1H-pyrazole-4-carboxamido)propanoic acid 40

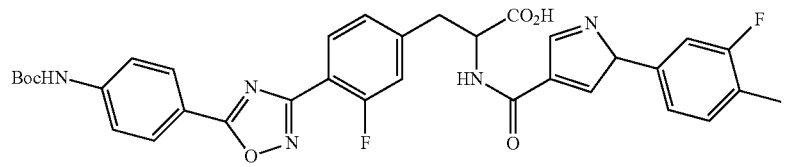 [SMILES: Cc1ccc(C2C=C(C(=O)NC(Cc3ccc(-c4noc(-c5ccc(NC(=O)OC(C)(C)C)cc5)n4)c(F)c3)C(=O)O)C=N2)cc1F]

Step A. Ethyl 3-(4-(5-(4-((tert-butoxycarbonyl)amino)phenyl)-1,2,4-oxadiazol-3-yl)-3-fluorophenyl)-2-(1H-pyrazole-4-carboxamido)propanoate. The title compound was prepared using the procedure as described in Example 6, substituting 1H-pyrazole-4-carboxylic acid for 5-p-tolyl-furan-2-carboxylic acid in Step G.

Step B. 3-(4-(5-(4-((tert-butoxycarbonyl)amino)phenyl)-1,2,4-oxadiazol-3-yl)-3-fluorophenyl)-2-(1-(3-fluoro-4-methylphenyl)-1H-pyrazole-4-carboxamido)propanoic acid. To a stirred solution of Ethyl 3-(4-(5-(4-((tert-butoxycarbonyl)amino)phenyl)-1,2,4-oxadiazol-3-yl)-3-fluorophenyl)-2-(1H-pyrazole-4-carboxamido)propanoate (65 mg, 0.1 mmol), copper acetate (18 mg) and molecular sieves (500 mg) in THF was added pyridine (0.1 ml) and (3-fluoro-4-methylphenyl)boronic acid (30 mg). After 12 h, the mixture was concentrated and chromatographed over silica gel to give the ethyl ester (14 mg), which hydrolyzed with LiOH as described in Example 1 Step H to give the title compound. EI-MS (m/z): 674 (M+H)+.

Method A6

Example 7

3-{4-[5-(4-tert-Butoxcarbonylamino-phenyl)-[1,2,4]oxadiazol-3-yl]-3-fluorophenyl}-2-(3-chloro-4-methyl-benzenesulfonylamino)-propionic acid 65

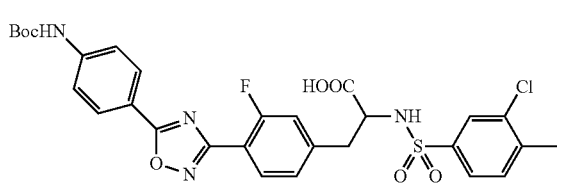 [SMILES: Cc1ccc(S(=O)(=O)NC(Cc2ccc(-c3noc(-c4ccc(NC(=O)OC(C)(C)C)cc4)n3)c(F)c2)C(=O)O)cc1Cl]

Step A. 3-{4-[5-(4-tert-Butoxycarbonylamino-phenyl)-[1,2,4]oxadiazol-3-yl]-3-fluoro-phenyl}-2-(3-chloro-4-methyl-benzenesulfonylamino)-propionic acid ethyl ester. 3-Chloro-4-methyl-benzenesulfonyl chloride (50 mg) was dissolved in 10% Na2CO3 aq. solution (3 mL) at 0° C. Orie equivalent of 2-amino-3-{4-[5-(4-tert-butoxycarbonylamino-phenyl)-[1,2,4]oxadiazol-3-yl]-3-fluoro-phenyl}-propionic acid ethyl ester in acetone (1.5 mL) was then added dropwise to the mixture over 5 min. After stirring at room temperature for 4 hrs. The mixture was extracted with EtOAc. The organic layer was concentrated to give the title compound (150 mg), which was used indirectly in the next step without further purification.

Step B. 3-{4-[5-(4-tert-Butoxycarbonylamino-phenyl)-[1,2,4]oxadiazol-3-yl]-3-fluoro-phenyl}-2-(3-chloro-4-methyl-benzenesulfonylamino)-propionic acid. To a mixture of 3-{4-[5-(4-tert-butoxycarbonylamino-phenyl)-[1,2,4]oxadiazol-3-yl]-3-fluoro-phenyl}-2-(3-chloro-4-methyl-benzenesulfonylamino)-propionic acid ethyl ester in acetone (3 mL) at 0° C. was added aq. NaOH solution (10%, 2 mL) dropwise in 5 min. After stirring for 1.5 hrs, the reaction mixture was acidified to pH 5 with diluted aq. HCl solution, and then extracted with EtOAc. The organic layer was concentrated to give the crude compound (about 70 mg), which was further purified by HPLC to give the title compound. 1H-NMR (400 MHz, DMSO-d6): δ 8.12 (d, J=8.8 Hz, 2H), 7.85 (t, J=8.0 Hz, 1H), 7.76 (d J=8.8 Hz, 2H), 7.41 (s, 1H), 7.35 (m, 2H), 7.16 (d, J=9.6 Hz, 2H), 4.01 (m, 1H), 3.11 (m, 1H), 2.80 (m, 1H), 2.19 (s, 3H), 1.52 (s, 9H).

Method A7

Example 8

3-{4-[5-(4-tert-Butoxycarbonylamino-phenyl)-[1,2,4]oxadiazol-3-yl]-3-fluoro-phenyl}-2-[4-(4-methyl-benzyl)-piperazine-1-sulfonylamino]-propionic acid 73

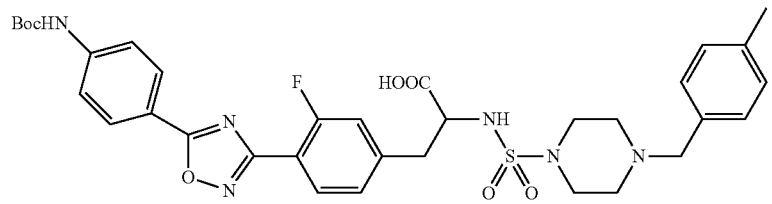 [SMILES: Cc1ccc(CN2CCN(S(=O)(=O)NC(Cc3ccc(-c4noc(-c5ccc(NC(=O)OC(C)(C)C)cc5)n4)c(F)c3)C(=O)O)CC2)cc1]

Step A. 3-{4-[5-(4-tert-Butoxycarbonylamino-phenyl)-[1,2,4]oxadiazol-3-yl]-3-fluoro-phenyl}-2-(2-oxo-oxazolidine-3-sulfonylamino)-propionic acid ethyl ester. To a 100 mL round-bottom flask charged with a solution of chlorosulfonyl isocyanate (338 mg, 2.4 mmol) in dichloromethane (10 mL) cooled to 0° C. was slowly added a solution of 2-bromoethanol (273 mg, 2.2 mmol) in dichloromethane (10 mL) under a nitrogen atmosphere to form a reaction mixture. After the reaction mixture was stirred for 40 min, a mixture of tert-butyl 4-(3-(4-(2-(ethoxycarbonyl)-2-aminoethyl)-2-fluorophenyl)-1,2,4-oxadiazol-5-yl)phenylcarbamate (940 mg, 2 mmol) and triethylamine (505 mg, 5 mmol) in dichloromethane (20 mL) was slowly added at 0° C. to the reaction mixture. The resulting mixture was stirred at room temperature for 30 min. TLC showed the reaction was completed. Dichloromethane (50 mL) and 1N aq. HCl solution (30 mL) were added to the solution, the layers were separated, and the aqueous portion was extracted with dichloromethane (30 mL). The combined organic layers were washed with brine (2×30 mL), dried over anhydrous sodium sulfate, filtered, and concentrated to give oxazolidione (1.1 g, 89% yield) as a yellow solid.

Step B. 3-{4-[5-(4-tert-Butoxycarbonylamino-phenyl)-[1,2,4]oxadiazol-3-yl]-3-fluoro-phenyl}-2-[4-(4-methyl-benzyl)-piperazine-1-sulfonylamino]-propionic acid ethyl ester. A mixture of oxazolidione from Step A (40 mg, 0.065 mmol), 1-(4-methylbenzyl)piperazine (24.7 mg, 0.13 mmol), and triethylamine (20 mg, 0.2 mmol) in acetonitrile (3 mL) was heated at 85° C. for 2.5 hrs. TLC showed the reaction was completed. The solution was concentrated. Ethyl acetate (20 mL) and 1N aq. HCl solution (10 mL) were added to the solution. The layers were separated, and the aqueous portion was extracted with ethyl acetate (20 mL). The combined organic layer was washed with brine (2×20 mL), dried over anhydrous sodium sulfate, filtered, and concentrated to give the title compound (32 mg, 69% yield) as a yellow solid.

Step C. 3-{4-[5-(4-tert-Butoxycarbonylamino-phenyl)-[1,2,4]oxadiazol-3-yl]-3-fluoro-phenyl}-2-[4-(4-methyl-benzyl)-piperazine-1-sulfonylamino]-propionic acid A289. A solution of 3-{4-[5-(4-tert-butoxycarbonylamino-phenyl)-[1,2,4]oxadiazol-3-yl]-3-fluoro-phenyl}-2-[4-(4-methyl-benzyl)-piperazine-1-sulfonylamino]-propionic acid ethyl ester (32 mg, 0.044 mmol) and 2N aq. LiOH solution (0.5 mL) in THF (3 mL) was stirred at room temperature overnight. TLC showed the reaction was completed. The solution was concentrated and adjusted to about pH 2 with 1N aq. HCl solution. The aqueous layer was extracted with ethyl acetate (3×20 mL). The combined organic layers were dried over anhydrous sodium sulfate, filtered, and concentrated to give a crude product, which was purified by preparative HPLC to afford the title compound (5.18 mg, 17% yield) as a white solid.

Method A8

Example 9

3-{4-[5-(4-tert-Butoxycarbonylamino-phenyl)-[1,2,4]oxadiazol-3-yl]-3-fluorophenyl}-2-{3-[5-(4-fluorophenyl)-2H-pyrazol-3-yl]-ureido}-propionic acid 193

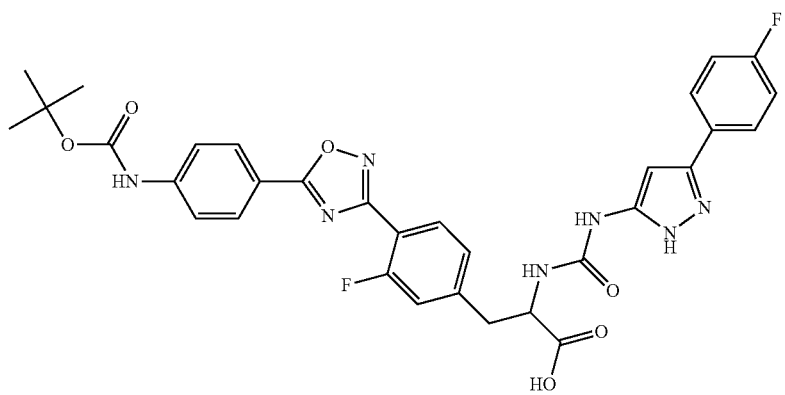 [SMILES: CC(C)(C)OC(=O)Nc1ccc(-c2nc(-c3ccc(CC(NC(=O)Nc4cc(-c5ccc(F)cc5)n[nH]4)C(=O)O)cc3F)no2)cc1]

Step A. 3-{4-[5-(4-tert-Butoxycarbonylamino-phenyl)-[1,2,4]oxadiazol-3-yl]-3-fluoro-phenyl}-2-{3-[5-(4-fluoro-phenyl)-2H-pyrazol-3-yl]-ureido}-propionic acid ethyl ester. To a solution of bis(trichloromethyl)carbonate (189 mg, 0.66 mmol) in dichloromethane (12 mL) and saturated aqueous NaHCO3 (0.8 mL) was slowly added a solution of tert-butyl 4-(3-(4-(2-(ethoxycarbonyl)-2-aminoethyl)-2-fluorophenyl)-1,2,4-oxadiazol-5-yl)phenylcarbamate (300 mg, 0.66 mmol) in dichloromethane (12 mL) at 0° C. The reaction mixture was then stirred at room temperature for 1 hr. TLC showed the reaction was completed. Saturated aqueous NaHCO3 (18 mL), pyridine (0.3 mL), and 3-(4-fluorophenyl)-1H-pyrazol-5-amine (177 mg, 1 mmol) were added to the reaction mixture. The resulting mixture was then stirred overnight. TLC showed the reaction was completed. The layers were separated and the aqueous portion was extracted with dichloromethane (2×50 mL). The combined organic layers were washed sequentially with aq. HCl solution (1N, 2×50 mL) and brine (50 mL), dried over anhydrous sodium sulfate, filtered, and concentrated to give the title compound (343 mg, 51% yield) as a yellow solid.

Step B. 3-{4-[5-(4-tert-Butoxycarbonylamino-phenyl)-[1,2,4]oxadiazol-3-yl]-3-fluoro-phenyl}-2-{3-[5-(4-fluoro-phenyl)-2H-pyrazol-3-yl]-ureido}-propionic acid A497. A solution of 3-{4-[5-(4-tert-butoxycarbonylamino-phenyl)-[1,2,4]oxadiazol-3-yl]-3-fluoro-phenyl}-2-{3-[5-(4-fluoro-phenyl)-2H-pyrazol-3-yl]-ureido}-propionic acid ethyl ester (343 mg, 0.51 mmol) and aq. LiOH solution (2N, 2 mL) in THF (12 mL) was stirred at room temperature for 1 hr. TLC showed the reaction was completed. The solution was concentrated and adjusted to about pH 2 with 1N aq. HCl solution. The aqueous layer was extracted with ethyl acetate (3×50 mL). The combined organic layers were dried over anhydrous sodium sulfate, filtered, concentrated, and purified with preparative HPLC to afford the title compound (93.5 mg, 28% yield) as a white solid. 1H NMR (400 MHz, DMSO-d6) δ 1.51 (s, 9H), 3.0-3.2 (m, 2H), 4.63 (m, 1H), 5.75 (s, 1H), 6.48 (s, 2H), 7.24-7.44 (m, 4H), 7.7 (m, 3H), 7.88 (q, 2H), 8.01 (t, 1H), 8.07 (d, 2H), 8.27 (d, 2H), 9.91 (s, 1H); MS (ESI) m/z: 646.1 (M+H)+.

Method A9

Example 10

3-{4-[5-(4-tert-Butoxycarbonylamino-phenyl)-[1,2,4]oxadiazol-3-yl]-3-fluoro-phenyl}-2-(2-piperidin-1-yl-pyrimidin-4-ylamino)-propionic acid 62

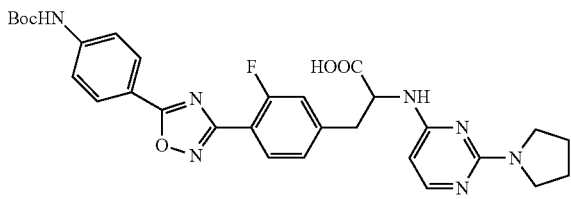 [SMILES: CC(C)(C)OC(=O)Nc1ccc(-c2nc(-c3ccc(CC(Nc4ccnc(N5CCCC5)n4)C(=O)O)cc3F)no2)cc1]

Step A. 3-{4-[5-(4-tert-Butoxycarbonylamino-phenyl)-[1,2,4]oxadiazol-3-yl]-3-fluoro-phenyl}-2-(2-chloro-pyrimidin-4-ylamino)-propionic acid ethyl ester. To solution of 2-Amino-3-{4-[5-(4-tert-butoxycarbonylamino-phenyl)-[1,2,4]oxadiazol-3-yl]-3-fluorophenyl}propionic acid ethyl ester in DMF (20 mL) were added sodium carbonate (360 mg, 3.4 mmol), potassium iodide (10 mg), TBAB (10 mg), and 2,4-dichloro-pyrimidine (503 mg, 3.4 mmol). The mixture was heated at 50° C. for 4 hrs. The mixture was cooled to room temperature and partitioned between ethyl acetate and water. The combined organic layers were washed with brine, dried over sodium sulfate, filtrated, concentrated, and purified by chromatography to give the title compound (96 mg).

Step B. 3-{4-[5-(4-tert-Butoxycarbonylamino-phenyl)-[1,2,4]oxadiazol-3-yl]-3-fluoro-phenyl}-2-(2-piperidin-1-yl-pyrimidin-4-ylamino)-propionic acid A498. The mixture of 3-{4-[5-(4-tert-butoxycarbonylamino-phenyl)-[1,2,4]oxadiazol-3-yl]-3-fluoro-phenyl}-2-(2-chloro-pyrimidin-4-ylamino)-propionic acid ethyl ester (50 mg, 0.086 mmol) and piperidine (22 mg, 0.26 mmol) in DMF (2 mL) was heated at 110° C. for 1 hr. The mixture was cooled to room temperature and partitioned between ethyl acetate and water. The combined organic layers were dried over sodium sulfate and concentrated to give a residue, which was dissolved in CH3OH (2 mL). Aqueous NaOH solution (1N) was added at 0° C. and the mixture was stirred for 5 hrs at room temperature. The mixture was acidified with AcOH and concentrated under reduced pressure. The residue was purified by HPLC to give the title compound (10 mg) as a white solid.

Method A10

Example 11

2-(4-tert-Butoxycarbonylamino-benzoylamino)-3-{4-[5-(4-tert-butoxycarbonylamino-phenyl)-[1,2,4]oxadiazol-3-yl]-3-fluorophenyl}-propionic acid 3

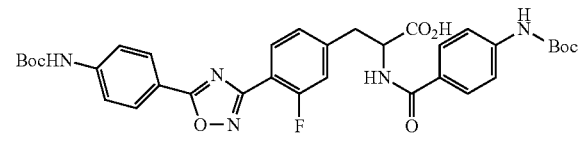 [SMILES: CC(C)(C)OC(=O)Nc1ccc(C(=O)NC(Cc2ccc(-c3noc(-c4ccc(NC(=O)OC(C)(C)C)cc4)n3)c(F)c2)C(=O)O)cc1]

Step A. 2-(4-tert-Butoxycarbonylamino-benzoylamino)-3-(4-cyano-3-fluoro-phenyl)-propionic acid ethyl ester. EDCI (560 mg, 2.92 mmol) was added to a solution of 4-tert-butoxycarbonylamino-benzoic acid (661 mg, 2.7 mmol) in dry CH2Cl2 (5 mL). After the mixture was stirred for 0.5 hr, 2-amino-3-(4-cyano-3-fluoro-phenyl)-propionic acid ethyl ester (627 mg, 2.66 mmol) was added and the mixture was stirred for another 5 hrs at room temperature. The mixture was partitioned between EtOAc and water. The combined organic layers were washed with brine, dried over anhydrous Na2SO4, concentrated under reduced pressure, and purified by silica gel chromatography to give the title compound as a white solid (906 mg, 75% yield).

Step B. 2-(4-tert-Butoxycarbonylamino-benzoylamino)-3-[3-fluoro-4-(N-hydroxycarbamimidoyl)-phenyl]-propionic acid ethyl ester. A mixture of 2-(4-tert-butoxycarbonylamino-benzoylamino)-3-(4-cyano-3-fluoro-phenyl)-propionic acid ethyl ester (214 mg, 0.47 mmol), NH2OH.HCl (49 mg 0.71 mmol), and NaHCO3 (79 mg, 0.94 mmol) in EtOH (10 mL) was heated under microwave at 120° C. for 20 min and then allowed to cool to room temperature. The mixture was filtered, concentrated in vacuo, and purified by silica gel chromatography to give the title compound (170 mg) as a white solid.

Step C. 2-(4-tert-Butoxycarbonylamino-benzoylamino)-3-{4-[5-(4-tert-butoxycarbonylamino-phenyl)-[1,2,4]oxadiazol-3-yl]-2-fluoro-phenyl}-propionic acid ethyl ester.

EDCI (10 mg, 0.05 mmol) was added to a solution of 4-tert-butoxycarbonylamino-benzoic acid (12 mg, 0.05 mmol) in dry CH2Cl2 (5 mL). After the mixture was stirred for 0.5 hrs, 2-(4-tert-butoxycarbonylamino-benzoylamino)-3-[3-fluoro-4-(N-hydroxycarbamimidoyl)-phenyl]-propionic acid ethyl ester (25 mg) was added and the mixture was heated for another 1 hr at 120° C. in a sealed tube. The mixture was partitioned between EtOAc and water. The combined organic layers were washed with brine, dried over anhydrous Na2SO4, concentrated under reduced pressure, and purified by silica gel chromatography to give the title compound (3 mg) as a white solid.

Step D. 2-(4-tert-Butoxycarbonylamino-benzoylamino)-3-{4-[5-(4-tert-butoxycarbonylamino-phenyl)-[1,2,4]oxadiazol-3-yl]-2-fluoro-phenyl}-propionic acid. 2-(4-tert-Butoxycarbonylamino-benzoylamino)-3-{4-[5-(4-tert-butoxycarbonylamino-phenyl)-[1,2,4]oxadiazol-3-yl]-2-fluoro-phenyl}-propionic acid ethyl ester (3 mg) was dissolved in THF/MeOH (1 mL, 1/1). LiOH in water (2M, 0.1 mL) was added. After stirring for 30 min, the mixture was quenched with 1N HCl and extracted with ethyl acetate. The combined organic layers were washed with brine, dried over anhydrous Na2SO4, concentrated under reduced pressure, and purified by silica gel chromatography to give the title compound (3 mg) as a white solid. ESI-MS m/z: 662.1 (M+H)+.

Method A11

Example 12

3-{3-Fluoro-4-[5-(4-methyl-piperidine-1-carbonyl)-[1,2,4]oxadiazol-3-yl]-phenyl}-2-[(4'-methyl-biphenyl-3-carbonyl)-amino]-propionic acid

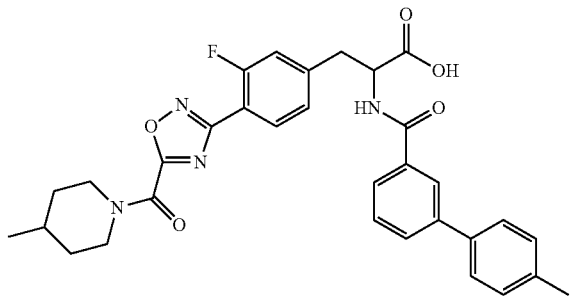

Step A. 2-(Benzhydrylidene-amino)-3-(4-cyano-3-fluoro-phenyl)-propionic acid tert-butyl ester. A mixture of 4-bromomethyl-2-fluoro-benzonitrile (20 g, 0.0935 mol), (benzhydrylidene-amino)acetic acid tert-butyl ester (30 g, 0.103 mol), and K2CO3 (28 g, 0.2 mol) in CH3CN (300 mL) was stirred for 3 days. The mixture were filtered, concentrated, washed with aq. NaCl solution (200 mL), dried over MgSO4, concentrated, and purified by chromatography to give the title compound (30 g, 75% yield).

Step B. 2-Amino-3-(4-cyano-3-fluoro-phenyl)-propionic acid tert-butyl ester. To a solution of 2-(benzhydrylidene-amino)-3-(4-cyano-3-fluoro-phenyl)-propionic acid tert-butyl ester (42.8 g, 0.1 mol) in THF (400 mL) was added aq. 1N HCl (400 mL, 0.4 mol). The mixture was stirred for 1 hr. TLC showed the reaction was completed. The mixture was concentrated, adjusted to pH 10 with NaHCO3, extracted with ethyl acetate (3×300 mL), dried over MgSO4, and concentrated to give the title compound (26 g, 98% yield).

Step C. 3-(4-Cyano-3-fluoro-phenyl)-2-[(4'-methyl-biphenyl-3-carbonyl)-amino]-propionic acid tert-butyl ester. To a solution of 2-amino-3-(4-cyano-3-fluoro-phenyl)-propionic acid tert-butyl ester (10.4 g, 0.04 mol) and Et3N (6.1 g, 0.06 mol) in CH2Cl2 (100 mL) was added dropwise a solution of 4'-methyl-biphenyl-3-carbonyl chloride (8.5 g, 0.04 mol) in CH2Cl2 (30 mL). The mixture was stirred for 2 hrs. TLC showed the reaction was completed. The mixture were washed with 1N aq. HCl solution and concentrated to give the title compound (10 g, 56% yield).

Step D. 3-[3-Fluoro-4-(hydroxy-hydroxyimino-methyl)-phenyl]-2-[(4'-methyl-biphenyl-3-carbonyl)-amino]-propionic acid tert-butyl ester. A mixture of 3-(4-cyano-3-fluoro-phenyl)-2-[(4'-methyl-biphenyl-3-carbonyl)-amino]-propionic acid tert-butyl ester (10 g, 0.02 mol), hydroxylamine hydrochloride salt (7 g, 0.1 mol), and NaHCO3 (10 g, 0.12 mol) in ethanol (150 mL) was refluxed overnight. TLC showed the reaction was completed. The mixture were filtered and concentrated to give the title compound (10 g, 93% yield).

Step E. 3-(4-{2-tert-Butoxycarbonyl-2-[(4'-methyl-biphenyl-3-carbonyl)-amino]-ethyl}-2-fluoro-phenyl)-[1,2,4]oxadiazole-5-carboxylic acid methyl ester. A mixture of 3-[3-fluoro-4-(hydroxy-hydroxyimino-methyl)-phenyl]-2-[(4'-methyl-biphenyl-3-carbonyl)-amino]-propionic acid tert-butyl ester (10 g, 0.02 mol) and methyl(chlorocarbonyl)formate (5 g, 0.04 mol), and pyridine (1 mL) in toluene (150 mL) was refluxed overnight. TLC showed the reaction was completed. An aqueous NaHCO3 solution (80 mL) was added to the reaction mixture, the layers were separated, and the aqueous portion was extracted with ethyl acetate (2×100 mL). The combined organic layers were washed with brine (2×30 mL), dried over anhydrous sodium sulfate, filtered, concentrated, and purified by chromatography and recrystallization to give the title compound (7 g, 64% yield) as a white solid.

Step F. 3-{3-Fluoro-4-[5-(4-methyl-piperidine-1-carbonyl)-[1,2,4]oxadiazol-3-yl]-phenyl}-2-[(4'-methyl-biphenyl-3-carbonyl)-amino]-propionic acid tert-butyl ester. A mixture of 3-(4-{2-tert-butoxycarbonyl-2-[(4'-methyl-biphenyl-3-carbonyl)-amino]-ethyl}-2-fluoro-phenyl)-[1,2,4]oxadiazole-5-carboxylic acid methyl ester (50 mg) and 4-methyl-piperidine (13.5 mg) in MeOH (3 mL) was heated at 55° C. for 25 min in a microwave reactor. TLC showed the reaction was completed. The mixture was concentrated, 10 mL of 1N aq. HCl solution and 20 mL of ethyl acetate were added. The layers were separated and the aqueous portion was extracted with ethyl acetate (2×10 mL). The combined organic layers were washed with brine (2×30 mL), dried over anhydrous sodium sulfate, filtered, and concentrated to give the title compound (40 mg, 71.4% yield).

Step G. 3-{3-Fluoro-4-[5-(4-methyl-piperidine-1-carbonyl)-[1,2,4]oxadiazol-3-yl]-phenyl}-2-[(4'-methyl-biphenyl-3-carbonyl)-amino]-propionic acid. To a solution of 3-{3-fluoro-4-[5-(4-methyl-piperidine-1-carbonyl)-[1,2,4]oxadiazol-3-yl]-phenyl}-2-[(4'-methyl-biphenyl-3-carbonyl)-amino]-propionic acid tert-butyl ester (50 mg) in CH2Cl2 (3 mL) was added TFA (1 mL). The mixture was then stirred at room temperature overnight. TLC showed the reaction was completed. The reaction mixture was concentrated and purified by preparative HPLC to afford the title compound (33.8 mg, 74% yield) as a white solid.

Method A12

Example 13

3-{4-[5-(4-tert-Butoxycarbonylamino-phenyl)-thiophen-2-yl]-3-fluorophenyl}-2-[(5-p-tolyl-furan-2-carbonyl)-amino]-propionic acid

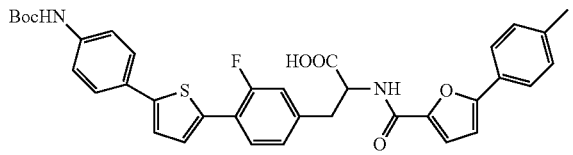 [SMILES: Cc1ccc(-c2ccc(C(=O)NC(Cc3ccc(-c4ccc(-c5ccc(NC(=O)OC(C)(C)C)cc5)s4)c(F)c3)C(=O)O)o2)cc1]

Step A. 3-(3-Fluoro-4-iodo-phenyl)-2-{[5-(4-fluoro-phenyl)-furan-2-carbonyl]-amino}-propionic acid methyl ester. The title compound was prepared using the procedures as described in Example 1, by substituting 2-fluoro-1-cyano-4-methyl-benzene with 2-fluoro-1-iodo-4-methyl-benzene in Step A.

Step B. To a solution of 3-(3-fluoro-4-iodo-phenyl)-2-{[5-(4-fluoro-phenyl)-furan-2-carbonyl]-amino}-propionic acid methyl ester (28 mg, 0.054 mmol) and 2-thipheneboronic acid (15 mg) in DMF (2 mL) were added K2CO3 (0.2 mL, 10%) and PdCl2(PPh3)2 (9 mg). The mixture was heated at 110° C. for 30 min. The mixture was then concentrated and purified by silica gel chromatography to give an ester as a white solid (28 mg).

Step C. To a solution of the ester prepared in Step B (176 mg, 0.37 mmol) in HOAc (2 mL) at 0° C. was added NaOAc (95 mg), followed by Br2 (0.5 mL, 2.0M in HOAc). The mixture was stirred for 30 min. The mixture was partitioned between EtOAc and saturated sodium bicarbonate. The organic layer were dried over Na2SO4 and concentrated. The crude product was used for next reaction without further purification.

Step D. To a solution of the compound prepared in Step C and 4-N-Boc-Ph-boronic acid (88 mg, 0.37 mmol) in DMF (4 mL) were added Pd(OAc)$_2$, P(tBu)-3-BF4 (3 mg), and K2CO3 (0.67 mL, 2 M in H2O). The mixture was heated at 120° C. for 1 hr. The mixture was then partitioned between EtOAc and water. The organic layers were dried and concentrated to give a crude product as a yellow solid. The crude product was redissolved in THF/MeOH (1/1, 5 mL), and LiOH (0.5 mL, 2.0 M) was added dropwise. After 30 min, the mixture was quenched with 1 N HCl and partitioned between EtOAc/water. The organic layers were dried, concentrated, and purified by preparative HPLC to give compound A465 as a white solid. ESI-MS (m/z): 641.0 (M+H)+.

Method A13

Example 14

3-{4-[5-(4-tert-Butoxycarbonylamino-phenyl)-[1,3,4]oxadiazol-2-yl]-3-fluorophenyl}-2-[(5-p-tolyl-furan-2-carbonyl)-amino]-propionic acid

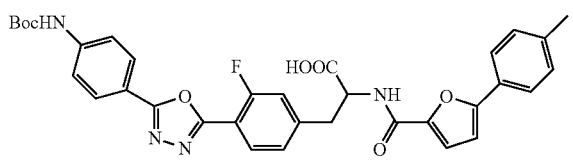 [SMILES: Cc1ccc(-c2ccc(C(=O)NC(Cc3ccc(-c4nnc(-c5ccc(NC(=O)OC(C)(C)C)cc5)o4)c(F)c3)C(=O)O)o2)cc1]

Step A. 3-[3-Fluoro-4-(2H-tetrazol-5-yl)-phenyl]-2-[(5-p-tolyl-furan-2-carbonyl)-amino]-propionic acid ethyl ester. To a solution of 3-(4-cyano-3-fluoro-phenyl)-2-[(5-p-tolyl-furan-2-carbonyl)-amino]-propionic acid ethyl ester (900 mg, 2.14 mmol) in DMF (20 mL) were added NaN3 (410 mg, 6.43 mmol) and NH4Cl (410 mg, 6.43 mmol). The mixture was then stirred at 100° C. for about 24 hrs. The mixture was poured into 50 mL H2O, extracted with EtOAc, dried over Na2SO4, filtered, concentrated, and purified with column chromatography to give the title compound (0.62 g, 62% yield).

Step B. 3-{4-[5-(4-tert-Butoxycarbonylamino-phenyl)-[1,3,4]oxadiazol-2-yl]-3-fluoro-phenyl}-2-[(5-p-tolyl-furan-2-carbonyl)-amino]-propionic acid A441. To a solution of 3-[3-fluoro-4-(2H-tetrazol-5-yl)-phenyl]-2-[(5-p-tolyl-furan-2-carbonyl)-amino]-propionic acid ethyl ester (0.37 g, 0.8 mmol) in THF and toluene (20 mL, 1:4) were added pyridine (1 mL) and (4-chlorocarbonyl-phenyl)-carbamic acid tert-butyl ester (1.2 mmol). The mixture was then refluxed overnight. The mixture was concentrated, and added H2O (30 mL) and EtOAc (50 mL). The organic layer was washed sequentially with 2N HCl, 2N NaOH, and brine, dried over Na2SO4, filtered, and purified by column chromatography to give an intermediate (110 mg). The intermediate was treated with a mixture of 2N LiOH (2 mL) in THF (2 mL). The resulting mixture was stirred about 3 hrs. The mixture was then acidified with 2N HCl to pH 7, extracted with DCM, dried over Na2SO4, filtered, concentrated, and purified by HPLC to give the title compound. 1H NMR (400 MHz, CD3OD) δ 1.55 (s, 9H), 2.34 (s, 3H), 3.29 (m, 1H), 3.50 (m, 1H), 4.97 (m, 1H), 6.82 (m, 1H), 7.18 (m, 1H), 7.22 (d, J=8.0 Hz, 2H), 7.36 (m, 2H), 7.63 (d, J=8.8 Hz, 2H), 7.70 (d, J=8.0 Hz, 2H), 7.98 (m, 3H)

Method A14

Example 15

3-{4-[5-(4-tert-Butoxycarbonylamino-phenyl)-[1,2,4]oxadiazol-3-yl]-3-cyano-phenyl}-2-[(5-p-tolyl-furan-2-carbonyl)-amino]-propionic acid

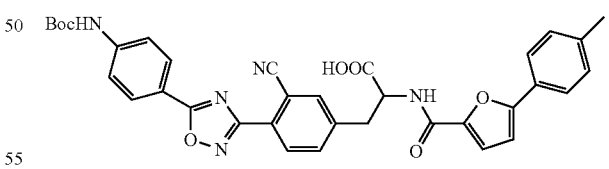

To a solution of 3-{3-bromo-4-[5-(4-tert-butoxycarbonylamino-phenyl)-[1,2,4]oxadiazol-3-yl]-phenyl}-2-[(5-p-tolyl-furan-2-carbonyl)-amino]-propionic acid (34 mg) and Pd(PPh3)4 (5 mg) in DMF (3 mL) was added Zn(CN)2 (20 mg) under argon. The mixture was heated at 120° C. for 2 hrs. The mixture was then concentrated under vacuum and purified by silica gel chromatography to give ethyl ester compound as a solid, which was then hydrolyzed with LiOH as described in Example 1 to furnish the title compound as a yellow solid. EI-MS (m/z): 634.0 (M+H)+.

Method A15

Example 16

3-{6-[5-(4-tert-Butoxycarbonylamino-phenyl)-[1,2,4]oxadiazol-3-yl]-pyridin-3-yl}-2-[(4'-methyl-biphenyl-3-carbonyl)-amino]-propionic acid

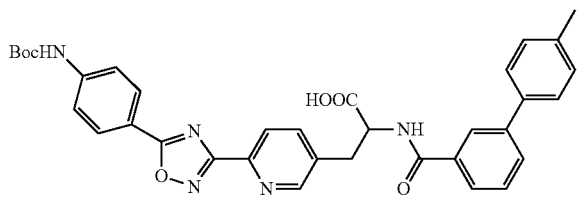 [SMILES: Cc1ccc(-c2cccc(C(=O)NC(Cc3ccc(-c4noc(-c5ccc(NC(=O)OC(C)(C)C)cc5)n4)nc3)C(=O)O)c2)cc1]

The title compound was prepared using the procedure as described in Example 1, substituting 2-fluoro-4-methylbenzonitrile with 5-methyl-pyridine-2-carbonitrile in Step A. 1H NMR (400 MHz, CD3OD) δ 1.53 (s, 9H), 2.31 (s, 3H), 3.24-3.29 (m, 1H), 3.50-3.55 (m, 1H), 4.86-5.01 (m, 1H), 7.19 (d, 2H), 7.47 (m, 3H), 7.59-7.73 (m, 6H), 7.90-7.96 (m, 2H), 8.06-8.14 (m, 3H), 8.62-8.63 (m, 1H).

Method B

Example 18

(R)-3-(4-(5-(4-((tert-butoxycarbonyl)amino)phenyl)-1,2,4-oxadiazol-3-yl)-3-fluorophenyl)-2-(5-(4-isopropylphenyl)furan-2-carboxamido)propanoic acid

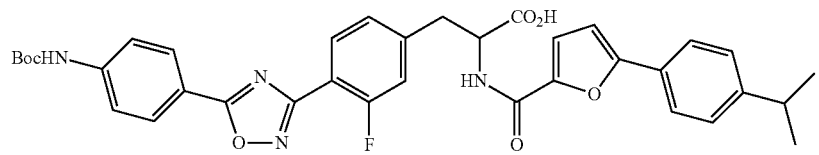 [SMILES: CC(C)c1ccc(-c2ccc(C(=O)NC(Cc3ccc(-c4noc(-c5ccc(NC(=O)OC(C)(C)C)cc5)n4)c(F)c3)C(=O)O)o2)cc1]

Step A. 4-bromo-2-fluoro-N'-hydroxybenzimidamide. To a suspension of 4-bromo-2-fluorobenzonitrile (21.82 g, 104 mmol) and NaHCO3 (13.1 g, 156 mmol) in ethanol (100 mL) and water (20 mL) was added hydroxylamine hydrochloride (8.68 g, 125 mmol). The mixture was stirred for 2 hrs at reflux in sealed tube. The mixture was then cooled and pooled to water. The mixture was filtered, washed with water and dried to give the title compound as a white solid (24 g, 100%).

Step B. tert-butyl-(3-(4-bromo-2-fluorophenyl)-1,2,4-oxadiazol-5-yl)phenyl)carbamate. To a solution of 4-((tert-butoxycarbonyl)amino)benzoic acid (8.2 g, 35.2 mmol) in dioxane (100 mL) was added EDCI (6.7 g, 35.2 mmol) in several portion. The solution was stirred at r.t. for 20 mins followed by addition of 4-bromo-2-fluoro-N-hydroxybenzimidamide (8.2 g, 35.2 mmol). The resulting solution was allowed to stir at r.t. for 2 hours and then heated by an oil bath to 130° C. for 4 hours. The solution was extracted with EtOAc (3 times). The combined organic layers were washed with water (2 times), dried and concentrated by evaporating under reduced pressure. The residue was chromatographied by a silica gel column (0-15% EtOAc/Hexane) to offer 7.1 g of 3-(4-bromo-2-fluorophenyl)-5-cyclopropyl-1,2,4-oxadiazole as a white solid.

Step C. (R)-methyl 2-amino-3-(4-(5-cyclopropyl-1,2,4-oxadiazol-3-yl)-3-fluorophenyl)propanoate. Zinc dust (6 g, 6 equiv), chlorotrimethylsilane (1 mL, 0.5 equiv), and anhydrous DMF (4 mL) were placed in an argon-purged, flame-dried, round-bottom flask fitted with a magnetic stirrer. The suspension was vigorously stirred at room temperature for min. The stirring was stopped to let the Zn* decant for 1 h. The chlorotrimethylsilane were then removed under vacuum. A solution of (R)-methyl 2-((((9H-fluoren-9-yl)methoxy)carbonyl)amino)-3-iodopropanoate (7.34 g, 16.5 mmol, 1.0 equiv) in anhydrous DMF (10 mL) was added dropwise to the activated anhydrous Zn*. The resulting suspension was stirred at room temperature for 30 min until the reaction had ended as judged by TLC. Bromide (7.15 g, 1.0 mol equiv), the catalyst Pd(OAc)2 (185 mg, 0.05 equiv), and tri-o-tolylphosphine (500 mg, 0.1 equiv) were quickly added to the Zn suspension. The mixture was and stirred at 65 C for 3 h. The reaction mixture was filtered through a Celite pad from which the Zn* was washed with ethyl acetate. The filtrate was combined with the reaction mixture, and the organic layer was washed with water and brine. The ethyl acetate solution was dried over anhydrous magnesium sulfate, vacuum filtered, and evaporated under reduced pressure. The crude product was reacted with pyrrodidine in DMF to give the crude amine, which was purified on silica gel using ethyl acetate/hexane as an eluant, leaving amine as a light yellow solid. Yield: 53% (4.0 g).

Step D. (R)-methyl 3-(4-(5-(4-((tert-butoxycarbonyl)amino)phenyl)-1,2,4-oxadiazol-3-yl)-3-fluorophenyl)-2-(5-(4-isopropylphenyl)furan-2-carboxamido)propanoate. Thionyl chloride (5 mL) was added to p-isopropylphenyl-furan-2-carboxylic acid (1.7 g, 7.23 mmol) and the mixture was heated under reflux for 10 min. After removal of excess thionyl chloride under vacuum, the resulting acetyl chloride was added to the mixture of 2-amino-3-{4-[5-(4-tert-butoxycarbonylamino-phenyl)-[1,2,4]oxadiazol-3-yl]-3-fluorophenyl}-propionic acid ethyl ester (3 g, 6.58 mmol), disopropylethylamine (1.3 g, 9.87 mmol) and the mixture was stirred for 30 min at room temperature. The mixture was partitioned between EtOAc and water. The combined organic layers were washed with brine, dried over anhydrous Na2SO4, and concentrated under reduced pressure to give the crude product, which was chromatographed on silica gel to give the title compound as a yellow solid (2.94 g).

Step E. (R)-3-(4-(5-(4-((tert-butoxycarbonyl)amino)phenyl)-1,2,4-oxadiazol-3-yl)-3-fluorophenyl)-2-(5-(4-isopropylphenyl)furan-2-carboxamido)propanoic acid. To a solution of 3-{4-[5-(4-tert-butoxycarbonylamino-phenyl)-[1,2,4]oxadiazol-3-yl]-3-fluorophenyl}-2-[(5-4-isopropylphenyl-furan-2-carbonyl)amino]-propionic acid methyl ester (2 g) in CH3OH (10 mL) was added 1N NaOH aqueous solution at 0° C. The mixture was stirred for 5 hrs at room temperature. The mixture was acidified with 1 N HCl and Extracted with ethyl acetate. The combined organic layers were concentrated under reduced pressure to give the title compound (1.8 g) as a white solid Method B1

Example 19

(R)-3-(4-((4-((tert-butoxycarbonyl)amino)phenyl)ethynyl)-3-fluorophenyl)-2-(5-(p-tolyl)furan-2-carboxamido)propanoic acid

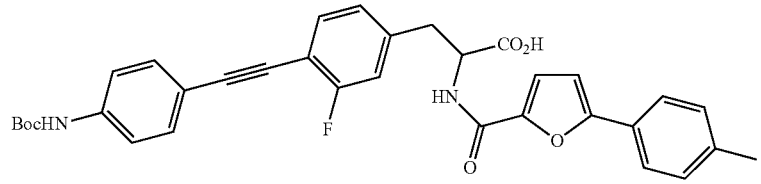 [SMILES: Cc1ccc(-c2ccc(C(=O)NC(Cc3ccc(C#Cc4ccc(NC(=O)OC(C)(C)C)cc4)c(F)c3)C(=O)O)o2)cc1]

Step A. tert-butyl (4-((4-bromo-2-fluorophenyl)ethynyl)phenyl)carbamate. To a suspension of 4-bromo-2-fluoro-1-iodobenzene (13.35 g, 44.4 mmol), PdCl2(PPh)3 (779 mg, 1.11 mmol), CuI (211 mg, 1.11 mmol) in DMF (50 mL) was added Et3N (8.3 mL, 60 mmol) followed by tert-butyl (4-ethynylphenyl)carbamate (8.22 g, 37 mmol). The mixture was heated at 60 C for 1 h. The mixture was then cooled and pooled to water and extracted with EtOAc. The combined organic layers were washed with water, dried and concentrated under reduced pressure. The residue was chromatographied by a silica gel column (0-15% EtOAc/Hexane) to offer 6.1 g of title compound as a brown solid Step B. (R)-3-(4-((4-((tert-butoxycarbonyl)amino)phenyl)ethynyl)-3-fluorophenyl)-2-(5-(p-tolyl)furan-2-carboxamido)propanoic acid. The title compound was prepared following the procedure as described in Example 1. 1H NMR (400 MHz, DMSO-d6): 0.72-0.75 (m, 2H) 0.96-1.01 (m, 2H) 1.50 (s, 9H) 1.93-1.97 (m, 1H) 3.17-3.26 (m, 2H) 4.68-4.75 (m, 1H) 7.00 (d, 1H) 7.15-7.19 (m, 3H) 7.36-7.45 (m, 2H) 7.70 (d, 2H) 7.77 (d, 2H) 7.99 (t, 1H) 8.06 (d, 2H) 8.75 (d, 1H) 9.93 (s, 1H). EI-MS (m/z): 583 (M+H)+.

Method B2

Example 20

(R)-3-{4-[5-(4-tert-Butoxycarbonylamino-phenyl)-[1,2,4]oxadiazol-3-yl]-3-fluorophenyl}-2-{[1-(4-tert-butyl-phenyl)-1H-[1,2,3]triazole-4-carbonyl]-amino}-propionic acid

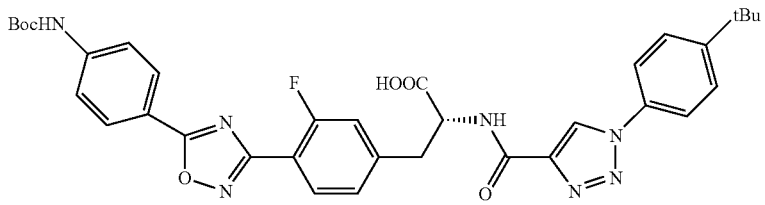 [SMILES: CC(C)(C)OC(=O)Nc1ccc(-c2nc(-c3ccc(C[C@@H](NC(=O)c4cn(-c5ccc(C(C)(C)C)cc5)nn4)C(=O)O)cc3F)no2)cc1]

The title compound (1.2 g) was obtained by chiral resolution of racemic compound A283 (2.5 g) with a Chirapac column eluting with 0.1% TFA in EtOH/THF.

Method B3

Example 21

(S)-3-{4-[5-(4-tert-Butoxycarbonylamino-phenyl)-[1,2,4]oxadiazol-3-yl]-3-fluorophenyl}-2-{[1-(4-tert-butylphenyl)-1H-[1,2,3]triazole-4-carbonyl]-amino}-propionic acid

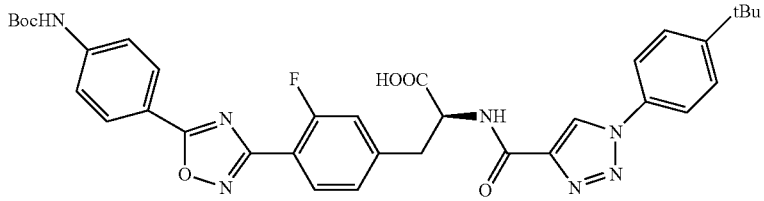 [SMILES: CC(C)(C)OC(=O)Nc1ccc(-c2nc(-c3ccc(C[C@H](NC(=O)c4cn(-c5ccc(C(C)(C)C)cc5)nn4)C(=O)O)cc3F)no2)cc1]

The title compound (1.6 g) was obtained by chiral resolution of racemic compound A283 (2.5 g) with a Chirapac column eluting with 0.1% TFA in EtOH/THF.

Method C

Example 22

5-[5-(4-tert-Butoxycarbonylamino-phenyl)-[1,2,4]oxadiazol-3-yl]-2-[(5-p-tolyl-furan-2-carbonyl)-amino]-indan-2-carboxylic acid

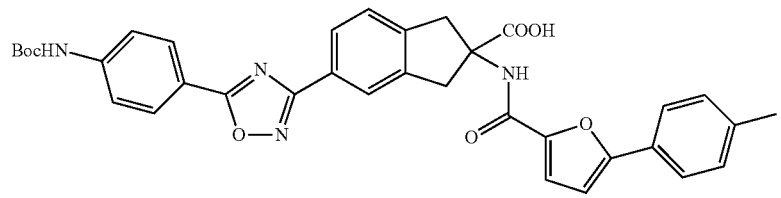 [SMILES: Cc1ccc(-c2ccc(C(=O)NC3(C(=O)O)Cc4ccc(-c5noc(-c6ccc(NC(=O)OC(C)(C)C)cc6)n5)cc4C3)o2)cc1]

Step A. 5-Bromo-2-[(5-p-tolyl-furan-2-carbonyl)-amino]-indan-2-carboxylic acid ethyl ester. To a solution of 5-p-Tolyl-furan-2-carboxylic acid (0.66 g, 3.26 mmol) in DCM (20 mL) were added EDC (0.70 g, 3.64 mmol), HOBt (10 mg), Et3N (1.0 mL, 0.72 mmol), and 2-amino-5-bromoindan-2-carboxylate (1.0 g, 3.12 mmol) (see, EP1849465). The mixture was then stirred overnight. The mixture was washed sequentially with 2N HCl, 2N NaOH, and brine, dried over Na2SO4, filtered, and concentrated to obtain the title compound (0.68 g, 46% yield), which was used directly without further purification in the next step.

Step B. 5-Cyano-2-[(5-p-tolyl-furan-2-carbonyl)-amino]-indan-2-carboxylic acid ethyl ester. To a solution of 5-bromo-2-[(5-p-tolyl-furan-2-carbonyl)-amino]-indan-2-carboxylic acid ethyl ester (0.60 g, 1.20 mmol) in DMF (10 mL) were added CuCN (0.40 g, 4.5 mmol) and Pd(PPh3)4 (50 mg). The mixture was stirred under microwave-irradiation for 3 hrs. The mixture was poured into H2O (50 mL), extracted with EtOAc, dried over Na2SO4, filtered, concentrated, and purified by column chromatography to yield the title compound (0.45 g, 85% yield).

Step C. 5-(N-Hydroxycarbamimidoyl)-2-[(5-p-tolyl-furan-2-carbonyl)-amino]-indan-2-carboxylic acid ethyl ester. To a solution of 5-cyano-2-[(5-p-tolyl-furan-2-carbonyl)-amino]-indan-2-carboxylic acid ethyl ester (0.40 g, 1.00 mmol) in EtOH (30 mL) were added NH2OH HCl (0.33 g, 5.0 mmol) and NaHCO3 (0.30 g, 5 mmol). The mixture was stirred at reflux for 5 hrs. The mixture was then filtered, concentrated, and purified by column chromatography to yield the title compound (0.33 g, 77% yield).

Step D. 5-[5-(4-tert-Butoxycarbonylamino-phenyl)-[1,2,4]oxadiazol-3-yl]-2-[(5-p-tolyl-furan-2-carbonyl)-amino]-indan-2-carboxylic acid D4. To a solution of 5-(N-hydroxycarbamimidoyl)-2-[(5-p-tolyl-furan-2-carbonyl)-amino]-indan-2-carboxylic acid ethyl ester (0.33 g, 0.8 mmol) in THF and toluene (20 mL, 1:4) were added pyridine (1 mL) and (4-chlorocarbonyl-phenyl)-carbamic acid tert-butyl ester (1.2 mmol). The mixture was stirred at reflux overnight. The mixture was then concentrated. H2O (30 mL) and EtOAc (50 mL) were added. The organic layer was washed sequentially with 2N HCl, 2N NaOH, and brine, dried over Na2SO4, filtered, and purified by column chromatography to give an intermediate (110 mg). The intermediate was treated with 2N LiOH (2 mL) in THF (2 mL). The resulting solution was stirred about 3 hrs. The solution was then acidified with 2N HCl to pH 7, extracted with DCM, dried over Na2SO4, filtered, concentrated, and purified by preparative HPLC to yield the title compound. 1H NMR (400 MHz, CD3OD) δ 1.56 (s, 9H), 2.36 (s, 3H), 3.62-3.65 (m, 2H), 3.79-3.81 (m, 2H), 6.82 (m, 1H), 7.23 (m, 3H), 7.41 (d, J=4.0 Hz, 1H), 7.66 (d, J=8.8 Hz, 2H), 7.73 (d, J=8.0 Hz, 2H), 7.96-8.00 (m, 2H), 8.09 (d, J=8.8 Hz, 1H).

Method D

Example 23

7-((4-((tert-butoxycarbonyl)amino)benzoyl)oxy)-2-((4-(tert-butyl)phenyl)sulfonyl)-6-methoxy-1,2,3,4-tetrahydroisoquinoline-3-carboxylic acid

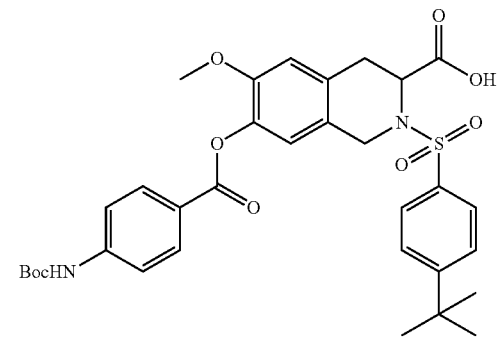 [SMILES: COc1cc2c(cc1OC(=O)c1ccc(NC(=O)OC(C)(C)C)cc1)CN(S(=O)(=O)c1ccc(C(C)(C)C)cc1)C(C(=O)O)C2]

Step A. Methyl 7-(benzyloxy)-6-methoxy-1,2,3,4-tetrahydroisoquinoline-3-carboxylate. The title compound was prepared analogy to the procedures by Guzman, Filadel et al from Journal of Medicinal Chemistry (1984), 27 (5), p 564 starting from 2-amino-3-(4-hydroxy-3-methoxyphenyl)propanoic acid.

Step B. 7-((4-((tert-butoxycarbonyl)amino)benzoyl)oxy)-2-((4-(tert-butyl)phenyl)sulfonyl)-6-methoxy-1,2,3,4-tetrahydroisoquinoline-3-carboxylic acid. The title compound was prepared using the procedure as described in Example 6, substituting 3-chloro-2-methylsulphonyl chloride with 4-tert-butylbenzenesulphonyl chloride in Step A. EI-MS (m/z): 637 (M−H)−

Example 24

Human GLP-1 Receptor Transfected Cell Assay

The glucagon-like peptide I receptor (GLP1R) is a class B Gs-coupled membrane receptor, an agonist of which activates adenylate cyclase (AC) and elevates intracellular cAMP level. In turn, the high content of secondary messengers can activate the cAMP response element binding protein (CREB), which can translocate into nucleus to activate gene transcription.

A reporter gene based screening assay was established to measure the effect of a compound on GLP1R. In this assay, a compound was incubated with CHO cells transiently transfected with a human GLP1R plasmid and a multiple response element (MRE)/cAMP response element (CRE)-driven luciferase reporter plasmid. Once luciferase was induced by the compound, its specific substrate can be activated to produce light signal for measurement.

Materials used in this assay included: (i) cell line: Chinese hamster ovary (CHO) cells (ATCC); (ii) fetal bovine serum (FBS) (Biochrom Co.); (iii) culture medium: RPMI1640 (Invitrogen Co.) supplemented with 10% FBS; (iv) LIPOFECTAMINE™ 2000 Reagent (Invitrogen Co.); (v) plasmids: pCMV-human GLP1R and pGL3-1905 reporter plasmid; (vi) GLP1 (7-36 amide) peptide (Sigma Co.); and (vii) BRIGHT-GLO™ Luciferase Assay System (Promega Co.).

Instruments used in this assay included: (i) Form a carbon dioxide incubator (Thermo Form a Co.); and (ii) Flexstation 3 (Molecular Device Co.).

Before transfection, CHO cells were plated into a 6-well culture plate at 800,000/2 mL/well, and cultured at 37° C. in 5% CO2 overnight. On the transfection day, cells were transfected with receptor plasmid and reporter plasmid using LIPOFECTAMINE™ 2000 reagent. After 6-hour transfection, cells were digested and seeded into 96-well plates at 20,000/100 μL/well. After 14-16 hour incubation, transfected cells were washed with 100 μL serum-free RPMII 640 medium first, and then added 50 μL of the culture medium. The GLP-1 standard and test compounds were respectively diluted to a series of concentrations, which were then added into the above 96-well culture plate at 50 μL/well. The cells were incubated at 37° C. in 5% CO2 for 6 hrs. The activity of luciferase was detected using BRIGHT-GLO™ Luciferase Analytic System, and the reading was performed with a Flexstation3 plate reader machine.

Example 25

Sensitizer Bioassay

Although GPCR have been studied for over 30 years, the concepts of sensitizer/modulator and recent GPCR dimers just were just recognized and accepted as physiological entities and not simply biochemical artifacts. Glucagon-like peptide1 (GLP1) receptor belongs to B-type GPCR family and activated by its natural agonist peptide, GLP1 peptide. We have found several small molecules which can increase GLP1 receptor activities in reporter gene assay and GLP1 insulinotropic activity when GLP1 treat beta-cell in the presence of compound. Further, in cell line model, these compounds can sensitize GLP1 effect by increasing GLP1 affinity and efficacy. These finding suggest GLP1 sensitizer can be a potential candidate for treatment of type 2 diabetes and/or obesity.

A reporter gene based screening assay was established to measure the effect of a compound on GLP1R. In this assay, a compound was incubated with CHO cells transiently transfected with a human GLP1R plasmid and a multiple response element (MRE)/cAMP response element (CRE)-driven luciferase reporter plasmid. Once luciferase was induced by the compound, its specific substrate can be activated to produce light signal for measurement.

Materials used in this assay included: Materials used in this assay included: (i) cell line: Chinese hamster ovary (CHO) cells (ATCC); (ii) fetal bovine serum (FBS) (Biochrom Co.); (iii) culture medium: RPMI1640 (Invitrogen Co.) supplemented with 10% FBS; (iv) LIPOFECTAMINE™ 2000 Reagent (Invitrogen Co.); (v) plasmids: pCMV-human GLP1R and pGL3-1905 reporter plasmid; (vi) GLP1 (7-36 amide) peptide (Sigma Co.); and (vii) BRIGHT-GLO™ Luciferase Assay System (Promega Co.).

Instruments used in this assay included: (i) Form a carbon dioxide incubator (Thermo Form a Co.); and (ii) Flexstation 3 (Molecular Device Co.).

Before the assay, seeding CHO cells onto a 96 well plate. First, remove and discard culture medium in large cell culture flask. Adding 0.7 ml of Trypsin-EDTA solution to flask until cell layer is dispersed (2-3 min), then, added 6 ml of culture medium and mixing gently. The cell numbers were counted and diluted into appropriately $2.5 \times 10^5$/ml. 100 μl of cell suspension was added to each well of 96 well plate. The culture plates were incubated at 37° C. incubator with 5% CO2 overnight. In the second day, the compounds were diluted to the concentrations from 25 μM and 5 μM with medium contains 3 nM GLP1 and mix.

The compounds solutions were then transferred into the wells of 40 μl per well. Each data points were tested for 3 duplicates for each sample. The final concentration is 25 μM and 5 μM. The cells treated with 100 nM of GLP1 peptide as positive control, and cells with medium is used as negative control, 6 duplicates for each. The plates were then incubated at at 37° C. in 5% CO2 incubator for 5~6 hours. 100 μl of Bright-Glo™ luciferase substrate was added to each well, and plates were shaked for 2 minutes on an orbital shaker. The lysates were transfected into a white detecting plate and measured in a luminometer.

In our data analysis, we defined Signal/Basal ratio=RLU GLP 1 (3 nM)/RLU basal. The compounds activity is defined as Signal/Basal ratio=RLU compounds/RLU basal. The sensitizer activity is determined by C.S.E which is defined as RLU compounds/RLU GLP1 (3 nM). The CV should be less than 0.15.

Example 26

Insulin Secretion Assay

GLP-1 stimulates insulin secretion in a glucose dependent manner via its receptor on beta cell. A rat insulinoma cell line (INS-1) was employed to test efficacies of compounds on a native GLP-1 receptor. This cell line secretes insulin in response to glucose concentrations in the physiological range.

Materials used in this assay included: (i) cell line: INS-1 insulinoma cells (ATCC); (ii) fetal bovine serum (FBS) (Biochrom Co.); (iii) culture medium: RPMI1640 (Invitrogen Co.) supplemented with 10% FBS; (iv) 10 mM HEPES (Invitrogen Co.); (v) 4 mM L-glutamine (Invitrogen Co.); (vi) 1 mM Sodium pyruvate (Invitrogen Co.); (vii) 0.1 mM 2-mercaptoethanol (Invitrogen Co.); (viii) assay buffer: HEPES balanced salt solution (HBSS), containing 114 mM NaCl, 4.7 mM KCl, 1.2 mM $KH_2PO_4$, 1.16 mM $MgSO_4$, 20 mM HEPES, 2.5 mM $CaCl_2$, and 25.5 mM $NaHCO_3$ at pH 7.4

(adjusted with NaOH); (ix) glucose (Sigma Co.); (x) vine serum albumin (Sigma Co.); (xi) poly-lysine (Sigma Co.); (xii) GLP-1 (7-36 amide) (Sigma Co.); and (xiii) insulin ELISA test kit (Xiamen Boson Biotechnology Co., China).

Instruments used in this assay included: (i) Form a carbon dioxide incubator (Thermo Form a Co.); and (ii) Flexstation 3 (Molecular Device Co.).

INS-1 cells were seeded at a density of 0.7-0.8×105/well in 200 μL medium for a poly-lysine coated 96-well plate on Day 1. Culture medium was changed on Day 3. The assay was performed on Day 4. INS-1 cells were washed twice with HBSS containing 3 mM glucose. The first wash was just a quick rinse. For the second wash, the HBSS was left on cells for 2 hrs. Test compounds were then diluted to a series of concentrations in HBSS containing 15 mM glucose. GLP-1 peptide (100 nM) was used as a standard control. For a 96-well plate, the test volume is 100 μL/well. Cells were incubated with test compounds for 1 hr. The supernatant was aspirated into equal volume of 2% BSA solution on ice for ELISA tests. Insulin was detected using the ELISA kit. The reading was performed on Flexstation at 463 nM.

Example 27

Competitive Binding Assay

A homologous competitive binding assay was used to determine receptor affinity (Kd) and density (Bmax) of test compounds. To ensure high-level of hGLP1 receptor surface expression, GLP-1 receptor membrane preparations were crude membrane preparations from HEK-293C3 cell line, which stably expressed human GLP1 receptor. The membrane preparations exhibited a Kd of 0.23 nM for [125I]-GLP-1. A full agonist of GLP1 receptor, exendin-4, was used as a positive control.

Materials used in this assay included: (i) radioligand: [125I] GLP-1(7-36) (Perkin Elmer Co.); (ii) exendin-4 (Sigma Co.); (iii) scintillation liquid: Betaplate scint (Perkin Elmer Co.); (iv) filtermat: printed filtermat B (Perkin Elmer Co.); (vi) Sample bag (Perkin Elmer Co.); (v) cassette: Microbeta 1450-104 (Perkin Elmer Co.); (vi) binding buffer: 50 mM HEPES, pH 7.4, 5 mM MgCl2, 1 mM CaCl2, 2 mM EDTA, 0.02% Tween20, filtered and stored at 4° C.; adding aprotinin to prepare working assay buffer containing 5 μg/mL aprotinin on the assay day; (vii) wash buffer: 50 mM HEPES, pH 7.4, 500 mM NaCl, 0.1% BSA, and 0.05% Tween 20, filtered and stored at 4° C.; (viii) filtermat blocking buffer: 0.33% polyethyleneimine; and (ix) filtermat wash buffer: 50 mM HEPES, pH 7.4, and 0.5% BSA, filtered and stored at 4° C.

Instruments used in this assay included: (i) Microbeta Plus 1450-011 (Wallac Co.); (ii) heat sealer 1295-012 (WALLAC Co.); and (iii) cell harvester 96 Mach III M (Tomtec Co.).

Titrated unlabeled competitors were prepared in 50 μL binding buffer per well. Unlabeled exendin 4 (100 nM) was used as a NSB control. A membranes solution was prepared in a concentration of 2-3 μg/well, and then combined with competitors and 50 pM [125I] GLP-1 (7-36). The mixtures were put on a shaker for 10 min at 100 rpm and then incubated at room temperature for 60 min. Prior to filtration, a printed filtermat was coated with 20 mL of 0.33% polyethyleneimine for 40-60 min, and then washed with 30 mL filtermat wash buffer. The binding reaction mixtures were collected on the blocked filtermat using a cell harvester. The filtermat was then dried and sealed with scintillation liquid in a sample bag. After heat-sealing, the sample bag was placed into Microbeta filter cassette for counting.

Exemplary compounds 1 to 327 as listed in Tables 1A, 2A, and 3A were prepared by using the methods described in the above Examples and Schemes. These compounds were also tested using the bioassay protocols described in the Examples above and showed biological activities which are summarized in Tables 1B, 2B, and 3B, wherein A represents a value no smaller than 60%, B represents a value between 40 to 60%, C represents a value between 20 to 40%, D represents a value between 10 to 20%, and E represents a value no greater than 10%. The activity of each compound in the tables is expressed as a percentage of the activity of the control at the concentration specified. It is also noted that Compounds in Table 1A, Table 2A, and Table 3A correspond to the tested compounds in Table 1B, Table 2B, and Table 3B, respectively. For example, Compound 1 in Table 1A corresponds to tested compound 1A in Table 1B; Compound 228 in Table 2A corresponds to tested compound 7A in Table 2B; and Compound 162 in Table 3A corresponds to tested compound 11A in Table 3B. Furthermore, the concentration (conc.) unit used in Tables 1B, 2B, and 3B is micromolar, i.e., μM.

TABLE 1A

Exemplary Compounds Showing Agonist Activity Only

| Number | Structure | Method | MS/HNMR |
|---|---|---|---|
| 1 | 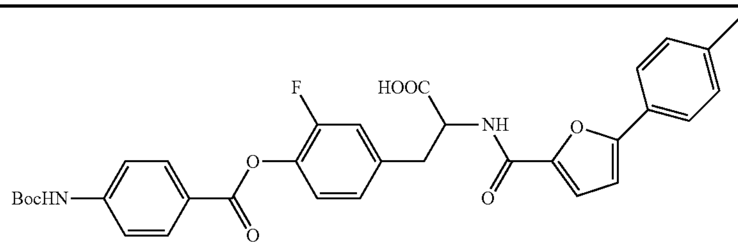 | A | 601 (M − H)− |
| 2 | 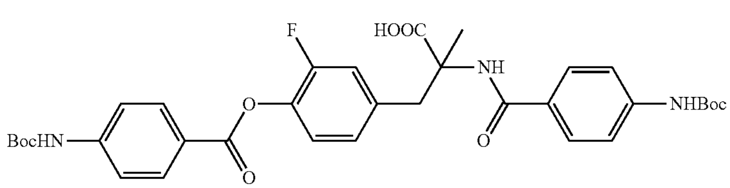 [SMILES: CC(C)(C)OC(=O)Nc1ccc(C(=O)NC(C)(Cc2ccc(OC(=O)c3ccc(NC(=O)OC(C)(C)C)cc3)c(F)c2)C(=O)O)cc1] | A | 650 (M − H)− |

TABLE 1A-continued

Exemplary Compounds Showing Agonist Activity Only

| Number | Structure | Method | MS/HNMR |
|---|---|---|---|
| 3 | 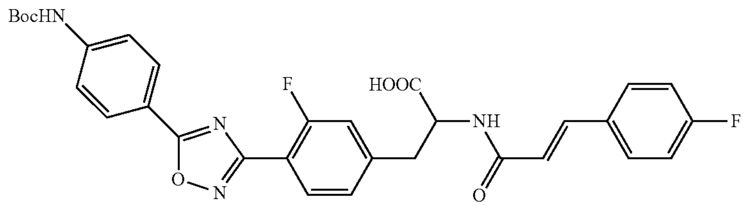 [SMILES: CC(C)(C)OC(=O)Nc1ccc(-c2nc(-c3ccc(CC(NC(=O)/C=C/c4ccc(F)cc4)C(=O)O)cc3F)no2)cc1] | A | 673 (M + H)+ |
| 4 | 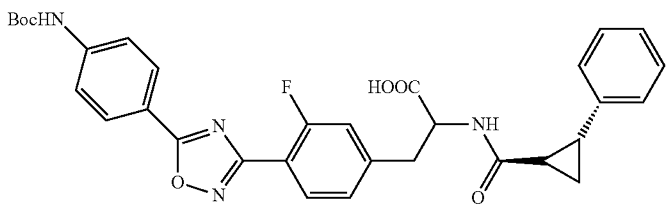 | A | 585 (M − H)− |
| 5 | 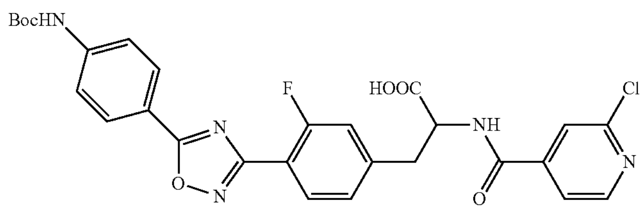 [SMILES: CC(C)(C)OC(=O)Nc1ccc(-c2nc(-c3ccc(CC(NC(=O)c4ccnc(Cl)c4)C(=O)O)cc3F)no2)cc1] | A | 580 (M − H)− |
| 6 | 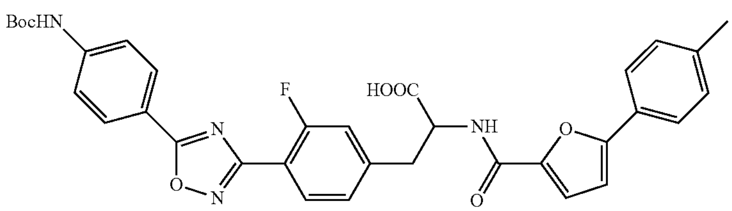 [SMILES: Cc1ccc(-c2ccc(C(=O)NC(Cc3ccc(-c4noc(-c5ccc(NC(=O)OC(C)(C)C)cc5)n4)c(F)c3)C(=O)O)o2)cc1] | A | 625 (M − H)− 9.89 (s, 1H), 8.73 (d, J = 8.8 Hz, 1H), 8.05 (d, J = 8.8 Hz, 2H), 7.98 (t, J = 8.0 Hz, 1H), 7.79 (d, J = 8.4 Hz, 2H), 7.70 (d, J = 8.8 Hz, 2H), 7.43 (d, J = 12.4 Hz, 1H), 7.37 (d, J = 8.0 Hz, 1H), 7.28 (d, J = 8.0 Hz, 2H), 7.15 (d, J = 3.6 Hz, 1H), 7.0 (d, J = 3.6 Hz, 1H), 4.71-4.77 (m, 1H), 3.19-3.25 (m, 2H), 2.34 (s, 3H), 1.49 (s, 9H) |
| 7 | 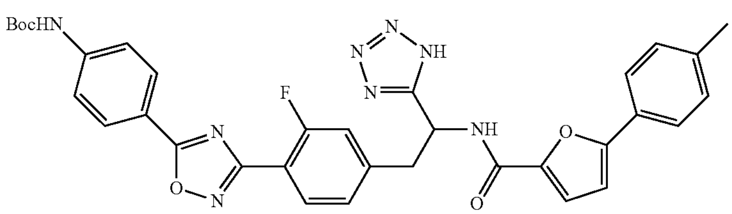 [SMILES: Cc1ccc(-c2ccc(C(=O)NC(Cc3ccc(-c4noc(-c5ccc(NC(=O)OC(C)(C)C)cc5)n4)c(F)c3)c3nnn[nH]3)o2)cc1] | A | 649 (M − H)− |
| 8 | 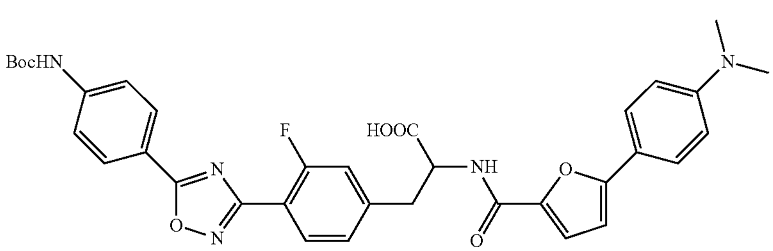 [SMILES: CN(C)c1ccc(-c2ccc(C(=O)NC(Cc3ccc(-c4noc(-c5ccc(NC(=O)OC(C)(C)C)cc5)n4)c(F)c3)C(=O)O)o2)cc1] | A2 | 654 (M − H)− |

TABLE 1A-continued

Exemplary Compounds Showing Agonist Activity Only

| Number | Structure | Method | MS/HNMR |
|---|---|---|---|
| 9 | 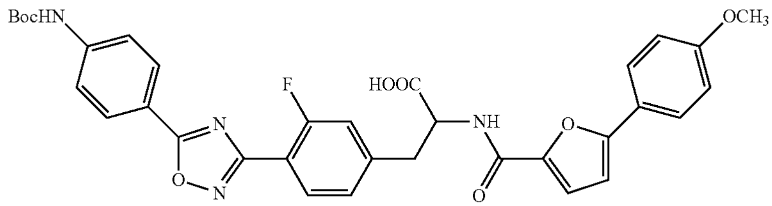 [SMILES: COc1ccc(-c2ccc(C(=O)NC(Cc3ccc(-c4noc(-c5ccc(NC(=O)OC(C)(C)C)cc5)n4)c(F)c3)C(=O)O)o2)cc1] | A2 | 641 (M − H)− |
| 10 | 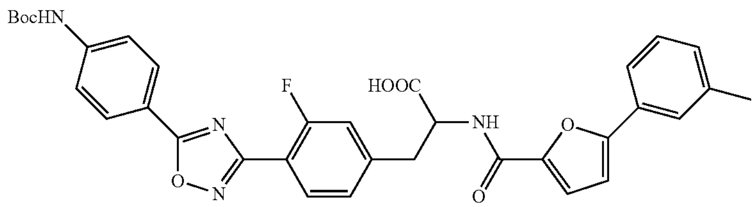 [SMILES: Cc1cccc(-c2ccc(C(=O)NC(Cc3ccc(-c4noc(-c5ccc(NC(=O)OC(C)(C)C)cc5)n4)c(F)c3)C(=O)O)o2)c1] | A2 | 625 (M − H)− |
| 11 | 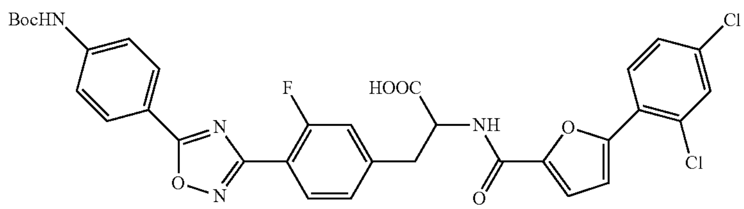 [SMILES: CC(C)(C)OC(=O)Nc1ccc(-c2nc(-c3ccc(CC(NC(=O)c4ccc(-c5ccc(Cl)cc5Cl)o4)C(=O)O)cc3F)no2)cc1] | A2 | 679 (M − H)− |
| 12 | 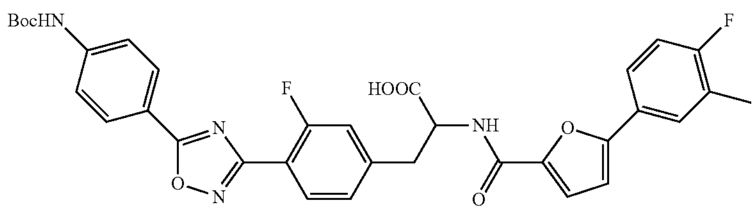 | A2 | 643 (M − H)− |
| 13 | 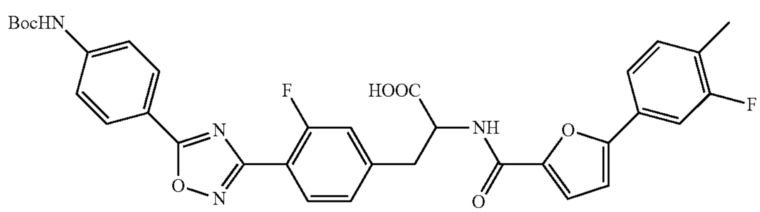 [SMILES: Cc1ccc(-c2ccc(C(=O)NC(Cc3ccc(-c4noc(-c5ccc(NC(=O)OC(C)(C)C)cc5)n4)c(F)c3)C(=O)O)o2)cc1F] | A2 | 643 (M − H)− |
| 14 | 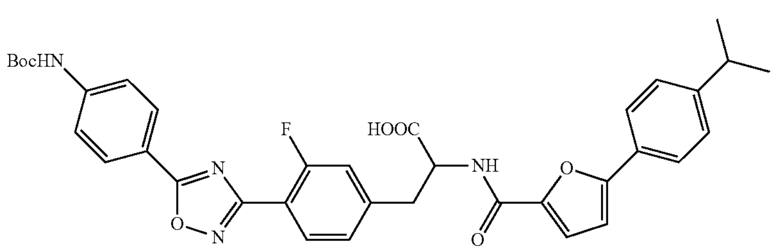 [SMILES: CC(C)c1ccc(-c2ccc(C(=O)NC(Cc3ccc(-c4noc(-c5ccc(NC(=O)OC(C)(C)C)cc5)n4)c(F)c3)C(=O)O)o2)cc1] | A2 | 653 (M − H)− |
| 15 | 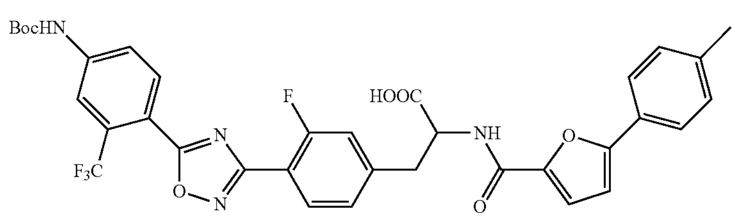 | A2 | 693 (M − H)− |

TABLE 1A-continued

Exemplary Compounds Showing Agonist Activity Only

| Number | Structure | Method | MS/HNMR |
|---|---|---|---|
| 16 | 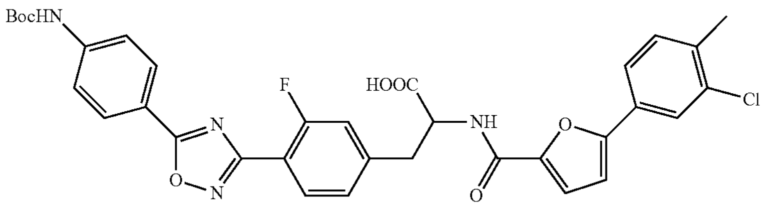 [SMILES: Cc1ccc(-c2ccc(C(=O)NC(Cc3ccc(-c4noc(-c5ccc(NC(=O)OC(C)(C)C)cc5)n4)c(F)c3)C(=O)O)o2)cc1Cl] | A2 | 659 (M − H)− |
| 17 | 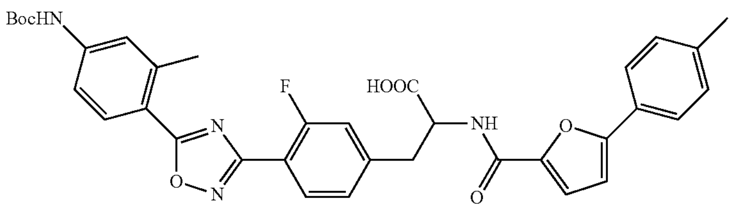 [SMILES: Cc1ccc(-c2ccc(C(=O)NC(Cc3ccc(-c4noc(-c5ccc(NC(=O)OC(C)(C)C)cc5C)n4)c(F)c3)C(=O)O)o2)cc1] | A2 | 639 (M − H)− |
| 18 | 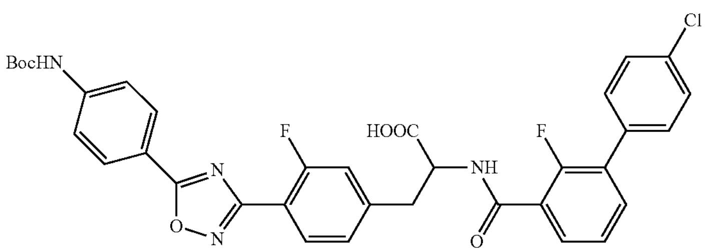 [SMILES: CC(C)(C)OC(=O)Nc1ccc(-c2nc(-c3ccc(CC(NC(=O)c4cccc(-c5ccc(Cl)cc5)c4F)C(=O)O)cc3F)no2)cc1] | A3 | 634 (M + H)+ |
| 19 | 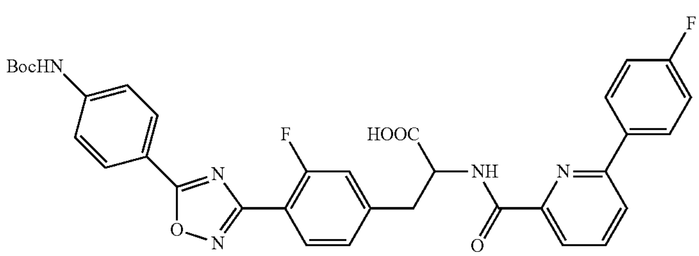 [SMILES: CC(C)(C)OC(=O)Nc1ccc(-c2nc(-c3ccc(CC(NC(=O)c4cccc(-c5ccc(F)cc5)n4)C(=O)O)cc3F)no2)cc1] | A3 | 639 (M − H)− |
| 20 | 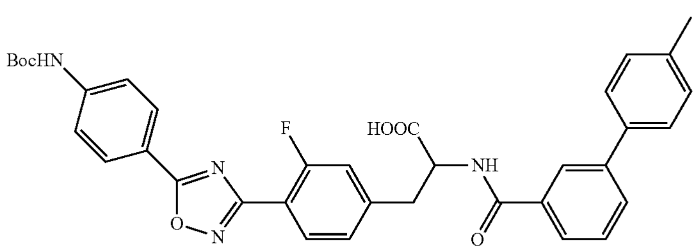 [SMILES: Cc1ccc(-c2cccc(C(=O)NC(Cc3ccc(-c4noc(-c5ccc(NC(=O)OC(C)(C)C)cc5)n4)c(F)c3)C(=O)O)c2)cc1] | A3 | 635 (M − H)− |
| 21 | 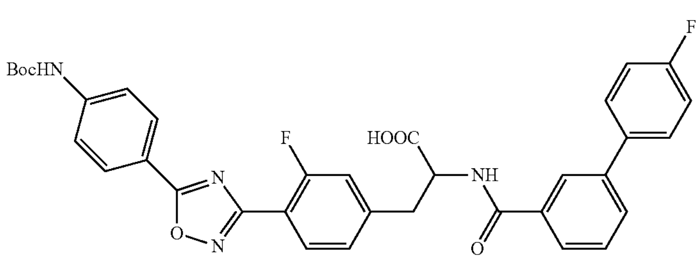 [SMILES: CC(C)(C)OC(=O)Nc1ccc(-c2nc(-c3ccc(CC(NC(=O)c4cccc(-c5ccc(F)cc5)c4)C(=O)O)cc3F)no2)cc1] | A3 | 639 (M − H)− |

TABLE 1A-continued

Exemplary Compounds Showing Agonist Activity Only

| Number | Structure | Method | MS/HNMR |
|---|---|---|---|
| 22 | 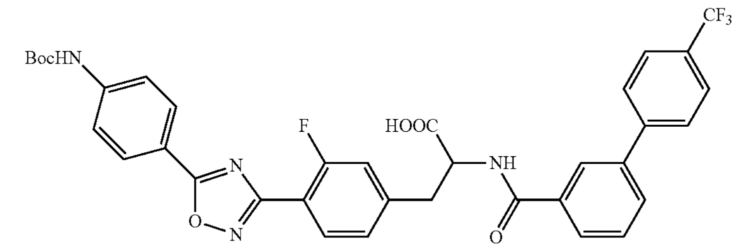 [SMILES: CC(C)(C)OC(=O)Nc1ccc(-c2nc(-c3ccc(CC(NC(=O)c4cccc(-c5ccc(C(F)(F)F)cc5)c4)C(=O)O)cc3F)no2)cc1] | A3 | 689 (M − H)− |
| 23 | 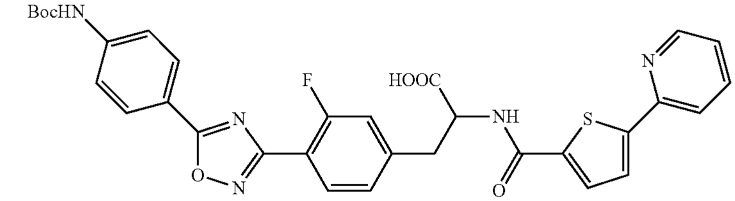 [SMILES: CC(C)(C)OC(=O)Nc1ccc(-c2nc(-c3ccc(CC(NC(=O)c4ccc(-c5ccccn5)s4)C(=O)O)cc3F)no2)cc1] | A2 | 628 (M − H)− |
| 24 | 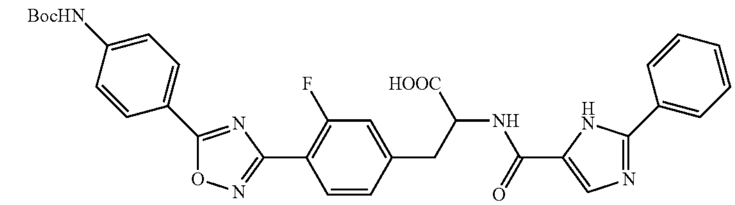 [SMILES: CC(C)(C)OC(=O)Nc1ccc(-c2nc(-c3ccc(CC(NC(=O)c4cnc(-c5ccccc5)[nH]4)C(=O)O)cc3F)no2)cc1] | A2 | 627 (M − H)− |
| 25 | 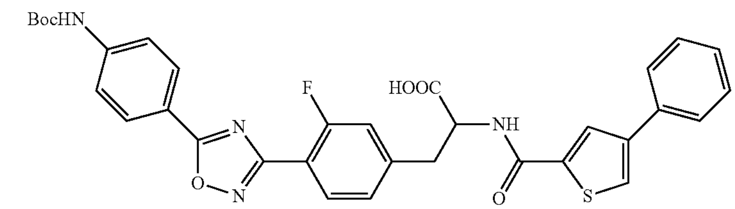 [SMILES: CC(C)(C)OC(=O)Nc1ccc(-c2nc(-c3ccc(CC(NC(=O)c4cc(-c5ccccc5)cs4)C(=O)O)cc3F)no2)cc1] | A2 | 627 (M − H)− |
| 26 | 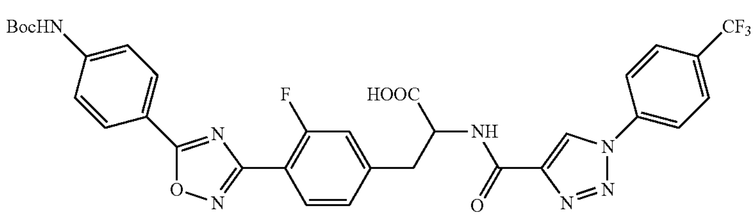 [SMILES: CC(C)(C)OC(=O)Nc1ccc(-c2nc(-c3ccc(CC(NC(=O)c4cn(-c5ccc(C(F)(F)F)cc5)nn4)C(=O)O)cc3F)no2)cc1] | A5 | 680 (M − H)− |
| 27 | 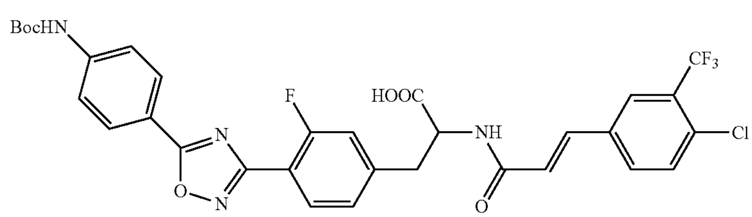 [SMILES: CC(C)(C)OC(=O)Nc1ccc(-c2nc(-c3ccc(CC(NC(=O)/C=C/c4ccc(Cl)c(C(F)(F)F)c4)C(=O)O)cc3F)no2)cc1] | A | 674 (M − H)− |

TABLE 1A-continued

Exemplary Compounds Showing Agonist Activity Only

| Number | Structure | Method | MS/HNMR |
|---|---|---|---|
| 28 | 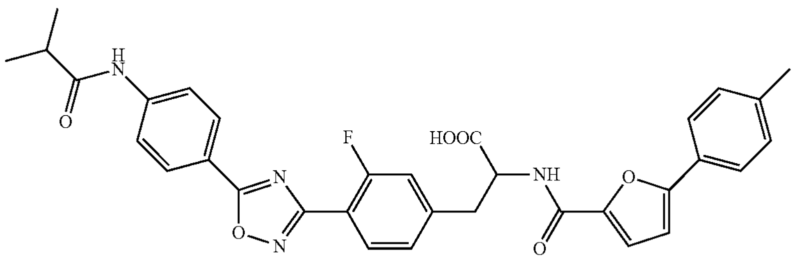 [SMILES: Cc1ccc(-c2ccc(C(=O)NC(Cc3ccc(-c4noc(-c5ccc(NC(=O)C(C)C)cc5)n4)c(F)c3)C(=O)O)o2)cc1] | A | 595 (M + H)+ |
| 29 | 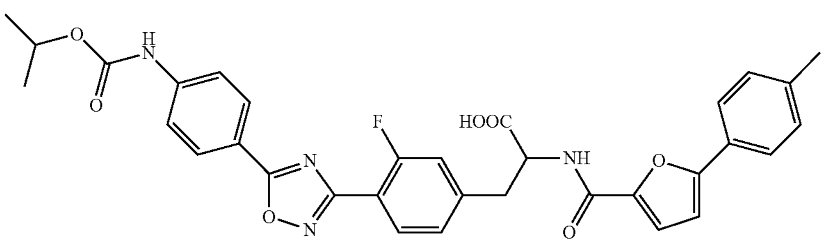 [SMILES: Cc1ccc(-c2ccc(C(=O)NC(Cc3ccc(-c4noc(-c5ccc(NC(=O)OC(C)C)cc5)n4)c(F)c3)C(=O)O)o2)cc1] | A | 611 (M − H)− |
| 30 | 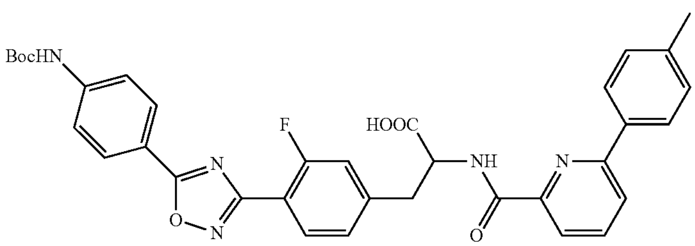 | A3 | 636 (M − H)− |
| 31 | 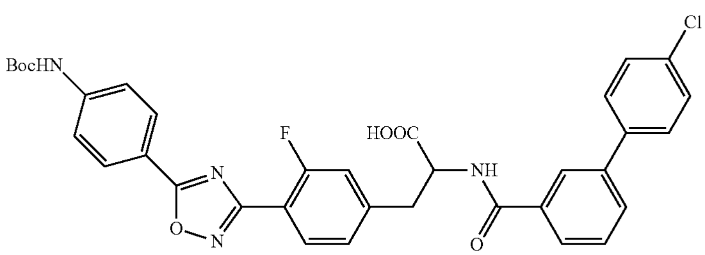 [SMILES: CC(C)(C)OC(=O)Nc1ccc(-c2nc(-c3ccc(CC(NC(=O)c4cccc(-c5ccc(Cl)cc5)c4)C(=O)O)cc3F)no2)cc1] | A1 | 657 (M − H)− |
| 32 | 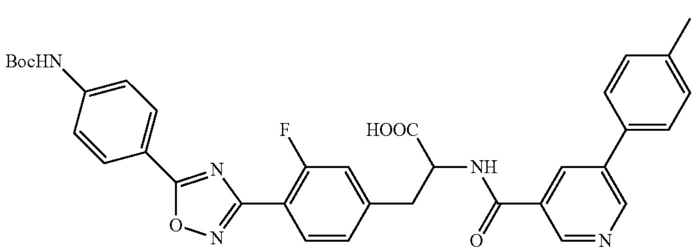 [SMILES: Cc1ccc(-c2cncc(C(=O)NC(Cc3ccc(-c4noc(-c5ccc(NC(=O)OC(C)(C)C)cc5)n4)c(F)c3)C(=O)O)c2)cc1] | A1 | 636 (M − H)− |

TABLE 1A-continued

Exemplary Compounds Showing Agonist Activity Only

| Number | Structure | Method | MS/HNMR |
|---|---|---|---|
| 33 | 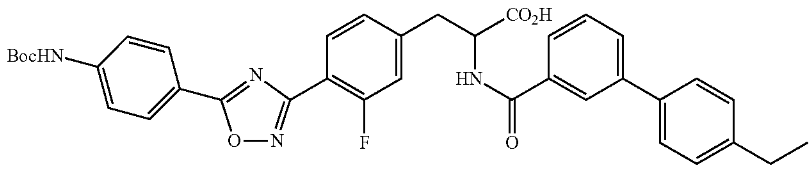 [SMILES: CCc1ccc(-c2cccc(C(=O)NC(Cc3ccc(-c4noc(-c5ccc(NC(=O)OC(C)(C)C)cc5)n4)c(F)c3)C(=O)O)c2)cc1] | A1 | 649 (M − H) 9.91 (s, 1H), 8.89 (d, J = 8.4 Hz, 1H), 8.05 (d, J = 8.8 Hz, 2H), 8.01 (t, J = 8.0 Hz, 2H), 7.80 (d, J = 8.0 Hz, 1H), 7.71-7.76 (m, 3H), 7.62 (d, J = 8.4 Hz, 2H), 7.54 (t, J = 8.0 Hz, 1H), 7.46 (d, J = 12.0 Hz, 1H), 7.41 (d, J = 12.0 Hz, 1H), 7.31 (d, J = 8.4 Hz, 2H), 4.74-4.80 (m, 1H), 3.25-3.30 (m, 1H), 3.16-3.20 (m, 1H), 2.63 (q, J = 7.6 Hz, 2H), 1.49 (s, 9H), 1.19 (t, J = 7.6 Hz, 3H). |
| 34 | 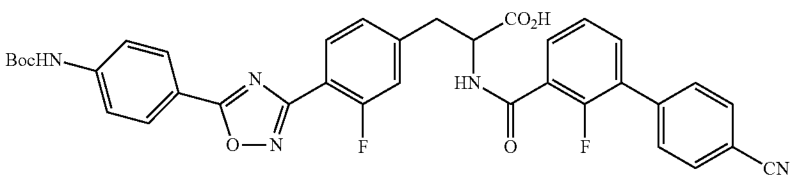 [SMILES: CC(C)(C)OC(=O)Nc1ccc(-c2nc(-c3ccc(CC(NC(=O)c4cccc(-c5ccc(C#N)cc5)c4F)C(=O)O)cc3F)no2)cc1] | A1 | 664 (M − H) 9.92 (s, 1H), 8.81 (d, J = 8.4 Hz, 1H), 8.07 (d, J = 8.8 Hz, 2H), 8.01 (t, J = 8.0 Hz, 1H), 7.96 (d, J = 8.4 Hz, 2H), 7.65-7.77 (m, 5H), 7.36-7.54 (m, 4H), 4.71-4.77 (m, 1H), 3.26-3.30 (m, 1H), 3.08-3.14 (m, 1H), 1.50 (s, 9H) |
| 35 | 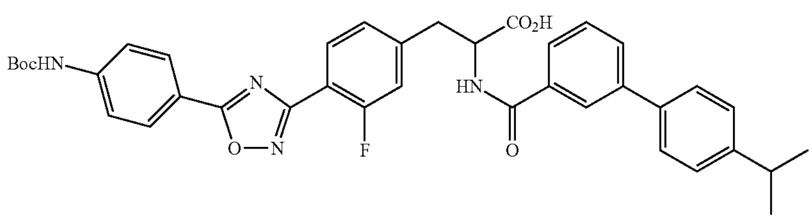 [SMILES: CC(C)c1ccc(-c2cccc(C(=O)NC(Cc3ccc(-c4noc(-c5ccc(NC(=O)OC(C)(C)C)cc5)n4)c(F)c3)C(=O)O)c2)cc1] | A1 | 663 (M − H) 9.92 (s, 1H), 8.89 (d, J = 8.4 Hz, 1H), 8.05 (d, J = 8.8 Hz, 2H), 7.99-8.02 (m, 2H), 7.79 (d, J = 7.6 Hz, 2H), 7.70-7.75 (m, 3H), 7.61 (d, J = 8.0 Hz, 2H), 7.53 (t, J = 8.0 Hz, 1H), 7.45 (d, J = 11.6 Hz, 1H), 7.39 (d, J = 8.4 Hz, 1H), 7.34 (d, J = 7.6 Hz, 2H), 4.74-4.80 (m, 1H), 3.25-3.30 (m, 1H), 3.15-3.20 (m, 1H), 2.88-2.96 (m, 1H), 1.50 (s, 9H), 1.22 (t, J = 7.6 Hz, 6H). |
| 36 | 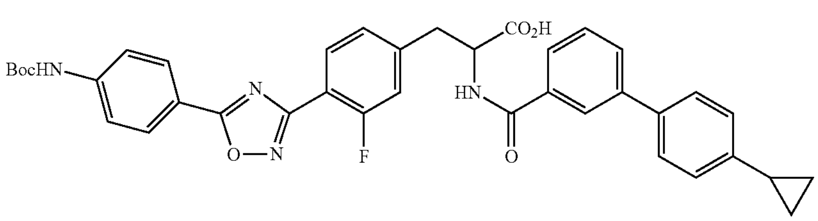 [SMILES: CC(C)(C)OC(=O)Nc1ccc(-c2nc(-c3ccc(CC(NC(=O)c4cccc(-c5ccc(C6CC6)cc5)c4)C(=O)O)cc3F)no2)cc1] | A1 | 661 (M − H) |

TABLE 1A-continued

Exemplary Compounds Showing Agonist Activity Only

| Number | Structure | Method | MS/HNMR |
|---|---|---|---|
| 37 | 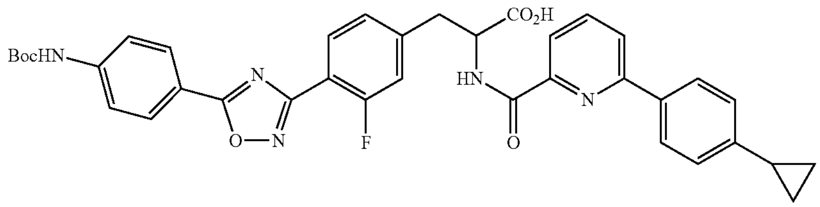 [SMILES: CC(C)(C)OC(=O)Nc1ccc(-c2nc(-c3ccc(CC(NC(=O)c4cccc(-c5ccc(C6CC6)cc5)n4)C(=O)O)cc3F)no2)cc1] | A1 | 662 (M − H) |
| 38 | 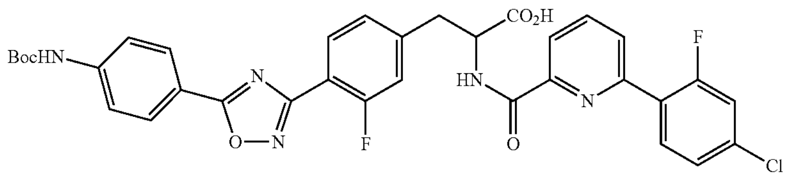 [SMILES: CC(C)(C)OC(=O)Nc1ccc(-c2nc(-c3ccc(CC(NC(=O)c4cccc(-c5ccc(Cl)cc5F)n4)C(=O)O)cc3F)no2)cc1] | A1 | 675 (M − H) |
| 39 | 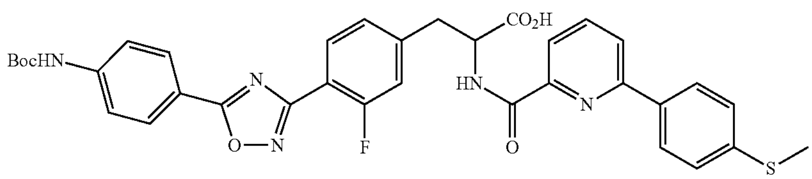 [SMILES: CSc1ccc(-c2cccc(C(=O)NC(Cc3ccc(-c4noc(-c5ccc(NC(=O)OC(C)(C)C)cc5)n4)c(F)c3)C(=O)O)n2)cc1] | A1 | 668 (M − H) |
| 40 | 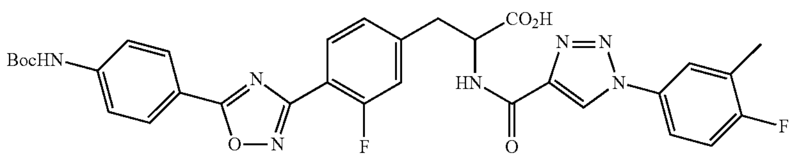 [SMILES: Cc1cc(-n2cc(C(=O)NC(Cc3ccc(-c4noc(-c5ccc(NC(=O)OC(C)(C)C)cc5)n4)c(F)c3)C(=O)O)nn2)ccc1F] | A5 | 644 (M − H) 8.82 (s, 1H), 8.02-8.09 (m, 3H), 8.06 (d, J = 8.8 Hz, 2H), 7.77 (d, J = 8.8 Hz, 1H), 7.64-7.70 (m, 3H), 7.21-7.32 (m, 3H), 4.99-5.03 (m, 1H), 3.46-3.51 (m, 1H), 3.25-3.31 (m, 1H) 2.36 (s, 3H), 1.54 (s, 9H). |
| 41 | 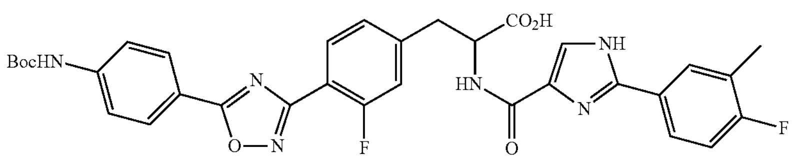 [SMILES: Cc1cc(-c2nc(C(=O)NC(Cc3ccc(-c4noc(-c5ccc(NC(=O)OC(C)(C)C)cc5)n4)c(F)c3)C(=O)O)c[nH]2)ccc1F] | A2 | 643 (M − H) 13.0 (brs, 1H), 9.92 (s, 1H), 8.06 (d, J = 8.8 Hz, 2H), 7.99 (t, J = 8.0 Hz, 1H), 7.93 (d, J = 7.6 Hz, 1H), 7.83 (brs, 1H), 7.70-7.76 (m, 3H), 7.32-7.39 (m, 2H), 7.26 (t, J = 8.8 Hz, 1H), 4.76-4.83 (m, 1H), 3.16-3.26 (m, 2H), 2.28 (s, 3H), 1.49 (s, 9H). |
| 42 | 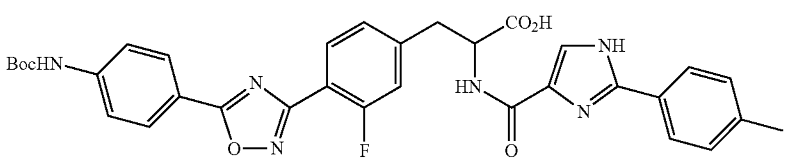 [SMILES: Cc1ccc(-c2nc(C(=O)NC(Cc3ccc(-c4noc(-c5ccc(NC(=O)OC(C)(C)C)cc5)n4)c(F)c3)C(=O)O)c[nH]2)cc1] | A2 | 625 (M − H) 12.9 (brs, 1H), 9.91 (s, 1H), 8.06 (d, J = 8.8 Hz, 2H), 7.99 (t, J = 8.0 Hz, 1H), 7.88 (d, J = 8.0 Hz, 2H), 7.70-7.74 (m, 3H), 7.37 (d, J = 12.0 Hz, 1H), 7.33 (d, J = 8.0 Hz, 1H), 7.28 (d, J = 8.0 Hz, 1H), 4.77-4.82 (m, 1H), 3.16-3.26 (m, 2H), 2.33 (s, 3H), 1.50 (s, 9H) |

TABLE 1A-continued
Exemplary Compounds Showing Agonist Activity Only
| Number | Structure | Method | MS/HNMR |
|---|---|---|---|
| 43 | 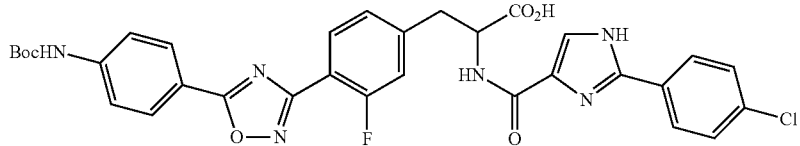 [SMILES: CC(C)(C)OC(=O)Nc1ccc(-c2nc(-c3ccc(CC(NC(=O)c4c[nH]c(-c5ccc(Cl)cc5)n4)C(=O)O)cc3F)no2)cc1] | A2 | 645 (M − H) |
| 44 | 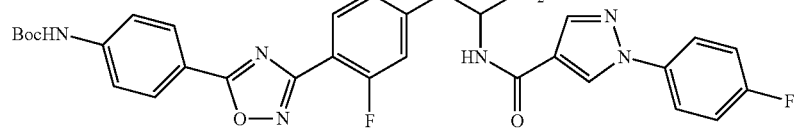 | A5 | 629 (M − H) |
| 45 | 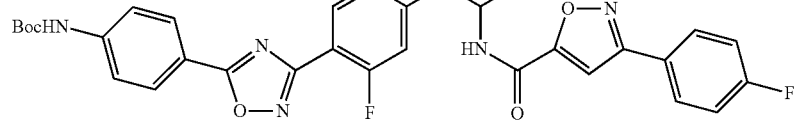 | A5 | 632 (M + H) |
| 46 | 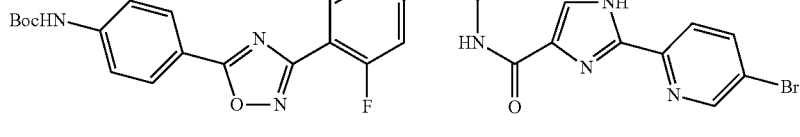 | A2 | 690 (M − H) 9.93 (s, 1H), 8.76 (d, J = 2.0 Hz, 1H), 8.27 (d, J = 8.4 Hz, 1H), 8.22 (dd, J = 2.4 Hz, 2.4 Hz, 1H), 8.05-8.07 (m, 3H), 7.98 (t, J = 8.0 Hz, 1H), 7.69-7.73 (m, 3H), 7.38 (d, J = 12.4 Hz, 1H), 7.33 (d, J = 8.0 Hz, 1H), 4.75-4.81 (m, 1H), 3.16-3.26 (m, 2H), 1.49 (s, 9H). |
| 47 | 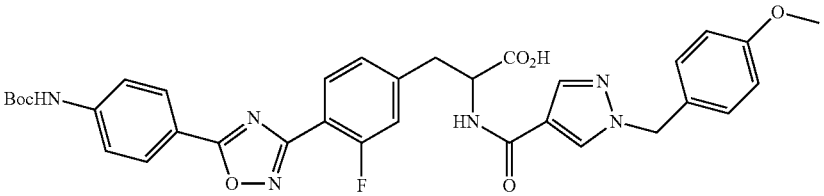 [SMILES: COc1ccc(Cn2cc(C(=O)NC(Cc3ccc(-c4noc(-c5ccc(NC(=O)OC(C)(C)C)cc5)n4)c(F)c3)C(=O)O)cn2)cc1] | A5 | 655 (M − H) |
| 48 | 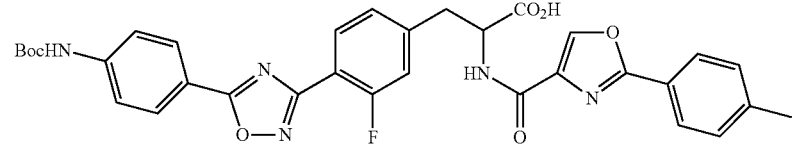 [SMILES: Cc1ccc(-c2nc(C(=O)NC(Cc3ccc(-c4noc(-c5ccc(NC(=O)OC(C)(C)C)cc5)n4)c(F)c3)C(=O)O)co2)cc1] | A2 | 626 (M − H) |
| 49 | 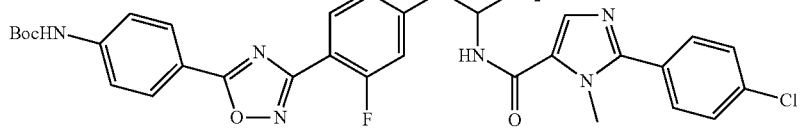 | A2 | 659 (M − H) 9.93 (s, 1H), 8.06 (d, J = 8.8 Hz, 2H), 7.95 (t, J = 8.0 Hz, 1H), 7.70-7.79 (m, 6H), 7.56 (d, J = 8.8 Hz, 2H), 7.27-7.33 (m, 2H), 4.63-4.72 (m, 1H), 3.76 (s, 3H) 3.16-3.26 (m, 2H), 1.50 (s, 9H) |

TABLE 1A-continued
Exemplary Compounds Showing Agonist Activity Only
| Number | Structure | Method | MS/HNMR |
|---|---|---|---|
| 50 | 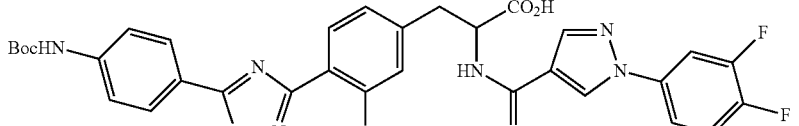 | A5 | 647 (M − H) |
| 51 | 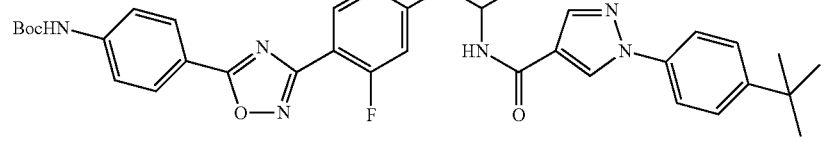 | A5 | 667 (M − H) 9.94 (s, 1H), 8.88 (s, 1H), 8.57 (d, J = 8.0 Hz, 1H), 8.15 (s, 1H), 8.07 (d, J = 8.8 Hz, 2H), 8.00 (t, J = 8.0 Hz, 1H), 7.71-7.76 (m, 4H), 7.53 (d, J = 8.4 Hz, 2H), 7.42 (d, J = 11.6 Hz, 1H), 7.37 (d, J = 7.6 Hz, 1H), 4.75-4.77 (m, 1H), 3.25-3.30 (m, 1H), 3.10-3.16 (m, 1H), 1.51 (s, 9H), 1.31 (s, 9H) |
| 52 | 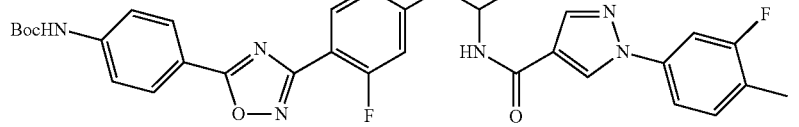 | A5 | 643 (M − H) |
| 53 | 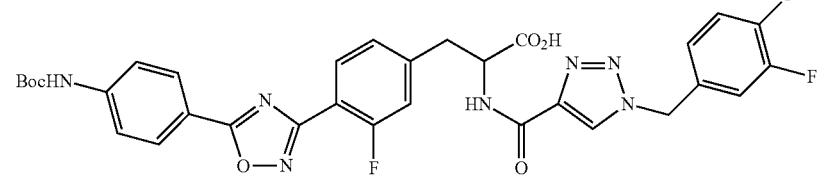 | A5 | 662 (M − H) 8.37 (s, 1H), 8.10 (d, J = 8.8 Hz, 2H), 8.03 (t, J = 8.0 Hz, 1H), 7.66 (d, J = 8.8 Hz, 2H), 7.23-7.34 (m, 4H), 7.13-7.16 (m, 1H), 5.62 (s, 2H), 4.91-4.98 (m, 1H), 3.43-3.48 (m, 1H), 3.21-3.28 (m, 1H), 1.55 (s, 9H) |
| 54 | 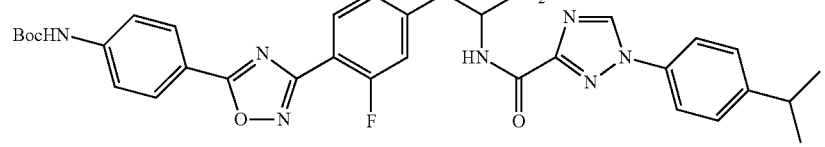 | A5 | 654 (M − H) 9.94 (s, 1H), 8.36 (s, 1H), 8.84 (d, J = 8.8 Hz, 1H), 8.07 (d, J = 8.8 Hz, 2H), 7.99 (t, J = 8.0 Hz, 1H), 7.80 (d, J = 8.4 Hz, 2H), 7.71 (d, J = 8.8 Hz, 2H), 7.45 (d, J = 8.4 Hz, 2H), 7.35-7.43 (m, 2H), 4.75-4.83 (m, 1H), 3.19-3.26 (m, 2H), 2.93-3.10 (m, 1H), 1.50 (s, 9H), 1.23 (d, J = 7.2 Hz, 6H). |
| 55 | 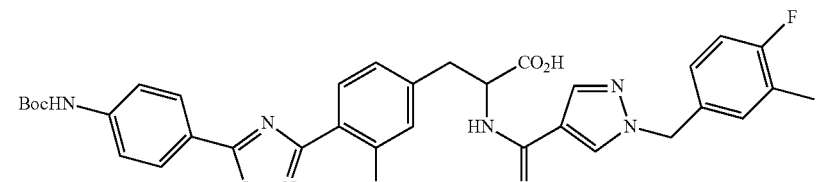 | A5 | 657 (M − H) |

TABLE 1A-continued

Exemplary Compounds Showing Agonist Activity Only

| Number | Structure | Method | MS/HNMR |
|---|---|---|---|
| 56 | 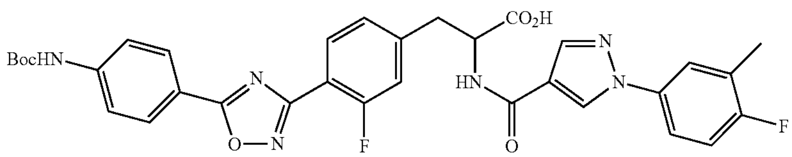 [SMILES: Cc1cc(-n2cc(C(=O)NC(Cc3ccc(-c4noc(-c5ccc(NC(=O)OC(C)(C)C)cc5)n4)c(F)c3)C(=O)O)cn2)ccc1F] | A5 | 643 (M − H) |
| 57 | 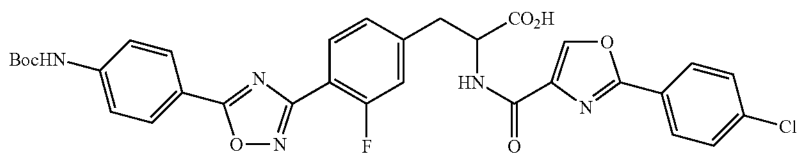 [SMILES: CC(C)(C)OC(=O)Nc1ccc(-c2nc(-c3ccc(CC(NC(=O)c4coc(-c5ccc(Cl)cc5)n4)C(=O)O)cc3F)no2)cc1] | A5 | 647 (M − H) |
| 58 | 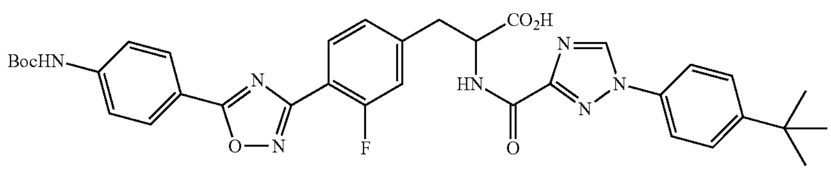 [SMILES: CC(C)(C)OC(=O)Nc1ccc(-c2nc(-c3ccc(CC(NC(=O)c4ncn(-c5ccc(C(C)(C)C)cc5)n4)C(=O)O)cc3F)no2)cc1] | A5 | 669 (M − H) |
| 59 | 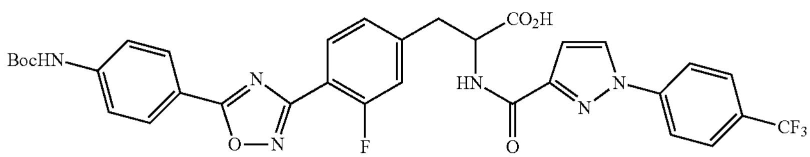 [SMILES: CC(C)(C)OC(=O)Nc1ccc(-c2nc(-c3ccc(CC(NC(=O)c4ccn(-c5ccc(C(F)(F)F)cc5)n4)C(=O)O)cc3F)no2)cc1] | A5 | 679 (M − H) 9.94 (s, 1H), 8.71 (s, 1H), 8.49 (s, 1H), 8.04-8.10 (m, 5H), 7.88-7.90 (m, 3H), 7.70 (d, J = 8.8 Hz, 2H), 7.15-7.22 (m, 2H), 6.93 (s, 1H), 4.19-4.21 (m, 1H), 3.21-3.27 (m, 2H), 1.49 (s, 9H) |
| 60 | 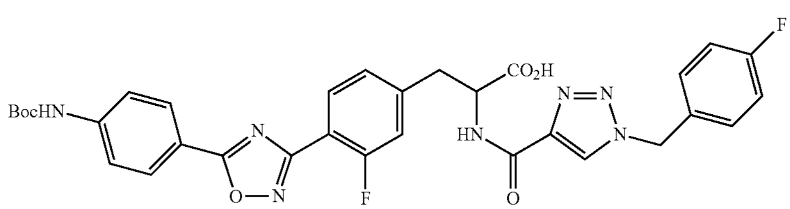 [SMILES: CC(C)(C)OC(=O)Nc1ccc(-c2nc(-c3ccc(CC(NC(=O)c4cn(Cc5ccc(F)cc5)nn4)C(=O)O)cc3F)no2)cc1] | A5 | 644 (M − H) 9.91 (s, 1H), 8.80 (d, J = 8.4 Hz, 1H), 8.04 (d, J = 8.8 Hz, 2H), 7.98 (d, J = 7.6 Hz, 2H), 7.68-7.73 (m, 4H), 7.46 (d, J = 12 Hz, 1H), 7.36-7.40 (m, 2H), 7.24 (d, J = 7.6 Hz, 1H), 7.18 (d, J = 3.2 Hz, 1H), 7.08 (d, J = 3.6 Hz, 1H), 4.69-4.75 (m, 1H), 3.33 (s, 2H), 3.19-3.26 (m, 2H), 2.91-2.97 (m, 1H), 1.48 (s, 9H) |
| 61 | 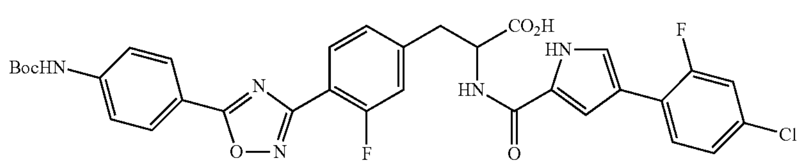 [SMILES: CC(C)(C)OC(=O)Nc1ccc(-c2nc(-c3ccc(CC(NC(=O)c4cc(-c5ccc(Cl)cc5F)c[nH]4)C(=O)O)cc3F)no2)cc1] | A5 | 663 (M − H) |
| 62 | 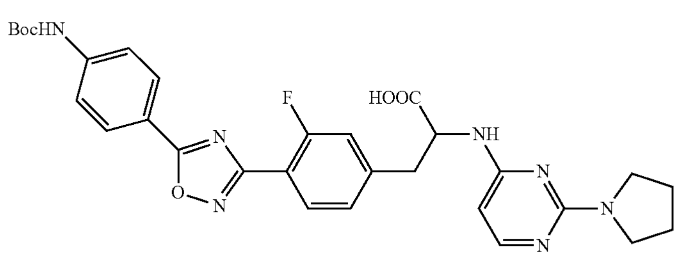 [SMILES: CC(C)(C)OC(=O)Nc1ccc(-c2nc(-c3ccc(CC(Nc4ccnc(N5CCCC5)n4)C(=O)O)cc3F)no2)cc1] | A9 | 663 (M − H) 1.55 (s, 9H), 1.63 (m, 4H), 1.70 (m, 2H), 3.04-3.10 (m, 1H), 3.44-3.48 (m, 1H), 3.63 (m, 4H), 4.57 (m, 1H), 6.11 (d, 1H), 7.24-7.28 (m, 2H), 7.45 (d, 1H), 7.67 (d, 2H), 8.00 (t, 1H), 8.10 (d, 2H). |

TABLE 1A-continued

Exemplary Compounds Showing Agonist Activity Only

| Number | Structure | Method | MS/HNMR |
|---|---|---|---|
| 63 | 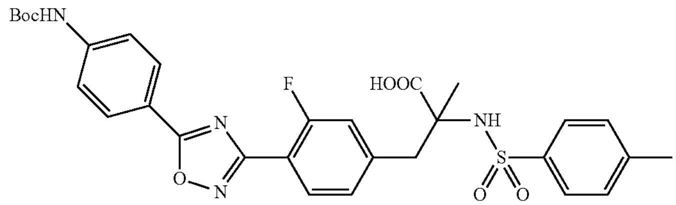 [SMILES: Cc1ccc(S(=O)(=O)NC(C)(Cc2ccc(-c3noc(-c4ccc(NC(=O)OC(C)(C)C)cc4)n3)c(F)c2)C(=O)O)cc1] | A6 | 609 (M − H)− |
| 64 | 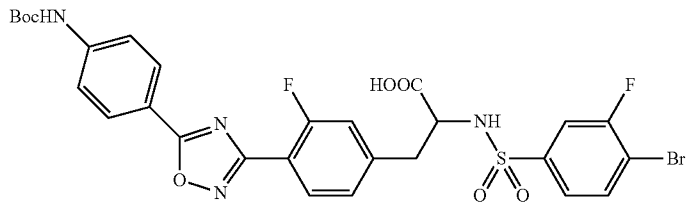 [SMILES: CC(C)(C)OC(=O)Nc1ccc(-c2nc(-c3ccc(CC(NS(=O)(=O)c4ccc(Br)c(F)c4)C(=O)O)cc3F)no2)cc1] | A6 | 677 (M − H)− |
| 65 | 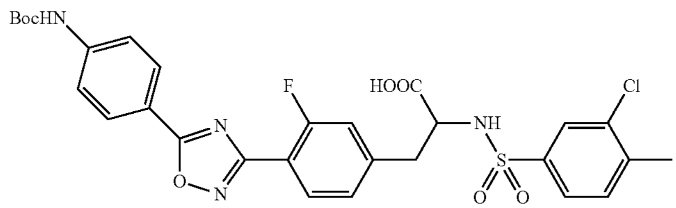 [SMILES: Cc1ccc(S(=O)(=O)NC(Cc2ccc(-c3noc(-c4ccc(NC(=O)OC(C)(C)C)cc4)n3)c(F)c2)C(=O)O)cc1Cl] | A6 | 630 (M − H)− |
| 66 | 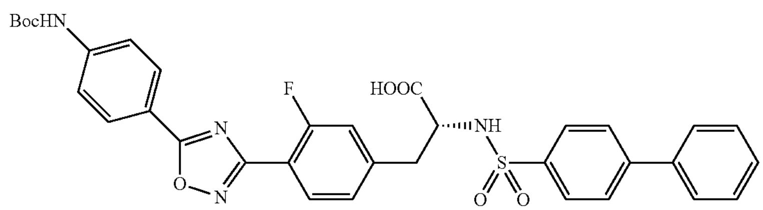 [SMILES: CC(C)(C)OC(=O)Nc1ccc(-c2nc(-c3ccc(C[C@@H](NS(=O)(=O)c4ccc(-c5ccccc5)cc4)C(=O)O)cc3F)no2)cc1] | A6 | 657 (M − H)− |
| 67 | 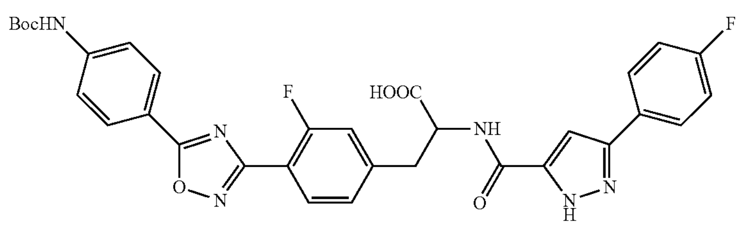 [SMILES: CC(C)(C)OC(=O)Nc1ccc(-c2nc(-c3ccc(CC(NC(=O)c4cc(-c5ccc(F)cc5)n[nH]4)C(=O)O)cc3F)no2)cc1] | A1 | 629 (M − H)− |
| 68 | 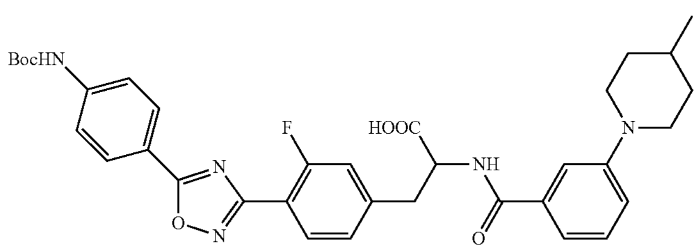 [SMILES: CC1CCN(c2cccc(C(=O)NC(Cc3ccc(-c4noc(-c5ccc(NC(=O)OC(C)(C)C)cc5)n4)c(F)c3)C(=O)O)c2)CC1] | A4 | 642 (M − H)− |
| 69 | 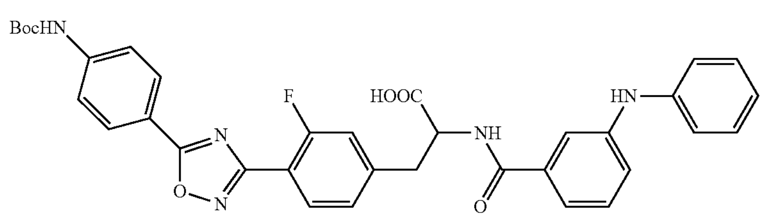 [SMILES: CC(C)(C)OC(=O)Nc1ccc(-c2nc(-c3ccc(CC(NC(=O)c4cccc(Nc5ccccc5)c4)C(=O)O)cc3F)no2)cc1] | A4 | 636 (M − H)− |

TABLE 1A-continued

Exemplary Compounds Showing Agonist Activity Only

| Number | Structure | Method | MS/HNMR |
|---|---|---|---|
| 70 | 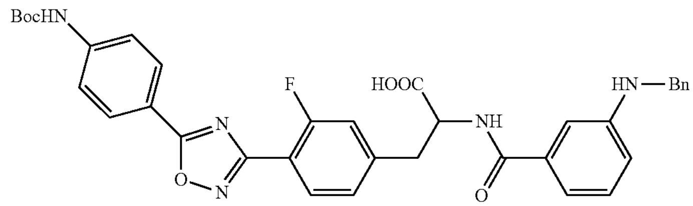 [SMILES: CC(C)(C)OC(=O)Nc1ccc(-c2nc(-c3ccc(CC(NC(=O)c4cccc(NCc5ccccc5)c4)C(=O)O)cc3F)no2)cc1] | A4 | 650 (M − H)− |
| 71 | 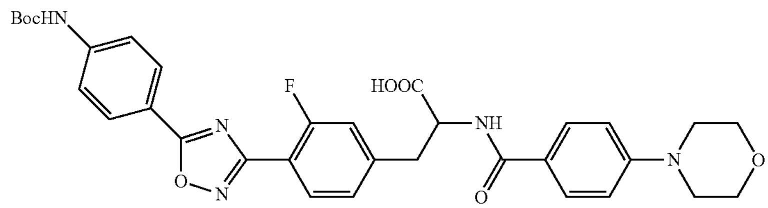 [SMILES: CC(C)(C)OC(=O)Nc1ccc(-c2nc(-c3ccc(CC(NC(=O)c4ccc(N5CCOCC5)cc4)C(=O)O)cc3F)no2)cc1] | A4 | 630 (M − H)− |
| 72 | 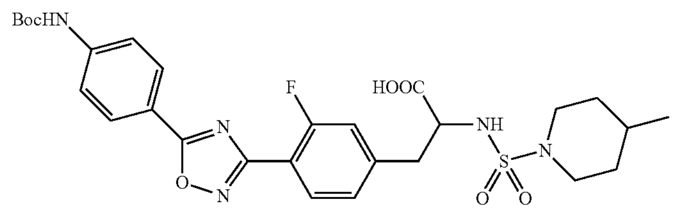 [SMILES: CC1CCN(S(=O)(=O)NC(Cc2ccc(-c3noc(-c4ccc(NC(=O)OC(C)(C)C)cc4)n3)c(F)c2)C(=O)O)CC1] | A7 | 604 (M + H)+ |
| 73 | 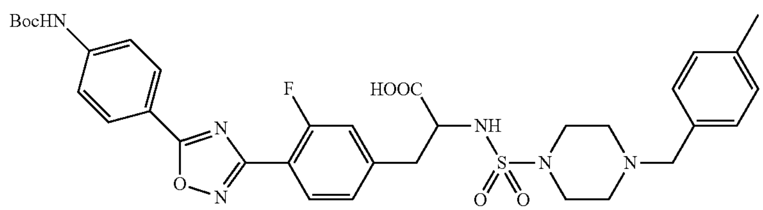 [SMILES: Cc1ccc(CN2CCN(S(=O)(=O)NC(Cc3ccc(-c4noc(-c5ccc(NC(=O)OC(C)(C)C)cc5)n4)c(F)c3)C(=O)O)CC2)cc1] | A7 | 695 (M + H)+. 1.51 (s, 9H), 2.51 (s, 3H), 2.91-3.13 (m, 10H), 3.97-4.19 (m, 3H), 7.15-7.25 (d, 4H), 7.38 (dd, J = 6.3 Hz, 2H), 7.75 (d, J = 6.3 Hz, 2H), 8.12 (m, 3H), 8.27 (s, 1H), 9.96 (s, 1H) |
| 74 | 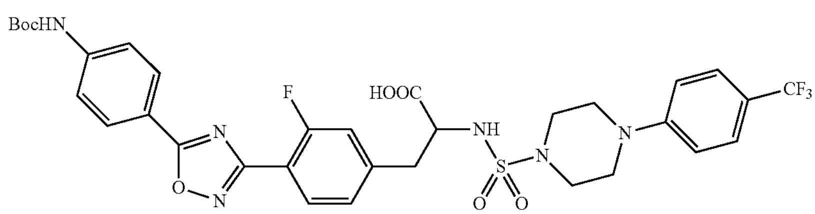 [SMILES: CC(C)(C)OC(=O)Nc1ccc(-c2nc(-c3ccc(CC(NS(=O)(=O)N4CCN(c5ccc(C(F)(F)F)cc5)CC4)C(=O)O)cc3F)no2)cc1] | A7 | 735 (M + H)+ |
| 75 | 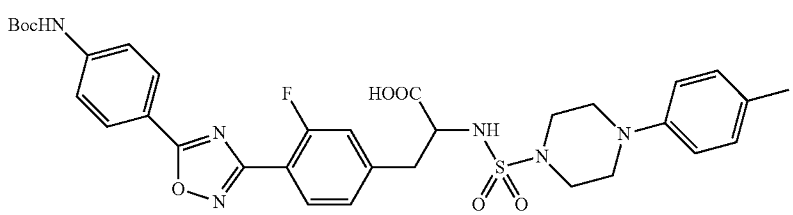 [SMILES: Cc1ccc(N2CCN(S(=O)(=O)NC(Cc3ccc(-c4noc(-c5ccc(NC(=O)OC(C)(C)C)cc5)n4)c(F)c3)C(=O)O)CC2)cc1] | A7 | 681 (M + H)+ 1.51 (s, 9H), 2.05 (s, 3H), 2.82-2.85 (m, 8H), 3.18-3.19 (m, 2H), 3.47 (s, 4H), 3.92 (m, 1H), 6.65 (d, 2H), 6.83 (d, 2H), 7.38-7.44 (m, 2H), 7.74 (d, 2H), 7.90-8.06 (m, 4H), 9.94 (s, 1H) |
| 76 | 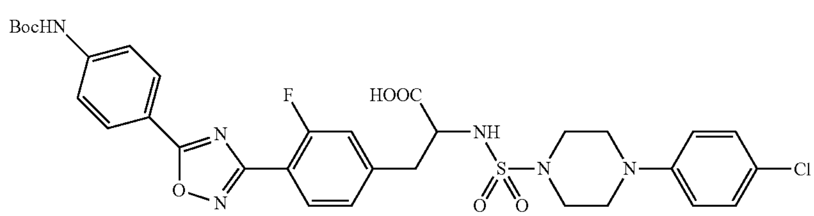 [SMILES: CC(C)(C)OC(=O)Nc1ccc(-c2nc(-c3ccc(CC(NS(=O)(=O)N4CCN(c5ccc(Cl)cc5)CC4)C(=O)O)cc3F)no2)cc1] | A7 | 700 (M + H)+ |

TABLE 1A-continued

Exemplary Compounds Showing Agonist Activity Only

| Number | Structure | Method | MS/HNMR |
|---|---|---|---|
| 77 | 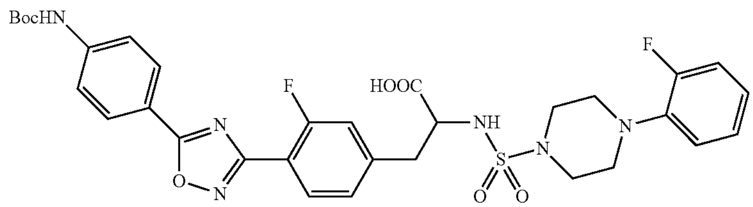 [SMILES: CC(C)(C)OC(=O)Nc1ccc(-c2nc(-c3ccc(CC(NS(=O)(=O)N4CCN(c5ccccc5F)CC4)C(=O)O)cc3F)no2)cc1] | A7 | 685 (M + H)+ 1.51 (s, 9H), 2.88-2.90 (m, 9H), 3.14-3.15 (m, 1H), 3.92 (m, 1H), 6.87-6.99 (m, 4H), 7.38-7.43 (m, 2H), 7.73 (d, 2H), 7.75-7.80 (m, 1H), 8.04-8.06 (m, 3H), 9.94 (s, 1H). |
| 78 | 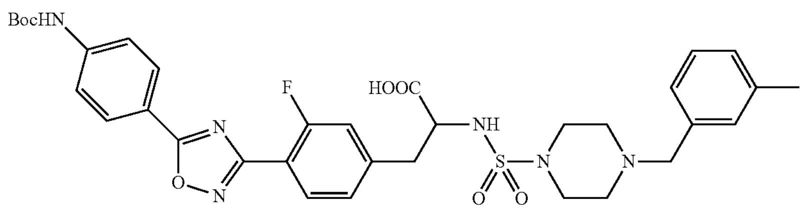 [SMILES: Cc1cccc(CN2CCN(S(=O)(=O)NC(Cc3ccc(-c4noc(-c5ccc(NC(=O)OC(C)(C)C)cc5)n4)c(F)c3)C(=O)O)CC2)c1] | A7 | 595 (M + H)+ |
| 79 | 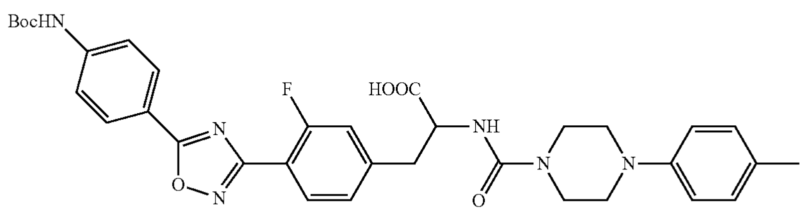 [SMILES: Cc1ccc(N2CCN(C(=O)NC(Cc3ccc(-c4noc(-c5ccc(NC(=O)OC(C)(C)C)cc5)n4)c(F)c3)C(=O)O)CC2)cc1] | A8 | 643 (M − H)− |
| 80 | 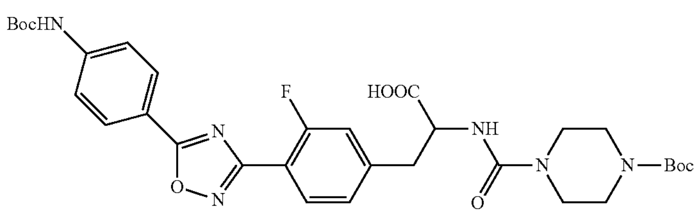 [SMILES: CC(C)(C)OC(=O)Nc1ccc(-c2nc(-c3ccc(CC(NC(=O)N4CCN(C(=O)OC(C)(C)C)CC4)C(=O)O)cc3F)no2)cc1] | A8 | 653 (M − H)− |
| 81 | 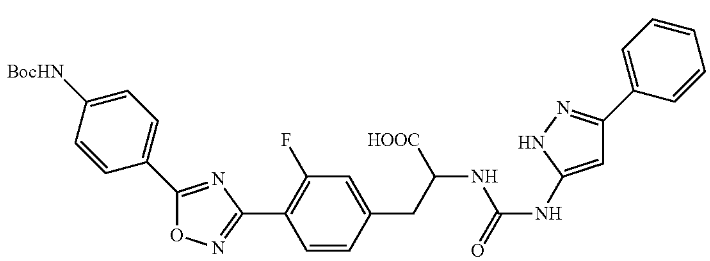 [SMILES: CC(C)(C)OC(=O)Nc1ccc(-c2nc(-c3ccc(CC(NC(=O)Nc4cc(-c5ccccc5)n[nH]4)C(=O)O)cc3F)no2)cc1] | A8 | 628 (M + H)+ |
| 82 | 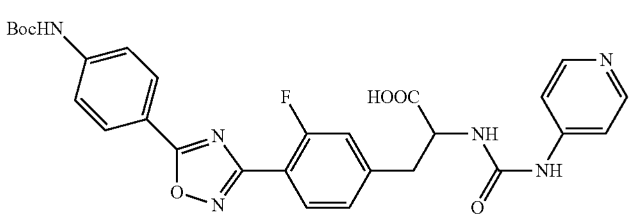 [SMILES: CC(C)(C)OC(=O)Nc1ccc(-c2nc(-c3ccc(CC(NC(=O)Nc4ccncc4)C(=O)O)cc3F)no2)cc1] | A8 | 561 (M − H)− |

TABLE 1A-continued

Exemplary Compounds Showing Agonist Activity Only

| Number | Structure | Method | MS/HNMR |
|---|---|---|---|
| 83 | 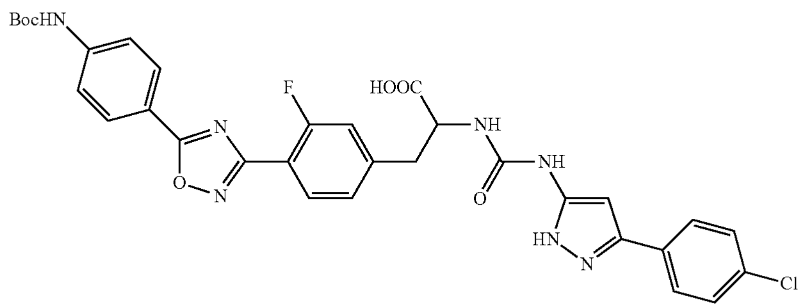 [SMILES: CC(C)(C)OC(=O)Nc1ccc(-c2nc(-c3ccc(CC(NC(=O)Nc4cc(-c5ccc(Cl)cc5)n[nH]4)C(=O)O)cc3F)no2)cc1] | A8 | 662 (M + H)+ |
| 84 | 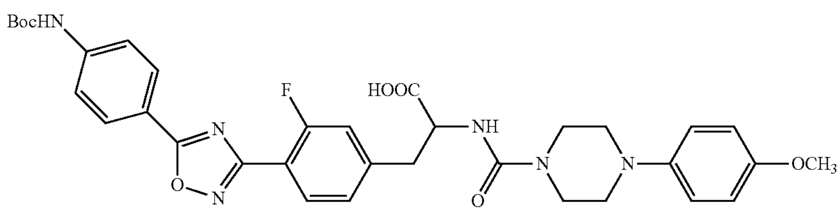 [SMILES: COc1ccc(N2CCN(C(=O)NC(Cc3ccc(-c4noc(-c5ccc(NC(=O)OC(C)(C)C)cc5)n4)c(F)c3)C(=O)O)CC2)cc1] | A8 | 675 (M + H)+ |
| 85 | 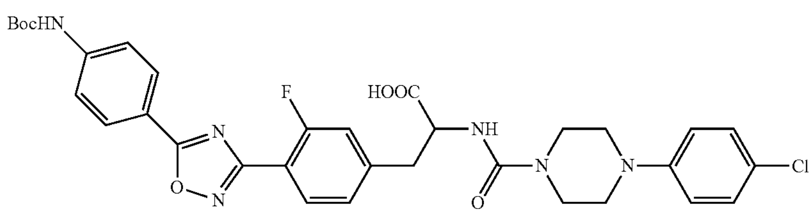 [SMILES: CC(C)(C)OC(=O)Nc1ccc(-c2nc(-c3ccc(CC(NC(=O)N4CCN(c5ccc(Cl)cc5)CC4)C(=O)O)cc3F)no2)cc1] | A8 | 663 (M − H)− |
| 86 | 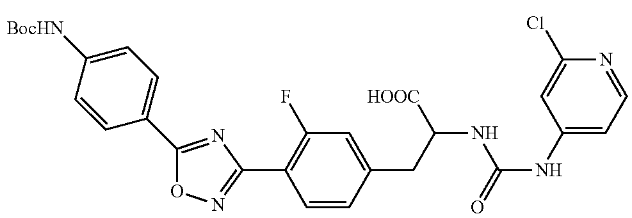 [SMILES: CC(C)(C)OC(=O)Nc1ccc(-c2nc(-c3ccc(CC(NC(=O)Nc4ccnc(Cl)c4)C(=O)O)cc3F)no2)cc1] | A8 | 595 (M − H)− |
| 87 | 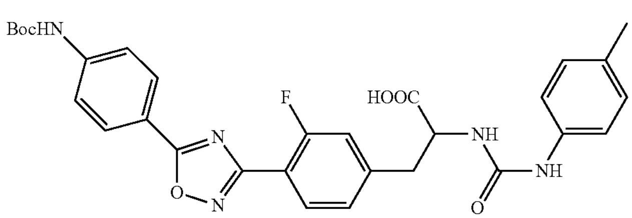 [SMILES: Cc1ccc(NC(=O)NC(Cc2ccc(-c3noc(-c4ccc(NC(=O)OC(C)(C)C)cc4)n3)c(F)c2)C(=O)O)cc1] | A8 | 574 (M − H)− |
| 88 | 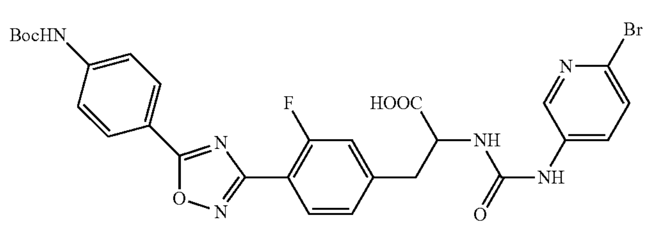 [SMILES: CC(C)(C)OC(=O)Nc1ccc(-c2nc(-c3ccc(CC(NC(=O)Nc4ccc(Br)nc4)C(=O)O)cc3F)no2)cc1] | A8 | 639 (M − H)− |

TABLE 1A-continued
Exemplary Compounds Showing Agonist Activity Only
| Number | Structure | Method | MS/HNMR |
|---|---|---|---|
| 89 | 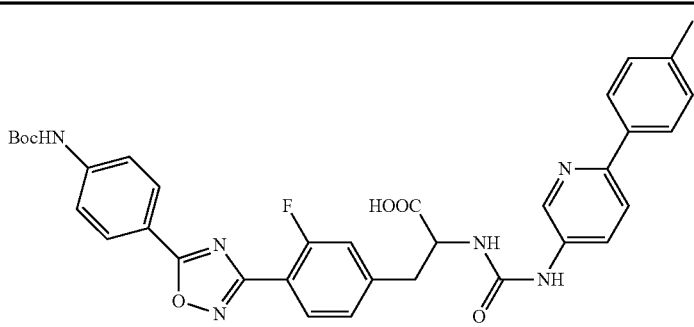 | A8 | 651 (M – H)– |
| 90 | 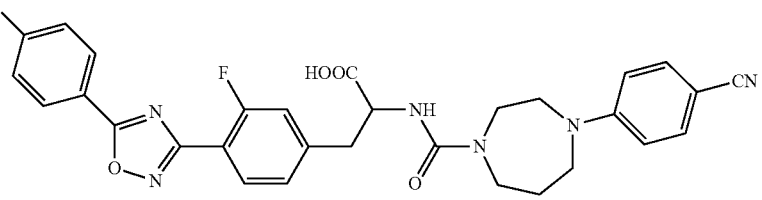 | A8 | 668 (M – H)– |
| 91 | 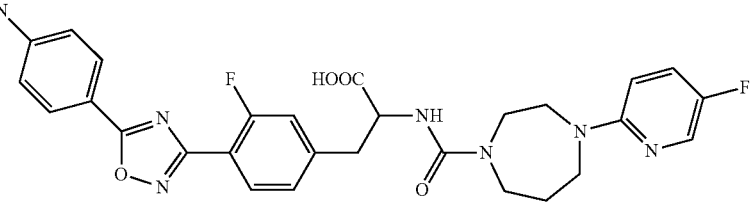 | A8 | 662 (M – H)– |
| 92 | 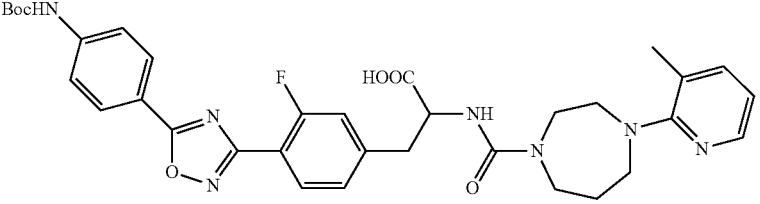 [SMILES: Cc1cccnc1N1CCCN(C(=O)NC(Cc2ccc(-c3noc(-c4ccc(NC(=O)OC(C)(C)C)cc4)n3)c(F)c2)C(=O)O)CC1] | A8 | 657 (M – H)– |
| 93 | 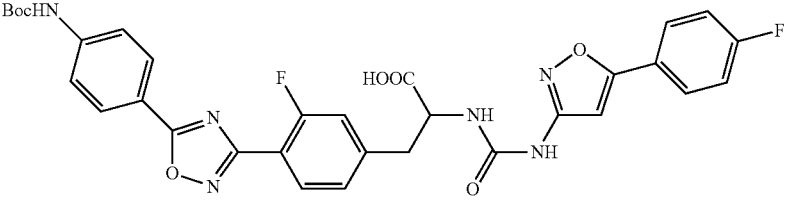 [SMILES: CC(C)(C)OC(=O)Nc1ccc(-c2nc(-c3ccc(CC(NC(=O)Nc4cc(-c5ccc(F)cc5)on4)C(=O)O)cc3F)no2)cc1] | A8 | 645 (M – H)– |
| 94 | 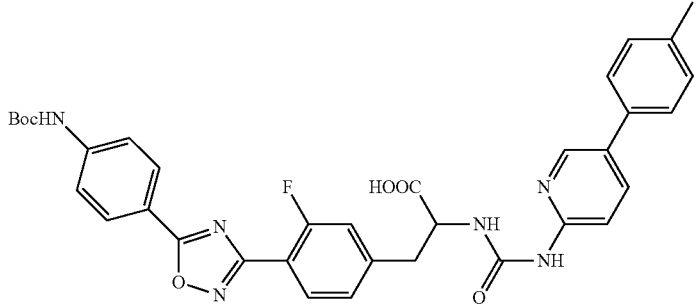 [SMILES: Cc1ccc(-c2ccc(NC(=O)NC(Cc3ccc(-c4noc(-c5ccc(NC(=O)OC(C)(C)C)cc5)n4)c(F)c3)C(=O)O)nc2)cc1] | A8 | 651 (M – H)– |

TABLE 1A-continued

Exemplary Compounds Showing Agonist Activity Only

| Number | Structure | Method | MS/HNMR |
|---|---|---|---|
| 95 | 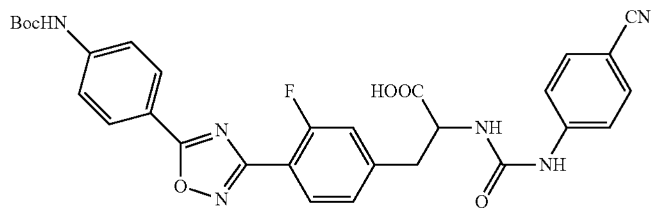 [SMILES: CC(C)(C)OC(=O)Nc1ccc(-c2nc(-c3ccc(CC(NC(=O)Nc4ccc(C#N)cc4)C(=O)O)cc3F)no2)cc1] | A8 | 585 (M − H)− |
| 96 | 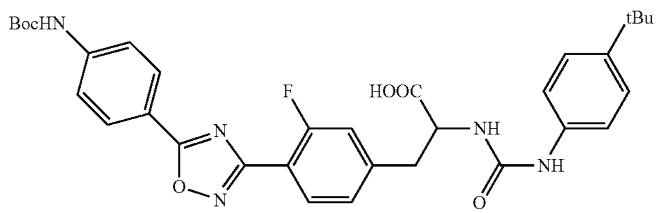 [SMILES: CC(C)(C)OC(=O)Nc1ccc(-c2nc(-c3ccc(CC(NC(=O)Nc4ccc(C(C)(C)C)cc4)C(=O)O)cc3F)no2)cc1] | A8 | 616 (M − H)− |
| 97 | 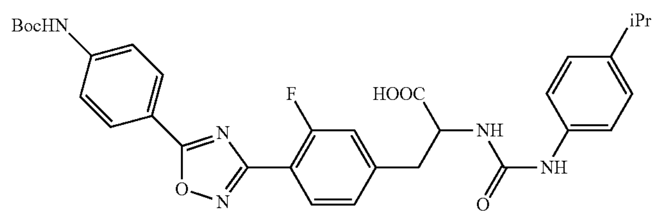 | A8 | 602 (M − H)− |
| 98 | 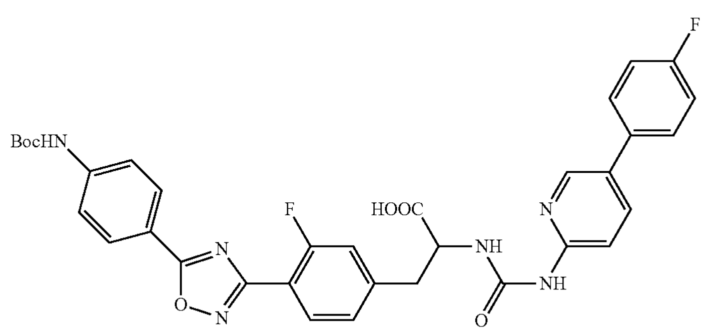 [SMILES: CC(C)(C)OC(=O)Nc1ccc(-c2nc(-c3ccc(CC(NC(=O)Nc4ccc(-c5ccc(F)cc5)cn4)C(=O)O)cc3F)no2)cc1] | A8 | 655 (M − H)− |
| 99 | 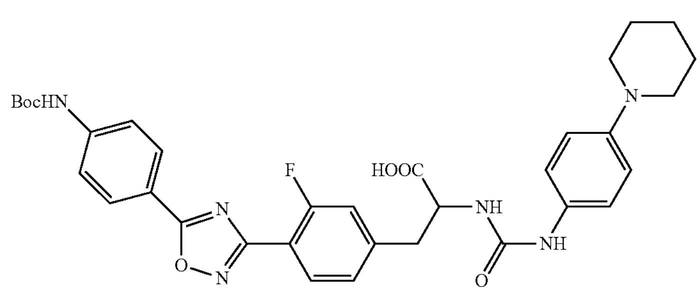 [SMILES: CC(C)(C)OC(=O)Nc1ccc(-c2nc(-c3ccc(CC(NC(=O)Nc4ccc(N5CCCCC5)cc4)C(=O)O)cc3F)no2)cc1] | A8 | 643 (M − H)− |

TABLE 1A-continued

Exemplary Compounds Showing Agonist Activity Only

| Number | Structure | Method | MS/HNMR |
|---|---|---|---|
| 100 | 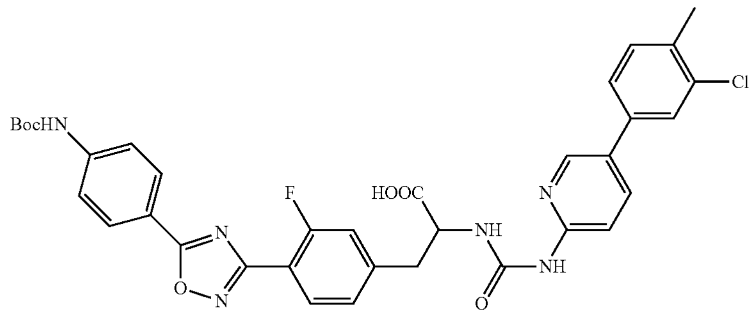 [SMILES: Cc1ccc(-c2ccc(NC(=O)NC(Cc3ccc(-c4noc(-c5ccc(NC(=O)OC(C)(C)C)cc5)n4)c(F)c3)C(=O)O)nc2)cc1Cl] | A8 | 685 (M − H)− |
| 101 | 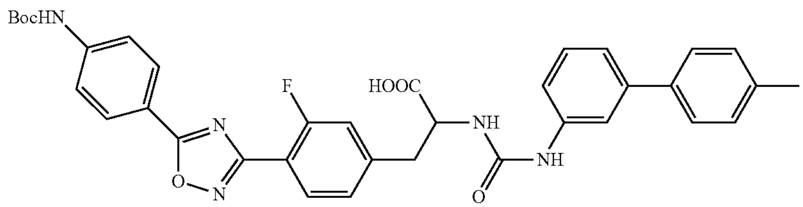 [SMILES: Cc1ccc(-c2cccc(NC(=O)NC(Cc3ccc(-c4noc(-c5ccc(NC(=O)OC(C)(C)C)cc5)n4)c(F)c3)C(=O)O)c2)cc1] | A8 | 650 (M − H)− |
| 102 | 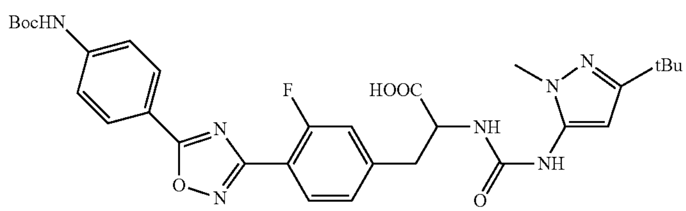 [SMILES: Cn1nc(C(C)(C)C)cc1NC(=O)NC(Cc1ccc(-c2noc(-c3ccc(NC(=O)OC(C)(C)C)cc3)n2)c(F)c1)C(=O)O] | A8 | 622 (M − H)− |
| 103 | 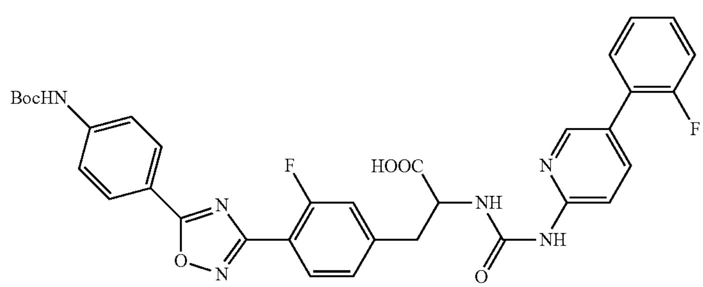 [SMILES: CC(C)(C)OC(=O)Nc1ccc(-c2nc(-c3ccc(CC(NC(=O)Nc4ccc(-c5ccccc5F)cn4)C(=O)O)cc3F)no2)cc1] | A8 | 655 (M − H)− |
| 104 | 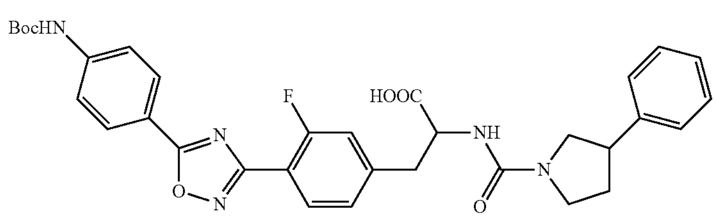 [SMILES: CC(C)(C)OC(=O)Nc1ccc(-c2nc(-c3ccc(CC(NC(=O)N4CCC(c5ccccc5)C4)C(=O)O)cc3F)no2)cc1] | A8 | 614 (M − H)− |

TABLE 1A-continued
Exemplary Compounds Showing Agonist Activity Only
| Number | Structure | Method | MS/HNMR |
|---|---|---|---|
| 105 | 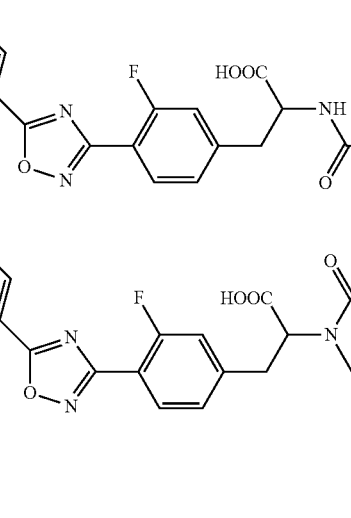 | A8 | 670 (M − H)− |
| 106 | 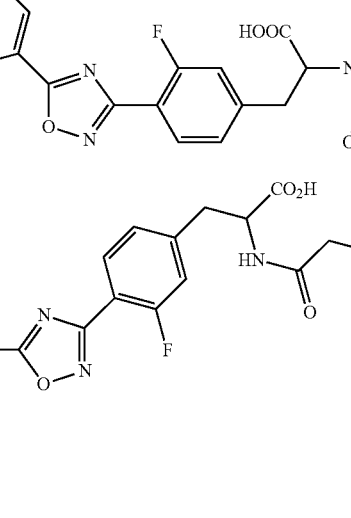 | A8 | 653 (M − H)+ |
| 107 | 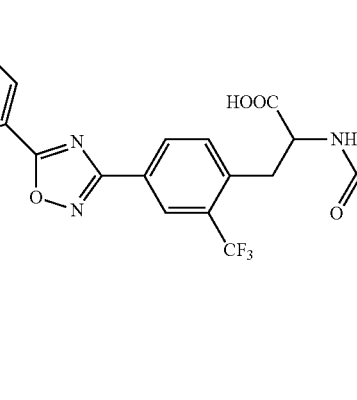 | A8 | 673 (M + H)+ |
| 108 | 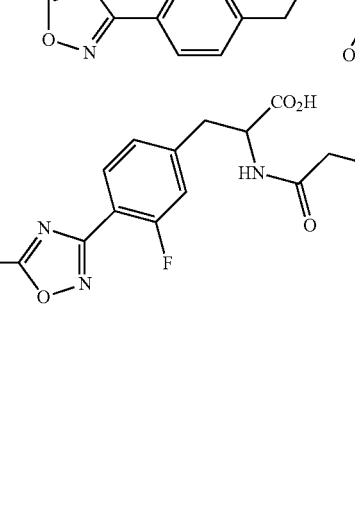 | A | 703 (M − H) 9.93 (s, 1H), 8.51 (d, J = 8.0 Hz, 1H), 8.03 (d, J = 8.8 Hz, 2H), 7.93 (t, J = 8.0 Hz, 1H), 7.72 (d, J = 8.8 Hz, 2H), 7.67 (d, J = 8.0 Hz, 2H) 7.53 (d, J = 8.4 Hz, 2H), 7.47 (d, J = 8.4 Hz, 2H), 7.31 (d, J = 12 Hz, 1H), 7.25 (d, J = 8.0 Hz, 1H), 7.11 (d, J = 8.0 Hz, 2H), 4.58-4.64 (m, 1H), 3.47-3.51 (m, 1H), 3.21-3.26 (m, 1H), 2.92-2.98 (m, 1H), 1.51 (s, 9H) |
| 109 | 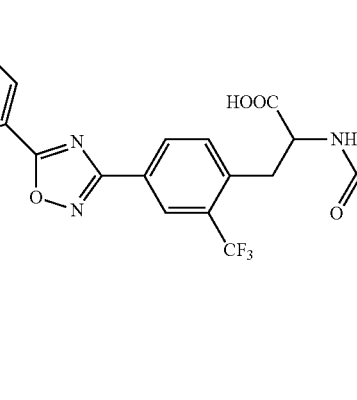 | A15 | 677 (M − H)− |

TABLE 1A-continued

Exemplary Compounds Showing Agonist Activity Only

| Number | Structure | Method | MS/HNMR |
|---|---|---|---|
| 110 | 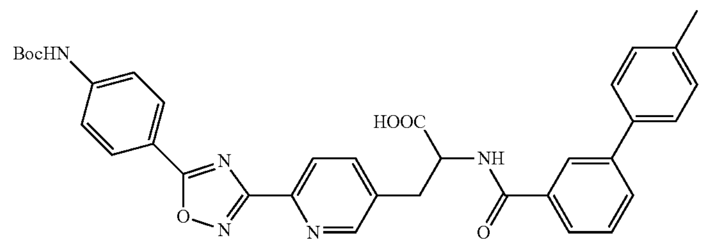 [SMILES: Cc1ccc(-c2cccc(C(=O)NC(Cc3ccc(-c4noc(-c5ccc(NC(=O)OC(C)(C)C)cc5)n4)nc3)C(=O)O)c2)cc1] | A15 | 1.53 (s, 9H), 2.31 (s, 3H), 3.24-3.29 (m, 1H), 3.50-3.55 (m, 1H), 4.86-5.01 (m, 1H), 7.19 (d, 2H), 7.47 (m, 3H), 7.59-7.73 (m, 6H), 7.90-7.96 (m, 2H), 8.06-8.14 (m, 3H), 8.62-8.63 (m, 1H). |
| 111 | 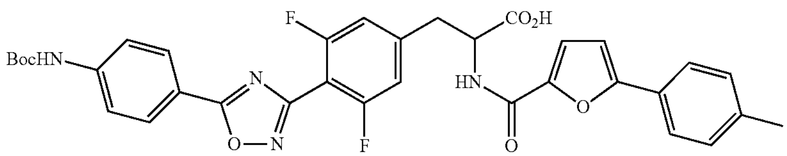 [SMILES: Cc1ccc(-c2ccc(C(=O)NC(Cc3cc(F)c(-c4noc(-c5ccc(NC(=O)OC(C)(C)C)cc5)n4)c(F)c3)C(=O)O)o2)cc1] | A15 | |
| 112 | 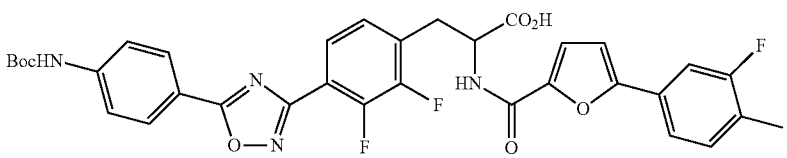 [SMILES: Cc1ccc(-c2ccc(C(=O)NC(Cc3ccc(-c4noc(-c5ccc(NC(=O)OC(C)(C)C)cc5)n4)c(F)c3F)C(=O)O)o2)cc1F] | A15 | 661 (M − H) 9.92 (s, 1H), 8.84 (d, J = 8.8 Hz, 1H), 8.04 (d, J = 8.8 Hz, 2H), 7.75-7.81 (m, 3H), 7.70 (d, J = 8.8 Hz, 2H), 7.40 (t, J = 7.2 Hz, 1H), 7.25 (t, J = 8.8 Hz, 1H), 7.16 (d, J = 3.6 Hz, 1H), 7.02 (d, J = 3.6 Hz, 1H), 4.73-4.79 (m, 1H), 3.16-3.26 (m, 2H), 2.29 (s, 3H), 1.49 (s, 9H) |
| 113 | 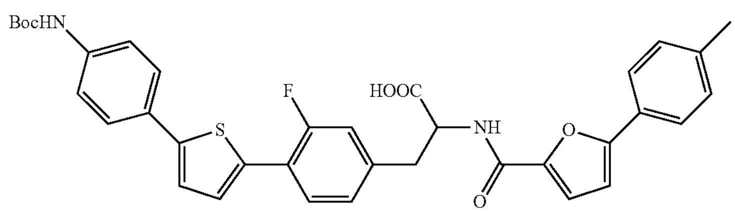 [SMILES: Cc1ccc(-c2ccc(C(=O)NC(Cc3ccc(-c4ccc(-c5ccc(NC(=O)OC(C)(C)C)cc5)s4)c(F)c3)C(=O)O)o2)cc1] | A12 | 641 (M + H)+ |
| 114 | 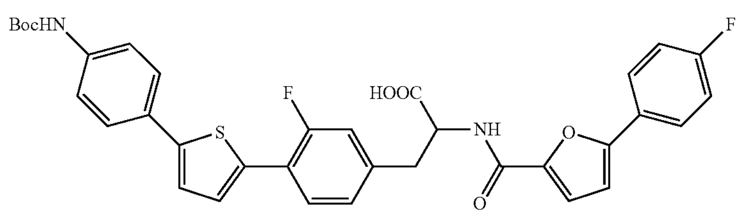 [SMILES: CC(C)(C)OC(=O)Nc1ccc(-c2ccc(-c3ccc(CC(NC(=O)c4ccc(-c5ccc(F)cc5)o4)C(=O)O)cc3F)s2)cc1] | A12 | 641 (M + H)+ |
| 115 | 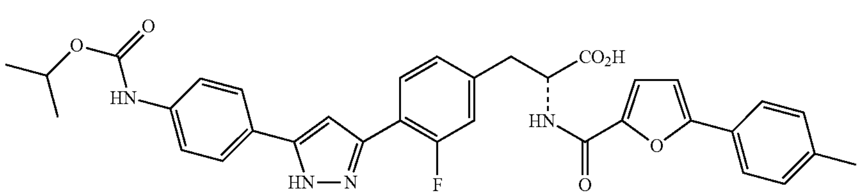 [SMILES: Cc1ccc(-c2ccc(C(=O)N[C@H](Cc3ccc(-c4cc(-c5ccc(NC(=O)OC(C)C)cc5)[nH]n4)c(F)c3)C(=O)O)o2)cc1] | A11 | 609 (M − H) |

TABLE 1A-continued

Exemplary Compounds Showing Agonist Activity Only

| Number | Structure | Method | MS/HNMR |
|---|---|---|---|
| 116 | 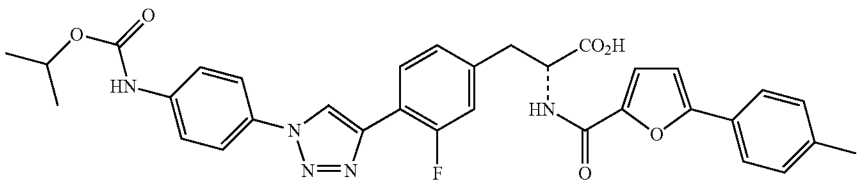 [SMILES: Cc1ccc(-c2ccc(C(=O)N[C@H](Cc3ccc(-c4cn(-c5ccc(NC(=O)OC(C)C)cc5)nn4)c(F)c3)C(=O)O)o2)cc1] | A11 | 610 (M − H) 9.88 (s, 1H), 8.87 (s, 1H), 8.58-8.60 (m, 1H), 8.01 (t, J = 8.0 Hz, 1H), 7.87 (d, J = 8.4 Hz, 2H), 7.78 (d, J = 8.0 Hz, 2H), 7.65 (d, J = 9.2 Hz, 2H 7.25-7.33 (m, 4H), 7.15 (d, J = 3.6 Hz, 1H), 7.02 (d, J = 3.6 Hz, 1H), 4.90-4.93 (m, 1H), 4.60-4.62 (m, 1H), 3.11-3.25 (m, 2H), 2.33 (s, 3H), 1.27 (d, J = 7.0 Hz, 6H). |
| 117 | 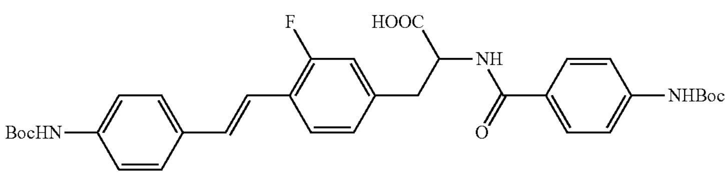 [SMILES: CC(C)(C)OC(=O)Nc1ccc(/C=C/c2ccc(CC(NC(=O)c3ccc(NC(=O)OC(C)(C)C)cc3)C(=O)O)cc2F)cc1] | A11 | 620 (M + H)+ |
| 118 | 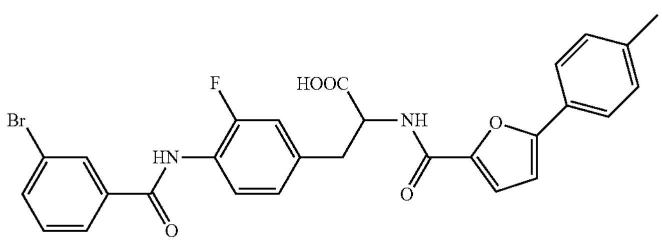 [SMILES: Cc1ccc(-c2ccc(C(=O)NC(Cc3ccc(NC(=O)c4cccc(Br)c4)c(F)c3)C(=O)O)o2)cc1] | A11 | 563 (M − H)− |
| 119 | 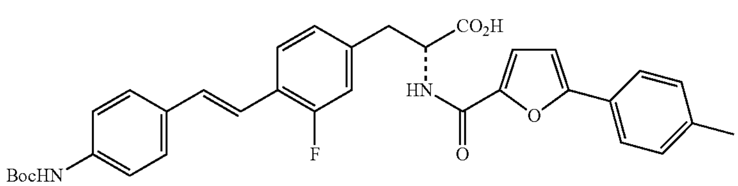 [SMILES: Cc1ccc(-c2ccc(C(=O)N[C@H](Cc3ccc(/C=C/c4ccc(NC(=O)OC(C)(C)C)cc4)c(F)c3)C(=O)O)o2)cc1] | A11 | 583 (M − H) |
| 120 | 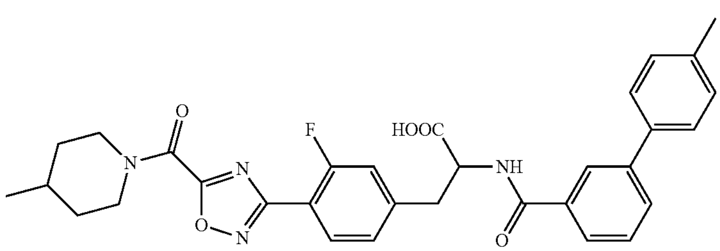 | A11 | 571.2 (M + H)+ 0.92 (d, 3H), 1.05-1.18 (m, 2H), 1.62-1.82 (m, 3H), 2.36 (s, 3H), 2.87-2.97 (m, 1H), 3.15-3.25 (m, 2H), 3.36-3.39 (m, 1H), 3.93 (d, 1H), 4.41 (d, 1H), 4.78 (m, 1H), 7.29-7.55 (m, 5H), 7.61 (d, 2H), 7.78 (dd, 2H), 7.95 (t, 1H), 8.02 (s, 1H), 8.90 (d, 1H), 13.01 (brs, 1H) |

TABLE 1A-continued

Exemplary Compounds Showing Agonist Activity Only

| Number | Structure | Method | MS/HNMR |
|---|---|---|---|
| 121 | 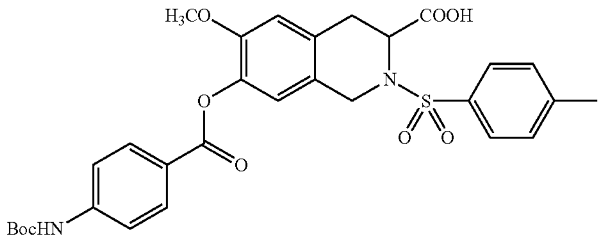 [SMILES: COc1cc2c(cc1OC(=O)c1ccc(NC(=O)OC(C)(C)C)cc1)CN(S(=O)(=O)c1ccc(C)cc1)C(C(=O)O)C2] | D | 595 (M − H)⁻ |
| 122 | 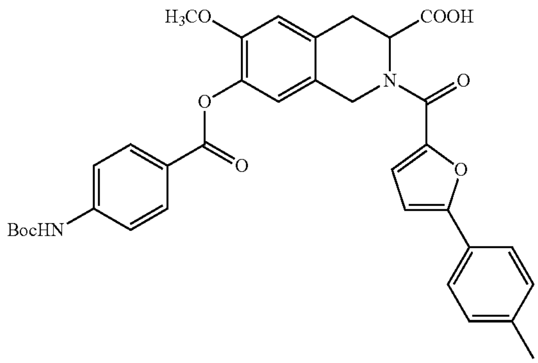 [SMILES: COc1cc2c(cc1OC(=O)c1ccc(NC(=O)OC(C)(C)C)cc1)CN(C(=O)c1ccc(-c3ccc(C)cc3)o1)C(C(=O)O)C2] | D | 625 (M − H)⁻ |
| 123 | 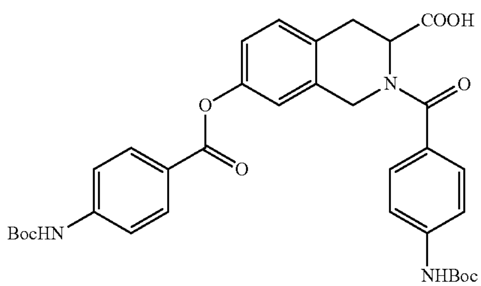 [SMILES: CC(C)(C)OC(=O)Nc1ccc(C(=O)Oc2ccc3c(c2)CN(C(=O)c2ccc(NC(=O)OC(C)(C)C)cc2)C(C(=O)O)C3)cc1] | D | 631 (M + H)⁺ |
| 124 | 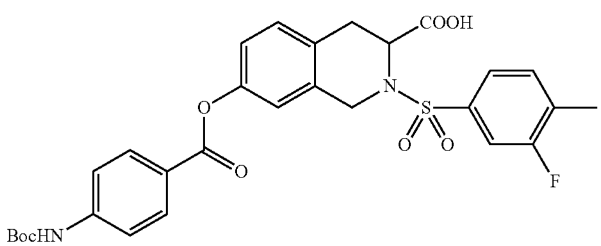 | D | 609 (M + H)⁺ |
| 125 | 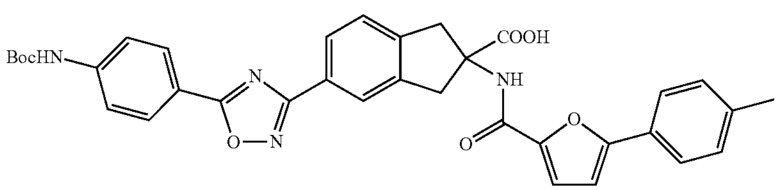 [SMILES: Cc1ccc(-c2ccc(C(=O)NC3(C(=O)O)Cc4ccc(-c5noc(-c6ccc(NC(=O)OC(C)(C)C)cc6)n5)cc4C3)o2)cc1] | C | 621 (M + H)+ 1.56 (s, 9H), 2.36 (s, 3H), 3.62-3.65 (m, 2H), 3.79-3.81 (m, 2H), 6.82 (m, 1H), 7.23 (m, 3H), 7.41 (d, J = 4.0 Hz, 1H), 7.66 (d, J = 8.8 Hz, 2H), 7.73 (d, J = 8.0 Hz, 2H), 7.96-8.00 (m, 2H), 8.09 (d, J = 8.8 Hz, 1H). |

TABLE 1A-continued
Exemplary Compounds Showing Agonist Activity Only
| Number | Structure | Method | MS/HNMR |
|---|---|---|---|
| 126 | 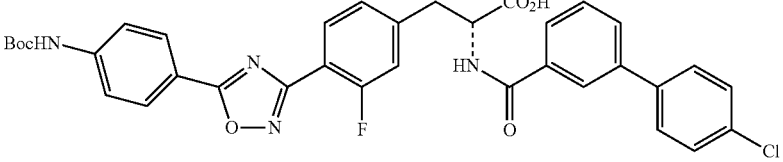 | B | 657 (M, M − 2)− 1.50 (s, 9H), 3.20-3.35 (m, 2H) 4.80 (m, 1H) 7.40-7.62 (m, 5H) 7.65-7.89 (m, 6H) 7.95-8.09 (m, 4H) 8.94 (d, 1H) 9.92 (s, 1H). |
| 127 | 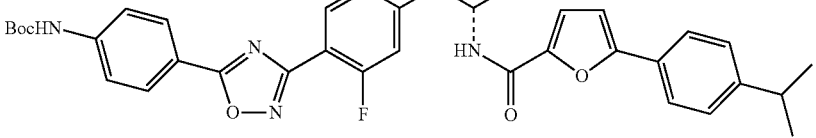 | B | 653 (M − H)− 1.22 (d, 6H) 1.50 (s, 9H) 2.89-2.95 (m, 1H) 3.18-3.29 (m, 2H) 4.70-4.76 (m, 1H) 7.02 (d, 1H) 7.17 (d, 1H) 7.33-7.38 (m, 3H) 7.45 (d, 1H) 7.70 (d, 2H) 7.82 (d, 2H) 7.99 (t, 1H) 8.06 (d, 2H) 8.76 (d, 1H) 9.91 (s, 1H). |
| 128 | 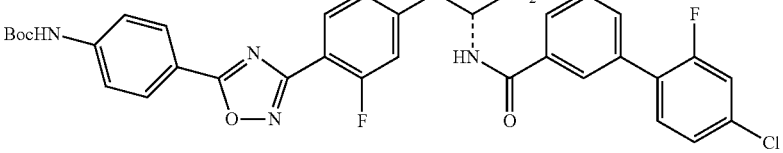 | B | 675 (M, M − 2)− 1.50 (s, 9H) 3.19-3.29 (m, 2H) 4.72-4.82 (m, 1H) 7.37-7.45 (m, 3H) 7.55-7.73 (m, 6H) 7.84-8.09 (m, 5H) 8.92 (d, 1H) 9.92 (s, 1H). |
| 129 | 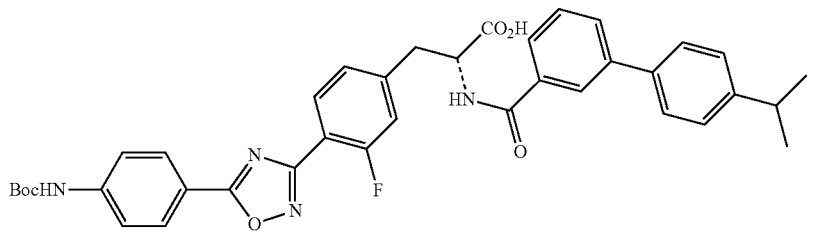 [SMILES: CC(C)c1ccc(-c2cccc(C(=O)N[C@H](Cc3ccc(-c4noc(-c5ccc(NC(=O)OC(C)(C)C)cc5)n4)c(F)c3)C(=O)O)c2)cc1] | B | 663 (M − H)− 1.20 (d, 6H) 1.49 (s, 9H) 2.86-2.89 (m, 1H) 3.25-3.41 (m, 2H) 4.88-4.96 (m, 1H) 7.18-7.25 (m, 4H) 7.39-7.51 (m, 3H) 7.64-7.71 (m, 4H) 7.85-8.03 (m, 5H) 9.02-9.06 (m, 1H). |
| 130 | 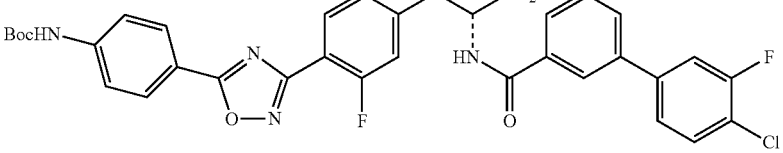 | B | 675 (M, M − 2)− 1.50 (s, 9H) 3.20-3.35 (m, 2H) 4.80 (m, 1H) 7.35-7.47 (m, 2H) 7.58-7.73 (m, 5H) 7.82-7.91 (m, 3H) 8.00-8.07 (m, 4H) 8.96 (d, 1H) 9.94 (s, 1H). |
| 131 | 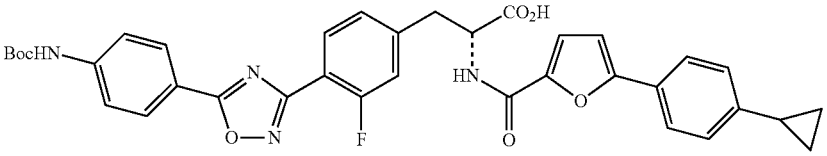 [SMILES: CC(C)(C)OC(=O)Nc1ccc(-c2nc(-c3ccc(C[C@@H](NC(=O)c4ccc(-c5ccc(C6CC6)cc5)o4)C(=O)O)cc3F)no2)cc1] | B | 610 (M + H)+ 0.72-0.75 (m, 2H) 0.96-1.01 (m, 2H) 1.50 (s, 9H) 1.93-1.97 (m, 1H) 3.17-3.26 (m, 2H) 4.68-4.75 (m, 1H) 7.00 (d, 1H) 7.15-7.19 (m, 3H) 7.36-7.45 (m, 2H) 7.70 (d, 2H) 7.77 (d, 2H) 7.99 (t, 1H) 8.06 (d, 2H) 8.75 (d, 1H) 9.93 (s, 1H). |

TABLE 1A-continued
Exemplary Compounds Showing Agonist Activity Only
| Number | Structure | Method | MS/HNMR |
|---|---|---|---|
| 132 | 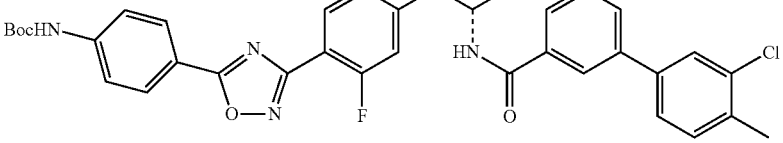 | B | 725 (M, M − 2)− |
| 133 | 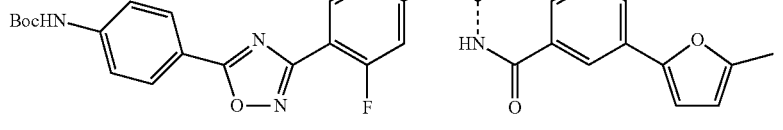 | B | 649 (M − H)− |
| 134 | 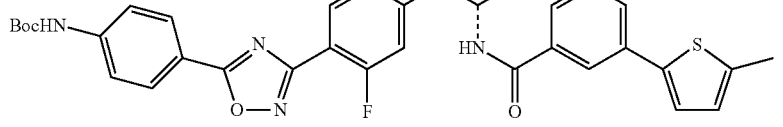 | B | 625 (M − H)− |
| 135 | 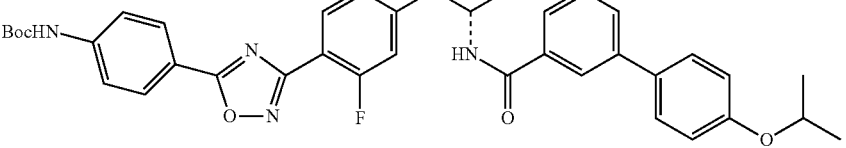 | B | 677 (M − H)− |
| 136 | 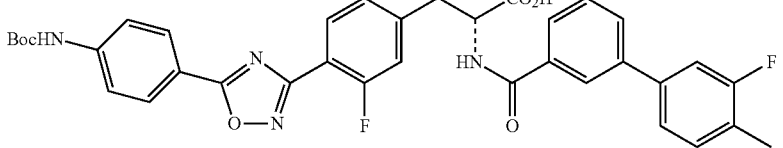 | B | 679 (M − H)− |
| 137 | 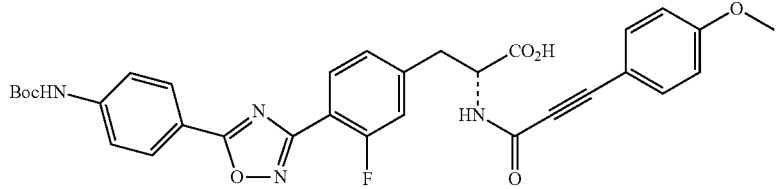 [SMILES: COc1ccc(C#CC(=O)N[C@H](Cc2ccc(-c3noc(-c4ccc(NC(=O)OC(C)(C)C)cc4)n3)c(F)c2)C(=O)O)cc1] | B | 653 (M − H)− |
| 138 | 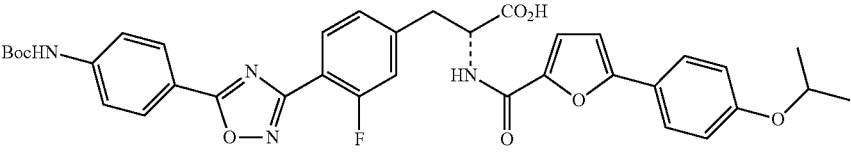 | B | 585 (M + H)+ |
| 139 | 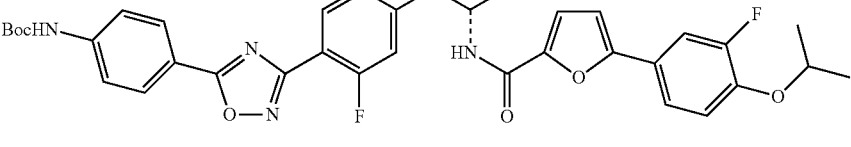 | B | 683 (M − H)− |

TABLE 1A-continued

Exemplary Compounds Showing Agonist Activity Only

| Number | Structure | Method | MS/HNMR |
|---|---|---|---|
| 140 | 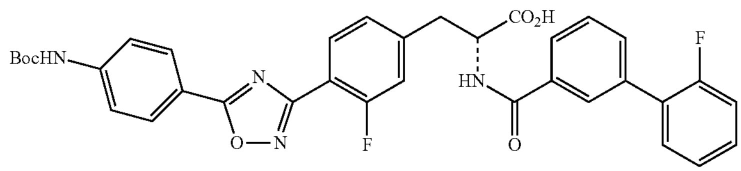 [SMILES: CC(C)(C)OC(=O)Nc1ccc(-c2nc(-c3ccc(C[C@@H](NC(=O)c4cccc(-c5ccccc5F)c4)C(=O)O)cc3F)no2)cc1] | B | 667 (M − H)−<br>1.51 (s, 9H) 3.19-3.29 (m, 2H) 4.72-4.82 (m, 1H) 7.32-7.45 (m, 5H) 7.56-7.60 (m, 2H) 7.70-7.74 (m, 3H) 7.83-8.08 (m, 5H) 8.90 (d, 1H) 9.92 (s, 1H). |
| 141 | 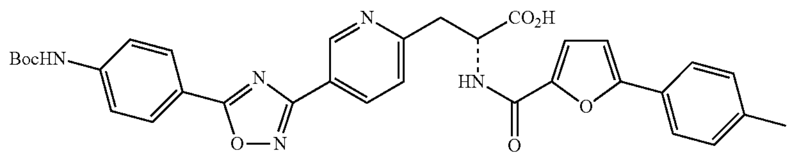 [SMILES: Cc1ccc(-c2ccc(C(=O)N[C@H](Cc3ccc(-c4noc(-c5ccc(NC(=O)OC(C)(C)C)cc5)n4)cn3)C(=O)O)o2)cc1] | B | 639 (M − H)− |
| 142 | 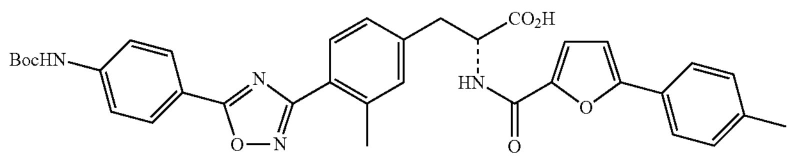 [SMILES: Cc1ccc(-c2ccc(C(=O)N[C@H](Cc3ccc(-c4noc(-c5ccc(NC(=O)OC(C)(C)C)cc5)n4)c(C)c3)C(=O)O)o2)cc1] | B | 621 (M − H)− |
| 143 | 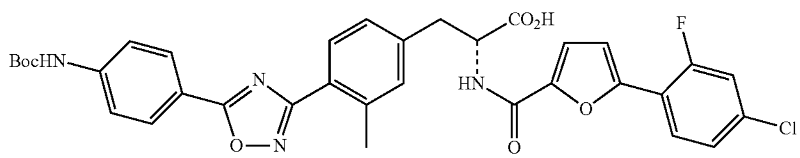 [SMILES: Cc1cc(C[C@@H](NC(=O)c2ccc(-c3ccc(Cl)cc3F)o2)C(=O)O)ccc1-c1noc(-c2ccc(NC(=O)OC(C)(C)C)cc2)n1] | B | 662 (M − H)− |
| 144 | 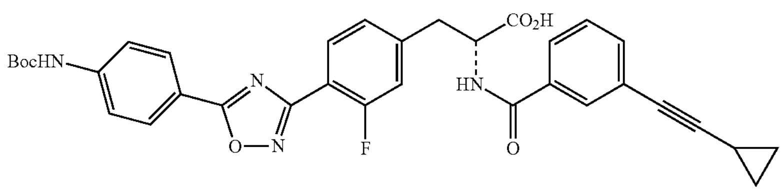 [SMILES: CC(C)(C)OC(=O)Nc1ccc(-c2nc(-c3ccc(C[C@@H](NC(=O)c4cccc(C#CC5CC5)c4)C(=O)O)cc3F)no2)cc1] | B | 609 (M − H)−<br>0.73-0.77 (m, 2H) 0.88-0.93 (m, 2H) 1.51 (s, 9H) 1.51-1.55 (m, 1H) 3.10-3.26 (m, 2H) 4.73 (m, 1H) 7.36-7.44 (m, 3H) 7.51 (d, 1H) 7.72-7.80 (m, 4H) 8.01 (t, 1H) 8.08 (d, 2H) 8.85 (d, 1H) 9.92 (s, 1H) |
| 145 | 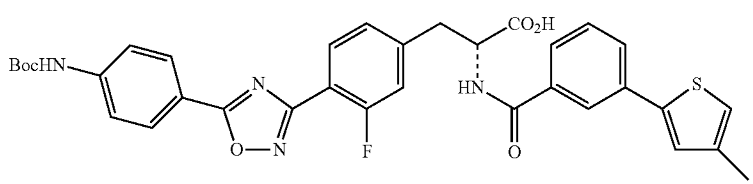 [SMILES: Cc1csc(-c2cccc(C(=O)N[C@H](Cc3ccc(-c4noc(-c5ccc(NC(=O)OC(C)(C)C)cc5)n4)c(F)c3)C(=O)O)c2)c1] | B | 641 (M − H)− |
| 146 | 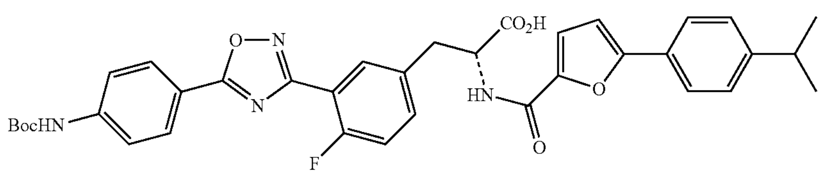 [SMILES: CC(C)c1ccc(-c2ccc(C(=O)N[C@H](Cc3ccc(F)c(-c4noc(-c5ccc(NC(=O)OC(C)(C)C)cc5)n4)c3)C(=O)O)o2)cc1] | B | 653 (M − H)− |
| 147 | 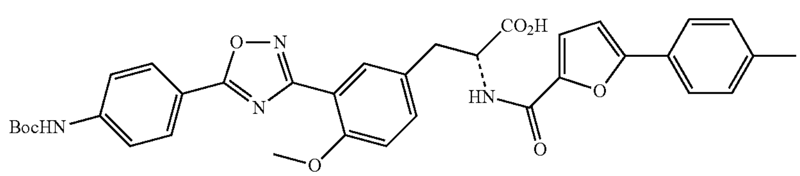 | B | 637 (M − H)− |

TABLE 1A-continued

Exemplary Compounds Showing Agonist Activity Only

| Number | Structure | Method | MS/HNMR |
|---|---|---|---|
| 148 | 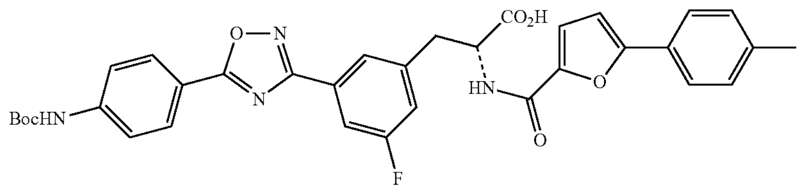 | B | 625 (M − H)− |
| 149 | 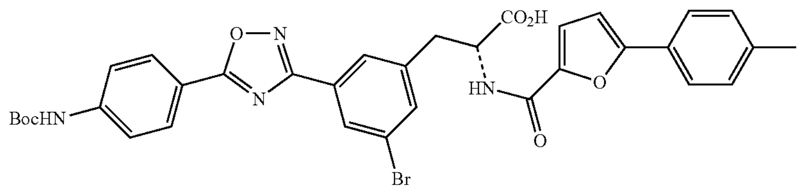 | B | 687 (M, M − 2)− |
| 150 | 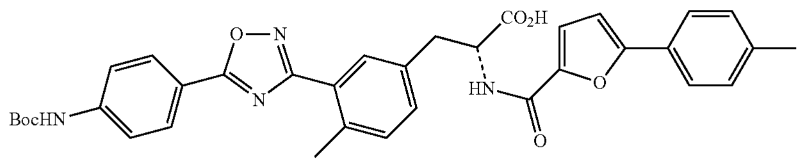 | B | 623 (M + H)+ |
| 151 | 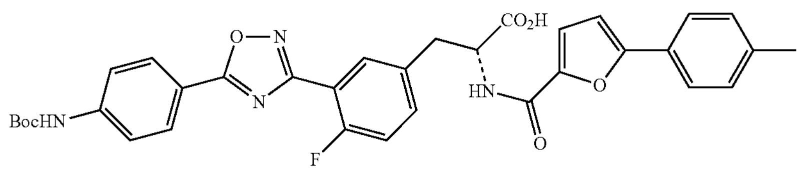 | B | 627 (M + H)+ |
| 152 | 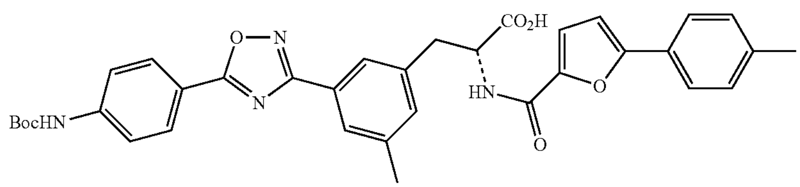 | B | 621 (M − H)− |
| 153 | 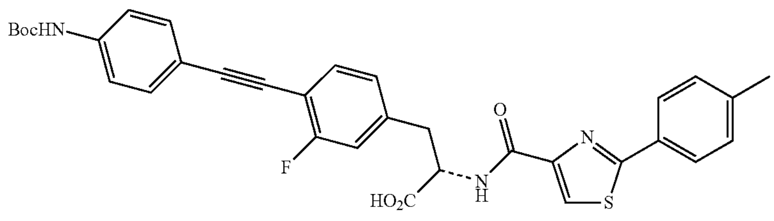 | B1 | 598 (M − H)− |
| 154 | 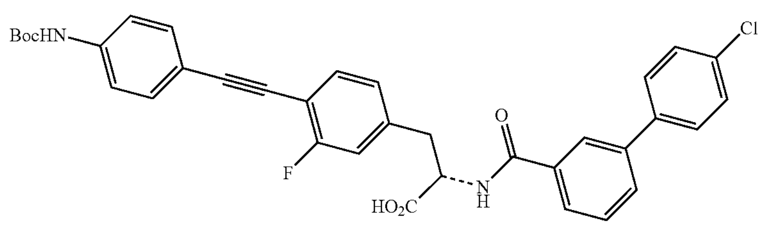 | B1 | 611 (M − H)− |

TABLE 1A-continued

Exemplary Compounds Showing Agonist Activity Only

| Number | Structure | Method | MS/HNMR |
|---|---|---|---|
| 155 | 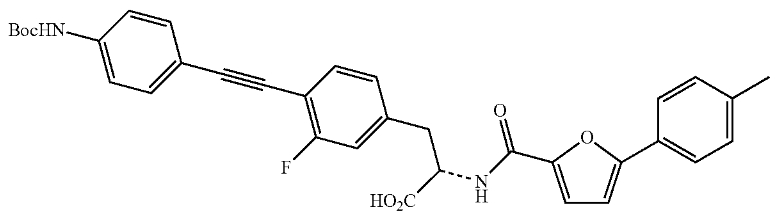 | B1 | 581 (M − H)− |
| 156 | 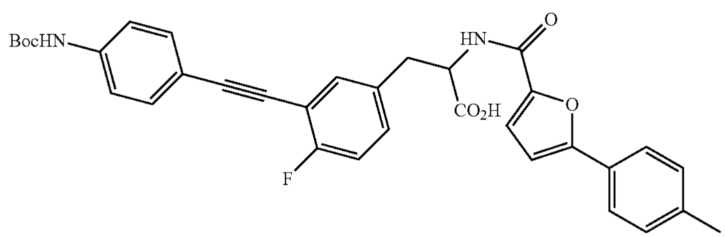 [SMILES: Cc1ccc(-c2ccc(C(=O)NC(Cc3ccc(F)c(C#Cc4ccc(NC(=O)OC(C)(C)C)cc4)c3)C(=O)O)o2)cc1] | B1 | 581 (M − H) |
| 157 | 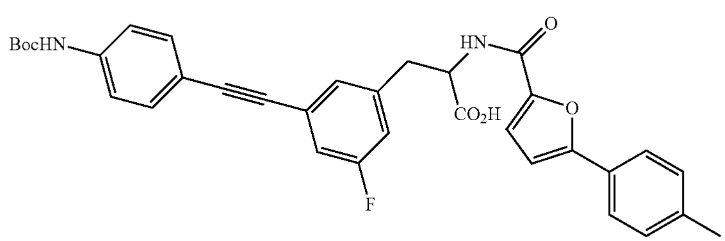 [SMILES: Cc1ccc(-c2ccc(C(=O)NC(Cc3cc(F)cc(C#Cc4ccc(NC(=O)OC(C)(C)C)cc4)c3)C(=O)O)o2)cc1] | B1 | 583 (M + H)+ |
| 158 | 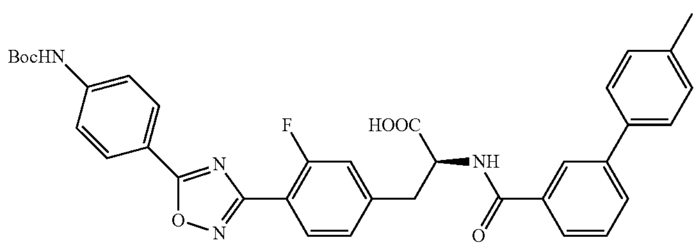 [SMILES: Cc1ccc(-c2cccc(C(=O)N[C@@H](Cc3ccc(-c4noc(-c5ccc(NC(=O)OC(C)(C)C)cc5)n4)c(F)c3)C(=O)O)c2)cc1] | B2 | 635 (M − 1) |
| 159 | 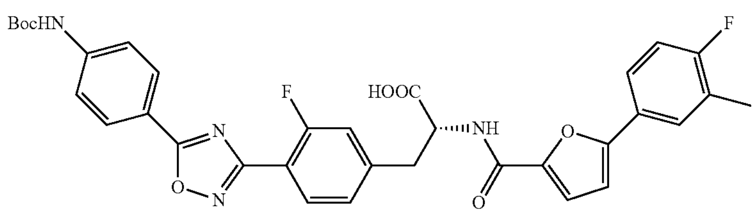 [SMILES: Cc1cc(-c2ccc(C(=O)N[C@H](Cc3ccc(-c4noc(-c5ccc(NC(=O)OC(C)(C)C)cc5)n4)c(F)c3)C(=O)O)o2)ccc1F] | B1 | 644 (M − 1) |
| 160 | 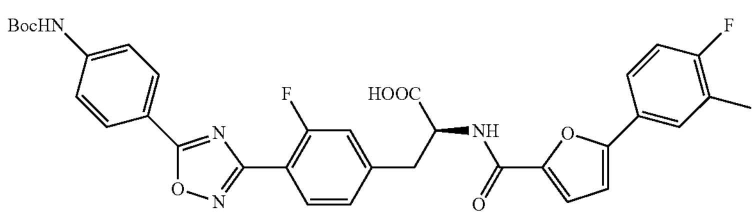 [SMILES: Cc1cc(-c2ccc(C(=O)N[C@@H](Cc3ccc(-c4noc(-c5ccc(NC(=O)OC(C)(C)C)cc5)n4)c(F)c3)C(=O)O)o2)ccc1F] | B2 | 644 (M − 1) |

TABLE 1A-continued

Exemplary Compounds Showing Agonist Activity Only

| Number | Structure | Method | MS/HNMR |
|---|---|---|---|
| 161 | (structure) | B1 | 625 (M − 1) |
| 162 | (structure) | B2 | 626 (M − 1) |

TABLE 1B

Biological Activities of Compounds with Agonist Activity Only

| Compound | Concentration | Activity | Compound | Concentration | Activity | Compound | Concentration | Activity | Compound | Concentration | Activity |
|---|---|---|---|---|---|---|---|---|---|---|---|
| 1A | 5 | A | 4A | 10 | B | 2V | 3.16 | B | 5V | 10 | A |
| 1B | 3.16 | A | 4B | 3.16 | B | 2W | 10 | A | 5W | 10 | A |
| 1C | 10 | A | 4C | 1 | A | 2X | 10 | A | 5X | 10 | A |
| 1D | 3.16 | C | 4D | 1 | A | 2Y | 3.16 | A | 5Y | 10 | A |
| 1F | 5 | A | 4F | 3.16 | B | 2Z | 3.16 | A | 5Z | 10 | A |
| 1G | 10 | A | 4G | 3.16 | A | 3A | 3.16 | A | 6A | 10 | A |
| 1H | 3.16 | A | 4H | 3.16 | A | 3B | 3.16 | A | 6B | 3.16 | B |
| 1I | 3.16 | A | 4I | 3.16 | A | 3C | 10 | A | 6C | 10 | A |
| 1J | 3.16 | A | 4J | 3.16 | B | 3D | 10 | A | 6D | 3 | C |
| 1K | 10 | A | 4K | 1 | A | 3F | 3.16 | C | 6F | 10 | A |
| 1L | 3.16 | A | 4L | 3.16 | B | 3G | 3 | B | 6G | 1 | B |
| 1M | 10 | A | 4M | 3.16 | A | 3H | 10 | C | 6H | 3.16 | A |
| 1N | 1 | A | 4N | 3.16 | C | 3I | 10 | B | 6I | 3 | C |
| 1O | 3.16 | C | 4O | 10 | A | 3J | 10 | B | 6J | 10 | A |
| 1P | 3.16 | A | 4P | 10 | A | 3K | 3 | C | 6K | 10 | A |
| 1Q | 3.16 | A | 4Q | 3.16 | A | 3L | 1 | C | 6L | 1 | C |
| 1R | 3 | C | 4R | 3 | C | 3M | 10 | C | 6M | 10 | C |
| 1S | 10 | B | 4S | 1 | B | 3N | 3.16 | C | 6N | 3 | B |
| 1T | 10 | B | 4T | 1 | B | 3O | 1 | C | 6O | 1 | C |
| 1U | 1 | A | 4U | 3 | B | 3P | 1 | B | 6P | 1 | B |
| 1V | 1 | B | 4V | 3 | B | 3Q | 1 | C | 6Q | 1 | B |
| 1W | 3 | A | 4W | 10 | B | 3R | 3 | A | 6R | 1 | A |
| 1X | 3 | B | 4X | 10 | A | 3S | 1 | A | 6S | 1 | C |
| 1Y | 10 | A | 4Y | 3 | C | 3T | 10 | B | 6T | 1 | C |
| 1Z | 10 | B | 4Z | 10 | B | 3U | 1 | C | 6U | 3 | B |
| 2A | 10 | A | 5A | 3 | B | 3V | 3 | C | 6V | 1 | C |
| 2B | 3 | B | 5B | 3 | B | 3W | 1 | B | 6W | 3 | C |
| 2C | 3 | B | 5C | 3 | A | 3X | 3 | A | 6X | 3 | B |
| 2D | 1 | B | 5D | 3 | A | 3Y | 10 | A | 6Y | 1 | A |
| 2F | 10 | D | 5F | 10 | A | 3Z | 3 | A | 6Z | 1 | B |
| 2G | 10 | B | 5G | 10 | A | 1E | 3 | B | 7E | 1 | A |
| 2H | 10 | C | 5H | 5 | A | 2E | 3 | B | 8E | 3 | A |
| 2I | 10 | B | 5I | 1 | A | 3E | 1 | B | 9E | 1 | A |
| 2J | 3.16 | A | 5J | 3.16 | A | 4E | 3 | C | 10E | 1 | A |
| 2K | 3.16 | A | 5K | 1 | A | 5E | 10 | A | 11E | 3.16 | A |
| 2L | 1 | A | 5L | 10 | A | 6E | 3.16 | A | 12E | 3.16 | A |
| 2M | 3.16 | A | 5M | 1 | A | | | | | | |
| 2N | 3.16 | A | 5N | 1 | A | | | | | | |
| 2O | 10 | A | 5O | 3.16 | A | | | | | | |
| 2P | 10 | A | 5P | 10 | A | | | | | | |
| 2Q | 3.16 | A | 5Q | 10 | A | | | | | | |
| 2R | 3.16 | A | 5R | 3.16 | B | | | | | | |
| 2S | 3.16 | A | 5S | 10 | A | | | | | | |
| 2T | 10 | A | 5T | 10 | A | | | | | | |
| 2U | 10 | A | 5U | 10 | A | | | | | | |

TABLE 2A

Exemplary Compounds Showing Sensitizer Activity Only

| Number | Structure | Method | MS/HNMR |
|---|---|---|---|
| 228 | 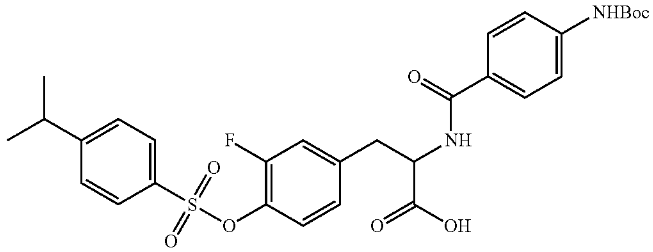 [SMILES: CC(C)c1ccc(S(=O)(=O)Oc2ccc(CC(NC(=O)c3ccc(NC(=O)OC(C)(C)C)cc3)C(=O)O)cc2F)cc1] | A | 601 (M + H) |
| 229 | 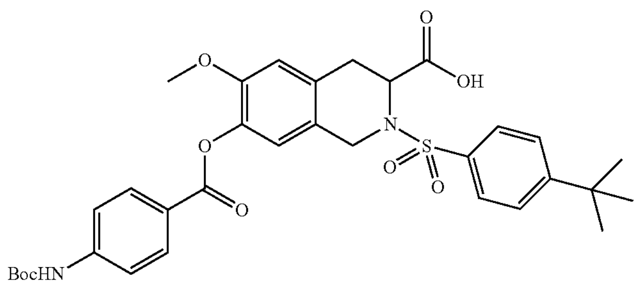 [SMILES: COc1cc2c(cc1OC(=O)c1ccc(NC(=O)OC(C)(C)C)cc1)CN(S(=O)(=O)c1ccc(C(C)(C)C)cc1)C(C(=O)O)C2] | A | 639 (M + H) |
| 230 | 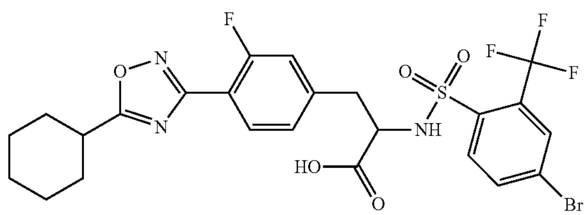 [SMILES: O=C(O)C(Cc1ccc(-c2noc(C3CCCCC3)n2)c(F)c1)NS(=O)(=O)c1ccc(Br)cc1C(F)(F)F] | A | 516 (M + H) 1.06 (m 6H) 1.28 (m 1H) 1.43 (m 2H) 1.62 (m 3H) 1.75 (m 2H) 2.07 (m 2H) 2.75 (m 2H) 3.06 (m 1H) 3.13 (m 1H) 3.90 (m 1H) 7.09 (t 2H) 7.14 (d 2H) 7.35 (d 2H) 7.73 (t 1H) 8.30 (d 1H) |
| 231 | 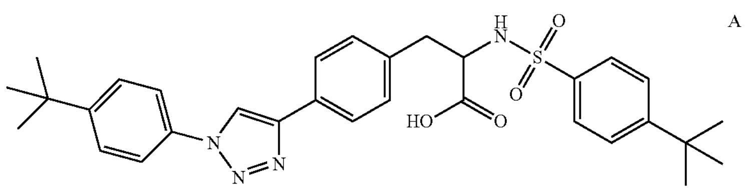 | A | 561 (M + H) |
| 232 | 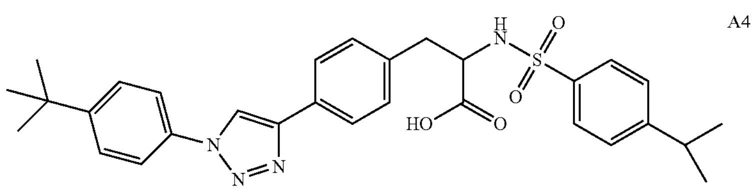 | A4 | 547 (M + H) |
| 233 | 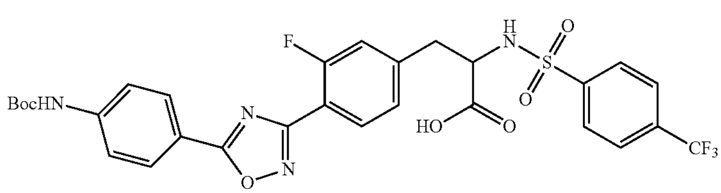 [SMILES: CC(C)(C)OC(=O)Nc1ccc(-c2nc(-c3ccc(CC(NS(=O)(=O)c4ccc(C(F)(F)F)cc4)C(=O)O)cc3F)no2)cc1] | A4 | 651 (M + H) |
| 234 | 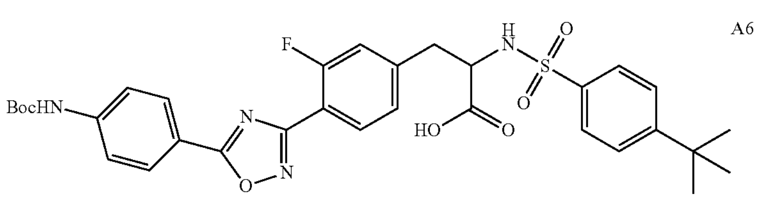 | A6 | 639 (M + H) |

TABLE 2A-continued

Exemplary Compounds Showing Sensitizer Activity Only

| Number | Structure | Method | MS/HNMR |
|---|---|---|---|
| 235 | 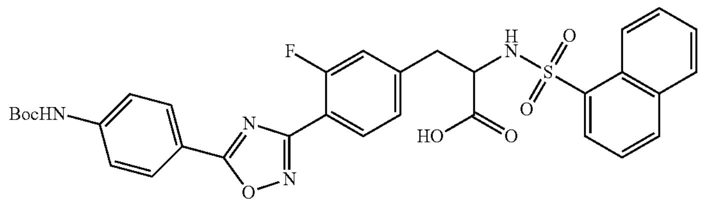 [SMILES: CC(C)(C)OC(=O)Nc1ccc(-c2nc(-c3ccc(CC(NS(=O)(=O)c4cccc5ccccc45)C(=O)O)cc3F)no2)cc1] | A4 | 633 (M + H) |
| 236 | 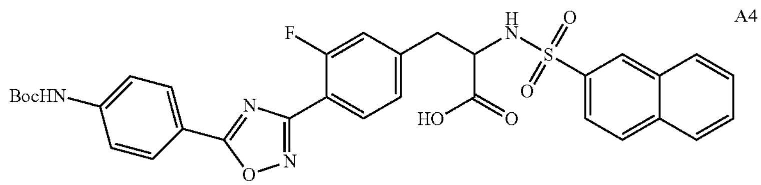 | A4 | 633 (M + H) |
| 237 | 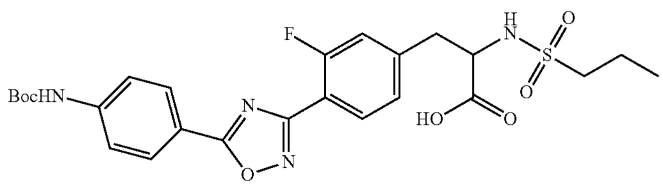 | A | 563 (M + H) |
| 238 | 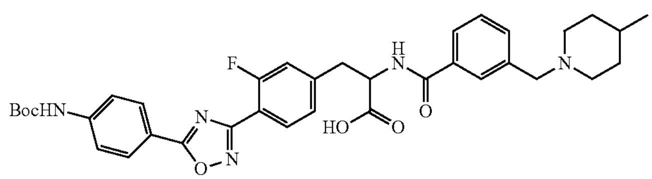 [SMILES: CC1CCN(Cc2cccc(C(=O)NC(Cc3ccc(-c4noc(-c5ccc(NC(=O)OC(C)(C)C)cc5)n4)c(F)c3)C(=O)O)c2)CC1] | A | 658 (M + H) |
| 239 | 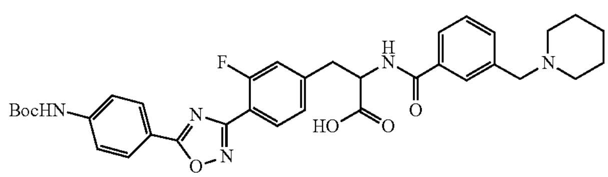 [SMILES: CC(C)(C)OC(=O)Nc1ccc(-c2nc(-c3ccc(CC(NC(=O)c4cccc(CN5CCCCC5)c4)C(=O)O)cc3F)no2)cc1] | A | 644 (M + H) |
| 240 | 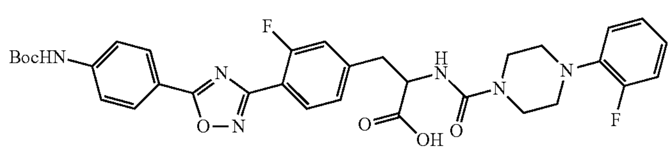 [SMILES: CC(C)(C)OC(=O)Nc1ccc(-c2nc(-c3ccc(CC(NC(=O)N4CCN(c5ccccc5F)CC4)C(=O)O)cc3F)no2)cc1] | A8 | 649 (M + H) |
| 241 | 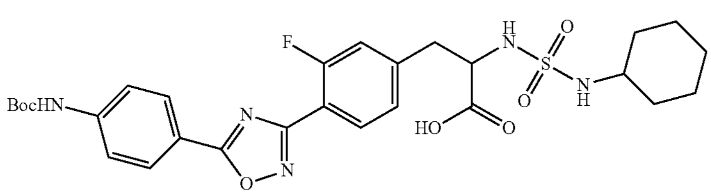 [SMILES: CC(C)(C)OC(=O)Nc1ccc(-c2nc(-c3ccc(CC(NS(=O)(=O)NC4CCCCC4)C(=O)O)cc3F)no2)cc1] | A | 604 (M + H) |
| 242 | 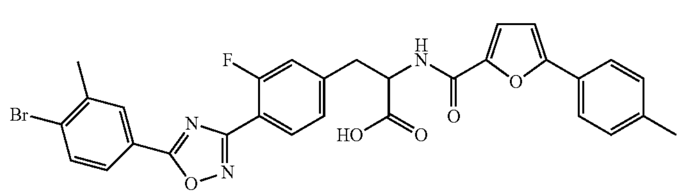 [SMILES: Cc1ccc(-c2ccc(C(=O)NC(Cc3ccc(-c4noc(-c5ccc(Br)c(C)c5)n4)c(F)c3)C(=O)O)o2)cc1] | A10 | 605 (M + H) |

TABLE 2A-continued

Exemplary Compounds Showing Sensitizer Activity Only

| Number | Structure | Method | MS/HNMR |
|---|---|---|---|
| 243 | 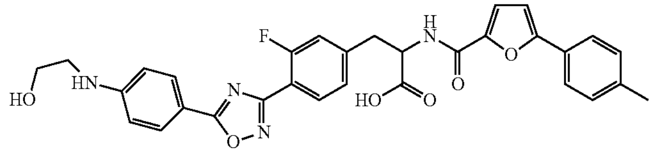 | A | 538 (M + H) |
| 244 | 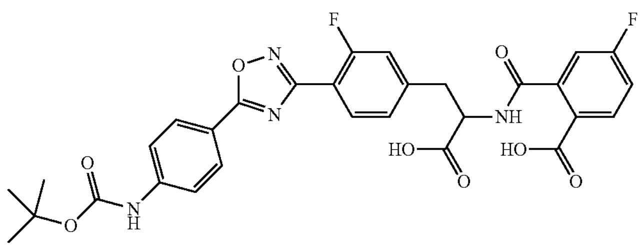 [SMILES: CC(C)(C)OC(=O)Nc1ccc(-c2nc(-c3ccc(CC(NC(=O)c4cc(F)ccc4C(=O)O)C(=O)O)cc3F)no2)cc1] | A | 609 (M + H) |
| 245 | 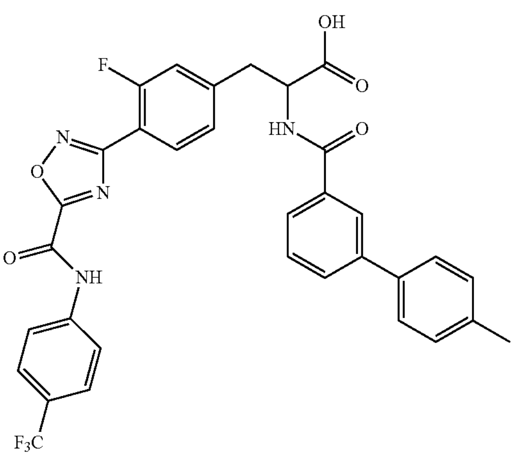 [SMILES: Cc1ccc(-c2cccc(C(=O)NC(Cc3ccc(-c4noc(C(=O)Nc5ccc(C(F)(F)F)cc5)n4)c(F)c3)C(=O)O)c2)cc1] | A | 633 (M + H) |
| 246 | 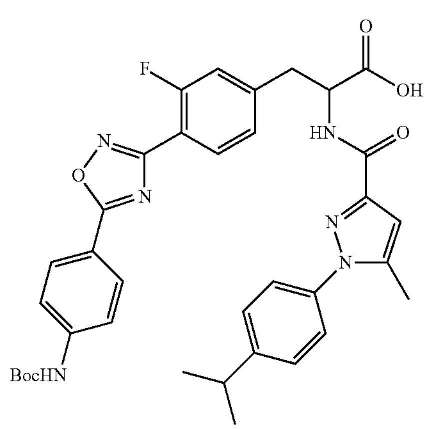 [SMILES: Cc1cc(C(=O)NC(Cc2ccc(-c3noc(-c4ccc(NC(=O)OC(C)(C)C)cc4)n3)c(F)c2)C(=O)O)nn1-c1ccc(C(C)C)cc1] | A2 | 669 (M + H) |

TABLE 2A-continued

Exemplary Compounds Showing Sensitizer Activity Only

| Number | Structure | Method | MS/HNMR |
|---|---|---|---|
| 247 | 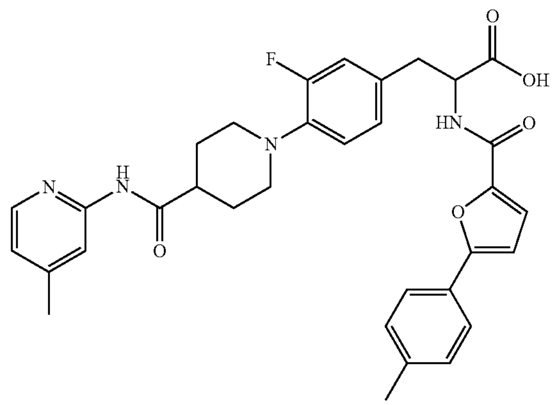 [SMILES: Cc1ccc(-c2ccc(C(=O)NC(Cc3ccc(N4CCC(C(=O)Nc5cc(C)ccn5)CC4)c(F)c3)C(=O)O)o2)cc1] | A | 585 (M + H) |
| 248 | 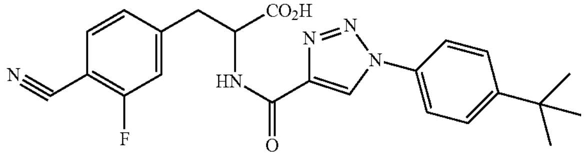 [SMILES: CC(C)(C)c1ccc(-n2cc(C(=O)NC(Cc3ccc(C#N)c(F)c3)C(=O)O)nn2)cc1] | A | 434 (M − H)− |
| 249 | 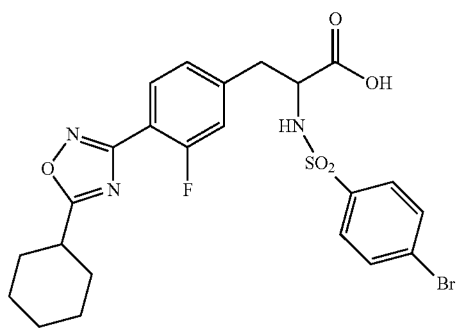 | A | 550 (M − H)− |
| 250 | 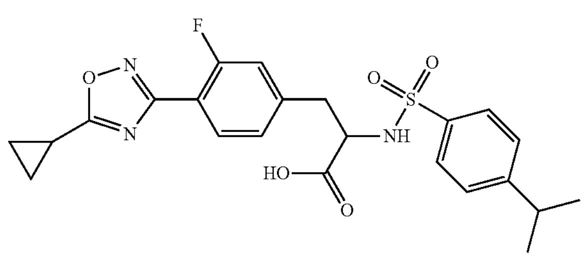 | A | 472 (M − H)− 1.18 (d 6H) 1.23 (m 2H) 1.28 (m 2H) 2.00 (m 1H) 2.42 (m 1H) 3.05 (m 3H) 7.10 (t 2H) 7.36 (d 2H) 7.60 (d 2H) 7.75 (t 1H) |
| 251 | 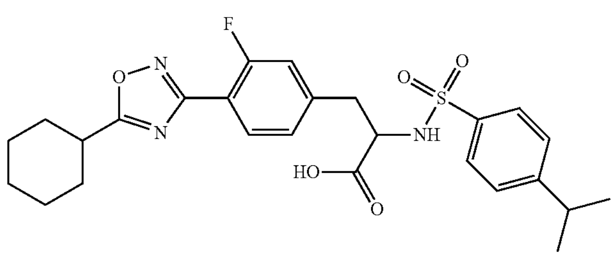 [SMILES: CC(C)c1ccc(S(=O)(=O)NC(Cc2ccc(-c3noc(C4CCCCC4)n3)c(F)c2)C(=O)O)cc1] | A | 514 (M − H)− 1.19 (m 2H) 1.31 (m 2H) 2.27 (s 3H) 2.44 (m 1H) 2.75 (m 1H) 3.07 (m 1H) 3.89 (m 1H) 7.04 (q 2H) 7.23 (t 1H) 7.43 (d 1H) 7.64 (m 2H) 8.62 (m 1H) |

TABLE 2A-continued

Exemplary Compounds Showing Sensitizer Activity Only

| Number | Structure | Method | MS/HNMR |
|---|---|---|---|
| 252 | 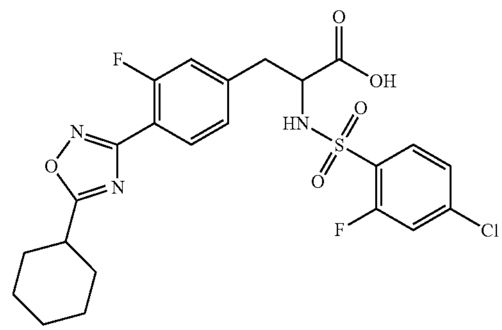 [SMILES: O=C(O)C(Cc1ccc(-c2noc(C3CCCCC3)n2)c(F)c1)NS(=O)(=O)c1ccc(Cl)cc1F] | A | 524 (M − H)− |
| 253 | 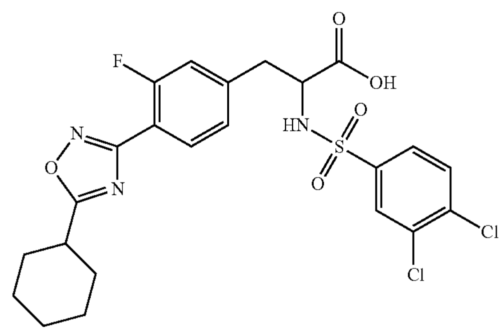 [SMILES: O=C(O)C(Cc1ccc(-c2noc(C3CCCCC3)n2)c(F)c1)NS(=O)(=O)c1ccc(Cl)c(Cl)c1] | A | 540 (M − H)− |
| 254 | 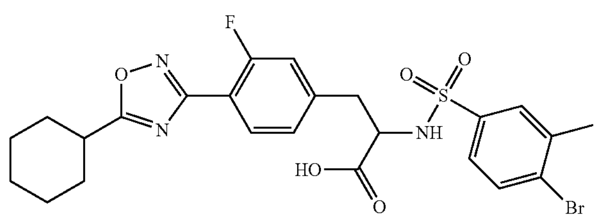 [SMILES: Cc1cc(S(=O)(=O)NC(Cc2ccc(-c3noc(C4CCCCC4)n3)c(F)c2)C(=O)O)ccc1Br] | A | 564 (M − H)− |
| 255 | 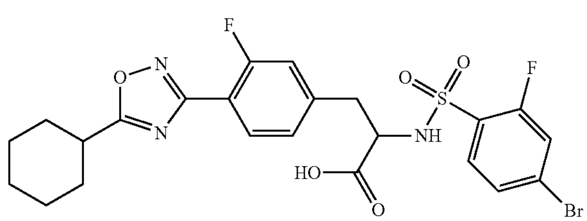 [SMILES: O=C(O)C(Cc1ccc(-c2noc(C3CCCCC3)n2)c(F)c1)NS(=O)(=O)c1ccc(Br)cc1F] | A | 568 (M − H)− |
| 256 | 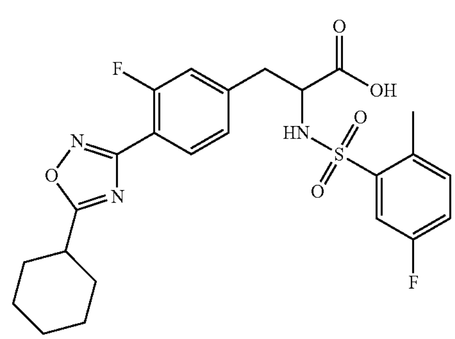 [SMILES: Cc1ccc(F)cc1S(=O)(=O)NC(Cc1ccc(-c2noc(C3CCCCC3)n2)c(F)c1)C(=O)O] | A | 504 (M − H)− |

TABLE 2A-continued

Exemplary Compounds Showing Sensitizer Activity Only

| Number | Structure | Method | MS/HNMR |
|---|---|---|---|
| 257 | 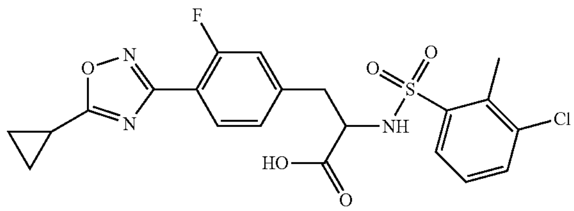 [SMILES: Cc1c(Cl)cccc1S(=O)(=O)NC(Cc1ccc(-c2noc(C3CC3)n2)c(F)c1)C(=O)O] | A | 478 (M − H)−<br>1.20 (m 2H) 1.31 (m 2H) 2.27 (s 3H) 2.44 (m 1H) 2.77 (t 1H) 3.07 (m 1H) 3.90 (m 1H) 7.04 (m 2H) 7.24 (m 1H) 7.43 (m 1H) 7.64 (m 2H) 8.64 (m 1H) |
| 258 | 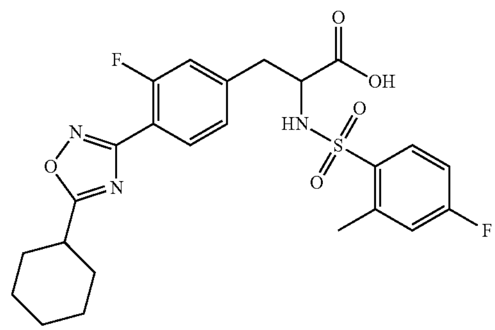 [SMILES: Cc1cc(F)ccc1S(=O)(=O)NC(Cc1ccc(-c2noc(C3CCCCC3)n2)c(F)c1)C(=O)O] | A | 506 (M − H)− |
| 259 | 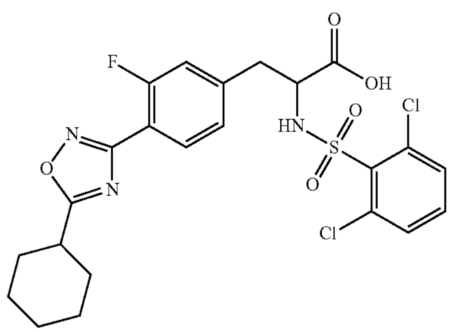 [SMILES: O=C(O)C(Cc1ccc(-c2noc(C3CCCCC3)n2)c(F)c1)NS(=O)(=O)c1c(Cl)cccc1Cl] | A | 540 (M − H)− |
| 260 | 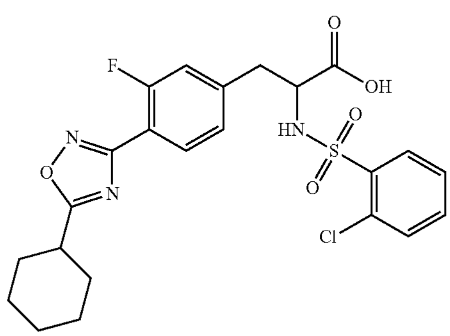 [SMILES: O=C(O)C(Cc1ccc(-c2noc(C3CCCCC3)n2)c(F)c1)NS(=O)(=O)c1ccccc1Cl] | A | 506 (M − H)− |
| 261 | 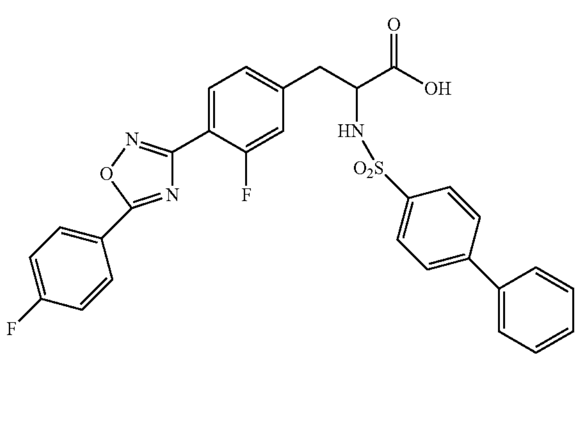 [SMILES: O=C(O)C(Cc1ccc(-c2noc(-c3ccc(F)cc3)n2)c(F)c1)NS(=O)(=O)c1ccc(-c2ccccc2)cc1] | A | 560 (M − H)− |

TABLE 2A-continued
Exemplary Compounds Showing Sensitizer Activity Only
| Number | Structure | Method | MS/HNMR |
|---|---|---|---|
| 262 | 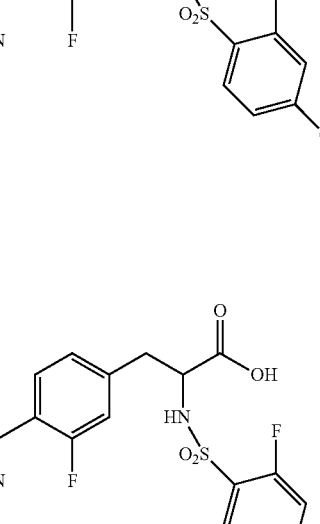 | A | 5454 (M − H)− |
| 263 | 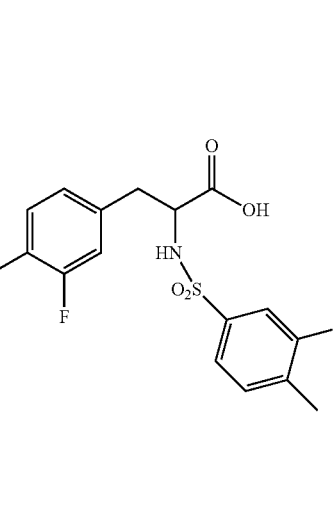 | A | 580 (M − H)− |
| 264 | 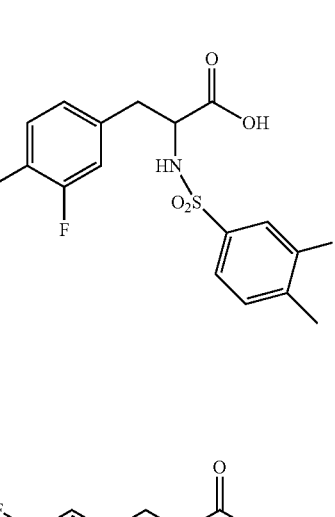 | A | 516 (M − H)− |
| 265 | 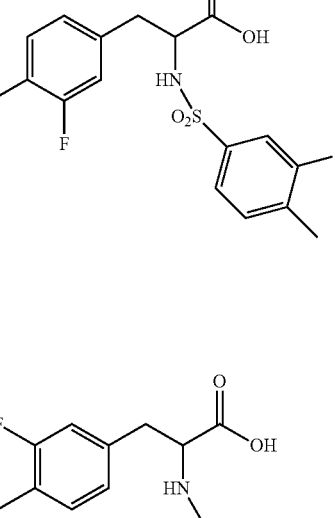 | A | 450 (M − H)− |

TABLE 2A-continued
Exemplary Compounds Showing Sensitizer Activity Only
| Number | Structure | Method | MS/HNMR |
|---|---|---|---|
| 266 | 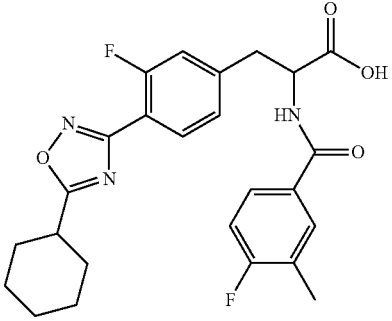 | A | 468 (M − H)− |
| 267 | 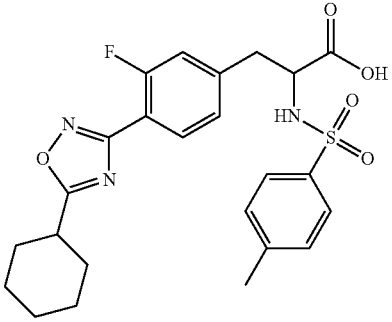 [SMILES: Cc1ccc(S(=O)(=O)NC(Cc2ccc(-c3noc(C4CCCCC4)n3)c(F)c2)C(=O)O)cc1] | A | 486 (M − H)− |
| 268 | 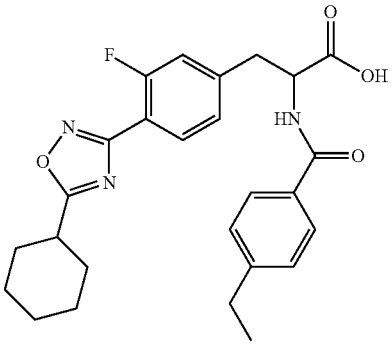 [SMILES: CCc1ccc(C(=O)NC(Cc2ccc(-c3noc(C4CCCCC4)n3)c(F)c2)C(=O)O)cc1] | A | 464 (M − H)− |
| 269 | 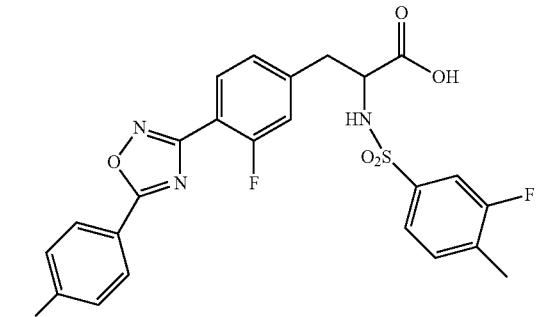 | A | 566 (M − H)− |

TABLE 2A-continued

Exemplary Compounds Showing Sensitizer Activity Only

| Number | Structure | Method | MS/HNMR |
|---|---|---|---|
| 270 | 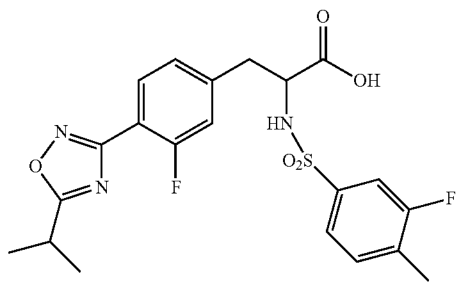 [SMILES: Cc1ccc(S(=O)(=O)NC(Cc2ccc(-c3noc(C(C)C)n3)c(F)c2)C(=O)O)cc1F] | A | 464 (M − H)− |
| 271 | 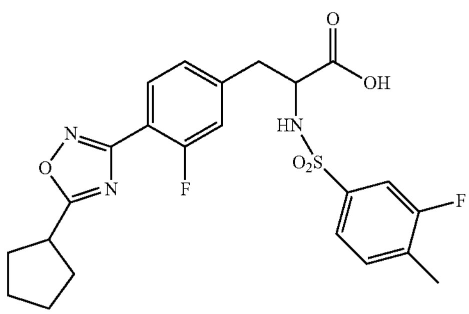 [SMILES: Cc1ccc(S(=O)(=O)NC(Cc2ccc(-c3noc(C4CCCC4)n3)c(F)c2)C(=O)O)cc1F] | A | 490 (M − H)− |
| 272 | 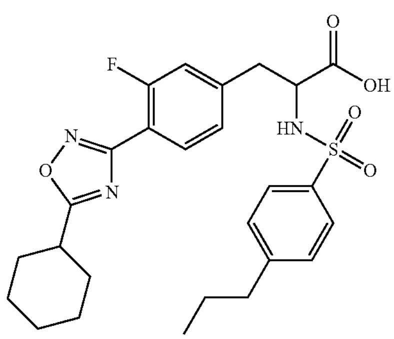 [SMILES: CCCc1ccc(S(=O)(=O)NC(Cc2ccc(-c3noc(C4CCCCC4)n3)c(F)c2)C(=O)O)cc1] | A | 514 (M − H)− |
| 273 | 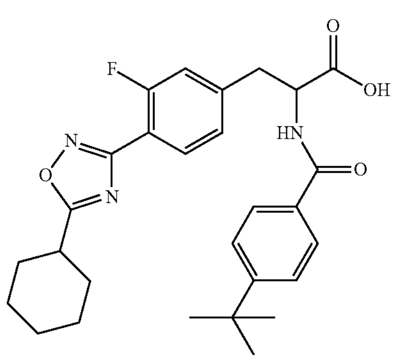 [SMILES: CC(C)(C)c1ccc(C(=O)NC(Cc2ccc(-c3noc(C4CCCCC4)n3)c(F)c2)C(=O)O)cc1] | A | 492 (M − H)− |

TABLE 2A-continued

Exemplary Compounds Showing Sensitizer Activity Only

| Number | Structure | Method | MS/HNMR |
|--------|-----------|--------|---------|
| 274 | 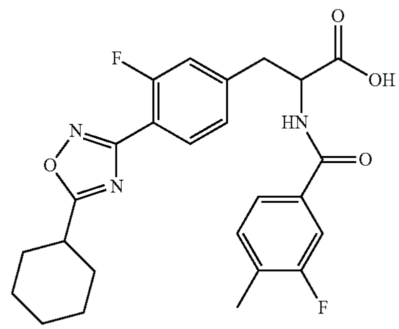 [SMILES: Cc1ccc(C(=O)NC(Cc2ccc(-c3noc(C4CCCCC4)n3)c(F)c2)C(=O)O)cc1F] | A | 468 (M − H)− |
| 275 | 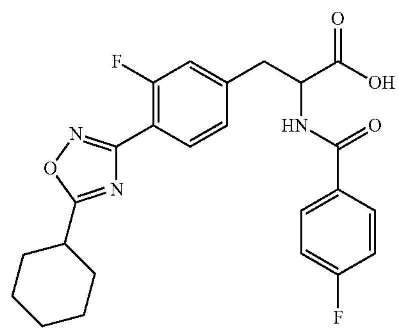 [SMILES: O=C(NC(Cc1ccc(-c2noc(C3CCCCC3)n2)c(F)c1)C(=O)O)c1ccc(F)cc1] | A | 454 (M − H)− |
| 276 | 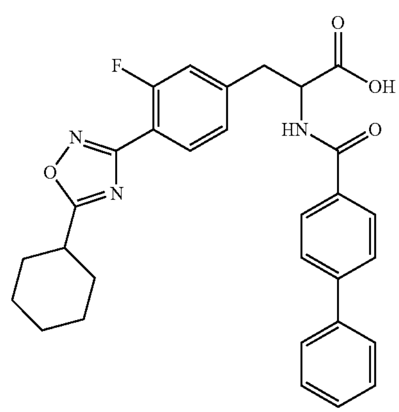 [SMILES: O=C(NC(Cc1ccc(-c2noc(C3CCCCC3)n2)c(F)c1)C(=O)O)c1ccc(-c2ccccc2)cc1] | A | 512 (M − H)− |
| 277 | 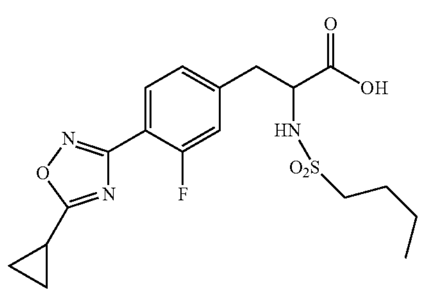 [SMILES: CCCCS(=O)(=O)NC(Cc1ccc(-c2noc(C3CC3)n2)c(F)c1)C(=O)O] | A6 | 410 (M − H)− |

TABLE 2A-continued

Exemplary Compounds Showing Sensitizer Activity Only

| Number | Structure | Method | MS/HNMR |
|---|---|---|---|
| 278 | 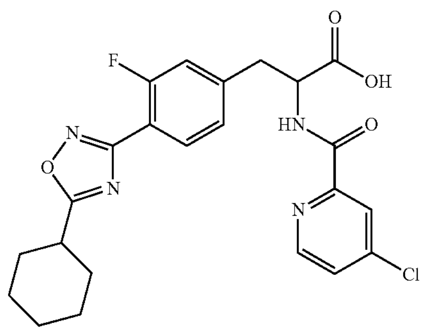 [SMILES: O=C(NC(Cc1ccc(-c2noc(C3CCCCC3)n2)c(F)c1)C(=O)O)c1cc(Cl)ccn1] | A | 471 (M − H)− |
| 279 | 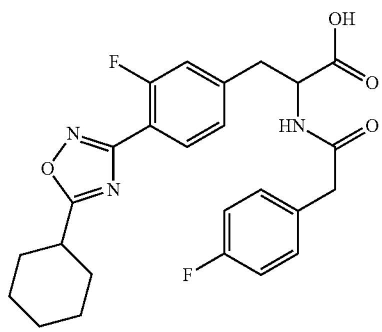 [SMILES: O=C(Cc1ccc(F)cc1)NC(Cc1ccc(-c2noc(C3CCCCC3)n2)c(F)c1)C(=O)O] | A | 468 (M − H)− |
| 280 | 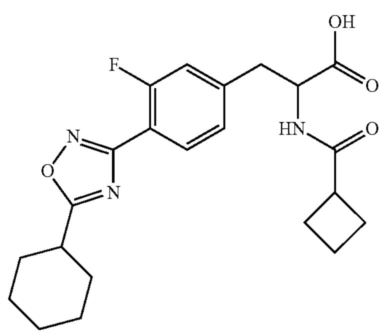 [SMILES: O=C(NC(Cc1ccc(-c2noc(C3CCCCC3)n2)c(F)c1)C(=O)O)C1CCC1] | A | 414 (M − H)− |
| 281 | 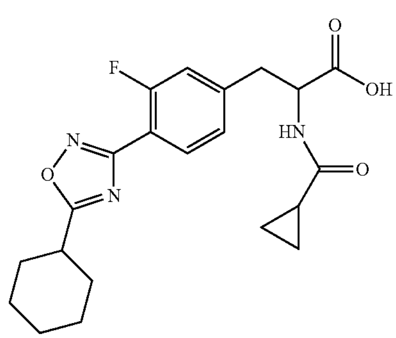 [SMILES: O=C(NC(Cc1ccc(-c2noc(C3CCCCC3)n2)c(F)c1)C(=O)O)C1CC1] | A | 400 (M − H)− |

TABLE 2A-continued

Exemplary Compounds Showing Sensitizer Activity Only

| Number | Structure | Method | MS/HNMR |
|---|---|---|---|
| 282 | 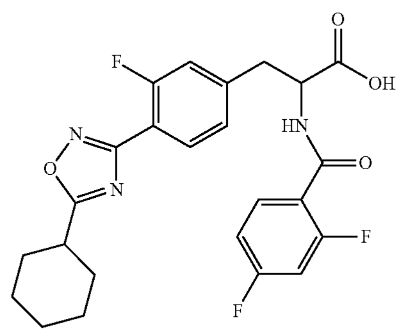 [SMILES: O=C(NC(Cc1ccc(-c2noc(C3CCCCC3)n2)c(F)c1)C(=O)O)c1ccc(F)cc1F] | A | 472 (M − H)− |
| 283 | 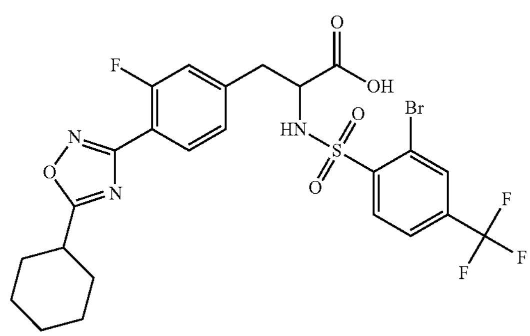 [SMILES: O=C(O)C(Cc1ccc(-c2noc(C3CCCCC3)n2)c(F)c1)NS(=O)(=O)c1ccc(C(F)(F)F)cc1Br] | A6 | 618 (M − H)− |
| 284 | 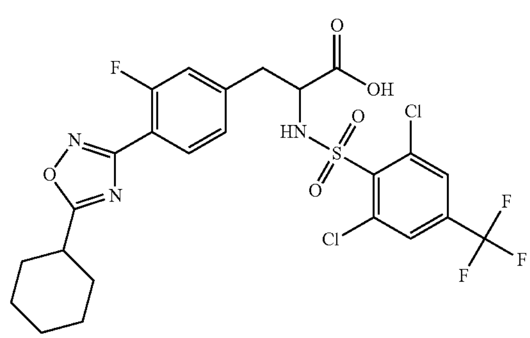 [SMILES: O=C(O)C(Cc1ccc(-c2noc(C3CCCCC3)n2)c(F)c1)NS(=O)(=O)c1c(Cl)cc(C(F)(F)F)cc1Cl] | A6 | 608 (M − H)− |
| 285 | 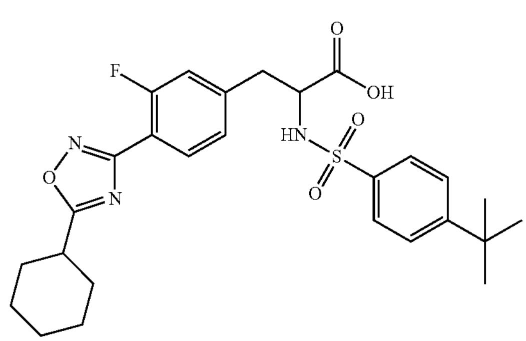 [SMILES: CC(C)(C)c1ccc(S(=O)(=O)NC(Cc2ccc(-c3noc(C4CCCCC4)n3)c(F)c2)C(=O)O)cc1] | A6 | 528 (M − H)− |

TABLE 2A-continued

Exemplary Compounds Showing Sensitizer Activity Only

| Number | Structure | Method | MS/HNMR |
|--------|-----------|--------|---------|
| 286 | 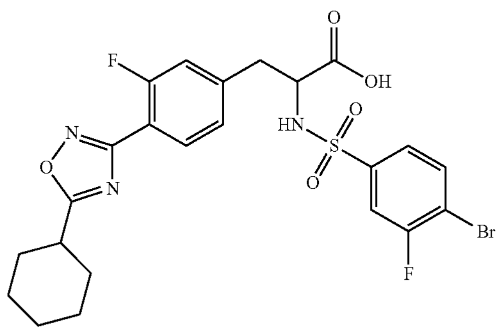 [SMILES: O=C(O)C(Cc1ccc(-c2noc(C3CCCCC3)n2)c(F)c1)NS(=O)(=O)c1ccc(Br)c(F)c1] | A6 | 568 (M − H)− |
| 287 | 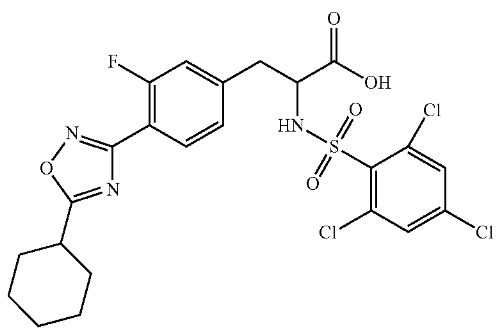 [SMILES: O=C(O)C(Cc1ccc(-c2noc(C3CCCCC3)n2)c(F)c1)NS(=O)(=O)c1c(Cl)cc(Cl)cc1Cl] | A6 | 574 (M − H)− |
| 288 | 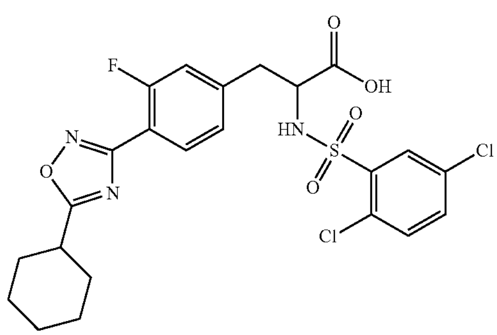 [SMILES: O=C(O)C(Cc1ccc(-c2noc(C3CCCCC3)n2)c(F)c1)NS(=O)(=O)c1cc(Cl)ccc1Cl] | A6 | 540 (M − H)− |
| 289 | 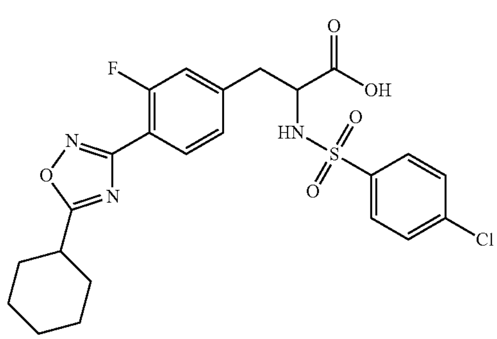 [SMILES: O=C(O)C(Cc1ccc(-c2noc(C3CCCCC3)n2)c(F)c1)NS(=O)(=O)c1ccc(Cl)cc1] | A6 | 506 (M − H)− |

TABLE 2A-continued

Exemplary Compounds Showing Sensitizer Activity Only

| Number | Structure | Method | MS/HNMR |
|---|---|---|---|
| 290 | 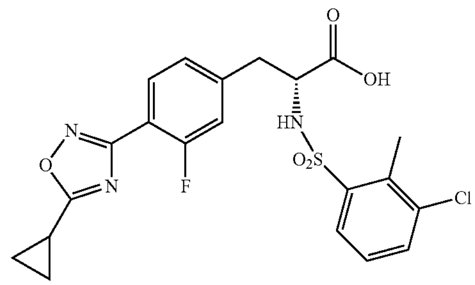 [SMILES: Cc1c(Cl)cccc1S(=O)(=O)N[C@H](Cc1ccc(-c2noc(C3CC3)n2)c(F)c1)C(=O)O] | A6 | 478 (M – H)– 1.20 (m 2H) 1.31 (m 2H) 2.27 (s 3H) 2.44 (m 1H) 2.76 (t 1H) 3.07 (dd 1H) 3.90 (dd 1H) 7.03 (q 2H) 7.23 (t 1H) 7.43 (d 1H) 7.65 (m 2H) 8.60 (m 1H) |
| 291 | 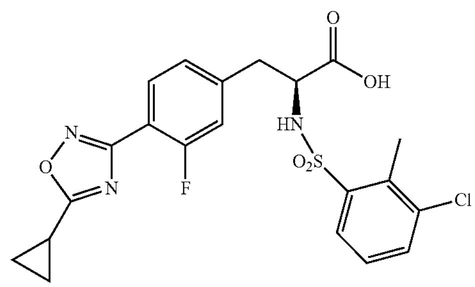 [SMILES: Cc1c(Cl)cccc1S(=O)(=O)N[C@@H](Cc1ccc(-c2noc(C3CC3)n2)c(F)c1)C(=O)O] | A6 | 478 (M – H)– |
| 292 | 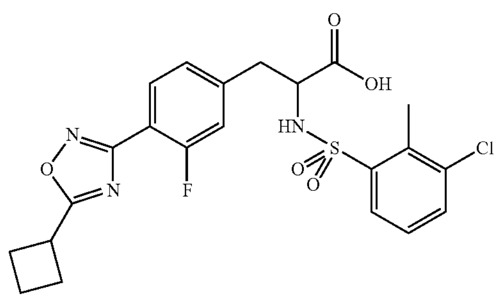 [SMILES: Cc1c(Cl)cccc1S(=O)(=O)NC(Cc1ccc(-c2noc(C3CCC3)n2)c(F)c1)C(=O)O] | A6 | 492 (M – H)– |
| 293 | 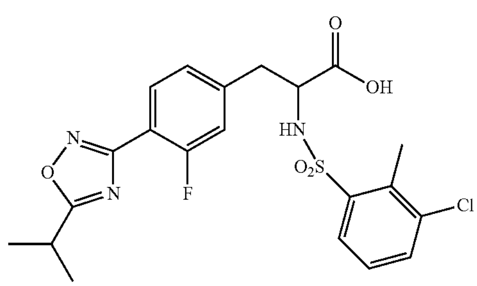 [SMILES: Cc1c(Cl)cccc1S(=O)(=O)NC(Cc1ccc(-c2noc(C(C)C)n2)c(F)c1)C(=O)O] | A6 | 480 (M – H)– |
| 294 | 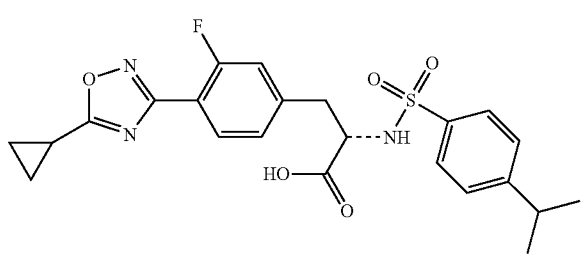 [SMILES: CC(C)c1ccc(S(=O)(=O)N[C@@H](Cc2ccc(-c3noc(C4CC4)n3)c(F)c2)C(=O)O)cc1] | B2 | 472 (M – H)– 1.08 (q 6H) 1.18 (m 2H) 1.31 (m 2H) 2.42 (m 1H) 2.76 (m 2H) 3.05 (dd 1H) 3.91 (m 1H) 7.10 (t 2H) 7.16 (d 2H) 7.36 (d 2H) 7.70 (t 1H) 8.27 (d 1H) |

TABLE 2A-continued

Exemplary Compounds Showing Sensitizer Activity Only

| Number | Structure | Method | MS/HNMR |
|---|---|---|---|
| 295 | 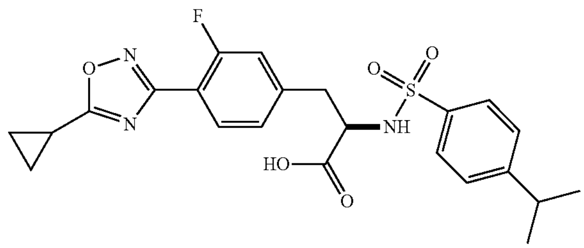 [SMILES: CC(C)c1ccc(S(=O)(=O)N[C@H](Cc2ccc(-c3noc(C4CC4)n3)c(F)c2)C(=O)O)cc1] | B1 | 472 (M − H)− 1.08 (q 6H) 1.18 (m 2H) 1.31 (m 2H) 2.42 (m 1H) 2.76 (m 2H) 3.05 (dd 1H) 3.91 (m 1H) 7.10 (t 2H) 7.16 (d 2H) 7.36 (d 2H) 7.70 (t 1H) 8.27 (d 1H) |
| 296 | 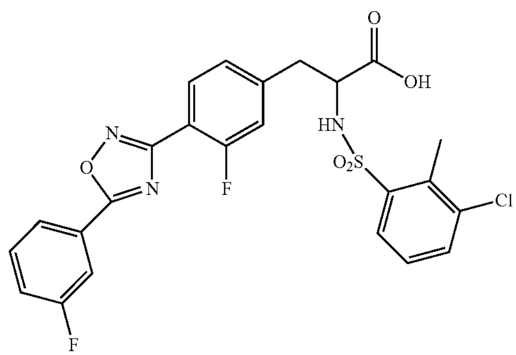 [SMILES: Cc1c(Cl)cccc1S(=O)(=O)NC(Cc1ccc(-c2noc(-c3cccc(F)c3)n2)c(F)c1)C(=O)O] | A6 | 532 (M − H)− |
| 297 | 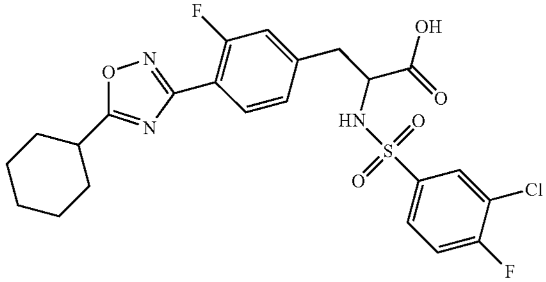 [SMILES: O=C(O)C(Cc1ccc(-c2noc(C3CCCCC3)n2)c(F)c1)NS(=O)(=O)c1ccc(F)c(Cl)c1] | A6 | 524 (M − H)− |
| 298 | 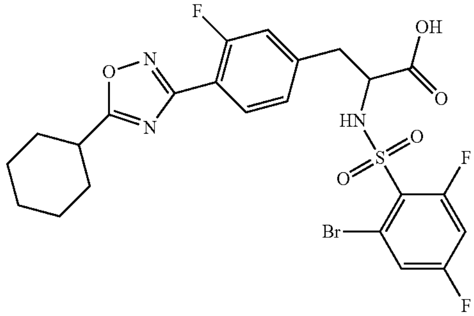 [SMILES: O=C(O)C(Cc1ccc(-c2noc(C3CCCCC3)n2)c(F)c1)NS(=O)(=O)c1c(F)cc(F)cc1Br] | A6 | 586 (M − H)− |
| 299 | 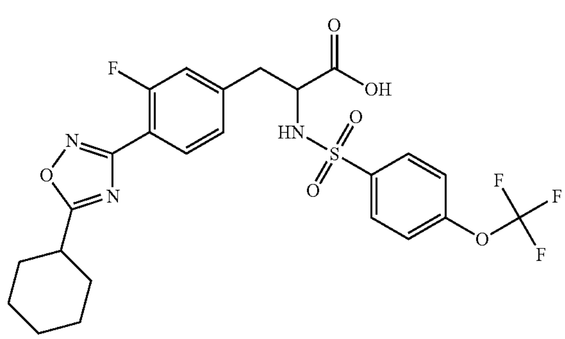 [SMILES: O=C(O)C(Cc1ccc(-c2noc(C3CCCCC3)n2)c(F)c1)NS(=O)(=O)c1ccc(OC(F)(F)F)cc1] | A6 | 556 (M − H)− |

TABLE 2A-continued
Exemplary Compounds Showing Sensitizer Activity Only
| Number | Structure | Method | MS/HNMR |
|---|---|---|---|
| 300 | 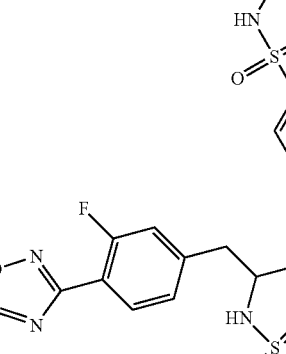 | A6 | 520 (M − H)− |
| 301 | 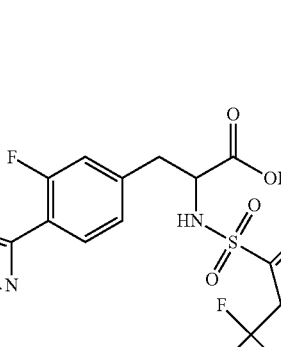 | A6 | 618 (M − H)− |
| 302 | 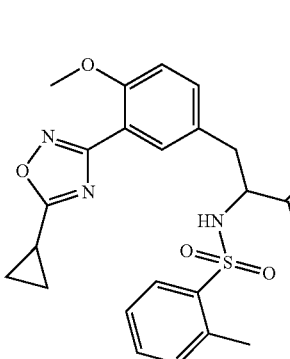 | A6 | 502 (M − H)− |
| 303 | 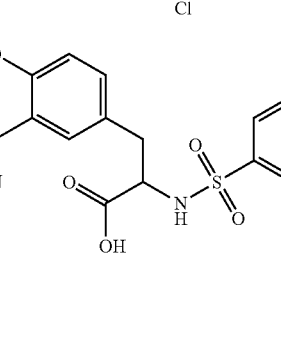 | B | 492 (M + H)+ |
| 304 | 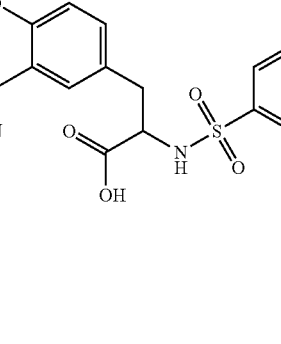 | A | 486 (M + H)+ |

TABLE 2A-continued

Exemplary Compounds Showing Sensitizer Activity Only

| Number | Structure | Method | MS/HNMR |
|---|---|---|---|
| 305 | 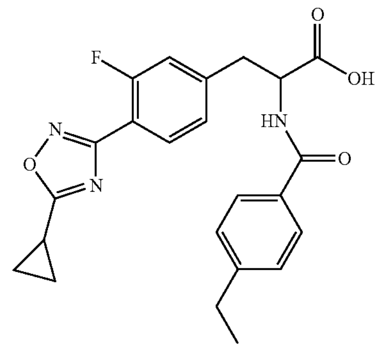 [SMILES: CCc1ccc(C(=O)NC(Cc2ccc(-c3noc(C4CC4)n3)c(F)c2)C(=O)O)cc1] | A | 422 (M − H)− |
| 306 | 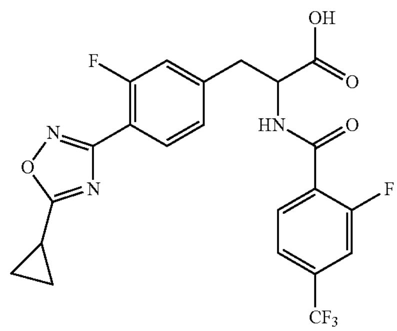 [SMILES: O=C(NC(Cc1ccc(-c2noc(C3CC3)n2)c(F)c1)C(=O)O)c1ccc(C(F)(F)F)cc1F] | A | 480 (M − H)− |
| 307 | 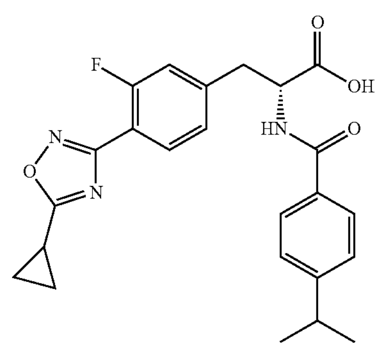 [SMILES: CC(C)c1ccc(C(=O)N[C@H](Cc2ccc(-c3noc(C4CC4)n3)c(F)c2)C(=O)O)cc1] | B | 436 (M − H)− |
| 308 | 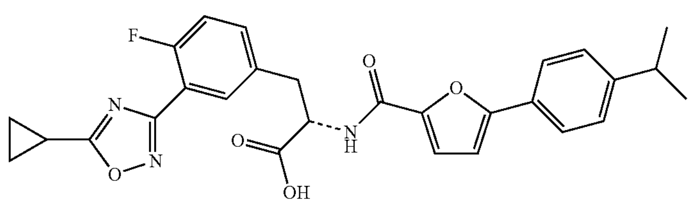 [SMILES: CC(C)c1ccc(-c2ccc(C(=O)N[C@@H](Cc3ccc(F)c(-c4noc(C5CC5)n4)c3)C(=O)O)o2)cc1] | B | 502 (M − H)− |
| 309 | 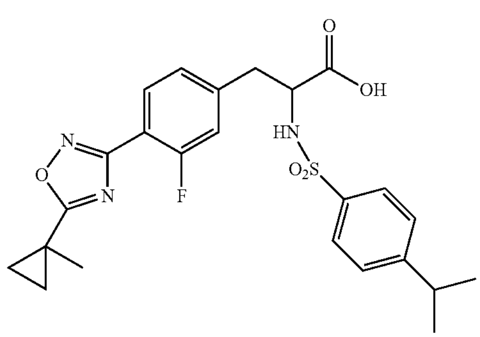 [SMILES: CC(C)c1ccc(S(=O)(=O)NC(Cc2ccc(-c3noc(C4(C)CC4)n3)c(F)c2)C(=O)O)cc1] | A4 | 486 (M − H)− |

TABLE 2A-continued

Exemplary Compounds Showing Sensitizer Activity Only

| Number | Structure | Method | MS/HNMR |
|---|---|---|---|
| 310 | 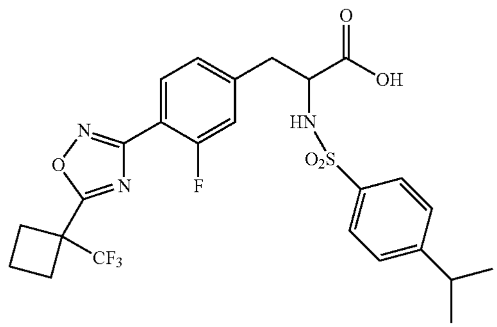 [SMILES: CC(C)c1ccc(S(=O)(=O)NC(Cc2ccc(-c3noc(C4(C(F)(F)F)CCC4)n3)c(F)c2)C(=O)O)cc1] | A4 | 554 (M − H)− |
| 311 | 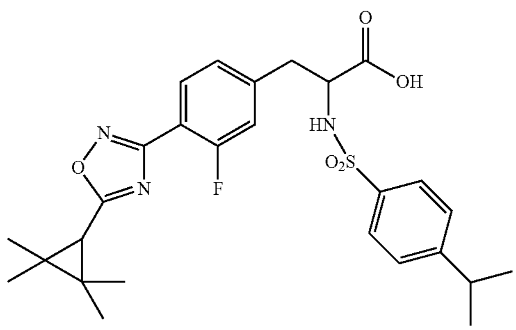 [SMILES: CC(C)c1ccc(S(=O)(=O)NC(Cc2ccc(-c3noc(C4C(C)(C)C4(C)C)n3)c(F)c2)C(=O)O)cc1] | A4 | 528 (M − H)− |
| 312 | 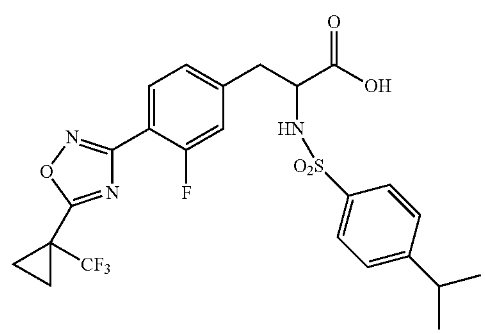 [SMILES: CC(C)c1ccc(S(=O)(=O)NC(Cc2ccc(-c3noc(C4(C(F)(F)F)CC4)n3)c(F)c2)C(=O)O)cc1] | A4 | 540 (M − H)− |
| 313 | 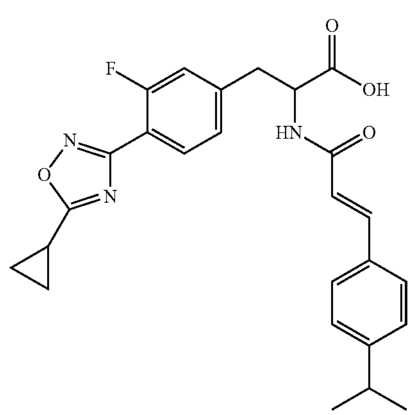 [SMILES: CC(C)c1ccc(/C=C/C(=O)NC(Cc2ccc(-c3noc(C4CC4)n3)c(F)c2)C(=O)O)cc1] | A | 462 (M − H)− |

TABLE 2A-continued

Exemplary Compounds Showing Sensitizer Activity Only

| Number | Structure | Method | MS/HNMR |
|---|---|---|---|
| 314 | 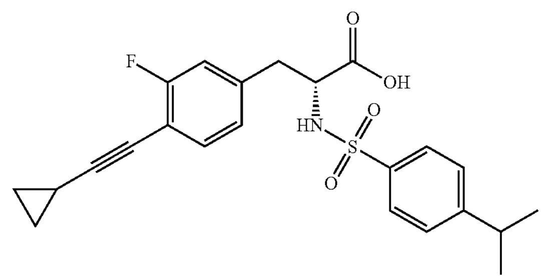 [SMILES: CC(C)c1ccc(S(=O)(=O)N[C@H](Cc2ccc(C#CC3CC3)c(F)c2)C(=O)O)cc1] | B | 428 (M − H)− |
| 315 | 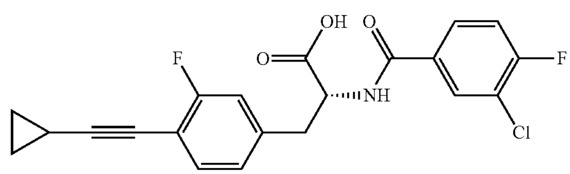 [SMILES: O=C(N[C@H](Cc1ccc(C#CC2CC2)c(F)c1)C(=O)O)c1ccc(F)c(Cl)c1] | A | 402 (M − H)− |
| 316 | 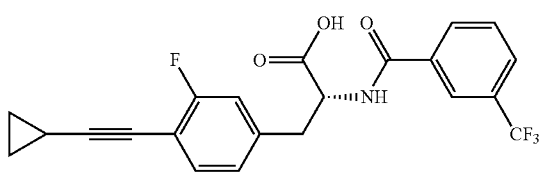 [SMILES: O=C(N[C@H](Cc1ccc(C#CC2CC2)c(F)c1)C(=O)O)c1cccc(C(F)(F)F)c1] | A | 418 (M − H)− |
| 317 | 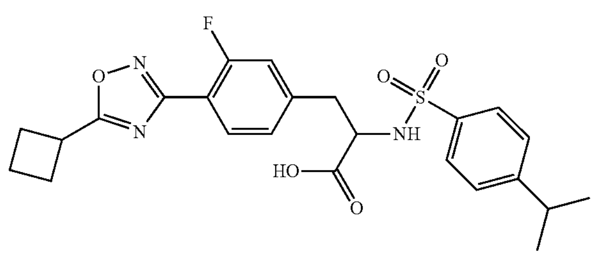 [SMILES: CC(C)c1ccc(S(=O)(=O)NC(Cc2ccc(-c3noc(C4CCC4)n3)c(F)c2)C(=O)O)cc1] | A | 486 (M − H)− |
| 318 | 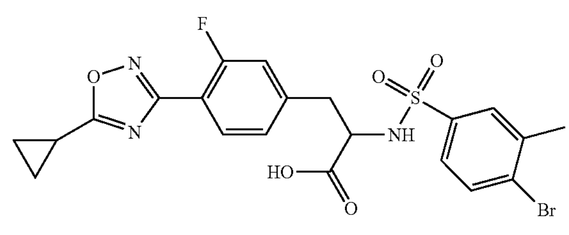 [SMILES: Cc1cc(S(=O)(=O)NC(Cc2ccc(-c3noc(C4CC4)n3)c(F)c2)C(=O)O)ccc1Br] | A | 521 (M − H)− |
| 319 | 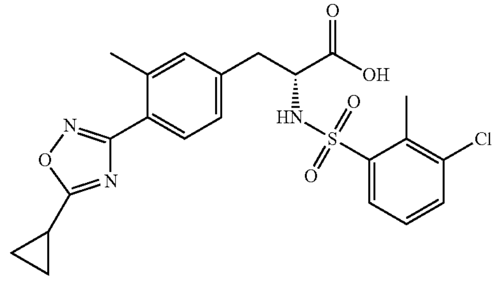 [SMILES: Cc1cc(C[C@@H](NS(=O)(=O)c2cccc(Cl)c2C)C(=O)O)ccc1-c1noc(C2CC2)n1] | B | 474 (M − H)− |

TABLE 2A-continued

Exemplary Compounds Showing Sensitizer Activity Only

| Number | Structure | Method | MS/HNMR |
|---|---|---|---|
| 320 | 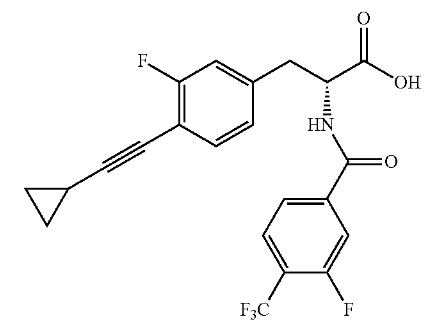 [SMILES: O=C(N[C@H](Cc1ccc(C#CC2CC2)c(F)c1)C(=O)O)c1ccc(C(F)(F)F)c(F)c1] | B1 | 436 (M − H)− |
| 321 | 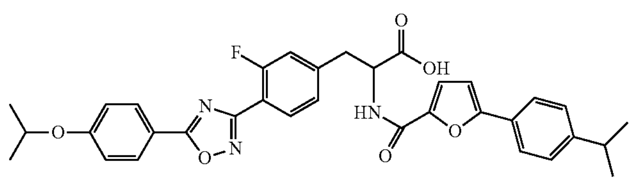 [SMILES: CC(C)Oc1ccc(-c2nc(-c3ccc(CC(NC(=O)c4ccc(-c5ccc(C(C)C)cc5)o4)C(=O)O)cc3F)no2)cc1] | A10 | 596 (M − H)− |
| 322 | 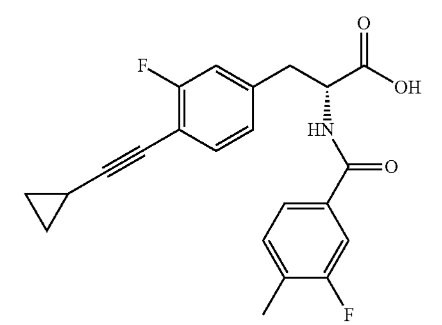 [SMILES: Cc1ccc(C(=O)N[C@H](Cc2ccc(C#CC3CC3)c(F)c2)C(=O)O)cc1F] | B1 | 382 (M − H)− |
| 323 | 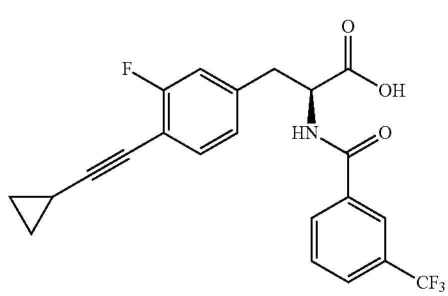 [SMILES: O=C(N[C@@H](Cc1ccc(C#CC2CC2)c(F)c1)C(=O)O)c1cccc(C(F)(F)F)c1] | B1 | 418 (M − H)− |
| 324 | 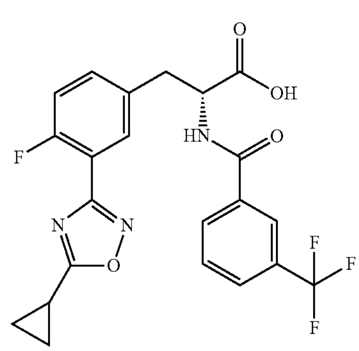 [SMILES: O=C(N[C@H](Cc1ccc(F)c(-c2noc(C3CC3)n2)c1)C(=O)O)c1cccc(C(F)(F)F)c1] | B1 | 462 (M − H)− |

TABLE 2A-continued

Exemplary Compounds Showing Sensitizer Activity Only

| Number | Structure | Method | MS/HNMR |
|---|---|---|---|
| 325 | 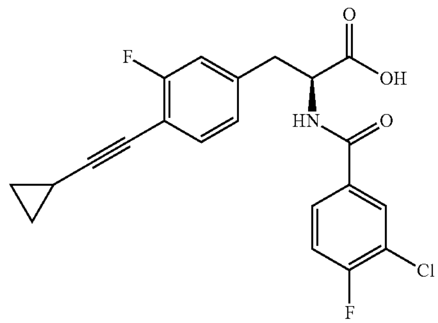 [SMILES: O=C(N[C@@H](Cc1ccc(C#CC2CC2)c(F)c1)C(=O)O)c1ccc(F)c(Cl)c1] | B1 | 402 (M – H)– |
| 326 | 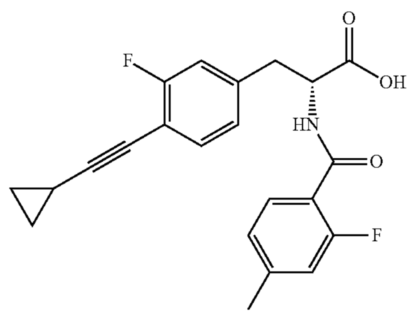 [SMILES: Cc1ccc(C(=O)N[C@H](Cc2ccc(C#CC3CC3)c(F)c2)C(=O)O)c(F)c1] | B1 | 382 (M – H)– |
| 327 | 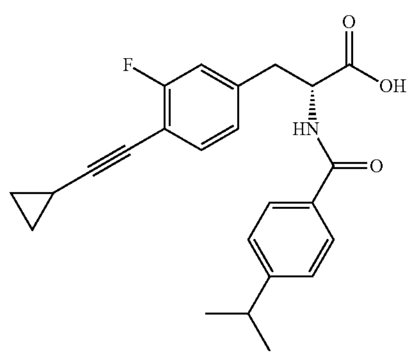 [SMILES: CC(C)c1ccc(C(=O)N[C@H](Cc2ccc(C#CC3CC3)c(F)c2)C(=O)O)cc1] | B1 | 392 (M – H)– |

TABLE 2B

Biological Activity of Sensitizer Compounds

| Compound | Concentration | Activity |
|---|---|---|
| 7A | 10 | A |
| 7B | 10 | A |
| 7C | 10 | A |
| 7D | 10 | B |
| 7F | 10 | A |
| 7G | 10 | A |
| 7H | 10 | A |
| 7I | 10 | A |
| 7J | 10 | A |
| 7K | 10 | A |
| 7L | 10 | A |
| 7M | 10 | A |
| 7N | 10 | A |
| 7O | 10 | A |
| 7P | 10 | B |
| 7Q | 10 | B |
| 7R | 10 | A |
| 7S | 10 | A |
| 7T | 10 | B |
| 7U | 10 | A |
| 7V | 5 | B |
| 7W | 20 | A |
| 7X | 5 | B |
| 7Y | 20 | B |
| 7Z | 20 | A |
| 8A | 20 | A |
| 8B | 20 | A |
| 8C | 20 | A |
| 8D | 20 | A |
| 8F | 20 | A |
| 8G | 20 | A |
| 8H | 20 | B |
| 8I | 20 | B |
| 8J | 20 | A |
| 8K | 20 | B |
| 8L | 20 | B |
| 8M | 20 | B |
| 8N | 20 | A |

TABLE 2B-continued

Biological Activity of Sensitizer Compounds

| Compound | Concentration | Activity |
|---|---|---|
| 8O | 20 | A |
| 8P | 20 | A |
| 8Q | 20 | A |
| 8R | 20 | A |
| 8S | 20 | A |
| 8T | 20 | A |
| 8U | 20 | A |
| 8V | 20 | B |
| 8W | 20 | A |
| 8X | 20 | A |
| 8Y | 5 | A |
| 8Z | 20 | A |
| 9A | 20 | A |
| 9B | 20 | A |
| 9C | 20 | A |
| 9D | 20 | A |
| 9F | 20 | A |
| 9G | 20 | A |
| 9H | 20 | A |
| 9I | 20 | A |
| 9J | 20 | A |
| 9K | 20 | A |
| 9L | 20 | A |
| 9M | 20 | A |
| 9N | 20 | A |
| 9O | 20 | A |
| 9P | 20 | A |
| 9Q | 20 | A |
| 9R | 20 | A |
| 9S | 20 | A |
| 9T | 20 | B |
| 9U | 20 | A |
| 9V | 20 | A |
| 9W | 20 | A |
| 9X | 20 | A |
| 9Y | 20 | A |
| 9Z | 20 | A |
| 10A | 20 | B |
| 10B | 20 | B |
| 10C | 20 | B |
| 10D | 20 | B |
| 10F | 20 | B |
| 10G | 20 | A |
| 10H | 20 | B |
| 10I | 20 | A |
| 10J | 20 | A |
| 10K | 20 | B |
| 10L | 20 | B |
| 10M | 20 | A |
| 10N | 20 | A |
| 10O | 20 | B |
| 10P | 20 | B |
| 10Q | 20 | A |
| 10R | 20 | B |
| 10S | 20 | A |
| 10T | 20 | A |
| 10U | 20 | A |
| 10V | 20 | B |
| 10W | 20 | B |
| 10X | 20 | B |
| 10Y | 20 | A |
| 10Z | 20 | A |

TABLE 3A

Exemplary Compounds Showing both Agonist and Sensitizer Activities

| Number | Structure | Method | MS |
|---|---|---|---|
| 163 | (structure) | A | 655 (M + H) |
| 164 | (structure) | A | 572 (M + H) |
| 165 | (structure) | A | 625 (M + H) |

TABLE 3A-continued

Exemplary Compounds Showing both Agonist and Sensitizer Activities

| Number | Structure | Method | MS |
|---|---|---|---|
| 166 | 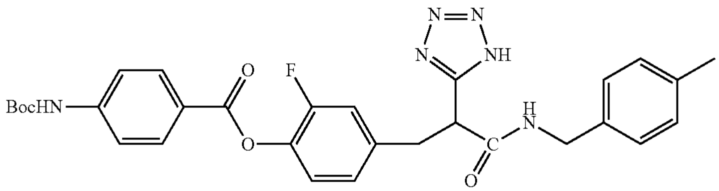 [SMILES: Cc1ccc(CNC(=O)C(Cc2ccc(OC(=O)c3ccc(NC(=O)OC(C)(C)C)cc3)c(F)c2)c2nnn[nH]2)cc1] | A | 575 (M + H) |
| 167 | 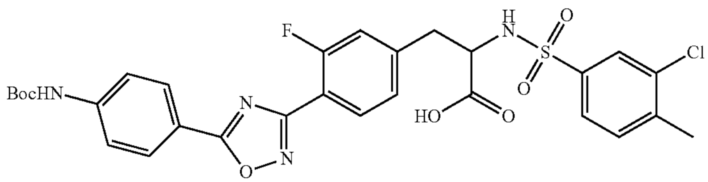 [SMILES: Cc1ccc(S(=O)(=O)NC(Cc2ccc(-c3noc(-c4ccc(NC(=O)OC(C)(C)C)cc4)n3)c(F)c2)C(=O)O)cc1Cl] | A6 | 632 (M + H) |
| 168 | 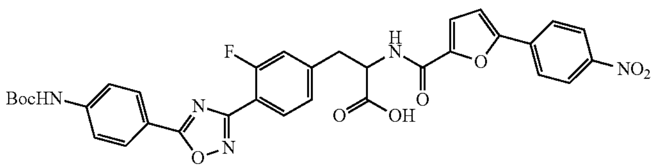 [SMILES: CC(C)(C)OC(=O)Nc1ccc(-c2nc(-c3ccc(CC(NC(=O)c4ccc(-c5ccc([N+](=O)[O-])cc5)o4)C(=O)O)cc3F)no2)cc1] | A2 | 658 (M + H) |
| 169 | 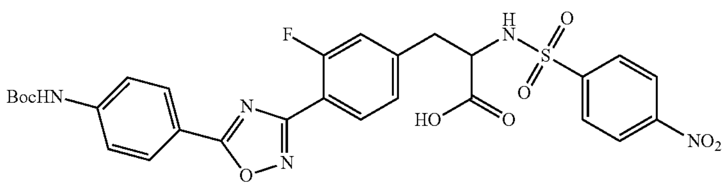 [SMILES: CC(C)(C)OC(=O)Nc1ccc(-c2nc(-c3ccc(CC(NS(=O)(=O)c4ccc([N+](=O)[O-])cc4)C(=O)O)cc3F)no2)cc1] | A6 | 628 (M + H) |
| 170 | 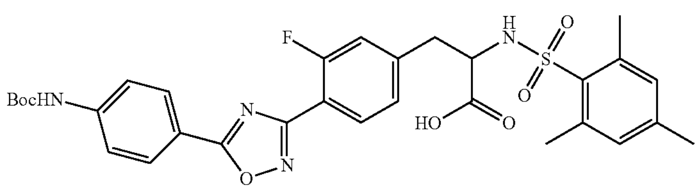 [SMILES: Cc1cc(C)c(S(=O)(=O)NC(Cc2ccc(-c3noc(-c4ccc(NC(=O)OC(C)(C)C)cc4)n3)c(F)c2)C(=O)O)c(C)c1] | A6 | 625 (M + H) |
| 171 | 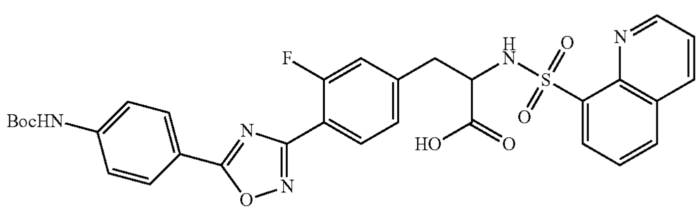 | A6 | 634 (M + H) |
| 172 | 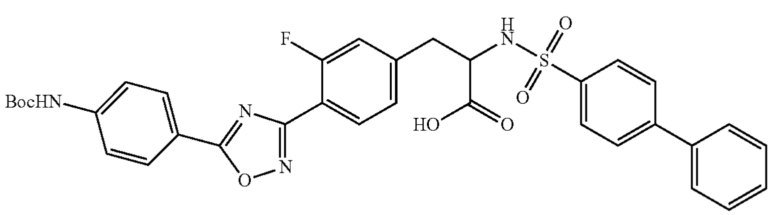 [SMILES: CC(C)(C)OC(=O)Nc1ccc(-c2nc(-c3ccc(CC(NS(=O)(=O)c4ccc(-c5ccccc5)cc4)C(=O)O)cc3F)no2)cc1] | A6 | 659 (M + H) |
| 173 | 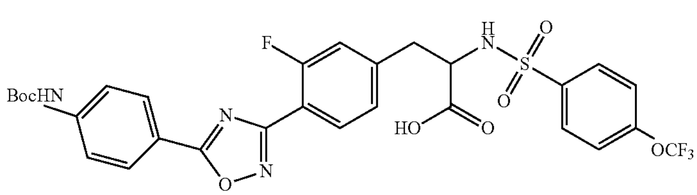 [SMILES: CC(C)(C)OC(=O)Nc1ccc(-c2nc(-c3ccc(CC(NS(=O)(=O)c4ccc(OC(F)(F)F)cc4)C(=O)O)cc3F)no2)cc1] | A6 | 667 (M + H) |

TABLE 3A-continued

Exemplary Compounds Showing both Agonist and Sensitizer Activities

| Number | Structure | Method | MS |
|---|---|---|---|
| 174 | 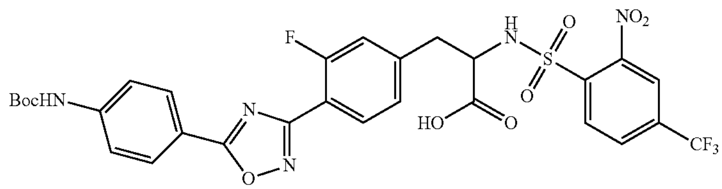 [SMILES: CC(C)(C)OC(=O)Nc1ccc(-c2nc(-c3ccc(CC(NS(=O)(=O)c4ccc(C(F)(F)F)cc4[N+](=O)[O-])C(=O)O)cc3F)no2)cc1] | A6 | 696 (M + H) |
| 175 | 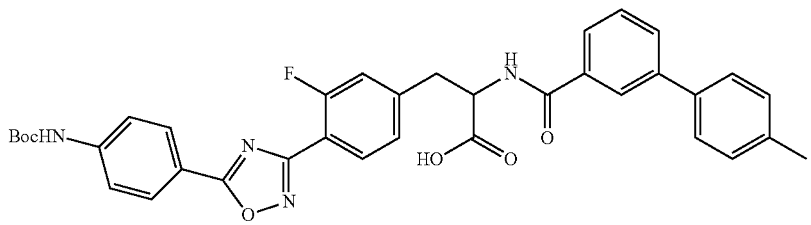 [SMILES: Cc1ccc(-c2cccc(C(=O)NC(Cc3ccc(-c4noc(-c5ccc(NC(=O)OC(C)(C)C)cc5)n4)c(F)c3)C(=O)O)c2)cc1] | A1 | 637 (M + H) |
| 176 | 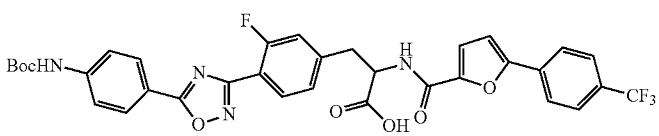 [SMILES: CC(C)(C)OC(=O)Nc1ccc(-c2nc(-c3ccc(CC(NC(=O)c4ccc(-c5ccc(C(F)(F)F)cc5)o4)C(=O)O)cc3F)no2)cc1] | A2 | 681 (M + H) |
| 177 | 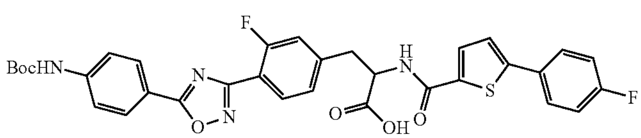 [SMILES: CC(C)(C)OC(=O)Nc1ccc(-c2nc(-c3ccc(CC(NC(=O)c4ccc(-c5ccc(F)cc5)s4)C(=O)O)cc3F)no2)cc1] | A2 | 647 (M + H) |
| 178 | 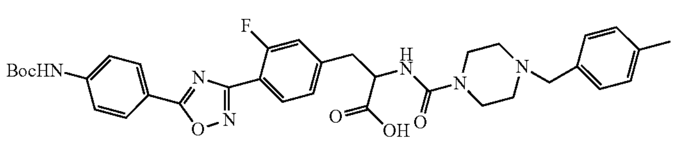 [SMILES: Cc1ccc(CN2CCN(C(=O)NC(Cc3ccc(-c4noc(-c5ccc(NC(=O)OC(C)(C)C)cc5)n4)c(F)c3)C(=O)O)CC2)cc1] | A8 | 659 (M + H) |
| 179 | 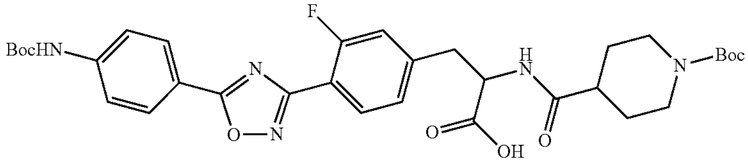 [SMILES: CC(C)(C)OC(=O)Nc1ccc(-c2nc(-c3ccc(CC(NC(=O)C4CCN(C(=O)OC(C)(C)C)CC4)C(=O)O)cc3F)no2)cc1] | A8 | 654 (M + H) |
| 180 | 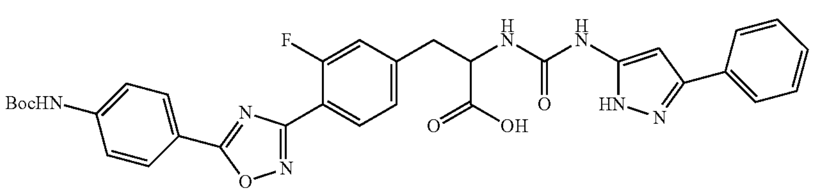 [SMILES: CC(C)(C)OC(=O)Nc1ccc(-c2nc(-c3ccc(CC(NC(=O)Nc4cc(-c5ccccc5)n[nH]4)C(=O)O)cc3F)no2)cc1] | A8 | 628 (M + H) |
| 181 | 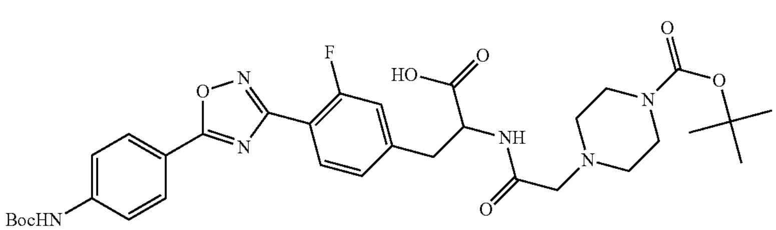 [SMILES: CC(C)(C)OC(=O)Nc1ccc(-c2nc(-c3ccc(CC(NC(=O)CN4CCN(C(=O)OC(C)(C)C)CC4)C(=O)O)cc3F)no2)cc1] | A | 669 (M + H) |

TABLE 3A-continued

Exemplary Compounds Showing both Agonist and Sensitizer Activities

| Number | Structure | Method | MS |
|---|---|---|---|
| 182 | 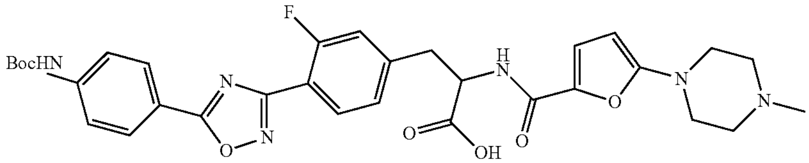 [SMILES: CN1CCN(c2ccc(C(=O)NC(Cc3ccc(-c4noc(-c5ccc(NC(=O)OC(C)(C)C)cc5)n4)c(F)c3)C(=O)O)o2)CC1] | A1 | 635 (M + H) |
| 183 | 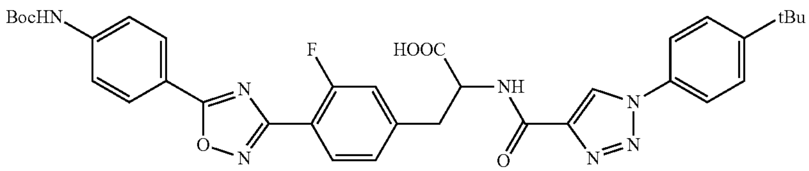 [SMILES: CC(C)(C)OC(=O)Nc1ccc(-c2nc(-c3ccc(CC(NC(=O)c4cn(-c5ccc(C(C)(C)C)cc5)nn4)C(=O)O)cc3F)no2)cc1] | A4 | 670 (M + H) |
| 184 | 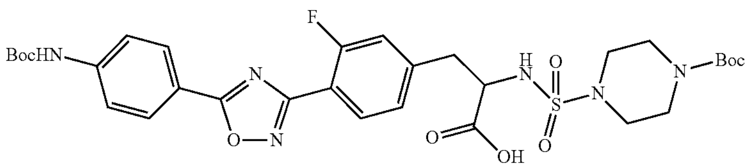 [SMILES: CC(C)(C)OC(=O)Nc1ccc(-c2nc(-c3ccc(CC(NS(=O)(=O)N4CCN(C(=O)OC(C)(C)C)CC4)C(=O)O)cc3F)no2)cc1] | A7 | 691 (M + H) |
| 185 | 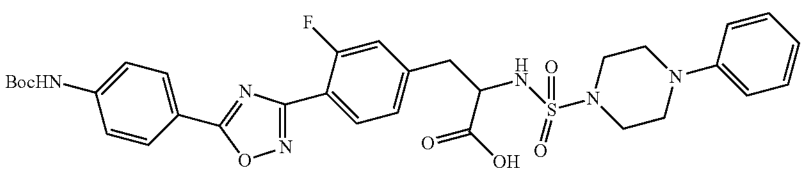 [SMILES: CC(C)(C)OC(=O)Nc1ccc(-c2nc(-c3ccc(CC(NS(=O)(=O)N4CCN(c5ccccc5)CC4)C(=O)O)cc3F)no2)cc1] | A7 | 667 (M + H) |
| 186 | 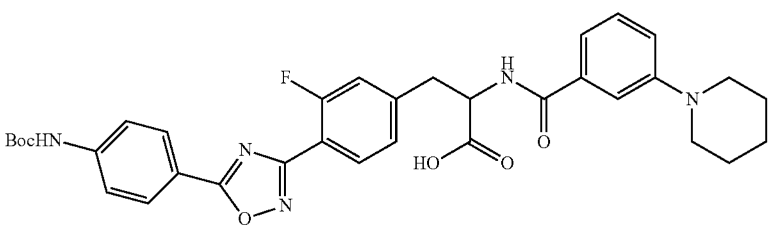 [SMILES: CC(C)(C)OC(=O)Nc1ccc(-c2nc(-c3ccc(CC(NC(=O)c4cccc(N5CCCCC5)c4)C(=O)O)cc3F)no2)cc1] | A3 | 630 (M + H) |
| 187 | 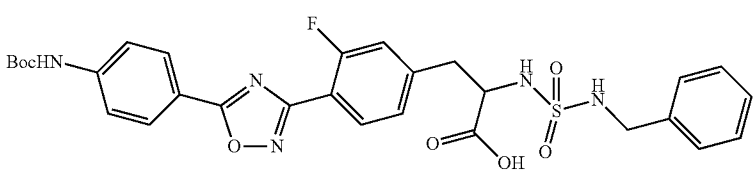 [SMILES: CC(C)(C)OC(=O)Nc1ccc(-c2nc(-c3ccc(CC(NS(=O)(=O)NCc4ccccc4)C(=O)O)cc3F)no2)cc1] | A7 | 612 (M + H) |
| 188 | 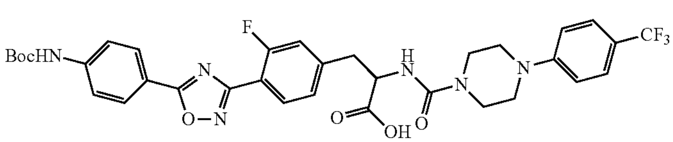 [SMILES: CC(C)(C)OC(=O)Nc1ccc(-c2nc(-c3ccc(CC(NC(=O)N4CCN(c5ccc(C(F)(F)F)cc5)CC4)C(=O)O)cc3F)no2)cc1] | A8 | 699 (M + H) |
| 189 | 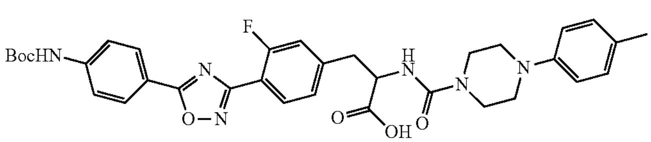 | A8 | 681 (M + H) |
| 190 | 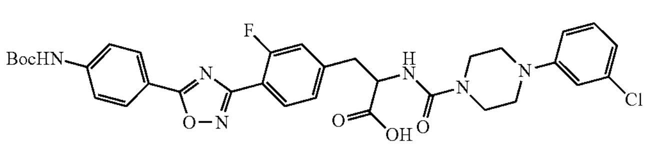 [SMILES: CC(C)(C)OC(=O)Nc1ccc(-c2nc(-c3ccc(CC(NC(=O)N4CCN(c5cccc(Cl)c5)CC4)C(=O)O)cc3F)no2)cc1] | A8 | 665 (M + H) |

TABLE 3A-continued

Exemplary Compounds Showing both Agonist and Sensitizer Activities

| Number | Structure | Method | MS |
|---|---|---|---|
| 191 | 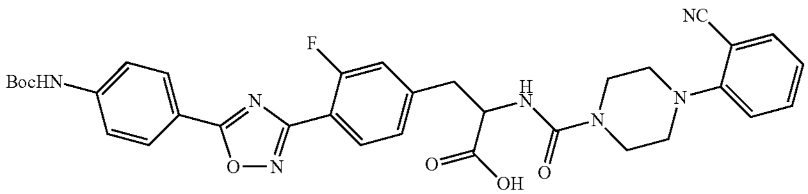 [SMILES: CC(C)(C)OC(=O)Nc1ccc(-c2nc(-c3ccc(CC(NC(=O)N4CCN(c5ccccc5C#N)CC4)C(=O)O)cc3F)no2)cc1] | A8 | 656 (M + H) |
| 192 | 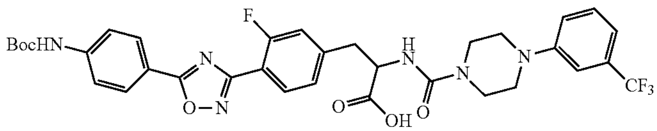 [SMILES: CC(C)(C)OC(=O)Nc1ccc(-c2nc(-c3ccc(CC(NC(=O)N4CCN(c5cccc(C(F)(F)F)c5)CC4)C(=O)O)cc3F)no2)cc1] | A8 | 699 (M + H) |
| 193 | 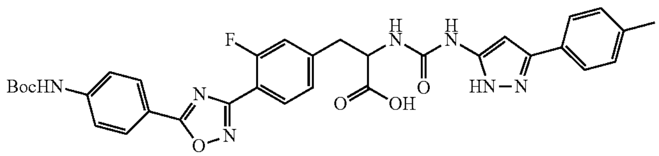 [SMILES: Cc1ccc(-c2cc(NC(=O)NC(Cc3ccc(-c4noc(-c5ccc(NC(=O)OC(C)(C)C)cc5)n4)c(F)c3)C(=O)O)[nH]n2)cc1] | A8 | 642 (M + H) |
| 194 | 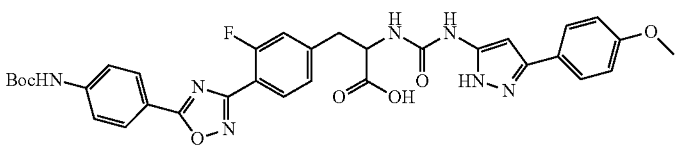 [SMILES: COc1ccc(-c2cc(NC(=O)NC(Cc3ccc(-c4noc(-c5ccc(NC(=O)OC(C)(C)C)cc5)n4)c(F)c3)C(=O)O)[nH]n2)cc1] | A8 | 658 (M + H) |
| 195 | 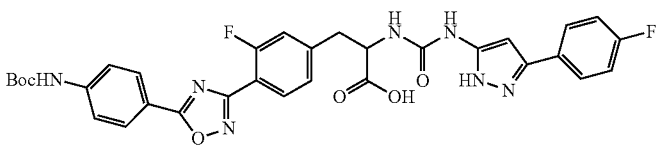 [SMILES: CC(C)(C)OC(=O)Nc1ccc(-c2nc(-c3ccc(CC(NC(=O)Nc4cc(-c5ccc(F)cc5)n[nH]4)C(=O)O)cc3F)no2)cc1] | A8 | 646 (M + H) |
| 196 | 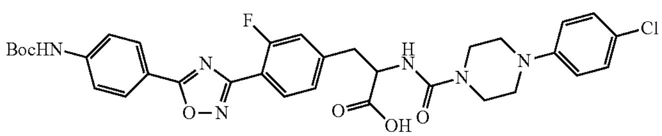 [SMILES: CC(C)(C)OC(=O)Nc1ccc(-c2nc(-c3ccc(CC(NC(=O)N4CCN(c5ccc(Cl)cc5)CC4)C(=O)O)cc3F)no2)cc1] | A8 | 665 (M + H) |
| 197 | 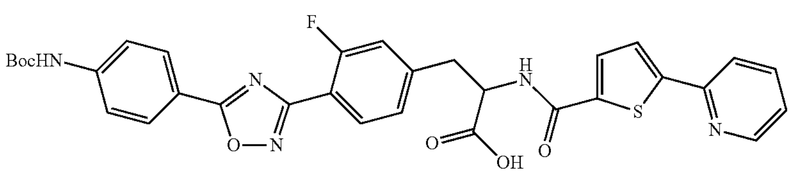 [SMILES: CC(C)(C)OC(=O)Nc1ccc(-c2nc(-c3ccc(CC(NC(=O)c4ccc(-c5ccccn5)s4)C(=O)O)cc3F)no2)cc1] | A8 | 630 (M + H) |
| 198 | 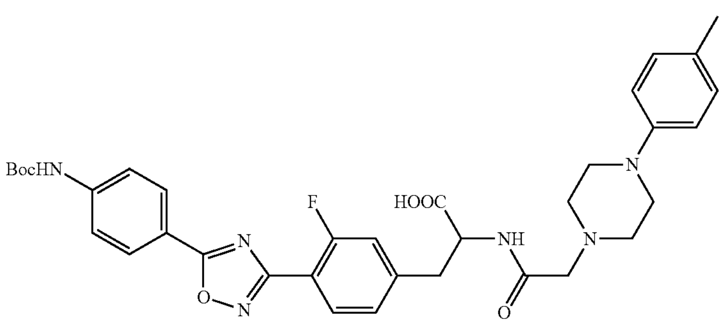 | A8 | 673 (M + H) |

TABLE 3A-continued

Exemplary Compounds Showing both Agonist and Sensitizer Activities

| Number | Structure | Method | MS |
|---|---|---|---|
| 199 | 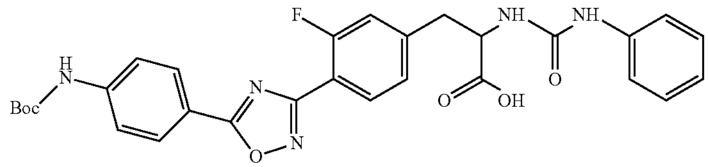 [SMILES: CC(C)(C)OC(=O)Nc1ccc(-c2nc(-c3ccc(CC(NC(=O)Nc4ccccc4)C(=O)O)cc3F)no2)cc1] | A8 | 562 (M + H) |
| 200 | 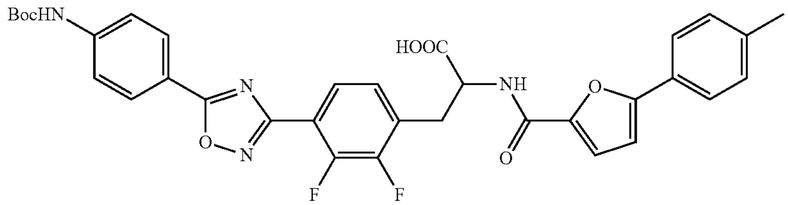 [SMILES: Cc1ccc(-c2ccc(C(=O)NC(Cc3ccc(-c4noc(-c5ccc(NC(=O)OC(C)(C)C)cc5)n4)c(F)c3F)C(=O)O)o2)cc1] | A15 | 645 (M + H) |
| 201 | 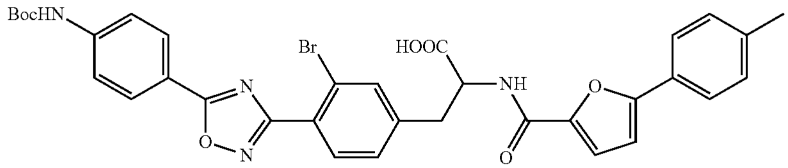 [SMILES: Cc1ccc(-c2ccc(C(=O)NC(Cc3ccc(-c4noc(-c5ccc(NC(=O)OC(C)(C)C)cc5)n4)c(Br)c3)C(=O)O)o2)cc1] | A15 | 685 (M − H) |
| 202 | 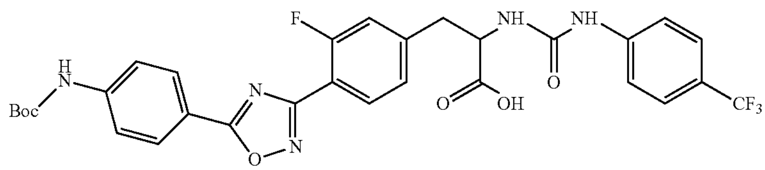 [SMILES: CC(C)(C)OC(=O)Nc1ccc(-c2nc(-c3ccc(CC(NC(=O)Nc4ccc(C(F)(F)F)cc4)C(=O)O)cc3F)no2)cc1] | A8 | 630 (M + H) |
| 203 | 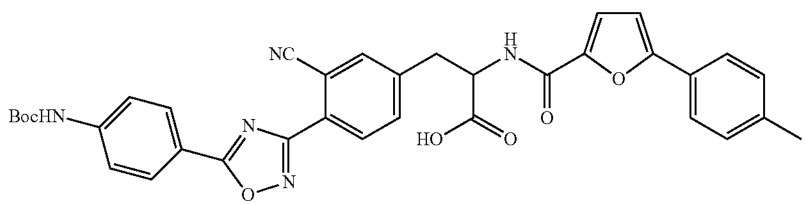 [SMILES: Cc1ccc(-c2ccc(C(=O)NC(Cc3ccc(-c4noc(-c5ccc(NC(=O)OC(C)(C)C)cc5)n4)c(C#N)c3)C(=O)O)o2)cc1] | A14 | 634 (M + H) |
| 204 | 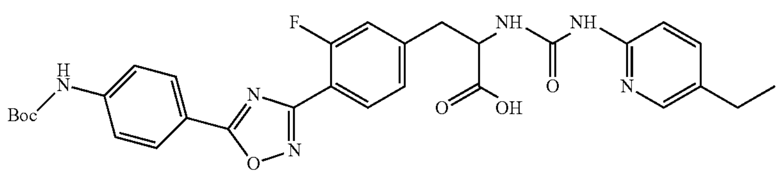 [SMILES: CCc1ccc(NC(=O)NC(Cc2ccc(-c3noc(-c4ccc(NC(=O)OC(C)(C)C)cc4)n3)c(F)c2)C(=O)O)nc1] | A8 | 590 (M + H) |
| 205 | 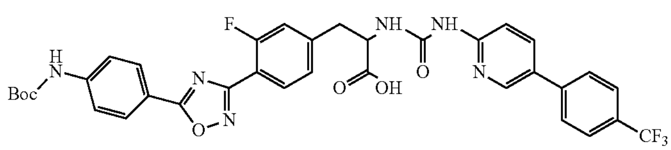 [SMILES: CC(C)(C)OC(=O)Nc1ccc(-c2nc(-c3ccc(CC(NC(=O)Nc4ccc(-c5ccc(C(F)(F)F)cc5)cn4)C(=O)O)cc3F)no2)cc1] | A8 | 707 (M + H) |
| 206 | 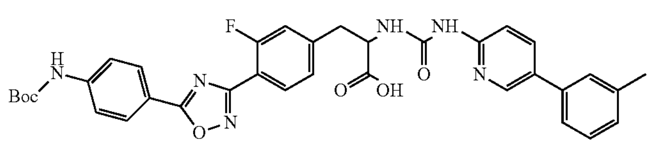 [SMILES: Cc1cccc(-c2ccc(NC(=O)NC(Cc3ccc(-c4noc(-c5ccc(NC(=O)OC(C)(C)C)cc5)n4)c(F)c3)C(=O)O)nc2)c1] | A8 | 653 (M + H) |
| 207 | 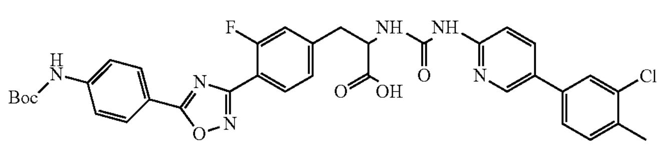 [SMILES: Cc1ccc(-c2ccc(NC(=O)NC(Cc3ccc(-c4noc(-c5ccc(NC(=O)OC(C)(C)C)cc5)n4)c(F)c3)C(=O)O)nc2)cc1Cl] | A8 | 689 (M + H) |

TABLE 3A-continued

Exemplary Compounds Showing both Agonist and Sensitizer Activities

| Number | Structure | Method | MS |
|---|---|---|---|
| 208 | 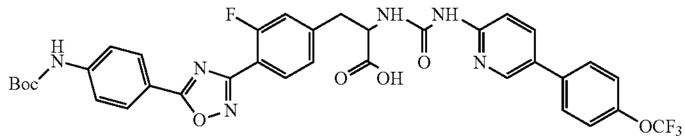 [SMILES: CC(C)(C)OC(=O)Nc1ccc(-c2nc(-c3ccc(CC(NC(=O)Nc4ccc(-c5ccc(OC(F)(F)F)cc5)cn4)C(=O)O)cc3F)no2)cc1] | A8 | 723 (M + H) |
| 209 | 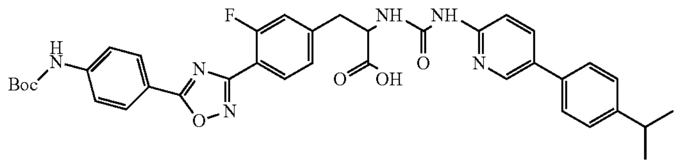 [SMILES: CC(C)c1ccc(-c2ccc(NC(=O)NC(Cc3ccc(-c4noc(-c5ccc(NC(=O)OC(C)(C)C)cc5)n4)c(F)c3)C(=O)O)nc2)cc1] | A8 | 681 (M + H) |
| 210 | 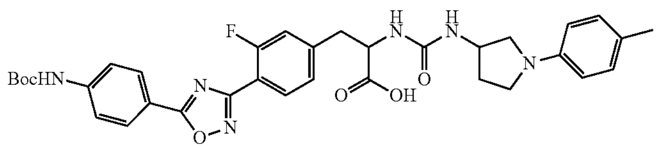 [SMILES: Cc1ccc(N2CCC(NC(=O)NC(Cc3ccc(-c4noc(-c5ccc(NC(=O)OC(C)(C)C)cc5)n4)c(F)c3)C(=O)O)C2)cc1] | A8 | 645 (M + H) |
| 211 | 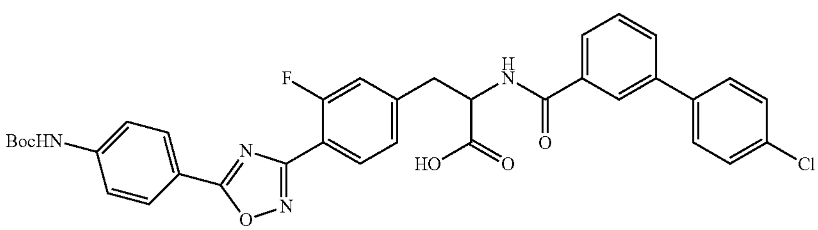 [SMILES: CC(C)(C)OC(=O)Nc1ccc(-c2nc(-c3ccc(CC(NC(=O)c4cccc(-c5ccc(Cl)cc5)c4)C(=O)O)cc3F)no2)cc1] | A8 | 658 (M + H) |
| 212 | 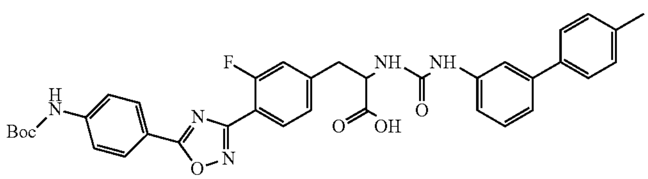 [SMILES: Cc1ccc(-c2cccc(NC(=O)NC(Cc3ccc(-c4noc(-c5ccc(NC(=O)OC(C)(C)C)cc5)n4)c(F)c3)C(=O)O)c2)cc1] | A8 | 650 (M − H) |
| 213 | 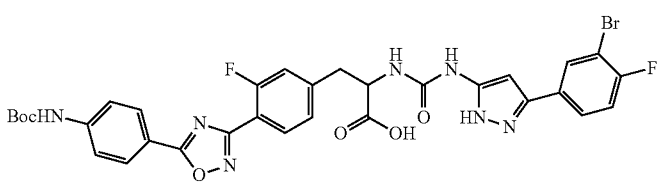 [SMILES: CC(C)(C)OC(=O)Nc1ccc(-c2nc(-c3ccc(CC(NC(=O)Nc4cc(-c5ccc(F)c(Br)c5)n[nH]4)C(=O)O)cc3F)no2)cc1] | A8 | 725 (M + H) |
| 214 | 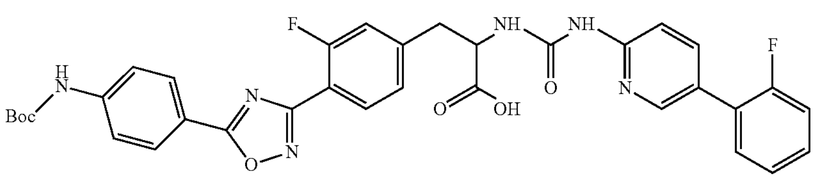 [SMILES: CC(C)(C)OC(=O)Nc1ccc(-c2nc(-c3ccc(CC(NC(=O)Nc4ccc(-c5ccccc5F)cn4)C(=O)O)cc3F)no2)cc1] | A8 | 657 (M + H) |
| 215 | 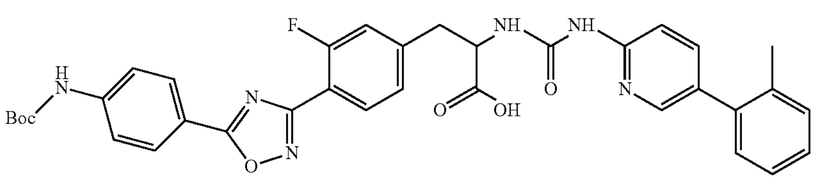 [SMILES: Cc1ccccc1-c1ccc(NC(=O)NC(Cc2ccc(-c3noc(-c4ccc(NC(=O)OC(C)(C)C)cc4)n3)c(F)c2)C(=O)O)nc1] | A8 | 653 (M + H) |
| 216 | 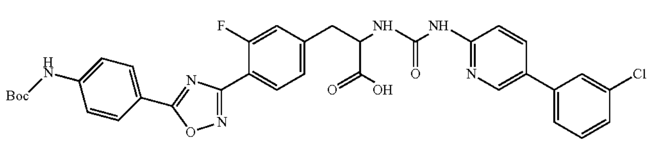 [SMILES: CC(C)(C)OC(=O)Nc1ccc(-c2nc(-c3ccc(CC(NC(=O)Nc4ccc(-c5cccc(Cl)c5)cn4)C(=O)O)cc3F)no2)cc1] | A8 | 673 (M + H) |

TABLE 3A-continued

Exemplary Compounds Showing both Agonist and Sensitizer Activities

| Number | Structure | Method | MS |
|---|---|---|---|
| 217 | 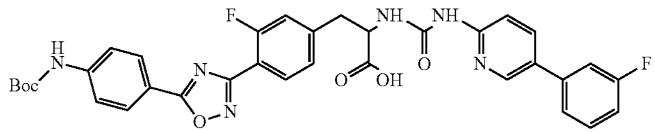 [SMILES: CC(C)(C)OC(=O)Nc1ccc(-c2nc(-c3ccc(CC(NC(=O)Nc4ccc(-c5cccc(F)c5)cn4)C(=O)O)cc3F)no2)cc1] | A8 | 657 (M + H) |
| 218 | 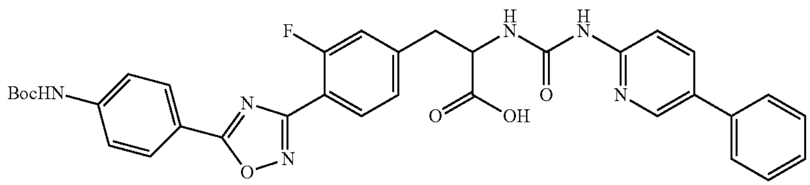 [SMILES: CC(C)(C)OC(=O)Nc1ccc(-c2nc(-c3ccc(CC(NC(=O)Nc4ccc(-c5ccccc5)cn4)C(=O)O)cc3F)no2)cc1] | A8 | 639 (M + H) |
| 219 | 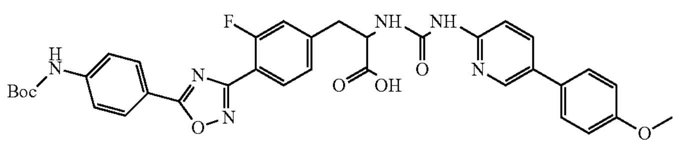 [SMILES: COc1ccc(-c2ccc(NC(=O)NC(Cc3ccc(-c4noc(-c5ccc(NC(=O)OC(C)(C)C)cc5)n4)c(F)c3)C(=O)O)nc2)cc1] | A8 | 669 (M + H) |
| 220 | 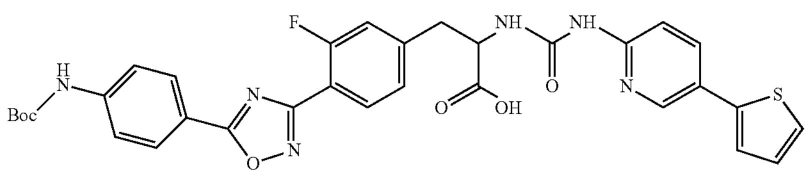 [SMILES: CC(C)(C)OC(=O)Nc1ccc(-c2nc(-c3ccc(CC(NC(=O)Nc4ccc(-c5cccs5)cn4)C(=O)O)cc3F)no2)cc1] | A8 | 645 (M + H) |
| 221 | 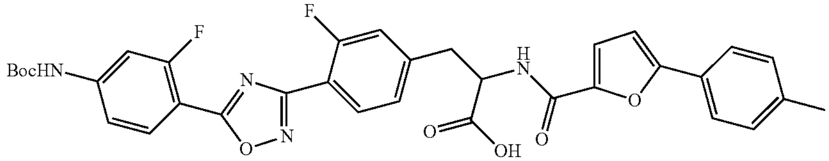 [SMILES: Cc1ccc(-c2ccc(C(=O)NC(Cc3ccc(-c4noc(-c5ccc(NC(=O)OC(C)(C)C)cc5F)n4)c(F)c3)C(=O)O)o2)cc1] | A | 645 (M + H) |
| 222 | 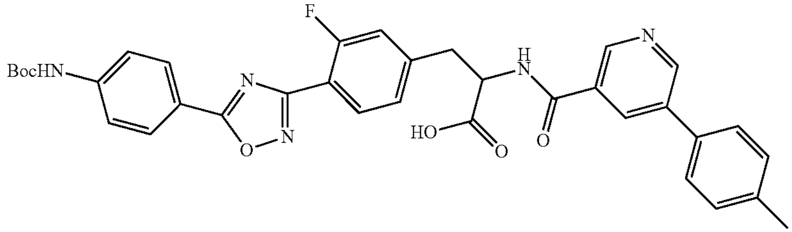 [SMILES: Cc1ccc(-c2cncc(C(=O)NC(Cc3ccc(-c4noc(-c5ccc(NC(=O)OC(C)(C)C)cc5)n4)c(F)c3)C(=O)O)c2)cc1] | A1 | 638 (M + H) |
| 223 | 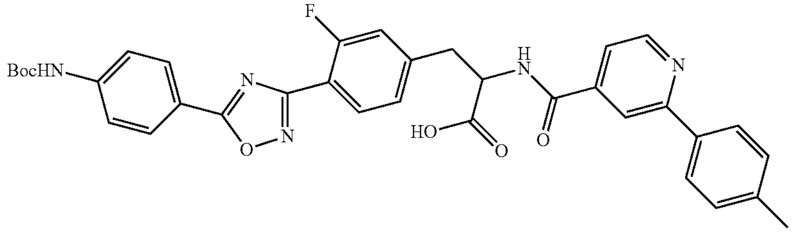 | A1 | 638 (M + H) |
| 224 | 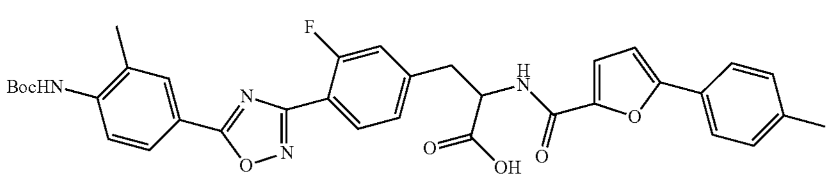 [SMILES: Cc1ccc(-c2ccc(C(=O)NC(Cc3ccc(-c4noc(-c5ccc(NC(=O)OC(C)(C)C)c(C)c5)n4)c(F)c3)C(=O)O)o2)cc1] | A | 641 (M + H) |

TABLE 3A-continued

Exemplary Compounds Showing both Agonist and Sensitizer Activities

| Number | Structure | Method | MS |
|---|---|---|---|
| 225 | 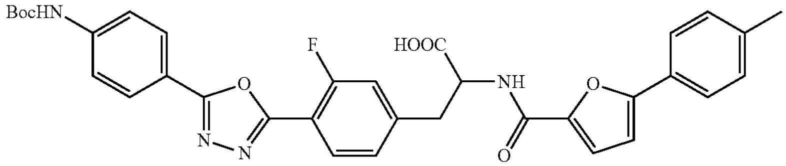 [SMILES: Cc1ccc(-c2ccc(C(=O)NC(Cc3ccc(-c4nnc(-c5ccc(NC(=O)OC(C)(C)C)cc5)o4)c(F)c3)C(=O)O)o2)cc1] | A13 | 627 (M + H) |
| 226 | 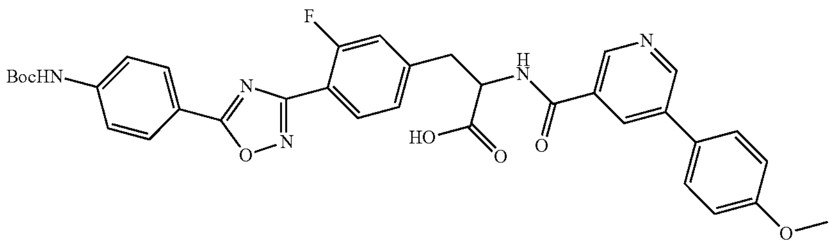 [SMILES: COc1ccc(-c2cncc(C(=O)NC(Cc3ccc(-c4noc(-c5ccc(NC(=O)OC(C)(C)C)cc5)n4)c(F)c3)C(=O)O)c2)cc1] | A1 | 654 (M + H) |
| 227 | 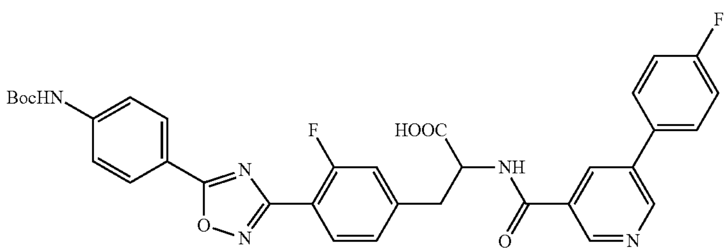 [SMILES: CC(C)(C)OC(=O)Nc1ccc(-c2nc(-c3ccc(CC(NC(=O)c4cncc(-c5ccc(F)cc5)c4)C(=O)O)cc3F)no2)cc1] | A1 | 640 (M − H)− |

TABLE 3B

Biological Activity of Compounds with both Agonist and Sensitizer Activities

| # | Sensitizer Conc. | Sensitizer Activity | Agonist Conc. | Agonist Activity |
|---|---|---|---|---|
| 11A | 10 | B | 10 | A |
| 11B | 10 | A | 10 | B |
| 11C | 10 | A | 10 | C |
| 11D | 10 | A | 10 | C |
| 11F | 10 | A | 10 | B |
| 11G | 10 | A | 10 | A |
| 11H | 10 | A | 10 | B |
| 11I | 10 | A | 10 | B |
| 11J | 10 | A | 10 | A |
| 11K | 10 | A | 10 | A |
| 11L | 10 | A | 10 | C |
| 11M | 10 | A | 10 | A |
| 11N | 10 | A | 10 | A |
| 11O | 10 | A | 10 | A |
| 11P | 10 | A | 10 | C |
| 11Q | 10 | A | 10 | A |
| 11R | 10 | A | 10 | A |
| 11S | 10 | A | 10 | A |
| 11T | 10 | A | 10 | B |
| 11U | 10 | A | 10 | C |
| 11V | 10 | A | 10 | A |
| 11W | 10 | A | 10 | B |
| 11X | 10 | A | 10 | A |
| 11Y | 10 | A | 10 | C |
| 11Z | 10 | A | 10 | B |
| 12A | 10 | A | 10 | A |
| 12B | 10 | A | 10 | A |
| 12C | 10 | A | 10 | A |
| 12D | 10 | A | 10 | A |
| 12F | 10 | A | 10 | A |
| 12G | 10 | A | 10 | A |
| 12H | 10 | A | 10 | A |
| 12I | 10 | A | 10 | A |
| 13A | 10 | A | 10 | A |
| 13B | 10 | A | 10 | A |
| 13C | 10 | A | 10 | A |
| 13D | 10 | A | 10 | B |
| 13F | 10 | A | 10 | A |
| 13G | 10 | A | 3.16 | A |
| 13H | 10 | A | 10 | A |
| 13I | 10 | A | 10 | B |
| 13J | 10 | A | 10 | A |
| 13K | 10 | A | 10 | A |
| 13L | 10 | B | 10 | A |
| 13M | 10 | A | 10 | A |
| 13N | 10 | A | 10 | A |
| 13O | 10 | A | 10 | B |
| 13P | 10 | A | 10 | A |
| 13Q | 10 | A | 10 | A |
| 13R | 10 | C | 10 | A |
| 13S | 10 | A | 10 | A |
| 13T | 10 | A | 10 | A |
| 13U | 10 | A | 10 | A |
| 13V | 10 | A | 10 | A |
| 13W | 10 | A | 10 | A |
| 13X | 10 | A | 10 | A |
| 13Y | 10 | B | 10 | A |
| 13Z | 10 | A | 10 | A |
| 14A | 10 | A | 10 | A |
| 14B | 10 | A | 10 | A |
| 14C | 10 | B | 10 | A |
| 14D | 10 | A | 10 | B |

TABLE 3B-continued

Biological Activity of Compounds with both Agonist and Sensitizer Activities

| # | Sensitizer | | Agonist | |
|---|---|---|---|---|
| | Conc. | Activity | Conc. | Activity |
| 14F | 10 | A | 3.16 | B |
| 14G | 10 | A | 10 | A |
| 14H | 10 | A | 3.16 | A |

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference in their entireties as if each such publication, patent or patent application were specifically and individually indicated to be incorporated herein by reference.

What is claimed is:

1. A compound of Formula (I):

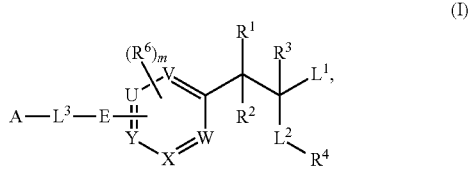

(I)

or a pharmaceutically acceptable salt, solvate, or prodrug thereof;

wherein:

A is $C_{3-8}$ carbocyclyl, $C_{6-14}$ aryl, $C_{7-15}$ aralkyl, heteroaryl, or heterocyclyl;

E is a bond, $C_{2-6}$ alkenylene, $C_{2-6}$ alkynylene, arylene, heteroarylene, carbocyclylene, heterocyclylene; with the proviso that E is not 4-oxo-imidazolidinylene;

$L^3$ is a bond, —C(O)—, —O—, —OC(O)O—, —OC(O)NR$^{1a}$—, —NR$^{1a}$C(O)O—, —OS(O)—, —S(O)O—, —OS(O)$_2$—, —S(O)$_2$O—, —OS(O)NR$^{1a}$—, —NR$^{1a}$S(O)O—, —OS(O)$_2$NR$^{1a}$—, —NR$^{1a}$S(O)$_2$O—, —NR$^{1a}$—, —NR$^{1a}$C(O)NR$^{1d}$—, —NR$^{1a}$S(O)NR$^{1d}$—, —NR$^{1a}$S(O)$_2$NR$^{1d}$—, —S—, —S(O)—, —S(O)$_2$—, —S(O)NR$^{1a}$—, —NR$^{1a}$S(O)—, —S(O)$_2$NR$^{1a}$—, or —NR$^{1a}$S(O)$_2$—; with the provisos that (a) E and $L^3$ are not both a bond at the same time; and (b) when $L^3$-E together is —O—, $R^6$ is not iodo or benzoxy;

m is an integer of 0, 1, 2, 3, or 4;

$L^1$ is a carboxylate bioisostere selected from the group consisting of —CH$_2$OH, —CONH$_2$, —CO$_2$H, —P(O)(OH)$_2$, —P(OH)$_2$, tetrazolyl, or 3-hydroxyisoxazolyl;

$L^2$ is —CH$_2$N(R$^5$)—, —N(R$^5$)CH$_2$—, —N(R$^5$)—, —O—, —S—, —C(O)NR$^5$—, —NR$^5$C(O)—, —CH$_2$C(O)NR$^5$—, —NR$^5$C(O)CH$_2$—, —CH=CH—C(O)NR$^5$—, —NR$^5$C(O)—CH=CH—, —C≡C—C(O)NR$^5$—, —NR$^5$C(O)—C≡C—, —S(O)NR$^5$—, —NR$^5$S(O)—, —S(O)$_2$NR$^5$—, —NR$^5$S(O)$_2$—, —NR$^5$C(O)NR$^{5a}$—, —NR$^5$S(O)$_2$NR$^{5a}$—, —CH$_2$NR$^5$S(O)$_2$NR$^{5a}$—, —NR$^5$S(O)$_2$NR$^{5a}$CH$_2$—, —NR$^5$C(O)-alkylene, —NR$^5$S(O)-alkylene, —NR$^5$S(O)$_2$-alkylene, —NR$^5$C(O)-alkenylene, —NR$^5$S(O)-alkenylene, or —NR$^5$S(O)$_2$-alkenylene; or alternatively; or alternatively, $L^2$ and V or W, together with other atoms to which they are attached, form 5- to 8-membered optionally substituted carbocyclyl or heterocyclyl; or alternatively, V or W and the carbon atom which is attached to $R^3$, $L^1$, and $L^2$, together with other atoms to which they are attached, form 5- to 8-membered optionally substituted carbocyclyl or heterocyclyl;

U, V, W, X, and Y are each independently C, CH, or N; and U, V, W, X, and Y, together with the carbon atom to which V and W are attached, form an aromatic 6-membered ring; with the proviso that at most 3 of U, V, W, X, and Y are N or NH;

$R^1$, $R^2$, and $R^3$ are selected from (i), (ii), (iii), and (iv):

(i) $R^1$, $R^2$, and $R^3$ are each independently (a) hydrogen, halo, or cyano; (b) $C_{1-6}$ alkyl, $C_{2-6}$ alkenyl, $C_{2-6}$ alkynyl, $C_{3-8}$ carbocyclyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

(ii) $R^1$ or $R^2$ forms a double bond with $R^3$; and the other of $R^1$ and $R^2$ is selected as in (i);

(iii) two of $R^1$, $R^2$, and $R^3$ are joined together to form $C_{3-8}$-carbocyclyl, or 3- to 8-membered heterocyclyl; and the third is selected as in (i); and (iv) $R^3$ and V or W, together with the other atoms to which are attached, form $C_{5-8}$ carbocyclyl, or 5- to 8-membered heterocyclyl; and $R^1$ and $R^2$ are selected as in (i);

$R^4$ is $C_{1-6}$ alkyl, $C_{2-6}$ alkenyl, $C_{2-6}$ alkynyl, $C_{3-7}$ carbocyclyl, $C_{6-14}$ aryl, $C_{7-15}$ aralkyl, heteroaryl, or heterocyclyl; or alternatively, $R^4$ and $R^5$ together with the N atom to which they are attached form heterocyclyl;

$R^5$ and $R^{5a}$ are each independently hydrogen, $C_{1-6}$ alkyl, —C(O)—$C_{1-6}$ alkyl; $C_{2-6}$ alkenyl, $C_{2-6}$ alkynyl, $C_{3-7}$ carbocyclyl, $C_{6-14}$ aryl, $C_{7-15}$ aralkyl, heteroaryl, or heterocyclyl; or alternatively, $R^4$ and $R^5$ are joined together to form heterocyclyl;

$R^6$ is cyano, halo, azido, nitro, $C_{1-6}$ alkyl, $C_{2-6}$ alkenyl, $C_{2-6}$ alkynyl, $C_{3-7}$ carbocyclyl, $C_{6-14}$ aryl, $C_{7-15}$ aralkyl, heteroaryl, heterocyclyl, —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

when U, V, W, X, and Y are each independently C or CH; $R^1$, $R^2$, and $R^3$ are hydrogen; $L^1$ is —CONH$_2$ or —CO$_2$H; $L^2$ is —NR$^5$C(O)—; and $R^4$ is -heteroaryl-aryl; then A-$L^3$-E- is cyano group;

each $R^{1a}$, $R^{1b}$, $R^{1c}$, and $R^{1d}$ is independently hydrogen, $C_{1-6}$ alkyl, $C_{2-6}$ alkenyl, $C_{2-6}$ alkynyl, $C_{3-7}$ carbocyclyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl;

wherein each alkyl, alkenyl, alkenylene, alkynyl, alkynylene, carbocyclyl, carbocyclylene, aryl, arylene, aralkyl, heteroaryl, heteroarylene, heterocyclyl, and heterocyclylene, in $R^1$, $R^2$, $R^3$, $R^4$, $R^5$, $R^{5a}$, $R^6$, $R^{1a}$, $R^{1b}$, $R^{1c}$, $R^{1d}$, A, and E is optionally substituted with one or more substituents Q, where each Q is independently selected from (a) cyano, halo, azido, and nitro;
(b) $C_{1-6}$ alkyl, $C_{2-6}$ alkenyl, $C_{2-6}$ alkynyl, $C_{3-7}$ carbocyclyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and
(c) —C(O)$R^a$, —C(O)O$R^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) $C_{1-6}$ alkyl, $C_{2-6}$ alkenyl, $C_{2-6}$ alkynyl, $C_{3-7}$ carbocyclyl, $C_{6-14}$ aryl, $C_{7-15}$ aralkyl, heteroaryl, or heterocyclyl, each optionally substituted with one or more, in one embodiment, one, two, three, or four, substituents $Q^a$; or (iii) R$^b$ and R$^c$ together with the N atom to which they are attached form heterocyclyl, optionally substituted with one or more, in one embodiment, one, two, three, or four, substituents $Q^a$; and wherein each $Q^a$ is independently selected from the group consisting of (a) cyano, halo, and nitro; (b) $C_{1-6}$ alkyl, $C_{2-6}$ alkenyl, $C_{2-6}$ alkynyl, $C_{3-7}$ carbocyclyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^i$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) $C_{1-6}$ alkyl, $C_{2-6}$ alkenyl, $C_{2-6}$ alkynyl, $C_{3-7}$ carbocyclyl, $C_{6-14}$ aryl, $C_{7-15}$ aralkyl, heteroaryl, or heterocyclyl; or (iii) R$^f$ and R$^g$ together with the N atom to which they are attached form heterocyclyl.

2. The comnound of claim 1, having the structure of Formula (II) or (III):

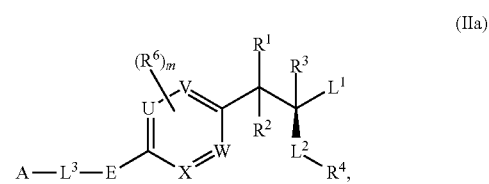
(II)

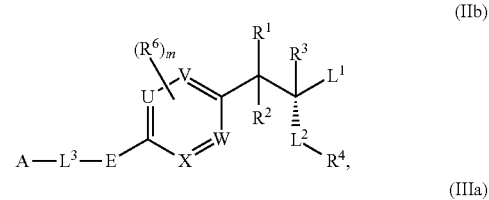
(III)

wherein A, $L^3$, $R^6$, E, m, Y, U, V, W, X, $R^1$, $R^2$, $R^3$, $L^1$, $L^2$, and $R^4$ are the same as defined in claim 1.

3. The compound of claim 2, having the structure of Formula (IIa), (IIb), (IIIa), or (Mb):

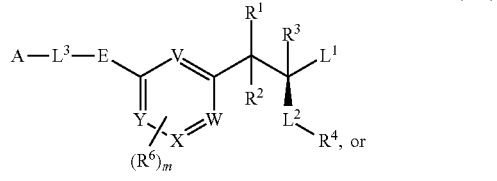
(IIa)

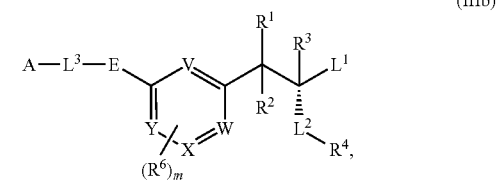
(IIb)

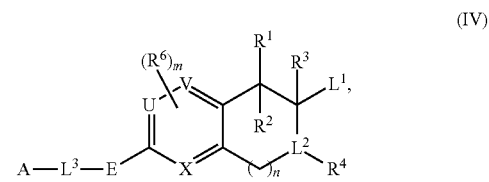
(IIIa)

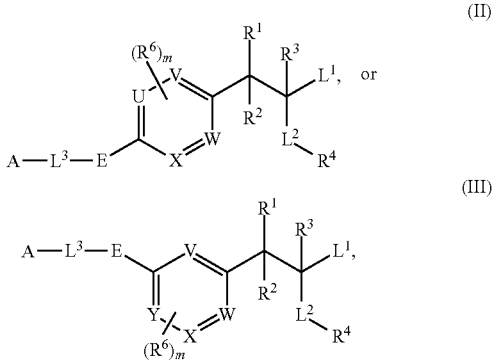
(IIIb)

wherein A, $L^3$, $R^6$, E, m, Y, U, V, W, X, $R^1$, $R^2$, $R^3$, $L^1$, $L^2$, and $R^4$ are the same as defined in claim 2.

4. The compound of claim 1, having the structure of Formula (IV):

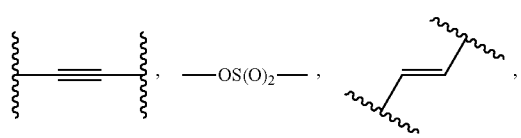
(IV)

wherein,
A, $L^3$, $R^6$, E, $R^1$, $R^2$, $R^3$, $L^1$, $L^2$, and $R^4$ are the same as defined in claim 1;
m is zero, 1, 2, or 3;
n is zero, 1, 2, or 3; when n is zero, $L^2$ is directly attached to the carbon atom adjacent to X to form a 5-membered ring; and
U, V, and X in (IIc) are independently CH or N.

5. The compound of claim 1, wherein -$L^3$-E- has the structure of:

-continued

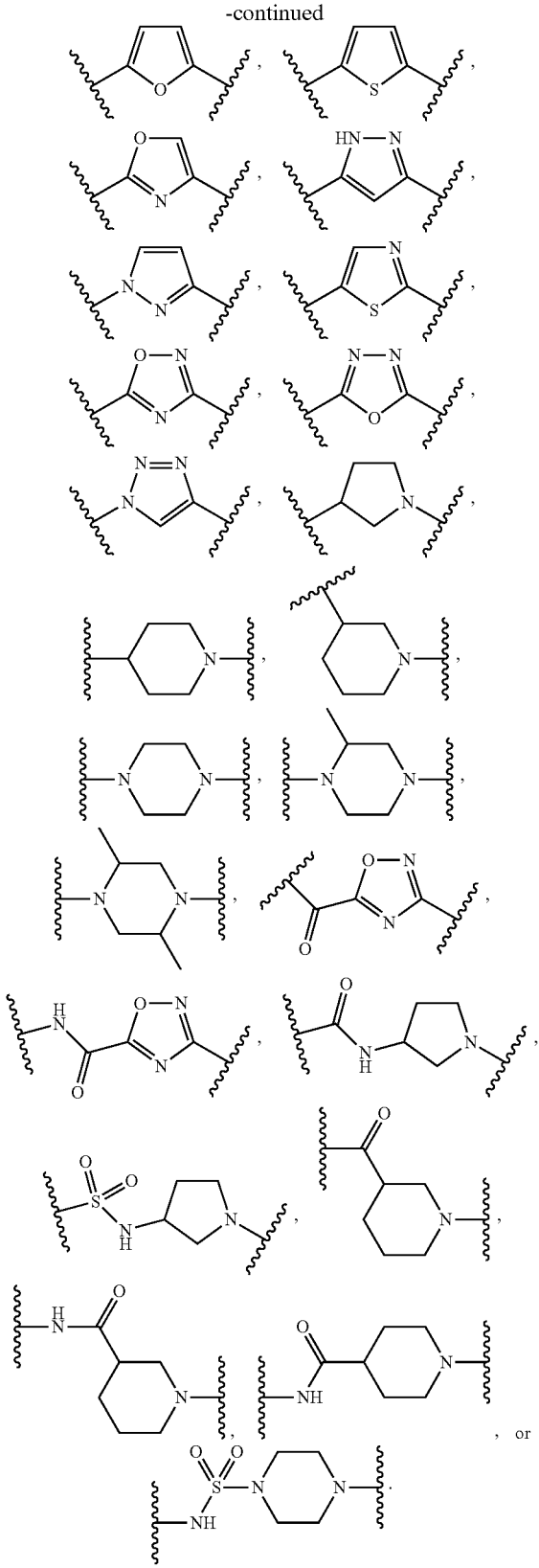

6. The compound of claim 1, wherein
E is a 5-membered heteroarylene or 6-membered heterocyclylene; and $L^3$ is a bond or —C(O)—, —OC(O)O—, —NR$^{1a}$C(O)NR$^{1d}$—, —OC(O)NR$^{1a}$—, —NR$^{1a}$C(O)O—, —OS(O)—, —S(O)O—, —OS(O)$_2$—, —S(O)$_2$O—, —S(O)$_2$NR$^{1a}$—, or —NR$^{1a}$S(O)$_2$—.

7. The compound of claim 1, wherein A is $C_{3-8}$ carbocyclyl or $C_{6-14}$ aryl, optionally substituted with one or more substituents Q, where each Q is independently selected from (a) cyano, halo, azido, and nitro; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) $C_{1-6}$ alkyl, $C_{2-6}$ alkenyl, $C_{2-6}$ alkynyl, $C_{3-7}$ carbocyclyl, $C_{6-14}$ aryl, $C_{7-15}$ aralkyl, heteroaryl, or heterocyclyl, each optionally substituted with one or more, in one embodiment, one, two, three, or four, substituents Q$^a$; or (iii) R$^b$ and R$^c$ together with the N atom to which they are attached form heterocyclyl, optionally substituted with one or more, in one embodiment, one, two, three, or four, substituents Q$^a$.

8. The compound of claim 1, wherein R$^1$ and R$^2$ are both hydrogen.

9. The compound of claim 1, wherein R$^3$ is hydrogen or $C_{1-6}$ alkyl.

10. The compound of claim 1, wherein -L$^2$-R$^4$ is selected from the group consisting of —NR$^5$S(O)$_2$—$C_{1-6}$ alkyl, —NR$^5$C(O)CH$_2$—$C_{3-7}$ carbocyclyl, —NR$^5$C(O)CH$_2$—$C_{6-14}$ aryl, —NR$^5$C(O)CH$_2$-heteroaryl, —NR$^5$C(O)CH$_2$-heterocyclyl, —N(R$^5$)—$C_{3-7}$ carbocyclyl, —N(R$^5$)—$C_{6-14}$ aryl, —N(R$^5$)-heteroaryl, —N(R$^5$)-heterocyclyl, —NR$^5$C(O)—CH═CH—$C_{3-7}$ carbocyclyl, —NR$^5$C(O)—CH═CH—$C_{6-14}$ aryl, —NR$^5$C(O)—CH═CH-heteroaryl, —NR$^5$C(O)—CH═CH-heterocyclyl, NR$^5$C(O)—C≡C—$C_{3-7}$ carbocyclyl, NR$^5$C(O)—C≡C—$C_{6-14}$ aryl, —NR$^5$C(O)—C≡C-heteroaryl, —NR$^5$C(O)—C≡C-heterocyclyl, —CH$_2$N(R$^5$)—$C_{3-8}$ carbocyclyl, —CH$_2$N(R$^5$)—$C_{6-14}$ aryl, —CH$_2$N(R$^5$)-heteroaryl, —CH$_2$N(R$^5$)-heterocyclyl, —NR$^5$C(O)—$C_{3-7}$ carbocyclyl, —NR$^5$S(O)$_2$—$C_{3-7}$ carbocyclyl, —NR$^5$C(O)NR$^{5a}$—$C_{3-7}$ carbocyclyl, —NR$^5$S(O)$_2$NR$^{5a}$—$C_{3-7}$ carbocyclyl, —NR$^5$C(O)—$C_{6-14}$ aryl, —NR$^5$S(O)$_2$—$C_{6-14}$ aryl, —NR$^5$C(O)NR$^{5a}$—$C_{6-14}$ aryl, —NR$^5$S(O)$_2$NR$^{5a}$—$C_{6-14}$ aryl, —NR$^5$C(O)-heteroaryl, —NR$^5$S(O)$_2$-heteroaryl, —NR$^5$C(O)NR$^{5a}$-heteroaryl, —NR$^5$S(O)$_2$NR$^{5a}$-heteroaryl, —NR$^5$C(O)-heterocyclyl, —NR$^5$S(O)$_2$-heterocyclyl, —NR$^5$C(O)NR$^{5a}$-heterocyclyl, and —NR$^5$S(O)$_2$NR$^{5a}$-heterocyclyl, where each of the $C_{1-6}$ alkyl, $C_{3-7}$ carbocyclyl, $C_{6-14}$ aryl, heteroaryl, heterocyclyl is optionally substituted with one or more substituents Q.

11. The compound of claim 1, wherein R$^5$ and R$^{5a}$ are each independently hydrogen, $C_{1-6}$ alkyl, or —C(O)—$C_{1-6}$ alkyl, where each $C_{1-6}$ alkyl is optionally substituted with one or more substituents Q.

12. The compound of claim 1, wherein the 6-membered ring formed by U, V, W, X, and Y is phenyl, pyridine, pyrimidine, or piperidine.

13. The compound of claim 1, wherein m is 1 or 2; and R$^6$ is (i) cyano or halo; or (ii) $C_{1-6}$ alkyl, optionally substituted with one or more substituents Q.

14. The compound of claim 1, having the structure of Formula (VI):

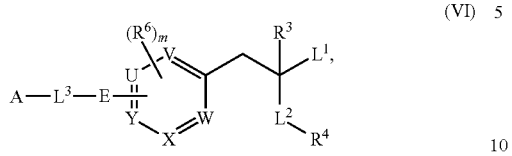

(VI)

wherein:
R³ is hydrogen or $C_{1-6}$ alkyl;
A is $C_{3-8}$-carbocyclyl, $C_{6-14}$ aryl, $C_{7-15}$ aralkyl, heteroaryl, or heterocyclyl;
-L³-E- is $C_{2-6}$ alkenylene, $C_{2-6}$ alkynylene, arylene, carbocyclylene, heteroarylene, heterocyclylene, —NR$^{1a}$S(O)$_2$-arylene-, —NR$^{1a}$S(O)$_2$-heteroarylene-, —NR$^{1a}$S(O)$_2$-heterocyclylene-, or —C(O)—;
U, V, W, X, and Y, together with the carbon atom to which V and W are attached, form a fully saturated or unsaturated 6-membered ring;
L¹ is —CH$_2$OH, —CONH$_2$, —CO$_2$H, —P(O)(OH)$_2$, —P(OH)$_2$, tetrazolyl, or 3-hydroxyisoxazolyl;
L² is —NR⁵C(O)—, —NR⁵S(O)—, —NR⁵S(O)$_2$—, or —NR⁵S(O)$_2$NR$^{5a}$, —NR⁵C(O)-alkylene, —NR⁵S(O)-alkylene, —NR⁵S(O)$_2$-alkylene, —NR⁵C(O)-alkenylene, —NR⁵S(O)-alkenylene, or —NR⁵S(O)$_2$-alkenylene; or alternatively, L² and V or W, together with other atoms to which they are attached, form 5- to 8-membered optionally substituted carbocyclyl or heterocyclyl;
R⁴ is $C_{1-6}$ alkyl, $C_{3-7}$ carbocyclyl, $C_{6-14}$ aryl, $C_{7-15}$ aralkyl, heteroaryl, or heterocyclyl;
R⁶ and m are the same as defined in claim 1; and
when U, V, W, X, and Y are each independently C or CH; R¹, R², and R³ are hydrogen; L¹ is —CONH$_2$ or —CO$_2$H; L² is —NR⁵C(O)—; and R⁴ is -heteroaryl-aryl; then A-L³-E- is cyano group;
when A is aryl, heteroaryl, carbocyclyl, or heterocyclyl; -L³-E- is heteroaryl, —NR⁵C(O)-heteroaryl, or —NR⁵C(O)-heterocyclyl; and -L²- is —NR⁵C(O)— or —NR⁵S(O)$_2$—; then R⁴ is substituted aryl or substituted heteroaryl wherein the substituent is optionally substituted aryl or optionally substituted heteroaryl;
wherein each alkyl, alkenyl, alkenylene, alkynyl, alkynylene, carbocyclyl, aryl, arylene, aralkyl, heteroaryl, heteroarylene, heterocyclyl, and heterocyclylene, in R³, R⁵, R$^{5a}$, R⁶, R$^{1a}$, R$^{1b}$, R$^{1c}$, R$^{1d}$, A, and E, is optionally substituted with one or more substituents Q as defined in claim 1;
wherein each alkyl, alkenyl, alkenylene, alkynyl, alkynylene, carbocyclyl, aryl, arylene, aralkyl, heteroaryl, heteroarylene, heterocyclyl, and heterocyclylene in R⁴ is optionally substituted with one or more substituents Q, where each Q is independently selected from (a), (b), and (c) as follows:
(a) cyano, halo, azido, and nitro;
(b) $C_{1-6}$ alkyl, $C_{2-6}$ alkenyl, and $C_{2-6}$ alkynyl, each of which is optionally substituted with one or more, in one embodiment, one, two, three, or four, substituents Q$^a$; and
(c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) $C_{1-6}$ alkyl, $C_{2-6}$ alkenyl, $C_{2-6}$ alkynyl, $C_{3-7}$ carbocyclyl, $C_{6-14}$ aryl, $C_{7-15}$ aralkyl, heteroaryl, or heterocyclyl, each optionally substituted with one or more, in one embodiment, one, two, three, or four, substituents Q$^a$; or (iii) R$^b$ and R$^c$ together with the N atom to which they are attached form heterocyclyl, optionally substituted with one or more substituents Q$^a$;
when -L³-E- is —C(O)—, then A is a $C_{6-14}$ aryl substituted with a $C_{6-14}$ aryl which is optionally substituted with one or more substituents Q$^a$;
when -L³-E- is —NR$^{1a}$C(O)-heteroarylene- or —NR$^{1a}$C(O)-heterocyclylene-, then A is a $C_{6-14}$ aryl or heteroaryl substituted with a $C_{6-14}$ aryl which is optionally substituted with one or more substituents Q$^a$.

15. The compound of claim 14, having the structure of Formula (VIa) or (VIb):

(VIa)

(VIb)

wherein A, L³, R⁶, E, m, Y, U, V, W, X, R³, L¹, L², and R⁴ are the same as defined in claim 14.

16. The compound of claim 14, wherein -L³-E- has the structure of:

-continued

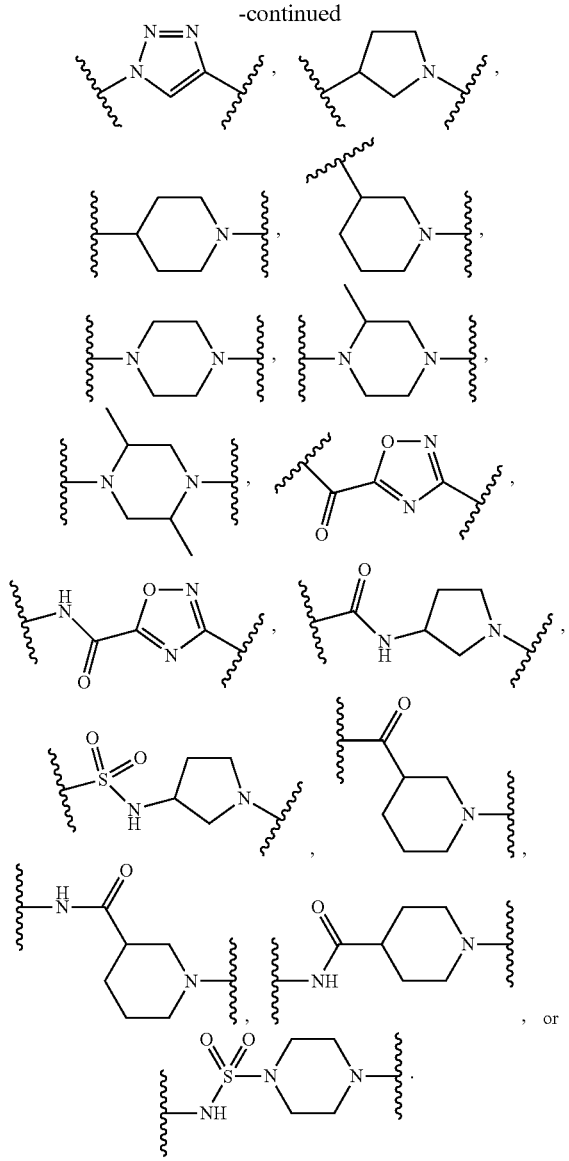

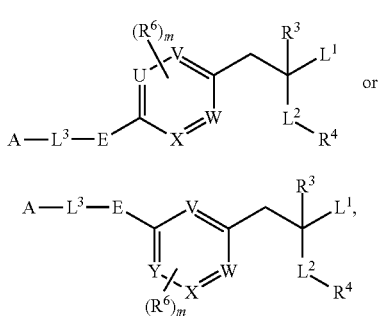

17. The compound of claim 14, having the structure of Formula (VII) or (VIII):

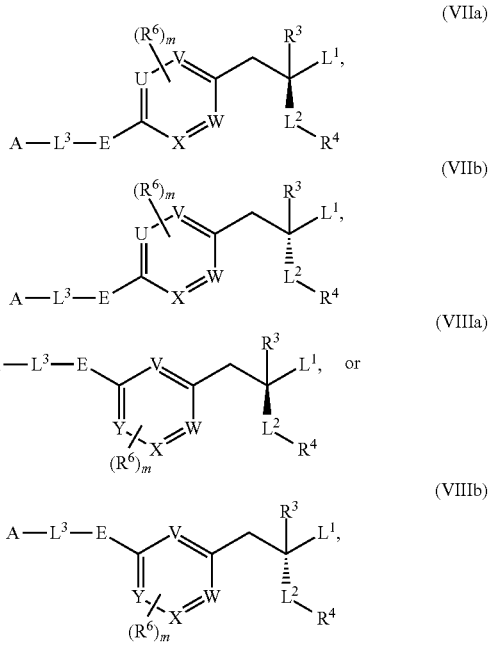

wherein A, L³, R⁶, E, m, Y, U, V, W, X, R³, L¹, L², and R⁴ are the same as defined in claim 14.

18. The compound of claim 17, having the structure of Formula (VIIa), (VIIb), (VIIIa), or (VIIIb):

(VIIa)

(VIIb)

(VIIIa)

(VIIIb)

wherein A, L³, R⁶, E, m, Y, U, V, W, X, R³, L¹, L², and R⁴ are the same as defined in claim 17.

19. The compound of claim 14, wherein Y, U, V, W, and X are independently CH or CH₂.

20. The compound of claim 14, wherein A-L³-E- is selected from the group consisting of carbocyclyl-C≡C—, aryl-C≡C—, heteroaryl-C≡C—, heterocyclyl-C≡C—, carbocyclyl-heteroarylene-, aryl-heteroarylene-, heteroaryl-heteroarylene-, heterocyclyl-heteroarylene-, aryl-S(O)₂O—, heteroaryl-S(O)₂O—, or aryl-C(O).

21. The compound of claim 14, wherein
L² is —NR⁵C(O)—, —NR⁵S(O)—, —NR⁵S(O)₂—, or —NR⁵S(O)₂NR⁵ᵃ—; and
R⁴ is C₁₋₆ alkyl, C₃₋₇ carbocyclyl, C₆₋₁₄ aryl, heteroaryl, or heterocyclyl.

22. The compound of claim 14, having the structure of Formula (IX):

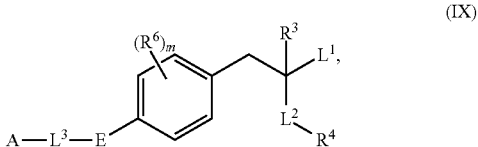

wherein
A-L³-E- is selected from the group consisting of carbocyclyl-C≡C—, aryl-C≡C—, heteroaryl-C≡C—, heterocyclyl-C≡C—, carbocyclyl-heteroarylene-, aryl-heteroarylene-, heteroaryl-heteroarylene-, heterocyclyl-heteroarylene-, aryl-S(O)₂O—, heteroaryl-S(O)₂O—, or aryl-C(O);
L² is —NR⁵C(O)—, —NR⁵C(O)CH₂—, —NR⁵S(O)—, —NR⁵S(O)₂—, or —NR⁵S(O)₂NR⁵ᵃ—; and
R⁴ is C₁₋₆ alkyl, C₃₋₇ carbocyclyl, C₆₋₁₄ aryl, heteroaryl, or heterocyclyl.

23. The compound of claim 22, having the structure of Formula (IXa) or (IXb):

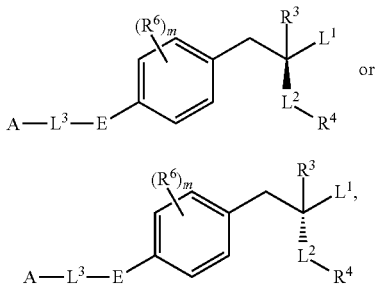

wherein A, L³, R⁶, E, m, R³, L¹, L², and R⁴ are the same as defined in claim 22.

24. The compound of claim 14, having the structure of Formula (X):

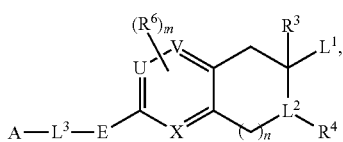

wherein
A, L³, R⁶, E, R³, L¹, L², and R⁴ are the same as defined in claim 14;
m is zero, 1, 2, or 3;
n is zero, 1, 2, or 3;
U, V, and X are independently CH or N.

25. The compound of claim 14, which has no agonist activity.

26. The compound of claim 1, having the structure of Formula (XII):

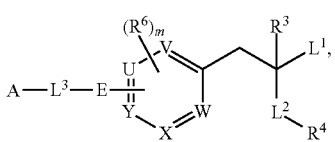

wherein:
R³ is hydrogen or $C_{1-6}$ alkyl;
A is $C_{3-8}$-carbocyclyl, $C_{6-14}$ aryl, $C_{7-15}$ aralkyl, heteroaryl, or heterocyclyl;
-L³-E- is $C_{2-6}$ alkenylene, $C_{2-6}$ alkynylene, arylene, carbocyclylene, heteroarylene, heterocyclylene, or —C(O)-heteroarylene;
U, V, W, X, and Y are independently CH, CH₂, or N;
L¹ is —CH₂OH, —CONH₂, —CO₂H, —P(O)(OH)₂, —P(OH)₂, tetrazolyl, or 3-hydroxyisoxazolyl;
L² is —N(R⁵)CH₂—, —N(R⁵)—, —O—, —S—, —NR⁵C(O)—, —CH₂NR⁵C(O)—, —NR⁵C(O)CH₂—, —NR⁵C(O)—CH═CH—, —NR⁵C(O)—C≡C—, —NR⁵S(O)—, —NR⁵S(O)₂—, or —NR⁵C(O)NR⁵ᵃ—;
or alternatively, L² and V or W, together with other atoms to which they are attached, form 5- to 8-membered optionally substituted carbocyclyl or heterocyclyl; or alternatively, V or W and the carbon atom which is attached to R³, L¹, and L², together with other atoms to which they are attached, form 5- to 8-membered optionally substituted carbocyclyl or heterocyclyl;
R⁶ and m are the same as defined in claim 1;
R⁴ is —R⁴ᵃ—R^q or —R⁴ᵇ;
R⁴ᵃ is $C_{3-7}$ carbocyclylene, $C_{6-14}$ arylene, heteroarylene, or heterocyclylene;
R^q is $C_{3-7}$ carbocyclyl, $C_{6-14}$ aryl, $C_{7-15}$ aralkyl, heteroaryl, heteroarylalkyl, or heterocyclyl;
R⁴ᵇ is $C_{3-7}$ carbocyclyl, $C_{6-14}$ aryl, heteroaryl, or heterocyclyl;
wherein each alkyl, alkenylene, alkynylene, carbocyclyl, aryl, aralkyl, heteroaryl, heterocyclyl, arylene, carbocyclylene, heteroarylene, and heterocyclylene in R³, R⁶, R^q, A, and -L³-E- is optionally substituted with one or more substitutents Q as defined in claim 1;
wherein each carbocyclylene, arylene, heteroarylene, and heterocyclylene in R⁴ᵃ and each carbocyclyl, aryl, heteroaryl, and heterocyclyl in R⁴ᵇ is optionally substituted with one or more substitutents Q, where each Q is independently selected from:

(a) cyano, halo, azido, and nitro;

(b) $C_{1-6}$ alkyl, $C_{2-6}$ alkenyl, and $C_{2-6}$ alkynyl, each of which is optionally substituted with one or more, in one embodiment, one, two, three, or four, substituents $Q^a$; and (c) —C(O)Rᵃ, —C(O)ORᵃ, —C(O)NRᵇRᶜ, —C(NRᵃ)NRᵇRᶜ, —ORᵃ, —OC(O)Rᵃ, —OC(O)ORᵃ, —OC(O)NRᵇRᶜ, —OC(═NRᵃ)NRᵇRᶜ, —OS(O)Rᵃ, —OS(O)₂Rᵃ, —OS(O)NRᵇRᶜ, —OS(O)₂NRᵇRᶜ, —NRᵇRᶜ, —NRᵃC(O)R^d, —NRᵃC(O)OR^d, —NRᵃC(O)NRᵇRᶜ, —NRᵃC(═NR^d)NRᵇRᶜ, —NRᵃS(O)R^d, —NRᵃS(O)₂R^d, —NRᵃS(O)NRᵇRᶜ, —NRᵃS(O)₂NRᵇRᶜ, —SRᵃ, —S(O)Rᵃ, —S(O)₂Rᵃ, —S(O)NRᵇRᶜ, and —S(O)₂NRᵇRᶜ, wherein each Rᵃ, Rᵇ, Rᶜ, and R^d is independently (i) hydrogen; (ii) $C_{1-6}$ alkyl, $C_{2-6}$ alkenyl, $C_{2-6}$ alkynyl, $C_{3-7}$ carbocyclyl, $C_{6-14}$ aryl, $C_{7-15}$ aralkyl, heteroaryl, or heterocyclyl, each optionally substituted with one or more, in one embodiment, one, two, three, or four, substituents $Q^a$; or (iii) Rᵇ and Rᶜ together with the N atom to which they are attached form heterocyclyl, optionally substituted with one or more substituents $Q^a$.

27. The compound of claim 26, wherein
when -L³-E- is $C_{2-6}$ alkenylene, or $C_{2-6}$ alkynylene; then R⁴ is —R⁴ᵃ—R^q.

28. The compound of claim 26, having the structure of Formula (XIIa) or (XIIb):

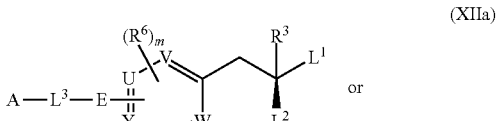

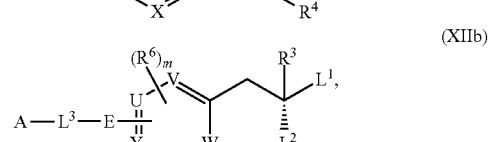

wherein A, L³, R⁶, E, m, Y, U, V, W, X, R³, L¹, L², and R⁴ are the same as defined in claim 26.

29. The compound of claim 26, having the structure of Formula (XIII) or (XIV):

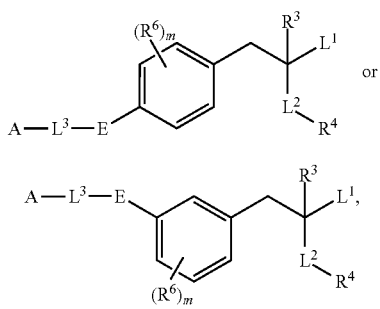

wherein A, $L^3$, $R^6$, E, m, $R^3$, $L^1$, $L^2$, and $R^4$ are the same as defined in claim 26.

30. The compound of claim 29, having the structure of Formula (XIIIa), (XIIIb), (XIVa), or (XIVb):

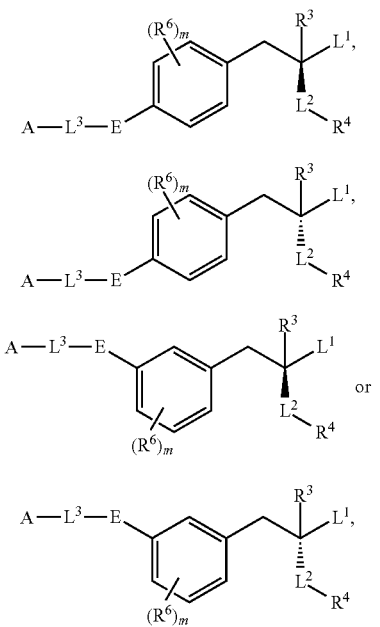

wherein A, $L^3$, $R^6$, E, m, $R^3$, $L^1$, $L^2$, and $R^4$ are the same as defined in claim 29.

31. The compound of claim 26, wherein A-$L^3$-E- is aryl-$C_{2-6}$ alkenylene, aryl-$C_{2-6}$ alkynylene, aryl-heteroarylene-, or heterocyclylene-C(O)-heteroarylene-.

32. The compound of claim 26, wherein m is 1 or 2; and $R^6$ is (i) cyano or halo; or (ii) $C_{1-6}$ alkyl, optionally substituted with one or more substituents Q.

33. The compound of claim 26, wherein
A-$L^3$-E- is aryl-$C_{2-6}$ alkenylene, aryl-$C_{2-6}$ alkynylene, aryl-heteroarylene-, or heterocyclylene-C(O)-heteroarylene-;
$L^2$ is —N($R^5$)$CH_2$—, —N($R^5$)—, —O—, —S—, —$NR^5$C(O)—, —$CH_2NR^5C(O)$—, —$NR^5C(O)CH_2$—, —$NR^5C(O)$—CH=CH—, —$NR^5C(O)$—C≡C—, —$NR^5S(O)$—, —$NR^5S(O)_2$—, or —$NR^5C(O)NR^{5a}$—; and
$R^4$ is —$R^{4a}$—$R^q$.

34. The compound of claim 26, having the structure of Formula (XV):

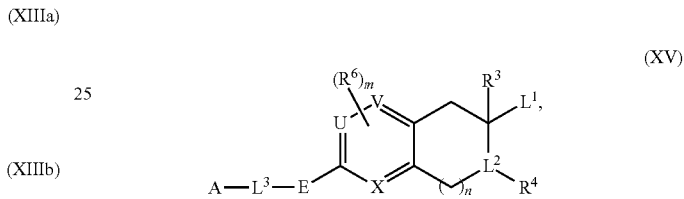

wherein,
-$L^3$-E- is arylene, or heteroarylene;
A is aryl or heteroaryl;
U, V, and X are independently C or CH;
n is zero, 1, or 2; and
$L^2$ is —$NR^5C(O)$— or —$NR^5S(O)_2$—.

35. The compound of claim 26, which has no sensitizer activity.

36. The compound of claim 1, having agonist activity level of A, B, or C and sensitizer activity level of A, B, or C at concentration of 2, 5, or 10 μM.

37. The compound of claim 36, having agonist activity level of A or B, and sensitizer activity level of A or B.

38. The compound of claim 36, selected from the group consisting of Compounds as shown below:

| Number | Structure |
|--------|-----------|
| 165 | 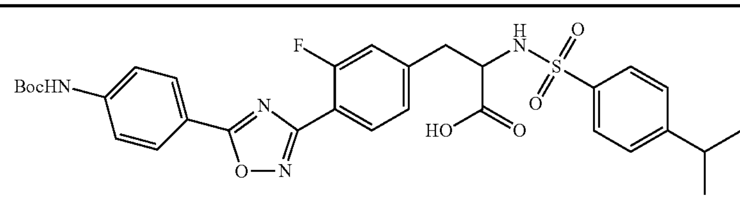 |
| 166 | 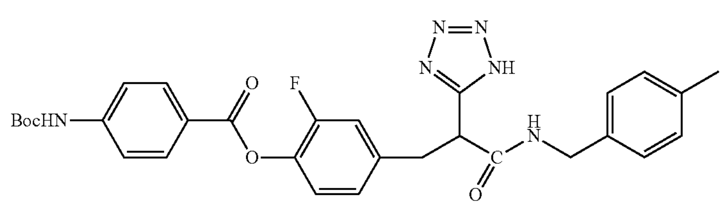 [SMILES: Cc1ccc(CNC(=O)C(Cc2ccc(OC(=O)c3ccc(NC(=O)OC(C)(C)C)cc3)c(F)c2)c2nnn[nH]2)cc1] |

-continued

| Number | Structure |
|---|---|
| 167 | 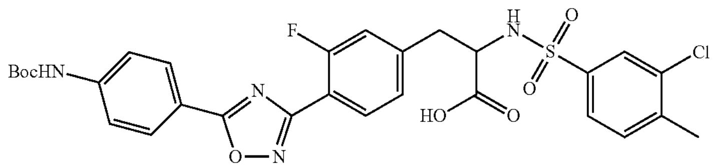 [SMILES: Cc1ccc(S(=O)(=O)NC(Cc2ccc(-c3noc(-c4ccc(NC(=O)OC(C)(C)C)cc4)n3)c(F)c2)C(=O)O)cc1Cl] |
| 168 | 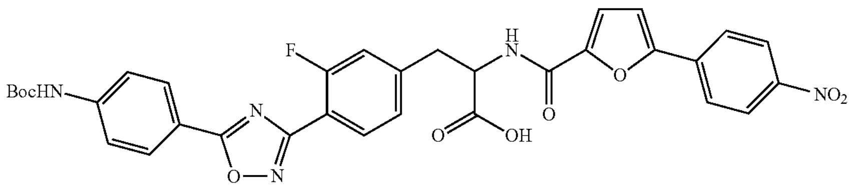 [SMILES: CC(C)(C)OC(=O)Nc1ccc(-c2nc(-c3ccc(CC(NC(=O)c4ccc(-c5ccc([N+](=O)[O-])cc5)o4)C(=O)O)cc3F)no2)cc1] |
| 169 | 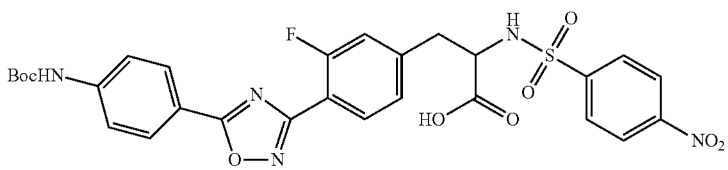 [SMILES: CC(C)(C)OC(=O)Nc1ccc(-c2nc(-c3ccc(CC(NS(=O)(=O)c4ccc([N+](=O)[O-])cc4)C(=O)O)cc3F)no2)cc1] |
| 170 | 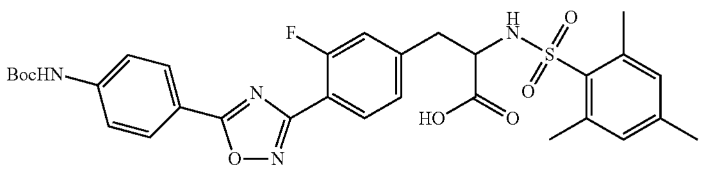 [SMILES: Cc1cc(C)c(S(=O)(=O)NC(Cc2ccc(-c3noc(-c4ccc(NC(=O)OC(C)(C)C)cc4)n3)c(F)c2)C(=O)O)c(C)c1] |
| 171 | 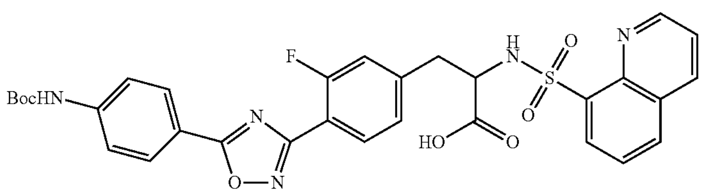 [SMILES: CC(C)(C)OC(=O)Nc1ccc(-c2nc(-c3ccc(CC(NS(=O)(=O)c4cccc5cccnc45)C(=O)O)cc3F)no2)cc1] |
| 172 | 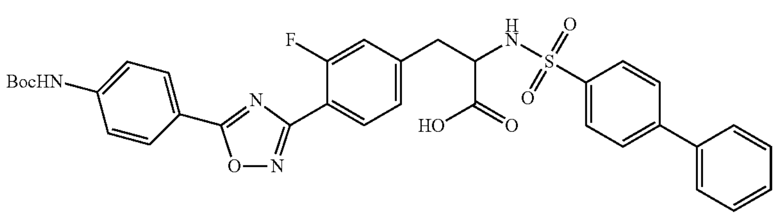 [SMILES: CC(C)(C)OC(=O)Nc1ccc(-c2nc(-c3ccc(CC(NS(=O)(=O)c4ccc(-c5ccccc5)cc4)C(=O)O)cc3F)no2)cc1] |
| 173 | 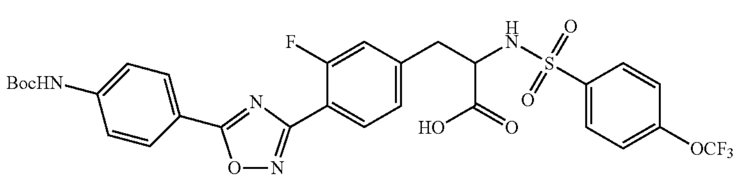 [SMILES: CC(C)(C)OC(=O)Nc1ccc(-c2nc(-c3ccc(CC(NS(=O)(=O)c4ccc(OC(F)(F)F)cc4)C(=O)O)cc3F)no2)cc1] |
| 174 | 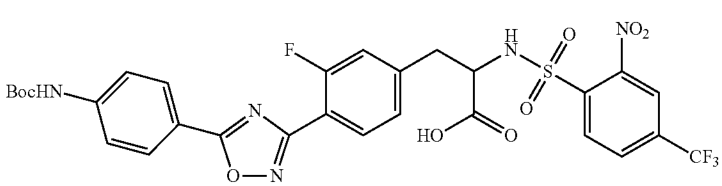 [SMILES: CC(C)(C)OC(=O)Nc1ccc(-c2nc(-c3ccc(CC(NS(=O)(=O)c4ccc(C(F)(F)F)cc4[N+](=O)[O-])C(=O)O)cc3F)no2)cc1] |

-continued
| Number | Structure |
|---|---|
| 175 | 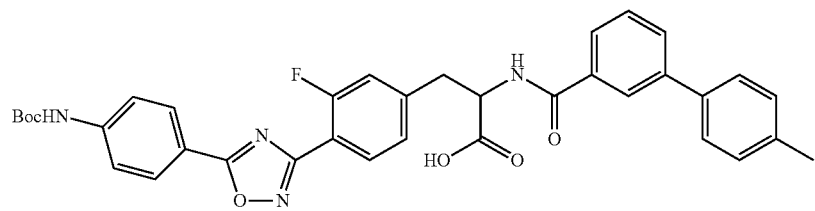 [SMILES: Cc1ccc(-c2cccc(C(=O)NC(Cc3ccc(-c4noc(-c5ccc(NC(=O)OC(C)(C)C)cc5)n4)c(F)c3)C(=O)O)c2)cc1] |
| 176 | 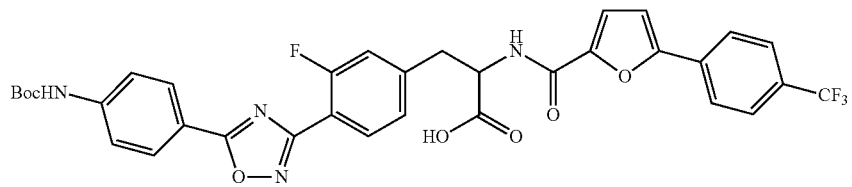 [SMILES: CC(C)(C)OC(=O)Nc1ccc(-c2nc(-c3ccc(CC(NC(=O)c4ccc(-c5ccc(C(F)(F)F)cc5)o4)C(=O)O)cc3F)no2)cc1] |
| 177 | 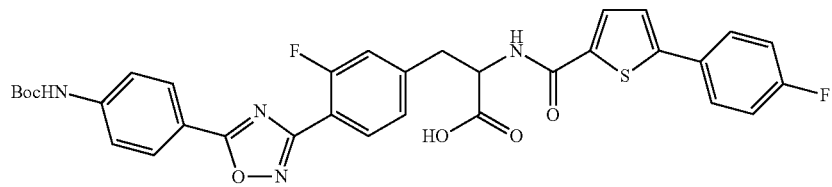 [SMILES: CC(C)(C)OC(=O)Nc1ccc(-c2nc(-c3ccc(CC(NC(=O)c4ccc(-c5ccc(F)cc5)s4)C(=O)O)cc3F)no2)cc1] |
| 178 | 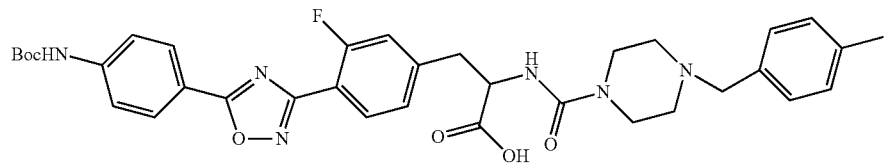 [SMILES: Cc1ccc(CN2CCN(C(=O)NC(Cc3ccc(-c4noc(-c5ccc(NC(=O)OC(C)(C)C)cc5)n4)c(F)c3)C(=O)O)CC2)cc1] |
| 179 | 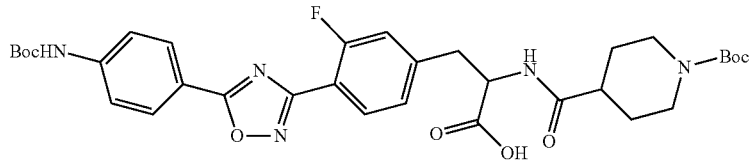 [SMILES: CC(C)(C)OC(=O)Nc1ccc(-c2nc(-c3ccc(CC(NC(=O)C4CCN(C(=O)OC(C)(C)C)CC4)C(=O)O)cc3F)no2)cc1] |
| 180 | 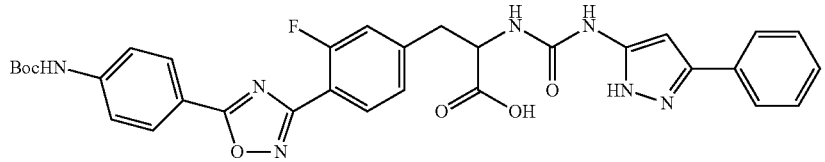 [SMILES: CC(C)(C)OC(=O)Nc1ccc(-c2nc(-c3ccc(CC(NC(=O)Nc4cc(-c5ccccc5)n[nH]4)C(=O)O)cc3F)no2)cc1] |
| 181 | 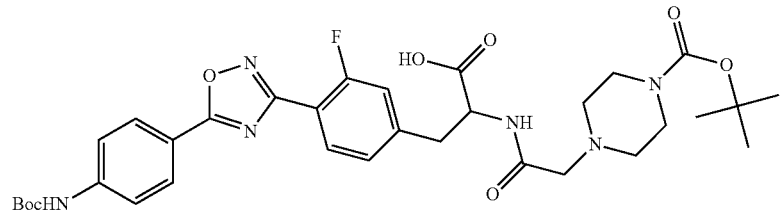 [SMILES: CC(C)(C)OC(=O)Nc1ccc(-c2nc(-c3ccc(CC(NC(=O)CN4CCN(C(=O)OC(C)(C)C)CC4)C(=O)O)cc3F)no2)cc1] |
| 182 | 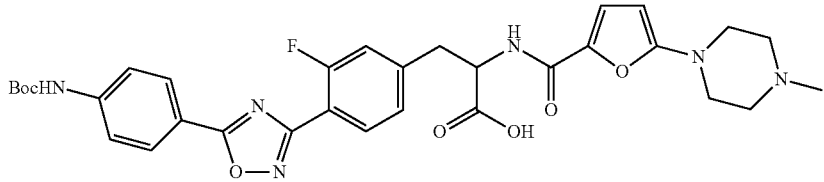 [SMILES: CN1CCN(c2ccc(C(=O)NC(Cc3ccc(-c4noc(-c5ccc(NC(=O)OC(C)(C)C)cc5)n4)c(F)c3)C(=O)O)o2)CC1] |

| Number | Structure |
|---|---|
| 183 | 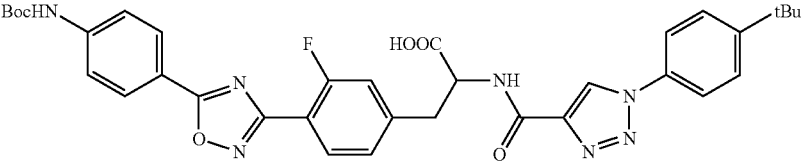 [SMILES: CC(C)(C)OC(=O)Nc1ccc(-c2nc(-c3ccc(CC(NC(=O)c4cn(-c5ccc(C(C)(C)C)cc5)nn4)C(=O)O)cc3F)no2)cc1] |
| 184 | 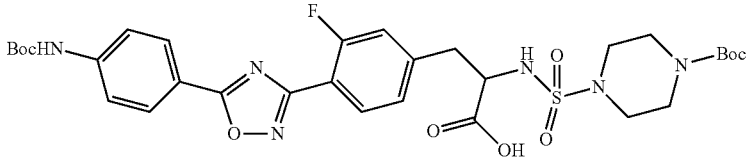 [SMILES: CC(C)(C)OC(=O)Nc1ccc(-c2nc(-c3ccc(CC(NS(=O)(=O)N4CCN(C(=O)OC(C)(C)C)CC4)C(=O)O)cc3F)no2)cc1] |
| 185 | 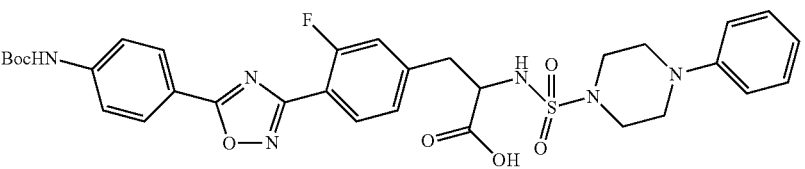 [SMILES: CC(C)(C)OC(=O)Nc1ccc(-c2nc(-c3ccc(CC(NS(=O)(=O)N4CCN(c5ccccc5)CC4)C(=O)O)cc3F)no2)cc1] |
| 186 | 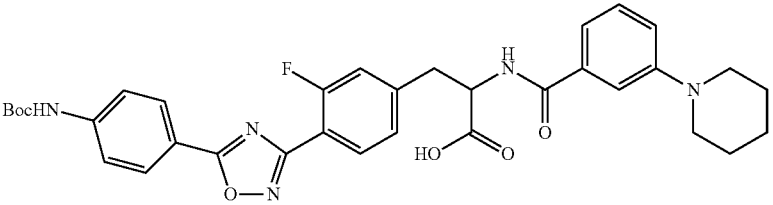 [SMILES: CC(C)(C)OC(=O)Nc1ccc(-c2nc(-c3ccc(CC(NC(=O)c4cccc(N5CCCCC5)c4)C(=O)O)cc3F)no2)cc1] |
| 187 | 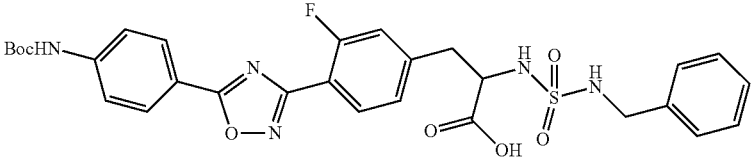 [SMILES: CC(C)(C)OC(=O)Nc1ccc(-c2nc(-c3ccc(CC(NS(=O)(=O)NCc4ccccc4)C(=O)O)cc3F)no2)cc1] |
| 188 | 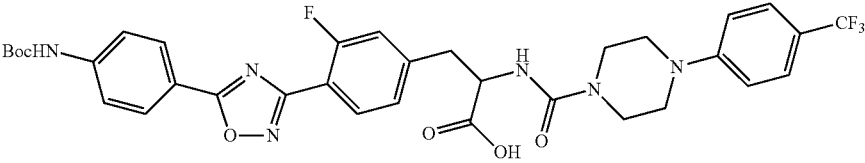 [SMILES: CC(C)(C)OC(=O)Nc1ccc(-c2nc(-c3ccc(CC(NC(=O)N4CCN(c5ccc(C(F)(F)F)cc5)CC4)C(=O)O)cc3F)no2)cc1] |
| 189 | 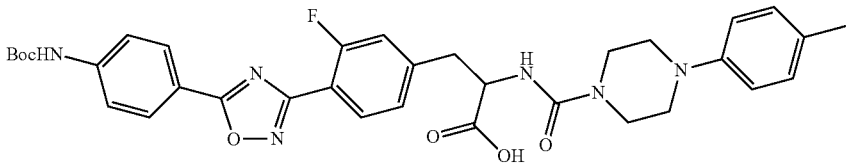 [SMILES: Cc1ccc(N2CCN(C(=O)NC(Cc3ccc(-c4noc(-c5ccc(NC(=O)OC(C)(C)C)cc5)n4)c(F)c3)C(=O)O)CC2)cc1] |
| 190 | 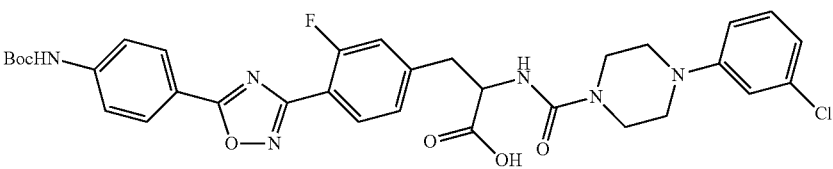 [SMILES: CC(C)(C)OC(=O)Nc1ccc(-c2nc(-c3ccc(CC(NC(=O)N4CCN(c5cccc(Cl)c5)CC4)C(=O)O)cc3F)no2)cc1] |

-continued
| Number | Structure |
|---|---|
| 191 | 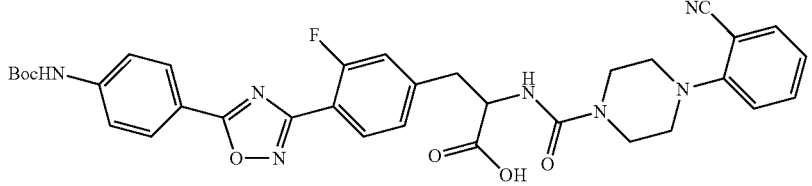 [SMILES: CC(C)(C)OC(=O)Nc1ccc(-c2nc(-c3ccc(CC(NC(=O)N4CCN(c5ccccc5C#N)CC4)C(=O)O)cc3F)no2)cc1] |
| 192 | 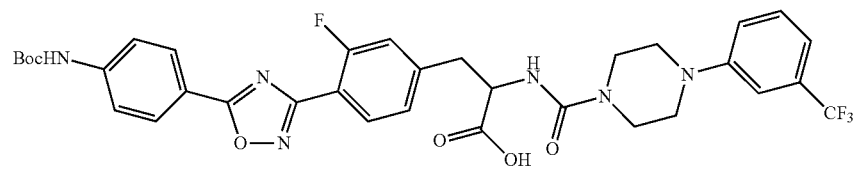 [SMILES: CC(C)(C)OC(=O)Nc1ccc(-c2nc(-c3ccc(CC(NC(=O)N4CCN(c5cccc(C(F)(F)F)c5)CC4)C(=O)O)cc3F)no2)cc1] |
| 193 | 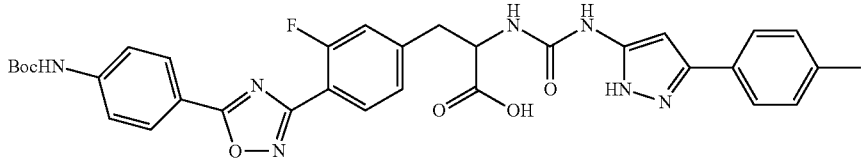 [SMILES: Cc1ccc(-c2cc(NC(=O)NC(Cc3ccc(-c4noc(-c5ccc(NC(=O)OC(C)(C)C)cc5)n4)c(F)c3)C(=O)O)[nH]n2)cc1] |
| 194 | 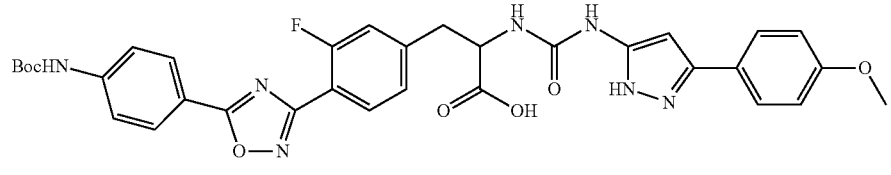 [SMILES: COc1ccc(-c2cc(NC(=O)NC(Cc3ccc(-c4noc(-c5ccc(NC(=O)OC(C)(C)C)cc5)n4)c(F)c3)C(=O)O)[nH]n2)cc1] |
| 195 | 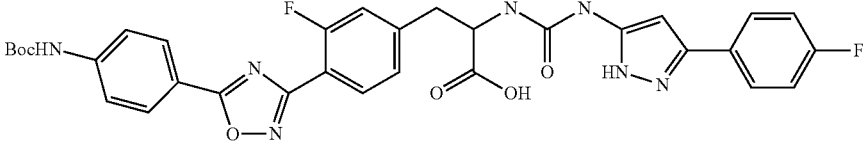 |
| 196 | 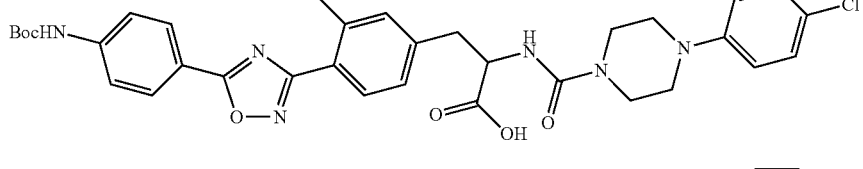 |
| 197 | 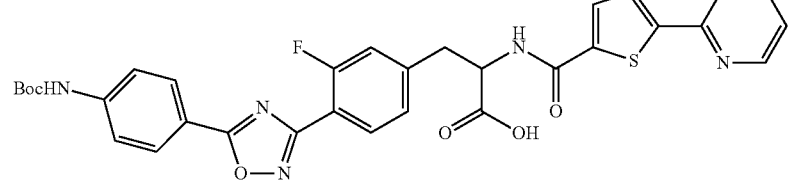 |
| 198 | 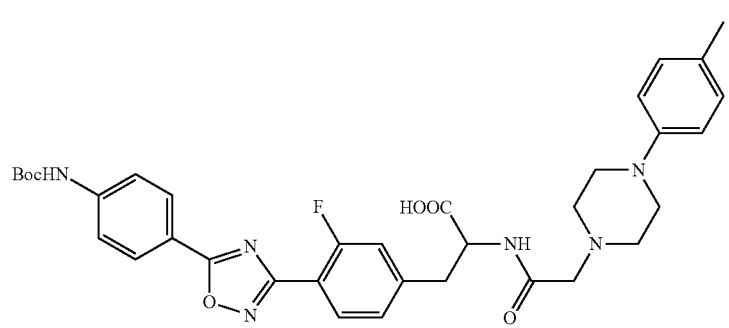 [SMILES: Cc1ccc(N2CCN(CC(=O)NC(Cc3ccc(-c4noc(-c5ccc(NC(=O)OC(C)(C)C)cc5)n4)c(F)c3)C(=O)O)CC2)cc1] |

-continued

| Number | Structure |
|---|---|
| 199 | 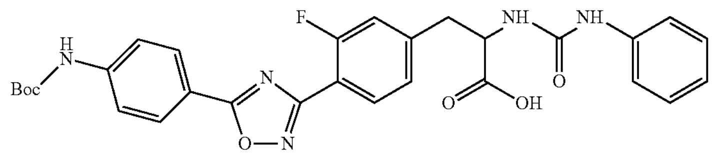 [SMILES: CC(C)(C)OC(=O)Nc1ccc(-c2nc(-c3ccc(CC(NC(=O)Nc4ccccc4)C(=O)O)cc3F)no2)cc1] |
| 200 | 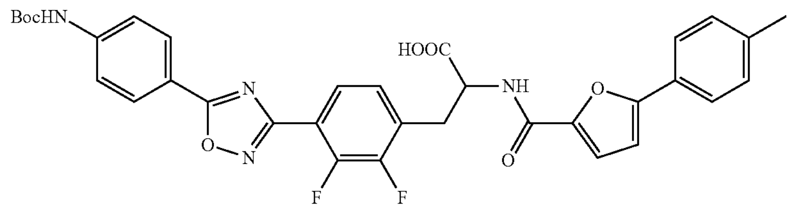 [SMILES: Cc1ccc(-c2ccc(C(=O)NC(Cc3ccc(-c4noc(-c5ccc(NC(=O)OC(C)(C)C)cc5)n4)c(F)c3F)C(=O)O)o2)cc1] |
| 201 | 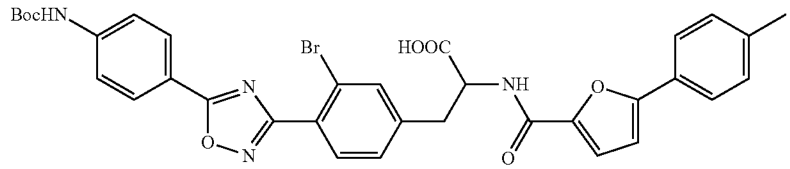 [SMILES: Cc1ccc(-c2ccc(C(=O)NC(Cc3ccc(-c4noc(-c5ccc(NC(=O)OC(C)(C)C)cc5)n4)c(Br)c3)C(=O)O)o2)cc1] |
| 202 | 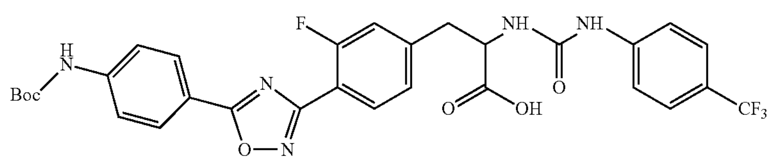 [SMILES: CC(C)(C)OC(=O)Nc1ccc(-c2nc(-c3ccc(CC(NC(=O)Nc4ccc(C(F)(F)F)cc4)C(=O)O)cc3F)no2)cc1] |
| 203 | 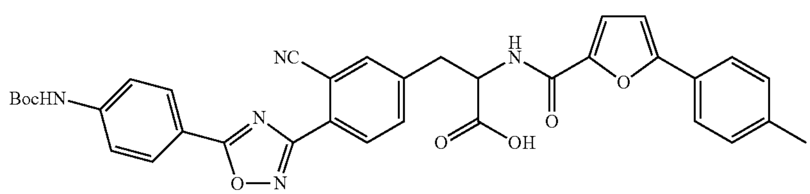 [SMILES: Cc1ccc(-c2ccc(C(=O)NC(Cc3ccc(-c4noc(-c5ccc(NC(=O)OC(C)(C)C)cc5)n4)c(C#N)c3)C(=O)O)o2)cc1] |
| 204 | 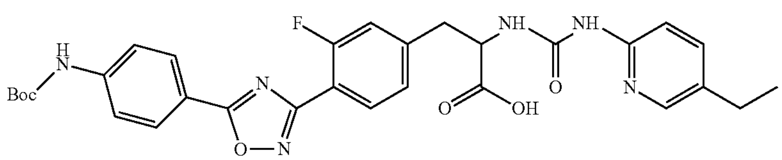 [SMILES: CCc1ccc(NC(=O)NC(Cc2ccc(-c3noc(-c4ccc(NC(=O)OC(C)(C)C)cc4)n3)c(F)c2)C(=O)O)nc1] |
| 205 | 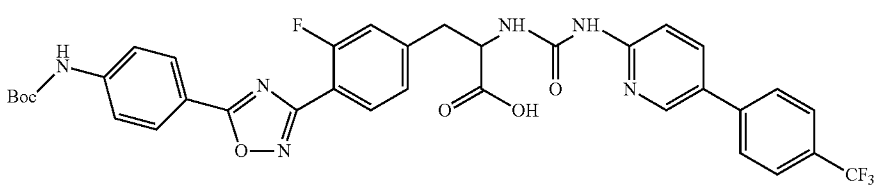 [SMILES: CC(C)(C)OC(=O)Nc1ccc(-c2nc(-c3ccc(CC(NC(=O)Nc4ccc(-c5ccc(C(F)(F)F)cc5)cn4)C(=O)O)cc3F)no2)cc1] |
| 206 | 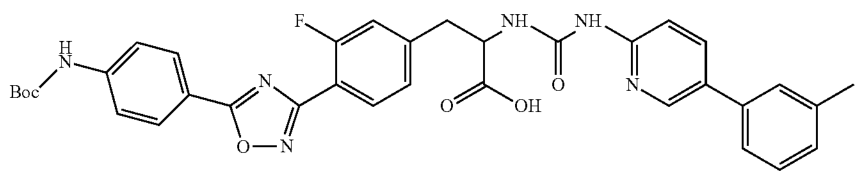 [SMILES: Cc1cccc(-c2ccc(NC(=O)NC(Cc3ccc(-c4noc(-c5ccc(NC(=O)OC(C)(C)C)cc5)n4)c(F)c3)C(=O)O)nc2)c1] |
| 207 | 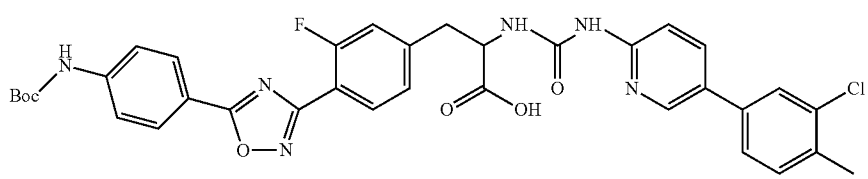 [SMILES: Cc1ccc(-c2ccc(NC(=O)NC(Cc3ccc(-c4noc(-c5ccc(NC(=O)OC(C)(C)C)cc5)n4)c(F)c3)C(=O)O)nc2)cc1Cl] |

-continued

| Number | Structure |
|---|---|
| 208 | 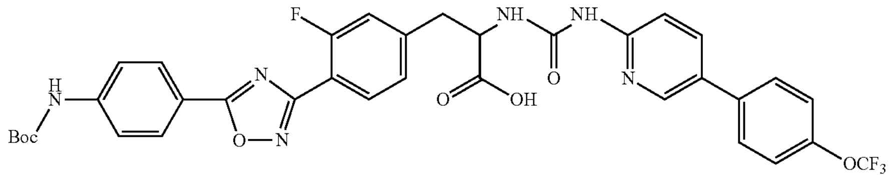 [SMILES: CC(C)(C)OC(=O)Nc1ccc(-c2nc(-c3ccc(CC(NC(=O)Nc4ccc(-c5ccc(OC(F)(F)F)cc5)cn4)C(=O)O)cc3F)no2)cc1] |
| 209 | 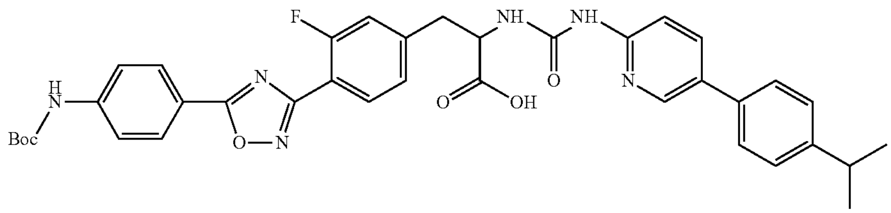 [SMILES: CC(C)c1ccc(-c2ccc(NC(=O)NC(Cc3ccc(-c4noc(-c5ccc(NC(=O)OC(C)(C)C)cc5)n4)c(F)c3)C(=O)O)nc2)cc1] |
| 210 | 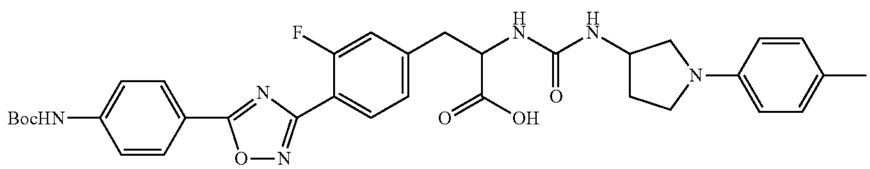 [SMILES: Cc1ccc(N2CCC(NC(=O)NC(Cc3ccc(-c4noc(-c5ccc(NC(=O)OC(C)(C)C)cc5)n4)c(F)c3)C(=O)O)C2)cc1] |
| 211 | 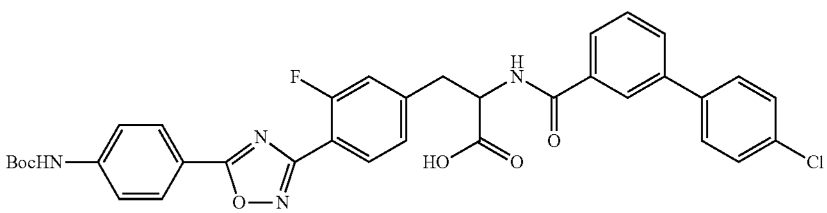 [SMILES: CC(C)(C)OC(=O)Nc1ccc(-c2nc(-c3ccc(CC(NC(=O)c4cccc(-c5ccc(Cl)cc5)c4)C(=O)O)cc3F)no2)cc1] |
| 212 | 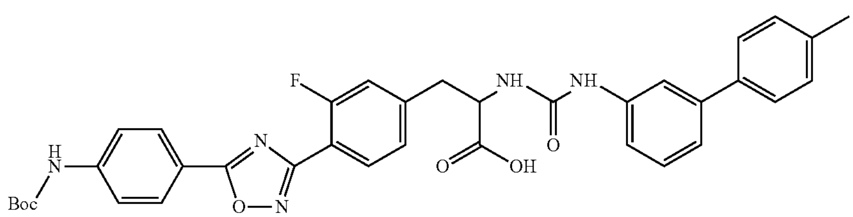 [SMILES: Cc1ccc(-c2cccc(NC(=O)NC(Cc3ccc(-c4noc(-c5ccc(NC(=O)OC(C)(C)C)cc5)n4)c(F)c3)C(=O)O)c2)cc1] |
| 213 | 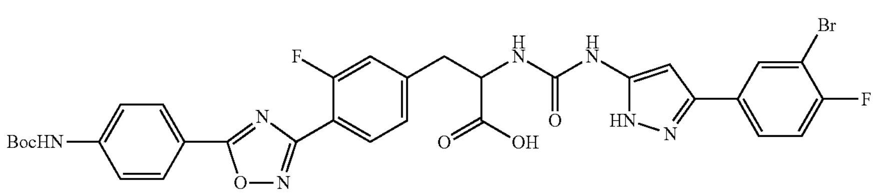 [SMILES: CC(C)(C)OC(=O)Nc1ccc(-c2nc(-c3ccc(CC(NC(=O)Nc4cc(-c5ccc(F)c(Br)c5)n[nH]4)C(=O)O)cc3F)no2)cc1] |
| 214 | 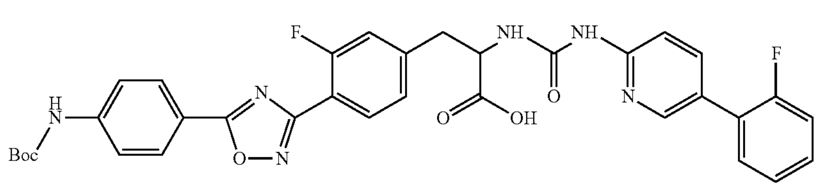 |
| 215 | 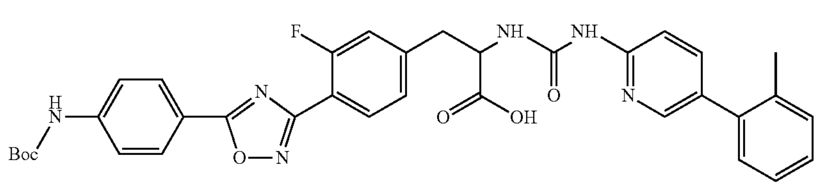 [SMILES: CC(C)(C)OC(=O)Nc1ccc(-c2nc(-c3ccc(CC(NC(=O)Nc4ccc(-c5ccccc5F)cn4)C(=O)O)cc3F)no2)cc1] |

-continued
| Number | Structure |
|---|---|
| 216 | 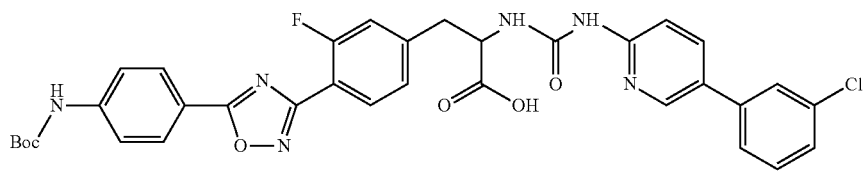 [SMILES: CC(C)(C)OC(=O)Nc1ccc(-c2nc(-c3ccc(CC(NC(=O)Nc4ccc(-c5cccc(Cl)c5)cn4)C(=O)O)cc3F)no2)cc1] |
| 217 | 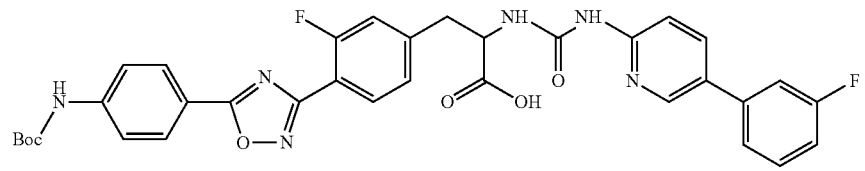 [SMILES: CC(C)(C)OC(=O)Nc1ccc(-c2nc(-c3ccc(CC(NC(=O)Nc4ccc(-c5cccc(F)c5)cn4)C(=O)O)cc3F)no2)cc1] |
| 218 | 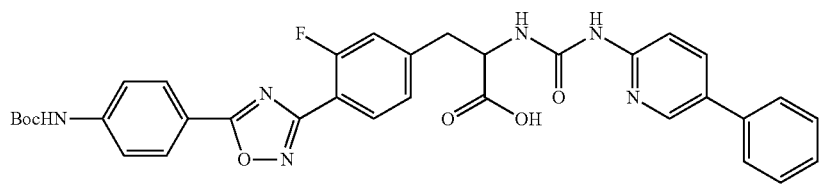 [SMILES: CC(C)(C)OC(=O)Nc1ccc(-c2nc(-c3ccc(CC(NC(=O)Nc4ccc(-c5ccccc5)cn4)C(=O)O)cc3F)no2)cc1] |
| 219 | 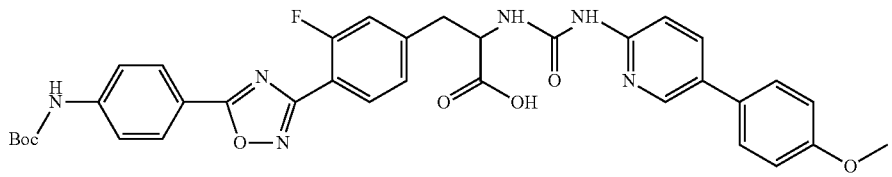 [SMILES: COc1ccc(-c2ccc(NC(=O)NC(Cc3ccc(-c4noc(-c5ccc(NC(=O)OC(C)(C)C)cc5)n4)c(F)c3)C(=O)O)nc2)cc1] |
| 220 | 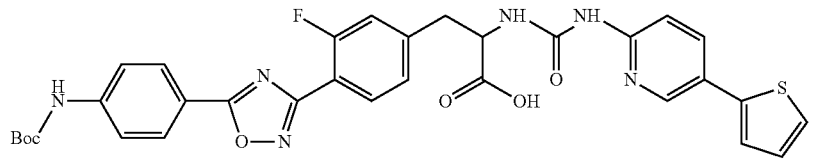 [SMILES: CC(C)(C)OC(=O)Nc1ccc(-c2nc(-c3ccc(CC(NC(=O)Nc4ccc(-c5cccs5)cn4)C(=O)O)cc3F)no2)cc1] |
| 221 | 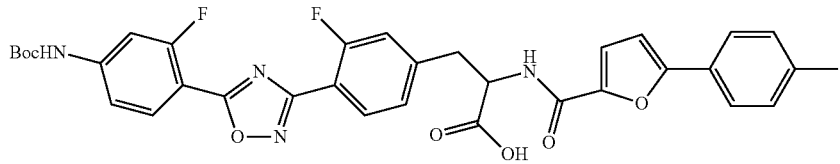 [SMILES: Cc1ccc(-c2ccc(C(=O)NC(Cc3ccc(-c4noc(-c5ccc(NC(=O)OC(C)(C)C)cc5F)n4)c(F)c3)C(=O)O)o2)cc1] |
| 222 | 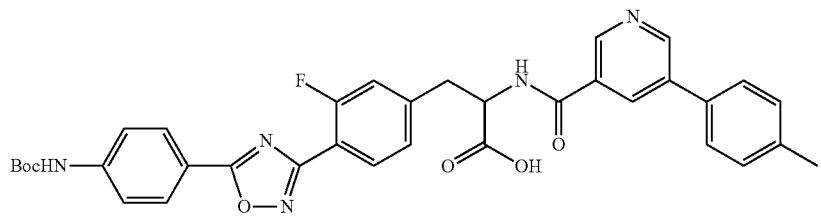 [SMILES: Cc1ccc(-c2cncc(C(=O)NC(Cc3ccc(-c4noc(-c5ccc(NC(=O)OC(C)(C)C)cc5)n4)c(F)c3)C(=O)O)c2)cc1] |
| 223 | 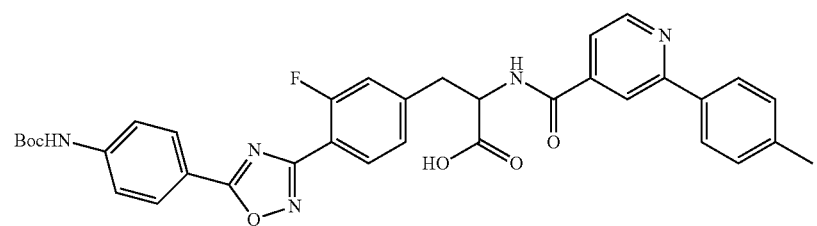 |

| Number | Structure |
|---|---|
| 224 | (structure shown) |
| 225 | (structure shown) |
| 226 | (structure shown) |
| 227 | (structure shown) |

39. The compound of claim 14, selected from the group consisting of Compounds as shown below:

| Number | Structure |
|---|---|
| 228 | (structure shown) |
| 230 | (structure shown) |

| Number | Structure |
|---|---|
| 231 | (4-tert-butylphenyl)triazole-phenyl-Ala-SO2-(4-tert-butylphenyl) |
| 232 | (4-tert-butylphenyl)triazole-phenyl-Ala-SO2-(4-isopropylphenyl) |
| 233 | BocHN-phenyl-oxadiazole-(2-F-phenyl)-Ala-SO2-(4-CF3-phenyl) |
| 234 | BocHN-phenyl-oxadiazole-(2-F-phenyl)-Ala-SO2-(4-tert-butylphenyl) |
| 235 | BocHN-phenyl-oxadiazole-(2-F-phenyl)-Ala-SO2-(1-naphthyl) |
| 236 | BocHN-phenyl-oxadiazole-(2-F-phenyl)-Ala-SO2-(2-naphthyl) |
| 237 | BocHN-phenyl-oxadiazole-(2-F-phenyl)-Ala-SO2-propyl |
| 238 | BocHN-phenyl-oxadiazole-(2-F-phenyl)-Ala-NHC(O)-(3-((4-methylpiperidin-1-yl)methyl)phenyl) |

-continued
| Number | Structure |
|---|---|
| 239 | 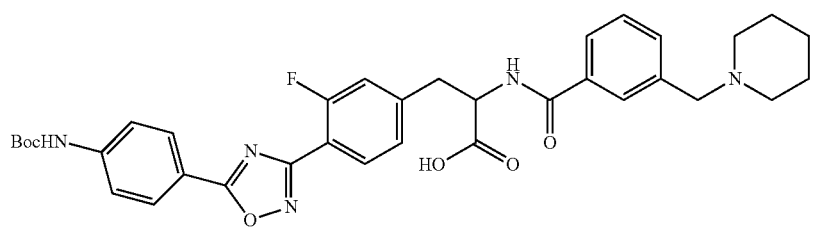 [SMILES: CC(C)(C)OC(=O)Nc1ccc(-c2nc(-c3ccc(CC(NC(=O)c4cccc(CN5CCCCC5)c4)C(=O)O)cc3F)no2)cc1] |
| 240 | 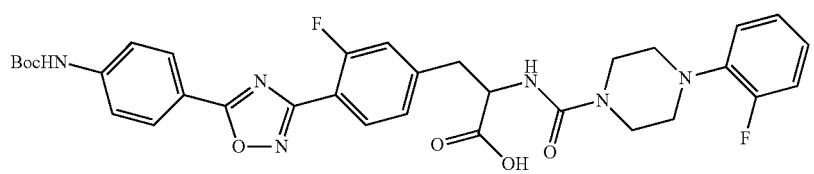 [SMILES: CC(C)(C)OC(=O)Nc1ccc(-c2nc(-c3ccc(CC(NC(=O)N4CCN(c5ccccc5F)CC4)C(=O)O)cc3F)no2)cc1] |
| 241 | 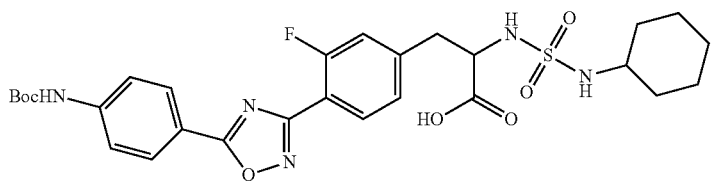 [SMILES: CC(C)(C)OC(=O)Nc1ccc(-c2nc(-c3ccc(CC(NS(=O)(=O)NC4CCCCC4)C(=O)O)cc3F)no2)cc1] |
| 242 | 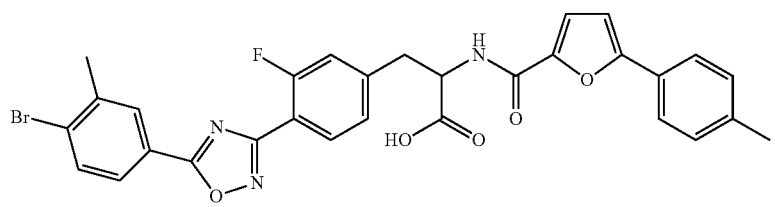 [SMILES: Cc1ccc(-c2ccc(C(=O)NC(Cc3ccc(-c4noc(-c5ccc(Br)c(C)c5)n4)c(F)c3)C(=O)O)o2)cc1] |
| 243 | 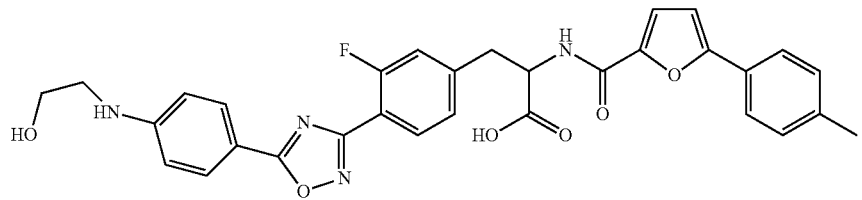 [SMILES: Cc1ccc(-c2ccc(C(=O)NC(Cc3ccc(-c4noc(-c5ccc(NCCO)cc5)n4)c(F)c3)C(=O)O)o2)cc1] |
| 244 | 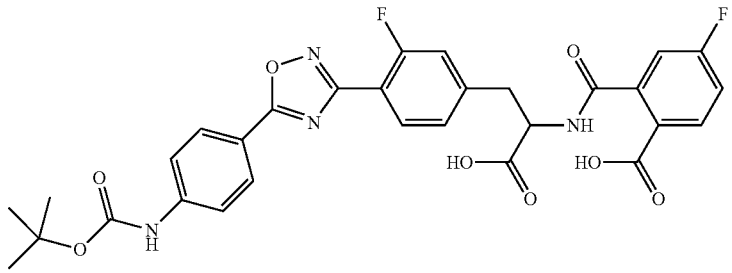 [SMILES: CC(C)(C)OC(=O)Nc1ccc(-c2nc(-c3ccc(CC(NC(=O)c4cc(F)ccc4C(=O)O)C(=O)O)cc3F)no2)cc1] |

-continued
| Number | Structure |
|---|---|
| 245 | 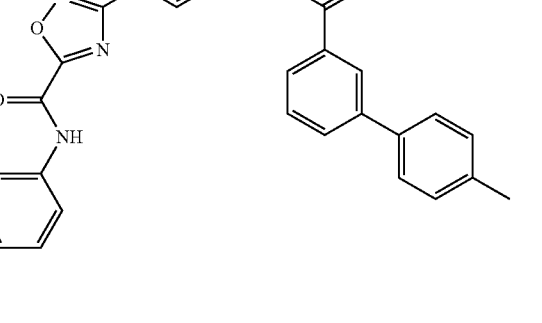 |
| 246 | 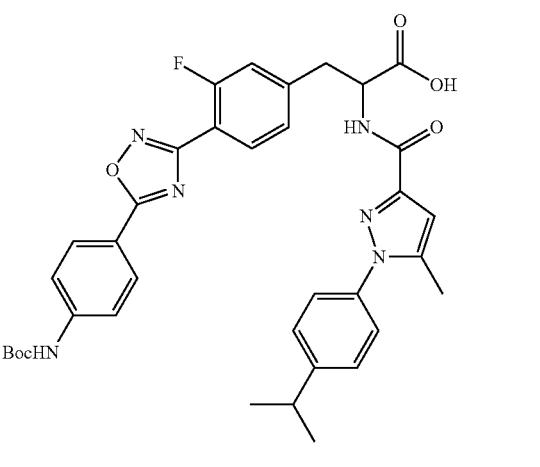 [SMILES: Cc1cc(C(=O)NC(Cc2ccc(-c3noc(-c4ccc(NC(=O)OC(C)(C)C)cc4)n3)c(F)c2)C(=O)O)nn1-c1ccc(C(C)C)cc1] |
| 247 | 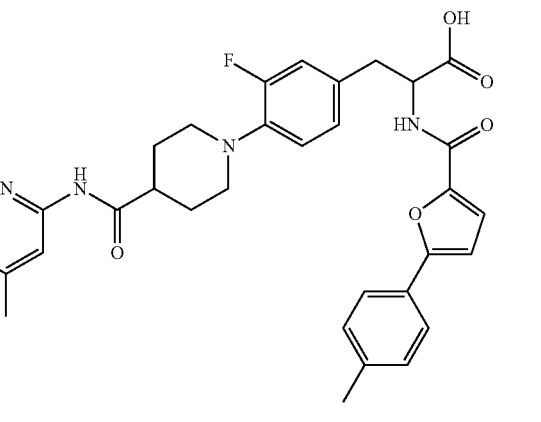 |
| 248 | 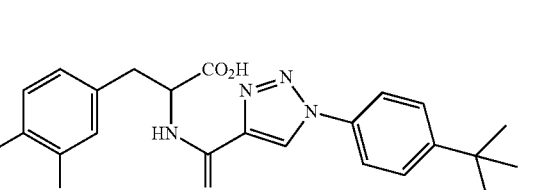 |

-continued
| Number | Structure |
|---|---|
| 249 | 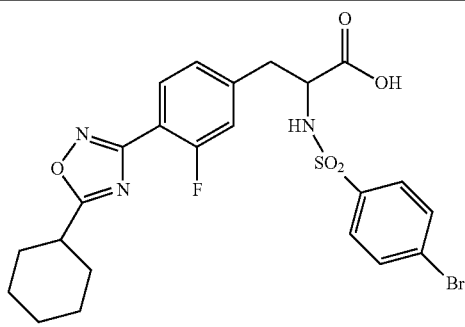 |
| 250 | 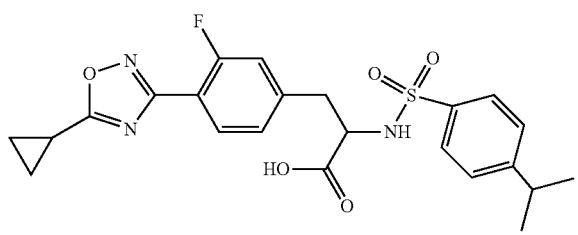 [SMILES: CC(C)c1ccc(S(=O)(=O)NC(Cc2ccc(-c3noc(C4CC4)n3)c(F)c2)C(=O)O)cc1] |
| 251 | 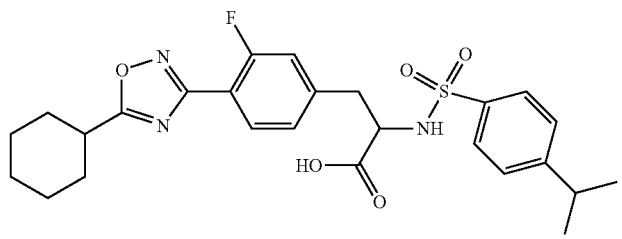 [SMILES: CC(C)c1ccc(S(=O)(=O)NC(Cc2ccc(-c3noc(C4CCCCC4)n3)c(F)c2)C(=O)O)cc1] |
| 252 | 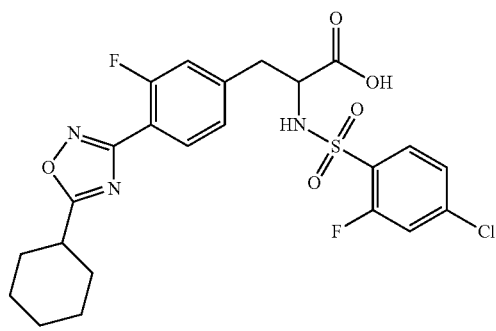 [SMILES: O=C(O)C(Cc1ccc(-c2noc(C3CCCCC3)n2)c(F)c1)NS(=O)(=O)c1ccc(Cl)cc1F] |
| 253 | 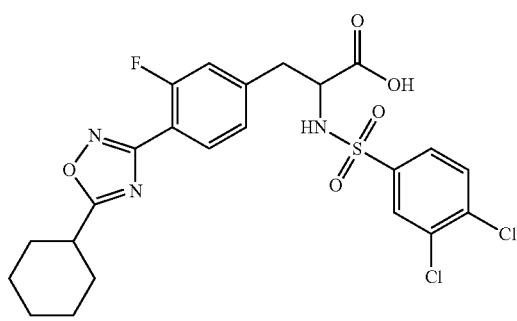 [SMILES: O=C(O)C(Cc1ccc(-c2noc(C3CCCCC3)n2)c(F)c1)NS(=O)(=O)c1ccc(Cl)c(Cl)c1] |

| Number | Structure |
|---|---|
| 254 | 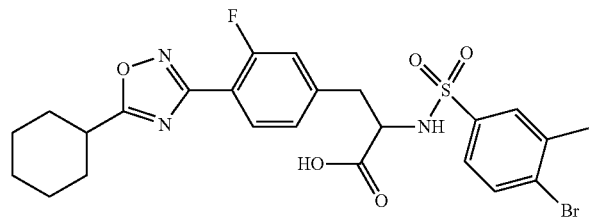 [SMILES: Cc1cc(S(=O)(=O)NC(Cc2ccc(-c3noc(C4CCCCC4)n3)c(F)c2)C(=O)O)ccc1Br] |
| 255 | 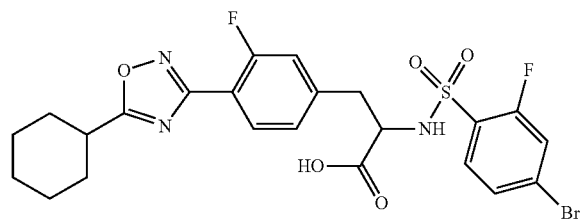 [SMILES: O=C(O)C(Cc1ccc(-c2noc(C3CCCCC3)n2)c(F)c1)NS(=O)(=O)c1ccc(Br)cc1F] |
| 256 | 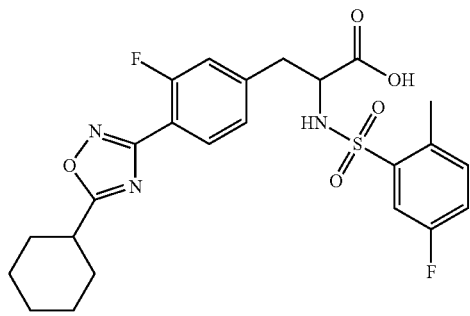 [SMILES: Cc1ccc(F)cc1S(=O)(=O)NC(Cc1ccc(-c2noc(C3CCCCC3)n2)c(F)c1)C(=O)O] |
| 257 | 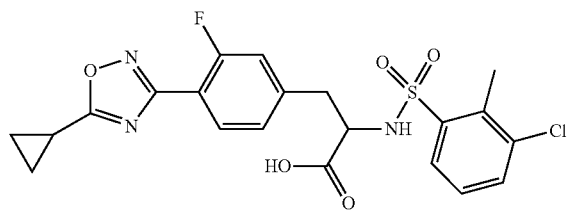 [SMILES: Cc1c(Cl)cccc1S(=O)(=O)NC(Cc1ccc(-c2noc(C3CC3)n2)c(F)c1)C(=O)O] |
| 258 | 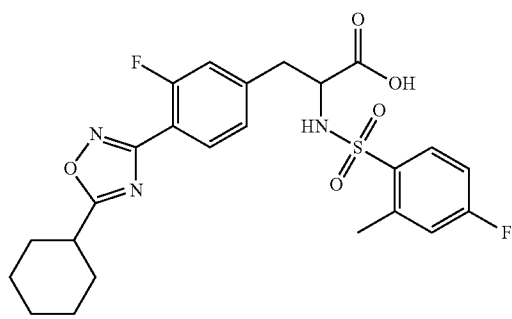 [SMILES: Cc1cc(F)ccc1S(=O)(=O)NC(Cc1ccc(-c2noc(C3CCCCC3)n2)c(F)c1)C(=O)O] |

| Number | Structure |
|---|---|
| 259 | 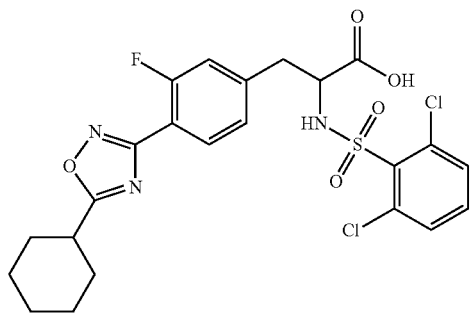 [SMILES: O=C(O)C(Cc1ccc(-c2noc(C3CCCCC3)n2)c(F)c1)NS(=O)(=O)c1c(Cl)cccc1Cl] |
| 260 | 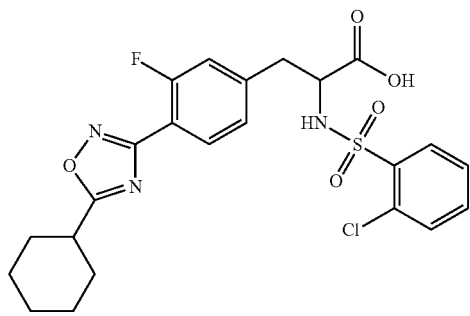 [SMILES: O=C(O)C(Cc1ccc(-c2noc(C3CCCCC3)n2)c(F)c1)NS(=O)(=O)c1ccccc1Cl] |
| 261 | 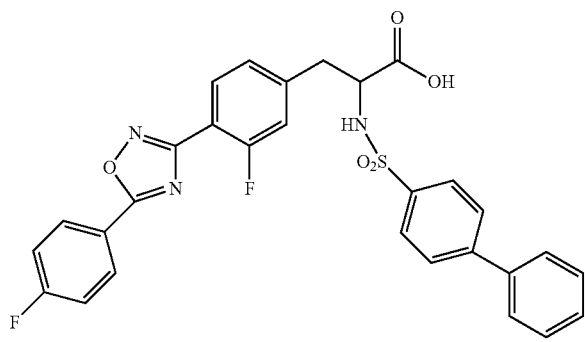 [SMILES: O=C(O)C(Cc1ccc(-c2noc(-c3ccc(F)cc3)n2)c(F)c1)NS(=O)(=O)c1ccc(-c2ccccc2)cc1] |
| 262 | 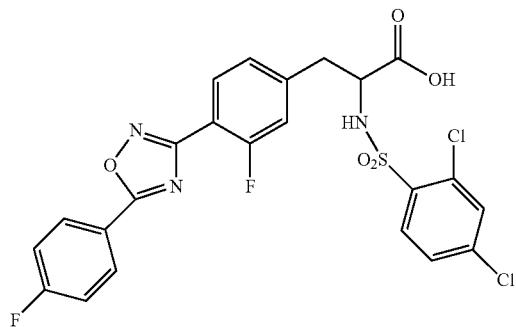 |

| Number | Structure |
|---|---|
| 263 | 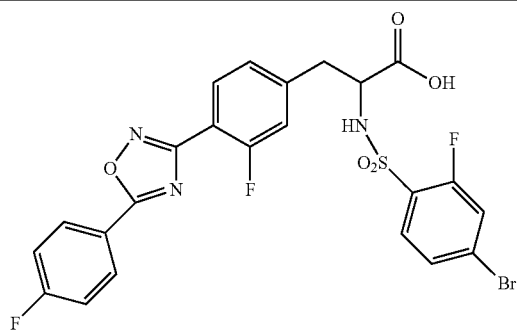 |
| 264 | 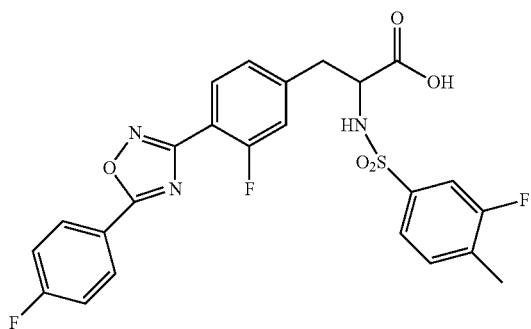 [SMILES: Cc1ccc(S(=O)(=O)NC(Cc2ccc(-c3noc(-c4ccc(F)cc4)n3)c(F)c2)C(=O)O)cc1F] |
| 265 | 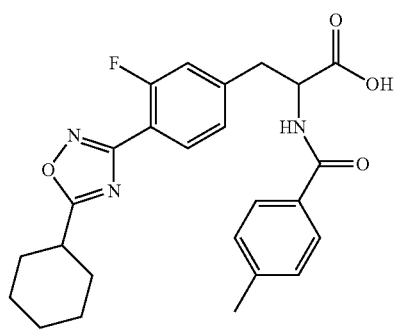 [SMILES: Cc1ccc(C(=O)NC(Cc2ccc(-c3noc(C4CCCCC4)n3)c(F)c2)C(=O)O)cc1] |
| 266 | 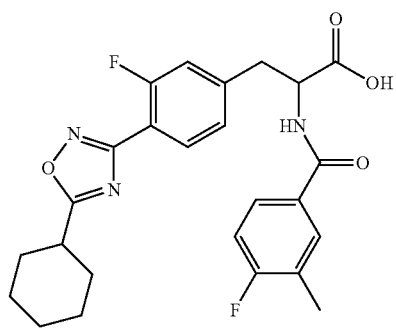 [SMILES: Cc1cc(C(=O)NC(Cc2ccc(-c3noc(C4CCCCC4)n3)c(F)c2)C(=O)O)ccc1F] |

-continued
| Number | Structure |
|---|---|
| 267 | 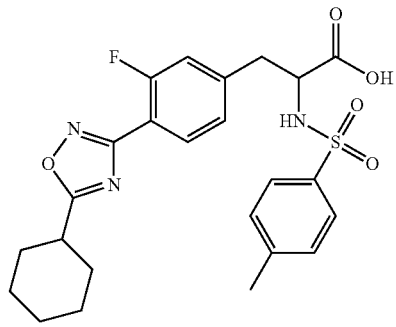 [SMILES: Cc1ccc(S(=O)(=O)NC(Cc2ccc(-c3noc(C4CCCCC4)n3)c(F)c2)C(=O)O)cc1] |
| 268 | 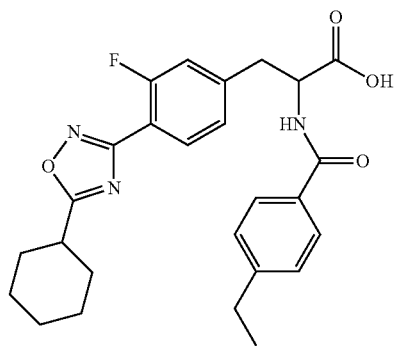 [SMILES: CCc1ccc(C(=O)NC(Cc2ccc(-c3noc(C4CCCCC4)n3)c(F)c2)C(=O)O)cc1] |
| 269 | 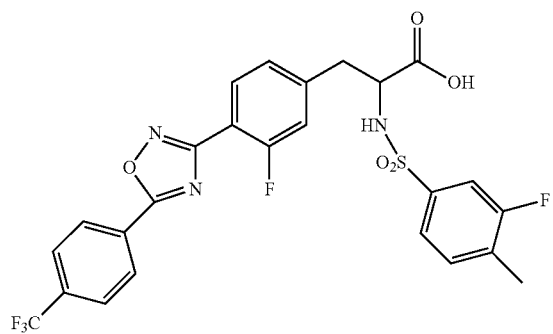 [SMILES: Cc1ccc(S(=O)(=O)NC(Cc2ccc(-c3noc(-c4ccc(C(F)(F)F)cc4)n3)c(F)c2)C(=O)O)cc1F] |
| 270 | 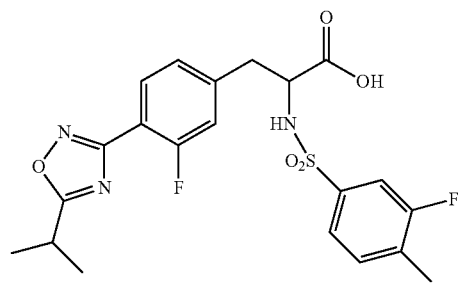 [SMILES: Cc1ccc(S(=O)(=O)NC(Cc2ccc(-c3noc(C(C)C)n3)c(F)c2)C(=O)O)cc1F] |
| 271 | 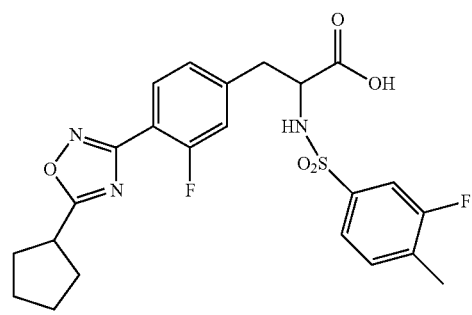 [SMILES: Cc1ccc(S(=O)(=O)NC(Cc2ccc(-c3noc(C4CCCC4)n3)c(F)c2)C(=O)O)cc1F] |

| Number | Structure |
|---|---|
| 272 | 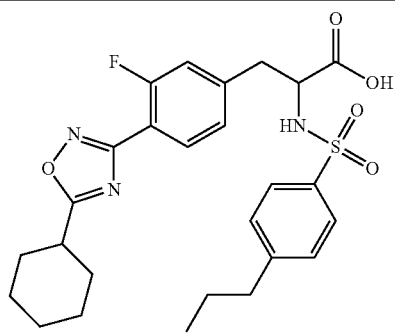 |
| 273 | 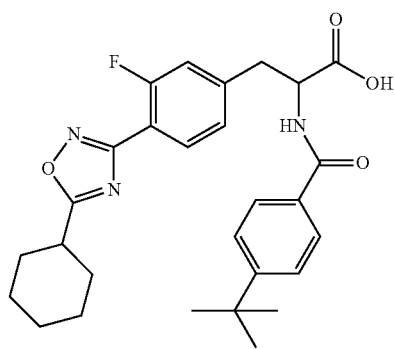 [SMILES: CC(C)(C)c1ccc(C(=O)NC(Cc2ccc(-c3noc(C4CCCCC4)n3)c(F)c2)C(=O)O)cc1] |
| 274 | 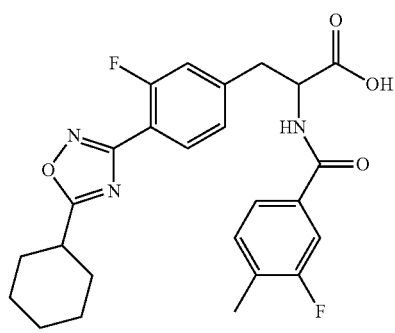 [SMILES: Cc1ccc(C(=O)NC(Cc2ccc(-c3noc(C4CCCCC4)n3)c(F)c2)C(=O)O)cc1F] |
| 275 | 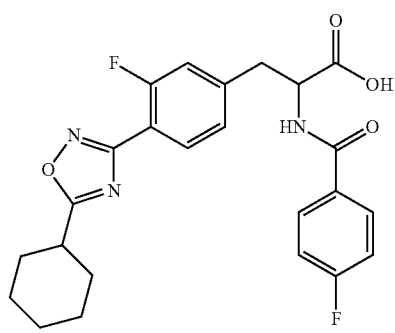 [SMILES: O=C(NC(Cc1ccc(-c2noc(C3CCCCC3)n2)c(F)c1)C(=O)O)c1ccc(F)cc1] |

-continued
| Number | Structure |
|---|---|
| 276 | 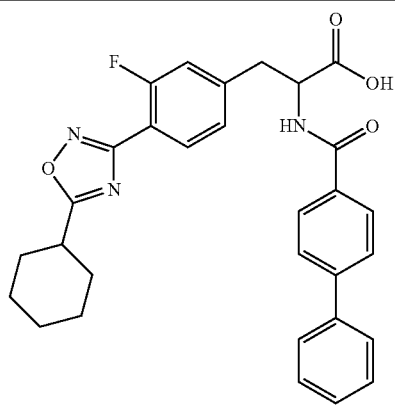 |
| 277 | 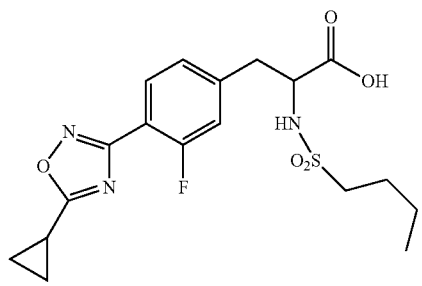 [SMILES: CCCCS(=O)(=O)NC(Cc1ccc(-c2noc(C3CC3)n2)c(F)c1)C(=O)O] |
| 278 | 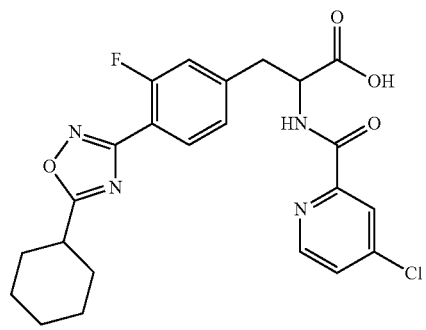 [SMILES: O=C(NC(Cc1ccc(-c2noc(C3CCCCC3)n2)c(F)c1)C(=O)O)c1cc(Cl)ccn1] |
| 279 | 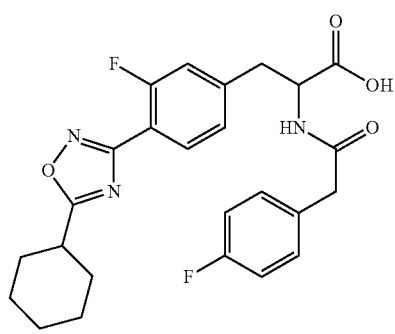 [SMILES: O=C(Cc1ccc(F)cc1)NC(Cc1ccc(-c2noc(C3CCCCC3)n2)c(F)c1)C(=O)O] |

| Number | Structure |
|---|---|
| 280 | 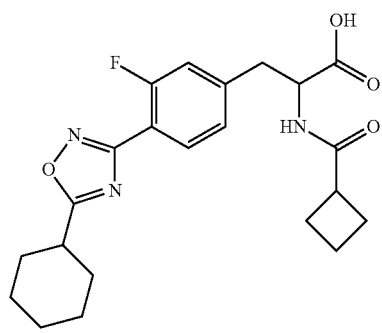 [SMILES: O=C(NC(Cc1ccc(-c2noc(C3CCCCC3)n2)c(F)c1)C(=O)O)C1CCC1] |
| 281 | 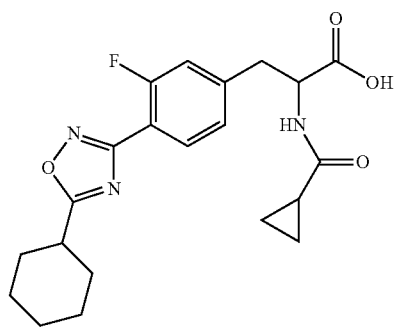 [SMILES: O=C(NC(Cc1ccc(-c2noc(C3CCCCC3)n2)c(F)c1)C(=O)O)C1CC1] |
| 282 | 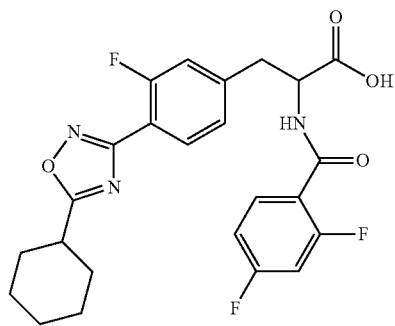 [SMILES: O=C(NC(Cc1ccc(-c2noc(C3CCCCC3)n2)c(F)c1)C(=O)O)c1ccc(F)cc1F] |
| 283 | 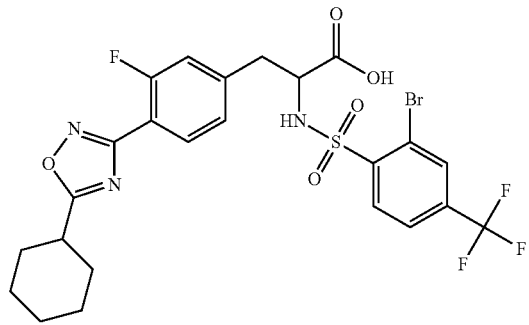 [SMILES: O=C(O)C(Cc1ccc(-c2noc(C3CCCCC3)n2)c(F)c1)NS(=O)(=O)c1ccc(C(F)(F)F)cc1Br] |

| Number | Structure |
|---|---|
| 284 | 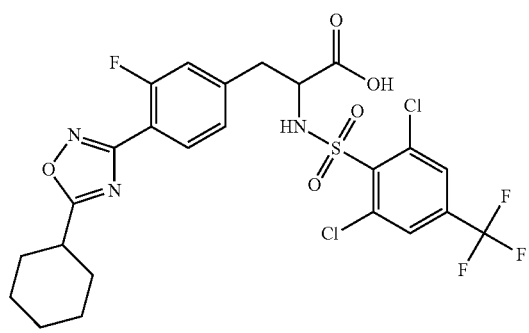 [SMILES: O=C(O)C(Cc1ccc(-c2noc(C3CCCCC3)n2)c(F)c1)NS(=O)(=O)c1c(Cl)cc(C(F)(F)F)cc1Cl] |
| 285 | 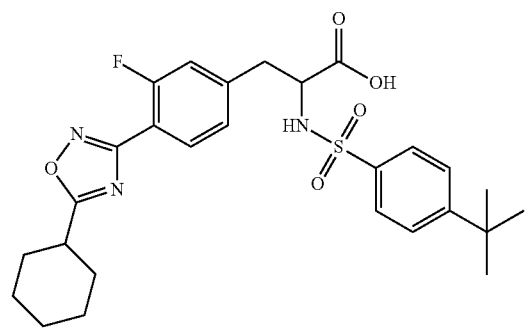 [SMILES: CC(C)(C)c1ccc(S(=O)(=O)NC(Cc2ccc(-c3noc(C4CCCCC4)n3)c(F)c2)C(=O)O)cc1] |
| 286 | 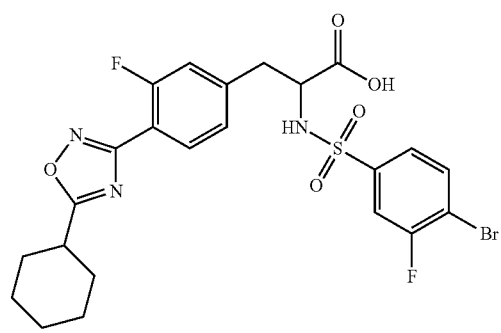 [SMILES: O=C(O)C(Cc1ccc(-c2noc(C3CCCCC3)n2)c(F)c1)NS(=O)(=O)c1ccc(Br)c(F)c1] |
| 287 | 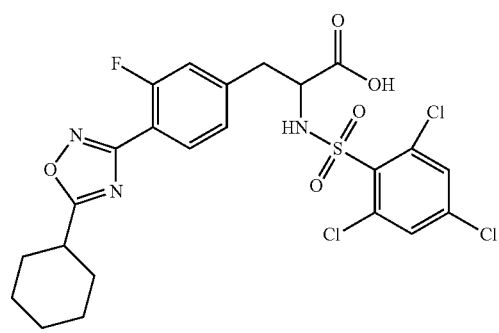 [SMILES: O=C(O)C(Cc1ccc(-c2noc(C3CCCCC3)n2)c(F)c1)NS(=O)(=O)c1c(Cl)cc(Cl)cc1Cl] |

-continued
| Number | Structure |
|---|---|
| 288 | 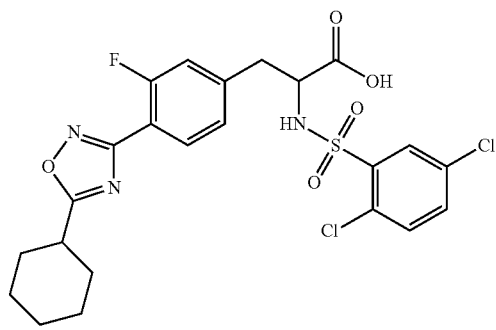 [SMILES: O=C(O)C(Cc1ccc(-c2noc(C3CCCCC3)n2)c(F)c1)NS(=O)(=O)c1cc(Cl)ccc1Cl] |
| 289 | 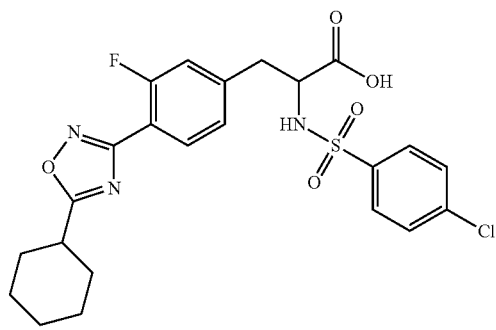 [SMILES: O=C(O)C(Cc1ccc(-c2noc(C3CCCCC3)n2)c(F)c1)NS(=O)(=O)c1ccc(Cl)cc1] |
| 290 | 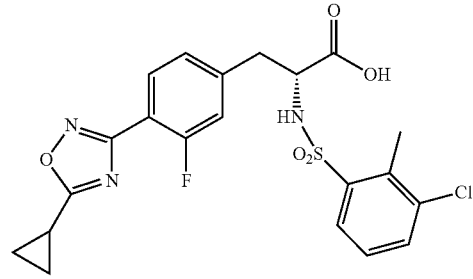 [SMILES: Cc1c(Cl)cccc1S(=O)(=O)N[C@H](Cc1ccc(-c2noc(C3CC3)n2)c(F)c1)C(=O)O] |
| 291 | 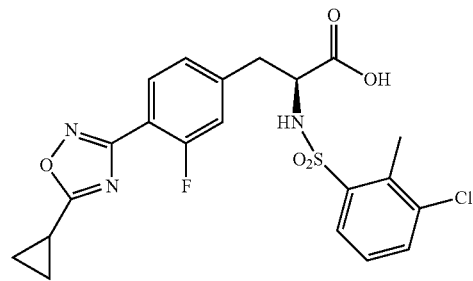 |
| 292 | 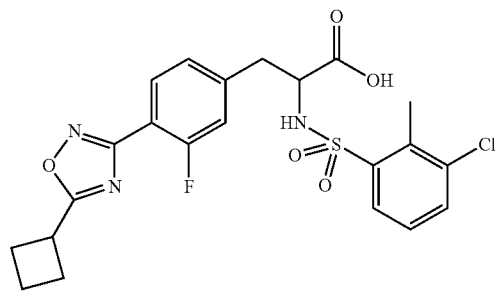 [SMILES: Cc1c(Cl)cccc1S(=O)(=O)NC(Cc1ccc(-c2noc(C3CCC3)n2)c(F)c1)C(=O)O] |

| Number | Structure |
|---|---|
| 293 | 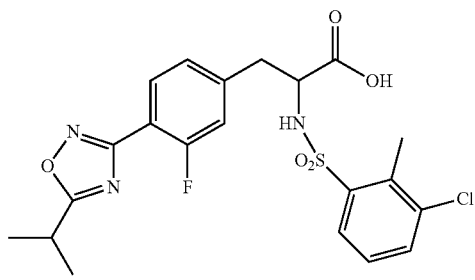 [SMILES: Cc1c(Cl)cccc1S(=O)(=O)NC(Cc1ccc(-c2noc(C(C)C)n2)c(F)c1)C(=O)O] |
| 294 | 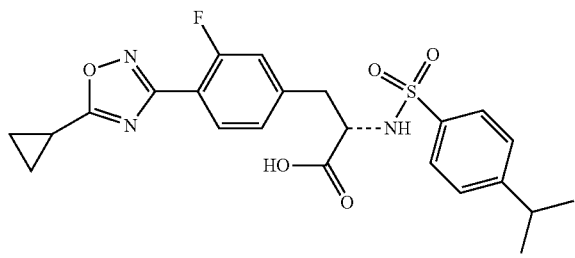 [SMILES: CC(C)c1ccc(S(=O)(=O)N[C@@H](Cc2ccc(-c3noc(C4CC4)n3)c(F)c2)C(=O)O)cc1] |
| 295 | 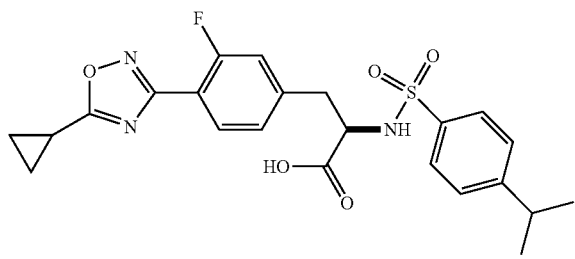 [SMILES: CC(C)c1ccc(S(=O)(=O)N[C@H](Cc2ccc(-c3noc(C4CC4)n3)c(F)c2)C(=O)O)cc1] |
| 296 | 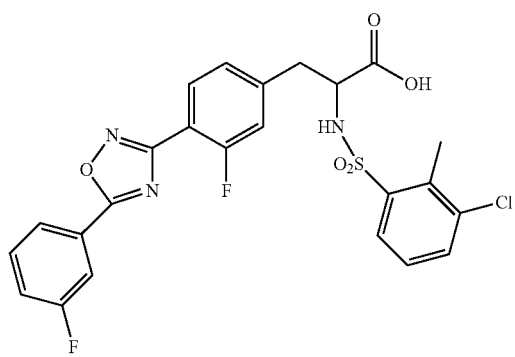 [SMILES: Cc1c(Cl)cccc1S(=O)(=O)NC(Cc1ccc(-c2noc(-c3cccc(F)c3)n2)c(F)c1)C(=O)O] |
| 297 | 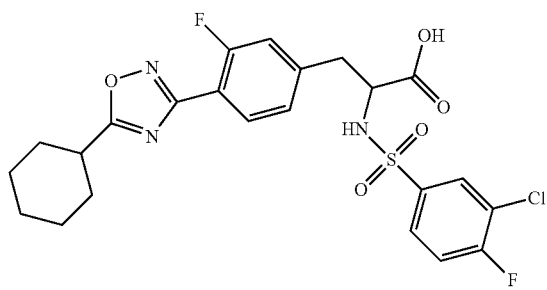 [SMILES: O=C(O)C(Cc1ccc(-c2noc(C3CCCCC3)n2)c(F)c1)NS(=O)(=O)c1ccc(F)c(Cl)c1] |

| Number | Structure |
|---|---|
| 298 | 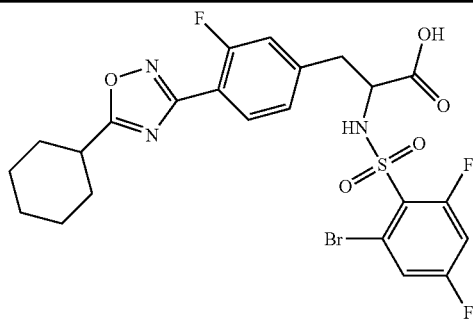 |
| 299 | 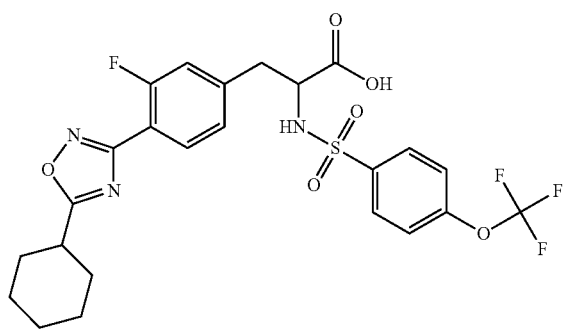 [SMILES: O=C(O)C(Cc1ccc(-c2noc(C3CCCCC3)n2)c(F)c1)NS(=O)(=O)c1ccc(OC(F)(F)F)cc1] |
| 300 | 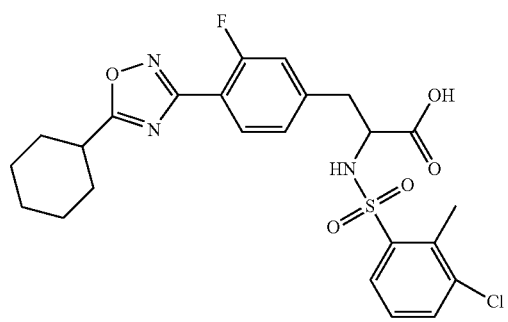 [SMILES: Cc1c(Cl)cccc1S(=O)(=O)NC(Cc1ccc(-c2noc(C3CCCCC3)n2)c(F)c1)C(=O)O] |
| 301 | 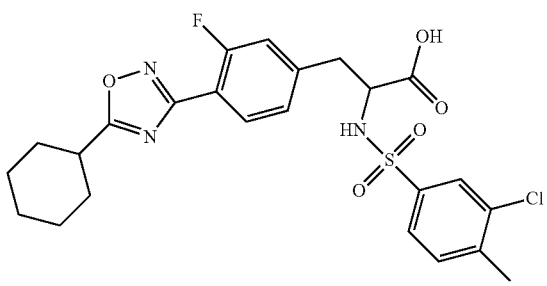 [SMILES: Cc1ccc(S(=O)(=O)NC(Cc2ccc(-c3noc(C4CCCCC4)n3)c(F)c2)C(=O)O)cc1Cl] |
| 302 | 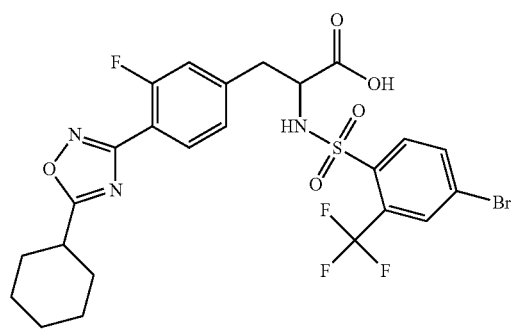 [SMILES: O=C(O)C(Cc1ccc(-c2noc(C3CCCCC3)n2)c(F)c1)NS(=O)(=O)c1ccc(Br)cc1C(F)(F)F] |

-continued
| Number | Structure |
|---|---|
| 303 | 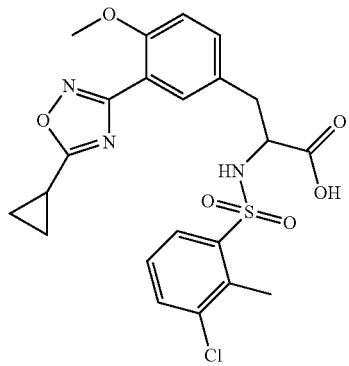 [SMILES: COc1ccc(CC(NS(=O)(=O)c2cccc(Cl)c2C)C(=O)O)cc1-c1noc(C2CC2)n1] |
| 304 | 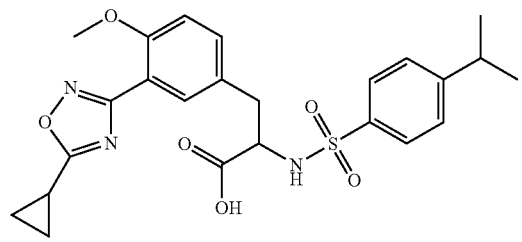 [SMILES: COc1ccc(CC(NS(=O)(=O)c2ccc(C(C)C)cc2)C(=O)O)cc1-c1noc(C2CC2)n1] |
| 305 | 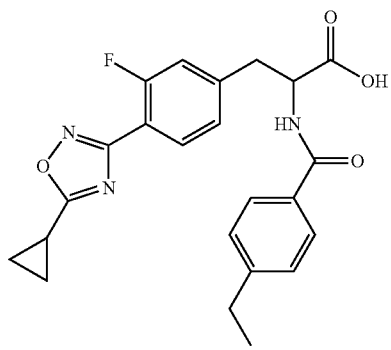 [SMILES: CCc1ccc(C(=O)NC(Cc2ccc(-c3noc(C4CC4)n3)c(F)c2)C(=O)O)cc1] |
| 306 | 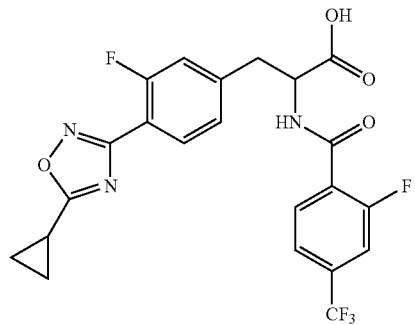 [SMILES: O=C(NC(Cc1ccc(-c2noc(C3CC3)n2)c(F)c1)C(=O)O)c1ccc(C(F)(F)F)cc1F] |

| Number | Structure |
|---|---|
| 307 | 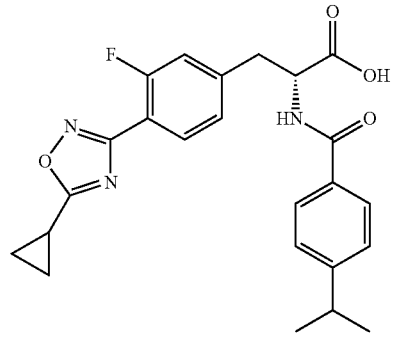 [SMILES: CC(C)c1ccc(C(=O)N[C@H](Cc2ccc(-c3noc(C4CC4)n3)c(F)c2)C(=O)O)cc1] |
| 308 | 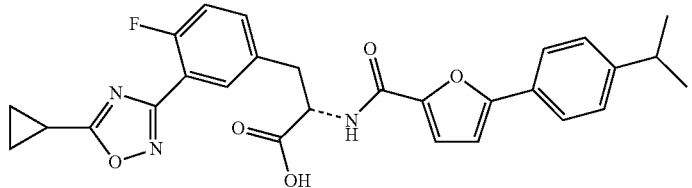 [SMILES: CC(C)c1ccc(-c2ccc(C(=O)N[C@@H](Cc3ccc(F)c(-c4noc(C5CC5)n4)c3)C(=O)O)o2)cc1] |
| 309 | 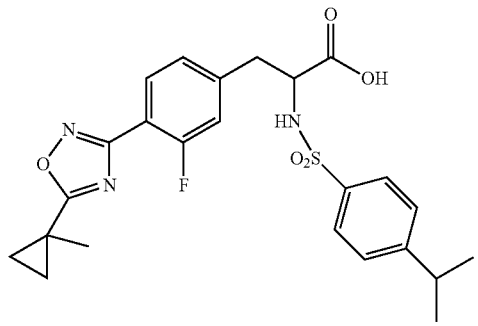 [SMILES: CC(C)c1ccc(S(=O)(=O)NC(Cc2ccc(-c3noc(C4(C)CC4)n3)c(F)c2)C(=O)O)cc1] |
| 310 | 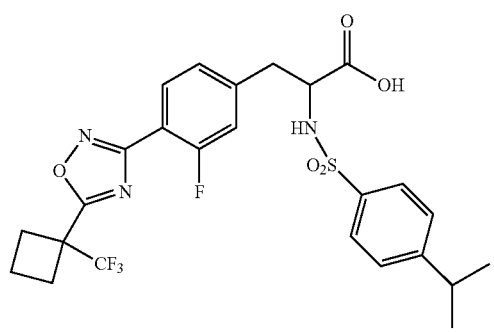 [SMILES: CC(C)c1ccc(S(=O)(=O)NC(Cc2ccc(-c3noc(C4(C(F)(F)F)CCC4)n3)c(F)c2)C(=O)O)cc1] |
| 311 | 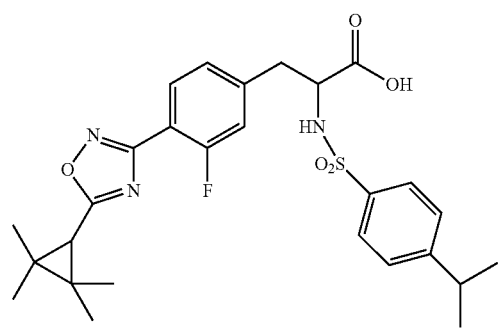 [SMILES: CC(C)c1ccc(S(=O)(=O)NC(Cc2ccc(-c3noc(C4C(C)(C)C4(C)C)n3)c(F)c2)C(=O)O)cc1] |

-continued
| Number | Structure |
|---|---|
| 312 | 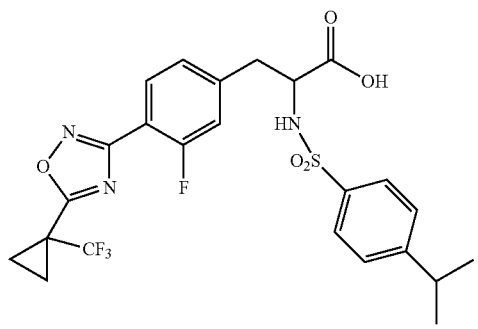 |
| 313 | 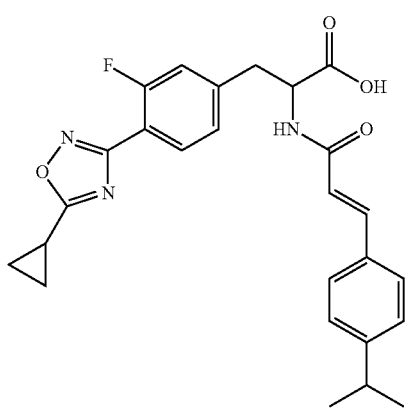 [SMILES: CC(C)c1ccc(/C=C/C(=O)NC(Cc2ccc(-c3noc(C4CC4)n3)c(F)c2)C(=O)O)cc1] |
| 314 | 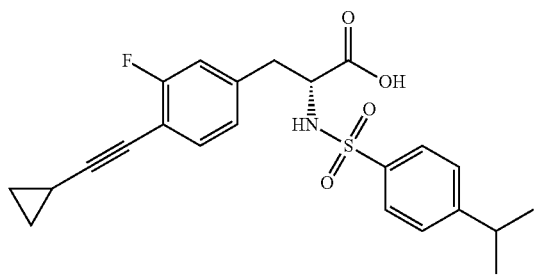 [SMILES: CC(C)c1ccc(S(=O)(=O)N[C@H](Cc2ccc(C#CC3CC3)c(F)c2)C(=O)O)cc1] |
| 315 | 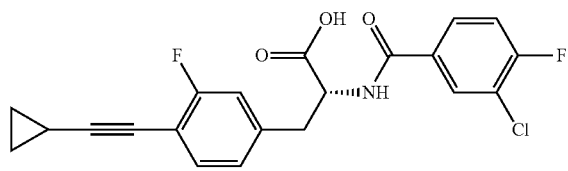 [SMILES: O=C(N[C@H](Cc1ccc(C#CC2CC2)c(F)c1)C(=O)O)c1ccc(F)c(Cl)c1] |
| 316 | 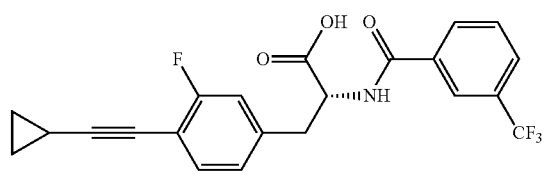 [SMILES: O=C(N[C@H](Cc1ccc(C#CC2CC2)c(F)c1)C(=O)O)c1cccc(C(F)(F)F)c1] |

-continued
| Number | Structure |
|---|---|
| 317 | 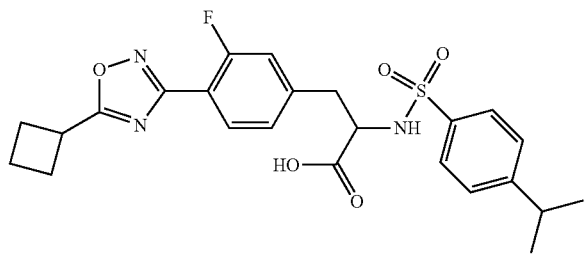 [SMILES: CC(C)c1ccc(S(=O)(=O)NC(Cc2ccc(-c3noc(C4CCC4)n3)c(F)c2)C(=O)O)cc1] |
| 318 | 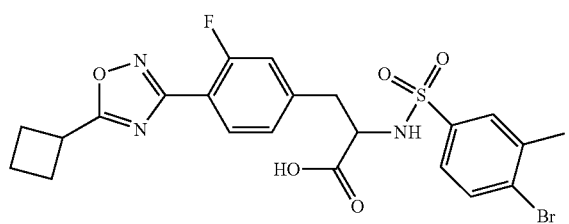 [SMILES: Cc1cc(S(=O)(=O)NC(Cc2ccc(-c3noc(C4CCC4)n3)c(F)c2)C(=O)O)ccc1Br] |
| 319 | 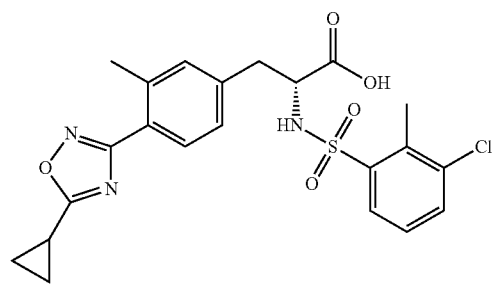 [SMILES: Cc1cc(C[C@@H](NS(=O)(=O)c2cccc(Cl)c2C)C(=O)O)ccc1-c1noc(C2CC2)n1] |
| 320 | 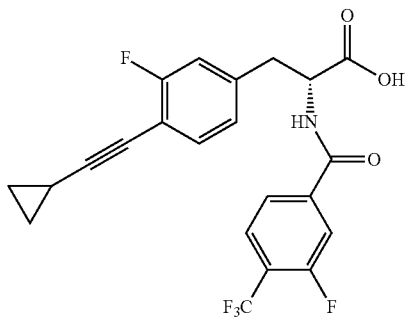 [SMILES: O=C(N[C@H](Cc1ccc(C#CC2CC2)c(F)c1)C(=O)O)c1ccc(C(F)(F)F)c(F)c1] |
| 321 | 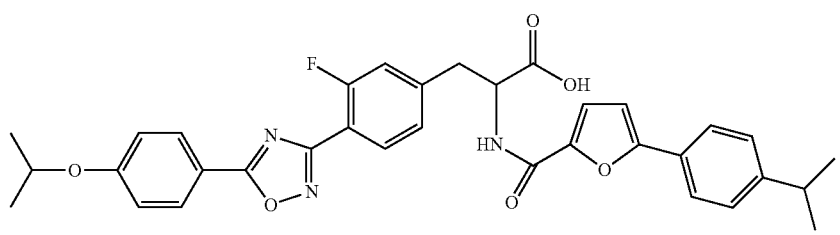 [SMILES: CC(C)Oc1ccc(-c2nc(-c3ccc(CC(NC(=O)c4ccc(-c5ccc(C(C)C)cc5)o4)C(=O)O)cc3F)no2)cc1] |

| Number | Structure |
|---|---|
| 322 | 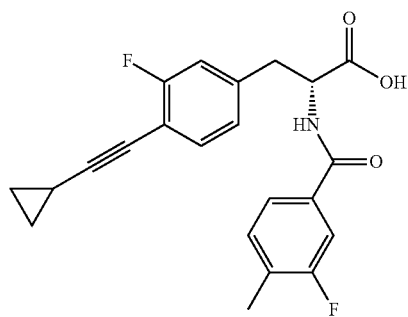 [SMILES: Cc1ccc(C(=O)N[C@H](Cc2ccc(C#CC3CC3)c(F)c2)C(=O)O)cc1F] |
| 323 | 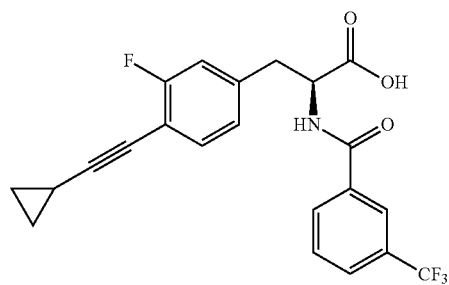 [SMILES: O=C(N[C@@H](Cc1ccc(C#CC2CC2)c(F)c1)C(=O)O)c1cccc(C(F)(F)F)c1] |
| 324 | 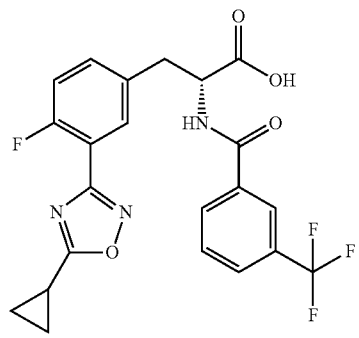 [SMILES: O=C(N[C@H](Cc1ccc(F)c(-c2noc(C3CC3)n2)c1)C(=O)O)c1cccc(C(F)(F)F)c1] |
| 325 | 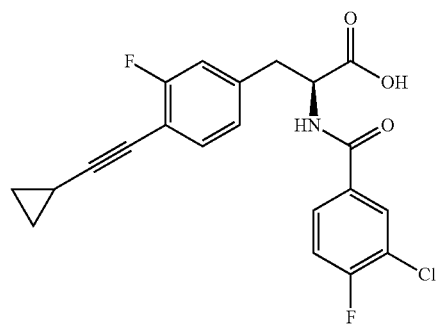 [SMILES: O=C(N[C@@H](Cc1ccc(C#CC2CC2)c(F)c1)C(=O)O)c1ccc(F)c(Cl)c1] |
| 326 | 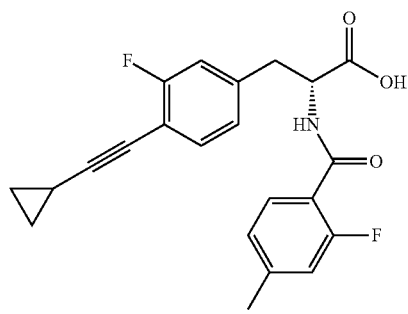 [SMILES: Cc1ccc(C(=O)N[C@H](Cc2ccc(C#CC3CC3)c(F)c2)C(=O)O)c(F)c1] |

| Number | Structure |
|---|---|
| 327 | 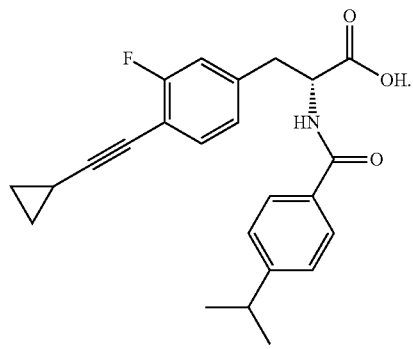 [SMILES: CC(C)c1ccc(C(=O)N[C@H](Cc2ccc(C#CC3CC3)c(F)c2)C(=O)O)cc1] |
40. The compound of claim 26, selected from the group consisting of Compounds as shown below:
| Number | Structure |
|---|---|
| 3 | 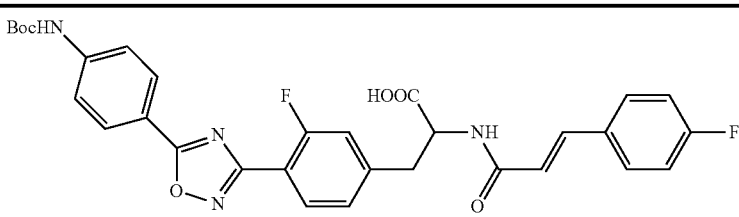 |
| 4 | 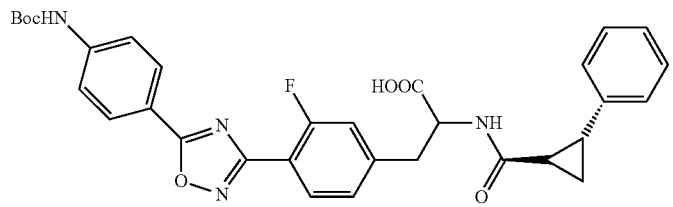 |
| 5 | 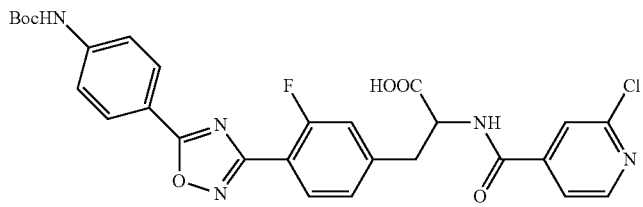 [SMILES: CC(C)(C)OC(=O)Nc1ccc(-c2nc(-c3ccc(CC(NC(=O)c4ccnc(Cl)c4)C(=O)O)cc3F)no2)cc1] |
| 6 | 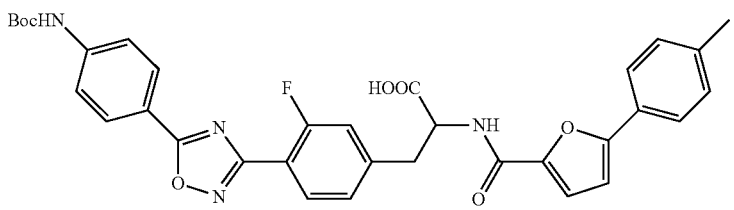 |
| 7 | 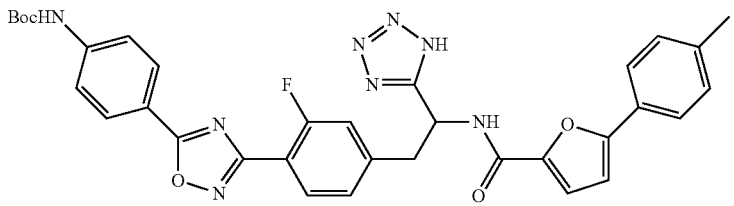 [SMILES: Cc1ccc(-c2ccc(C(=O)NC(Cc3ccc(-c4noc(-c5ccc(NC(=O)OC(C)(C)C)cc5)n4)c(F)c3)c3nnn[nH]3)o2)cc1] |

-continued
| Number | Structure |
|---|---|
| 8 | 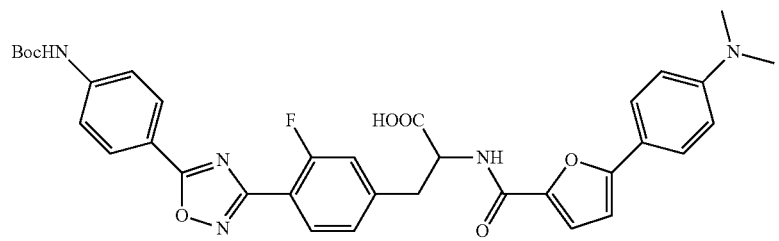 [SMILES: CN(C)c1ccc(-c2ccc(C(=O)NC(Cc3ccc(-c4noc(-c5ccc(NC(=O)OC(C)(C)C)cc5)n4)c(F)c3)C(=O)O)o2)cc1] |
| 9 | 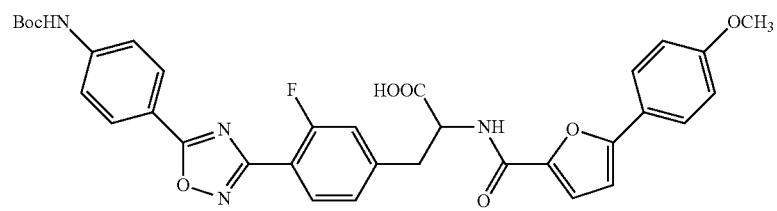 [SMILES: COc1ccc(-c2ccc(C(=O)NC(Cc3ccc(-c4noc(-c5ccc(NC(=O)OC(C)(C)C)cc5)n4)c(F)c3)C(=O)O)o2)cc1] |
| 10 | 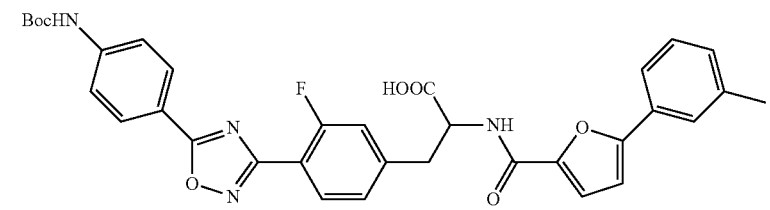 [SMILES: Cc1cccc(-c2ccc(C(=O)NC(Cc3ccc(-c4noc(-c5ccc(NC(=O)OC(C)(C)C)cc5)n4)c(F)c3)C(=O)O)o2)c1] |
| 11 | 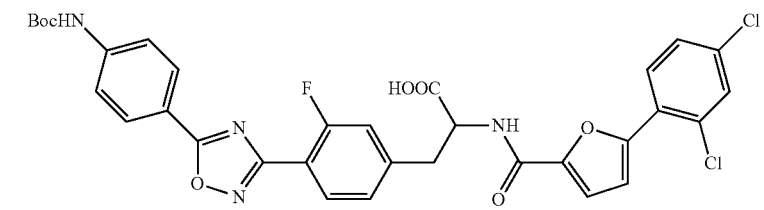 [SMILES: CC(C)(C)OC(=O)Nc1ccc(-c2nc(-c3ccc(CC(NC(=O)c4ccc(-c5ccc(Cl)cc5Cl)o4)C(=O)O)cc3F)no2)cc1] |
| 12 | 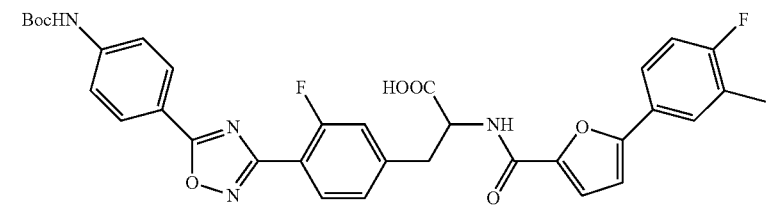 |
| 13 | 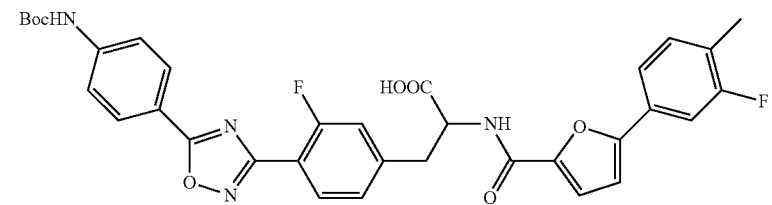 [SMILES: Cc1ccc(-c2ccc(C(=O)NC(Cc3ccc(-c4noc(-c5ccc(NC(=O)OC(C)(C)C)cc5)n4)c(F)c3)C(=O)O)o2)cc1F] |
| 14 | 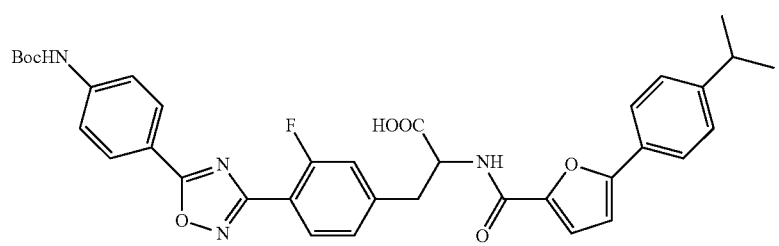 [SMILES: CC(C)c1ccc(-c2ccc(C(=O)NC(Cc3ccc(-c4noc(-c5ccc(NC(=O)OC(C)(C)C)cc5)n4)c(F)c3)C(=O)O)o2)cc1] |

| Number | Structure |
|---|---|
| 15 | 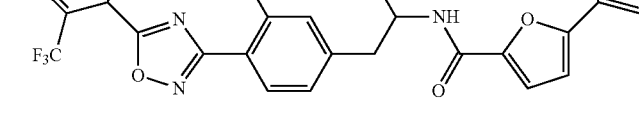 |
| 16 | 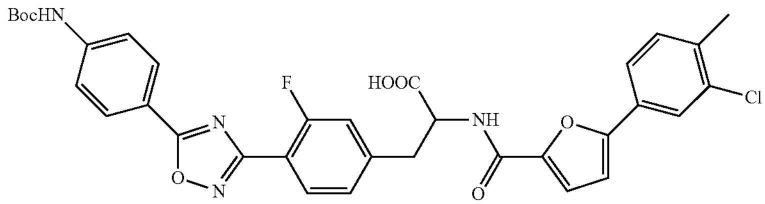 [SMILES: Cc1ccc(-c2ccc(C(=O)NC(Cc3ccc(-c4noc(-c5ccc(NC(=O)OC(C)(C)C)cc5)n4)c(F)c3)C(=O)O)o2)cc1Cl] |
| 17 | 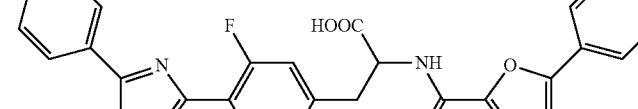 |
| 18 | 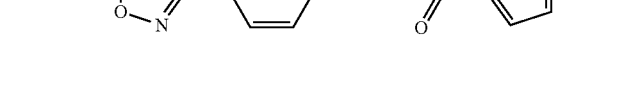 |
| 19 | 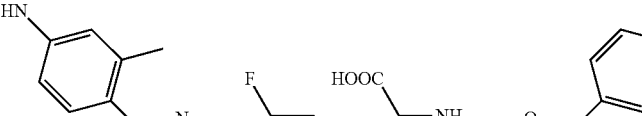 |
| 20 | 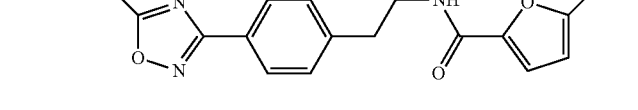 |

-continued
| Number | Structure |
|---|---|
| 21 | 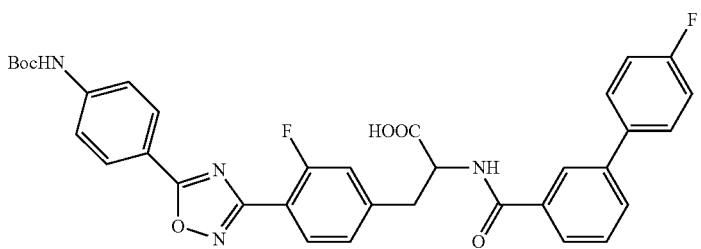 [SMILES: CC(C)(C)OC(=O)Nc1ccc(-c2nc(-c3ccc(CC(NC(=O)c4cccc(-c5ccc(F)cc5)c4)C(=O)O)cc3F)no2)cc1] |
| 22 | 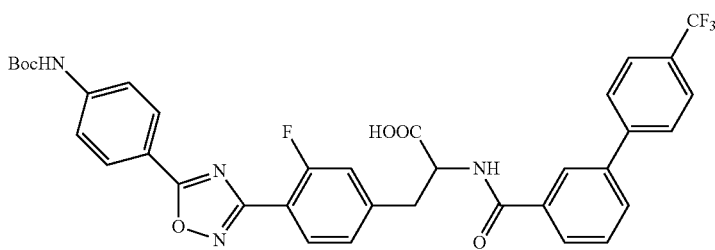 [SMILES: CC(C)(C)OC(=O)Nc1ccc(-c2nc(-c3ccc(CC(NC(=O)c4cccc(-c5ccc(C(F)(F)F)cc5)c4)C(=O)O)cc3F)no2)cc1] |
| 23 | 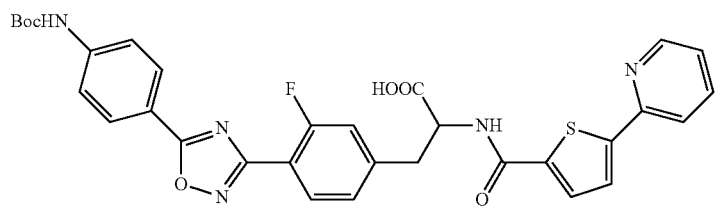 [SMILES: CC(C)(C)OC(=O)Nc1ccc(-c2nc(-c3ccc(CC(NC(=O)c4ccc(-c5ccccn5)s4)C(=O)O)cc3F)no2)cc1] |
| 24 | 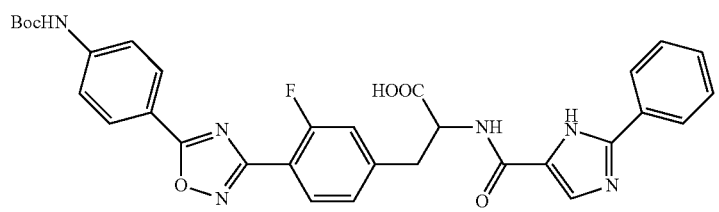 [SMILES: CC(C)(C)OC(=O)Nc1ccc(-c2nc(-c3ccc(CC(NC(=O)c4cnc(-c5ccccc5)[nH]4)C(=O)O)cc3F)no2)cc1] |
| 25 | 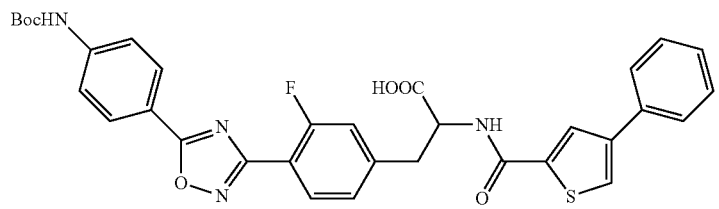 [SMILES: CC(C)(C)OC(=O)Nc1ccc(-c2nc(-c3ccc(CC(NC(=O)c4cc(-c5ccccc5)cs4)C(=O)O)cc3F)no2)cc1] |
| 26 | 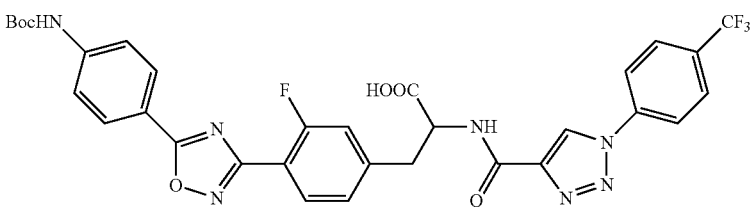 [SMILES: CC(C)(C)OC(=O)Nc1ccc(-c2nc(-c3ccc(CC(NC(=O)c4cn(-c5ccc(C(F)(F)F)cc5)nn4)C(=O)O)cc3F)no2)cc1] |
| 27 | 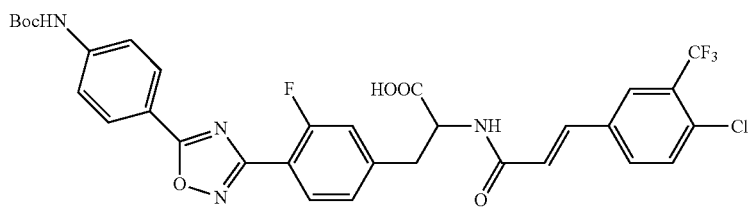 [SMILES: CC(C)(C)OC(=O)Nc1ccc(-c2nc(-c3ccc(CC(NC(=O)/C=C/c4ccc(Cl)c(C(F)(F)F)c4)C(=O)O)cc3F)no2)cc1] |

-continued
| Number | Structure |
|---|---|
| 28 | 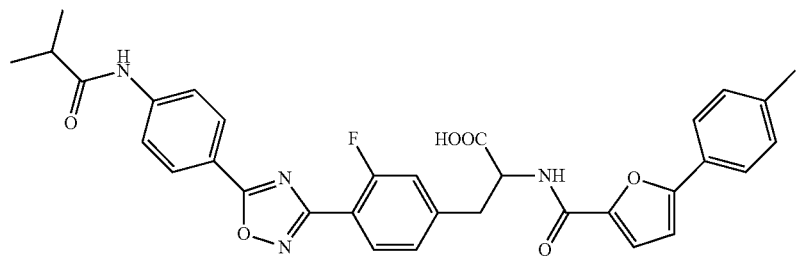 [SMILES: Cc1ccc(-c2ccc(C(=O)NC(Cc3ccc(-c4noc(-c5ccc(NC(=O)C(C)C)cc5)n4)c(F)c3)C(=O)O)o2)cc1] |
| 29 | 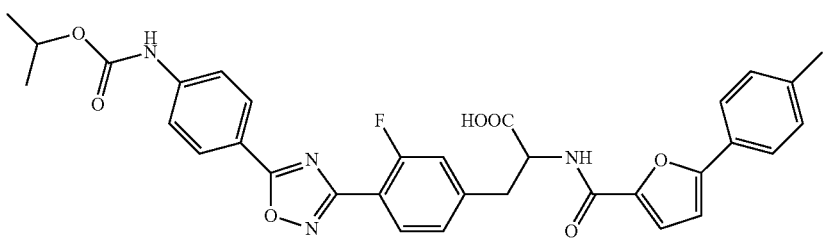 [SMILES: Cc1ccc(-c2ccc(C(=O)NC(Cc3ccc(-c4noc(-c5ccc(NC(=O)OC(C)C)cc5)n4)c(F)c3)C(=O)O)o2)cc1] |
| 30 | 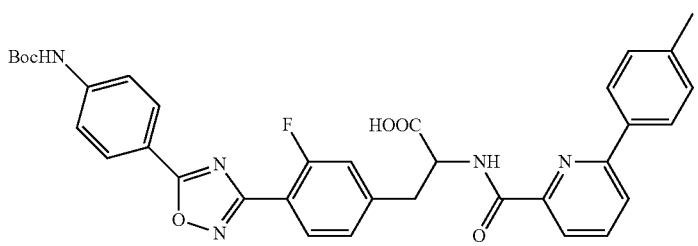 [SMILES: Cc1ccc(-c2cccc(C(=O)NC(Cc3ccc(-c4noc(-c5ccc(NC(=O)OC(C)(C)C)cc5)n4)c(F)c3)C(=O)O)n2)cc1] |
| 31 | 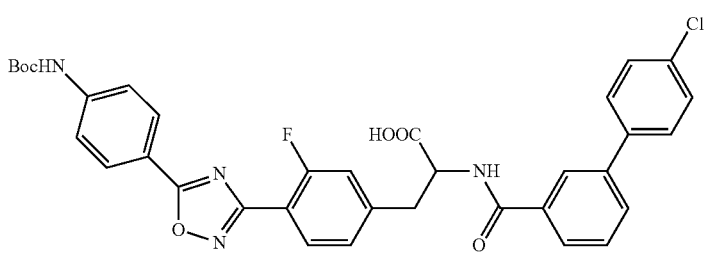 [SMILES: CC(C)(C)OC(=O)Nc1ccc(-c2nc(-c3ccc(CC(NC(=O)c4cccc(-c5ccc(Cl)cc5)c4)C(=O)O)cc3F)no2)cc1] |
| 32 | 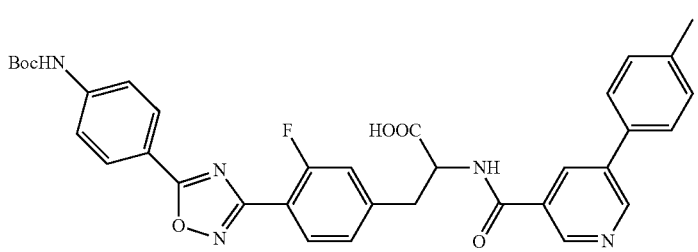 [SMILES: Cc1ccc(-c2cncc(C(=O)NC(Cc3ccc(-c4noc(-c5ccc(NC(=O)OC(C)(C)C)cc5)n4)c(F)c3)C(=O)O)c2)cc1] |
| 33 | 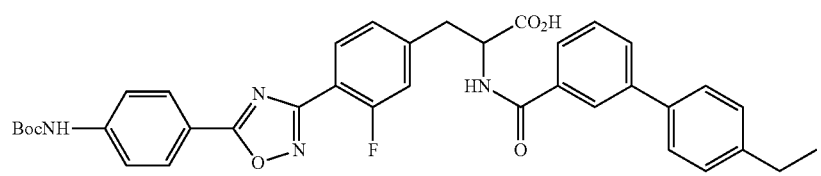 [SMILES: CCc1ccc(-c2cccc(C(=O)NC(Cc3ccc(-c4noc(-c5ccc(NC(=O)OC(C)(C)C)cc5)n4)c(F)c3)C(=O)O)c2)cc1] |
| 34 | 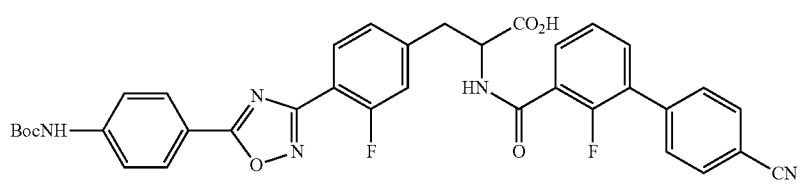 [SMILES: CC(C)(C)OC(=O)Nc1ccc(-c2nc(-c3ccc(CC(NC(=O)c4cccc(-c5ccc(C#N)cc5)c4F)C(=O)O)cc3F)no2)cc1] |

| Number | Structure |
|---|---|
| 35 | 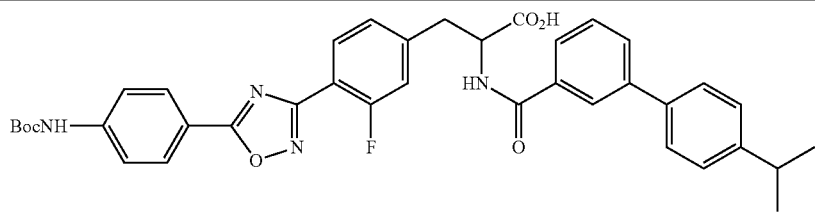 |
| 36 | 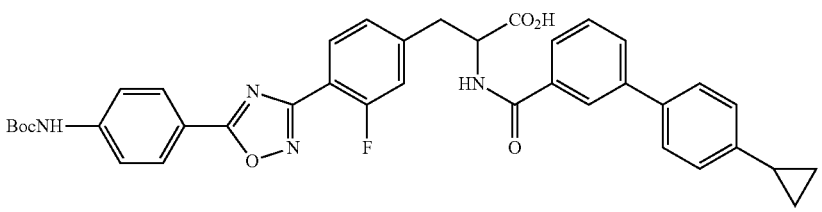 [SMILES: CC(C)(C)OC(=O)Nc1ccc(-c2nc(-c3ccc(CC(NC(=O)c4cccc(-c5ccc(C6CC6)cc5)c4)C(=O)O)cc3F)no2)cc1] |
| 37 | 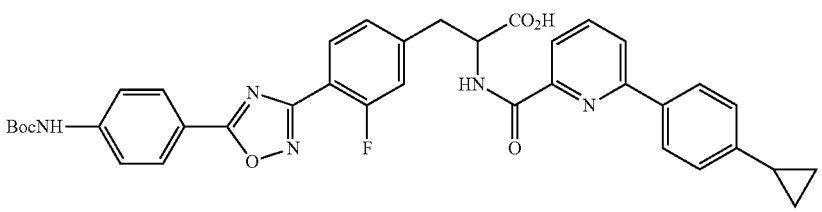 |
| 38 | 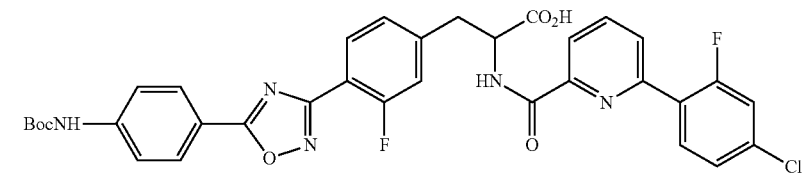 [SMILES: CC(C)(C)OC(=O)Nc1ccc(-c2nc(-c3ccc(CC(NC(=O)c4cccc(-c5ccc(Cl)cc5F)n4)C(=O)O)cc3F)no2)cc1] |
| 39 | 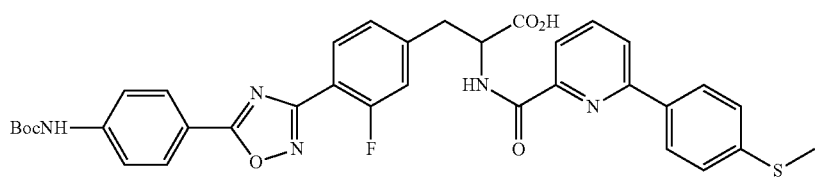 [SMILES: CSc1ccc(-c2cccc(C(=O)NC(Cc3ccc(-c4noc(-c5ccc(NC(=O)OC(C)(C)C)cc5)n4)c(F)c3)C(=O)O)n2)cc1] |
| 40 | 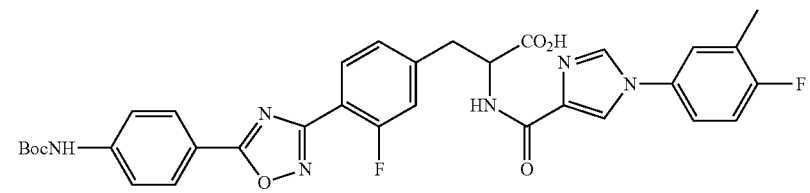 [SMILES: Cc1cc(-n2cnc(C(=O)NC(Cc3ccc(-c4noc(-c5ccc(NC(=O)OC(C)(C)C)cc5)n4)c(F)c3)C(=O)O)c2)ccc1F] |
| 41 | 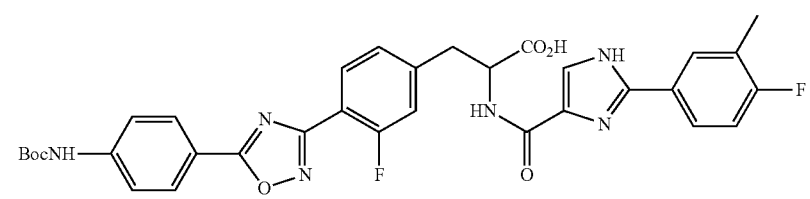 [SMILES: Cc1cc(-c2nc(C(=O)NC(Cc3ccc(-c4noc(-c5ccc(NC(=O)OC(C)(C)C)cc5)n4)c(F)c3)C(=O)O)c[nH]2)ccc1F] |
| 42 | 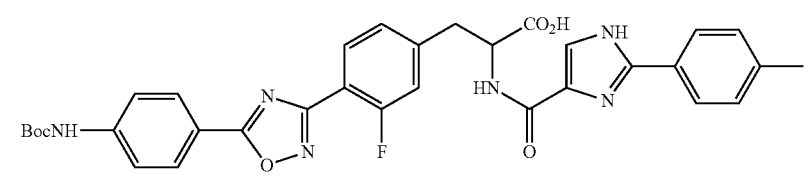 [SMILES: Cc1ccc(-c2nc(C(=O)NC(Cc3ccc(-c4noc(-c5ccc(NC(=O)OC(C)(C)C)cc5)n4)c(F)c3)C(=O)O)c[nH]2)cc1] |

-continued

| Number | Structure |
|---|---|
| 43 | 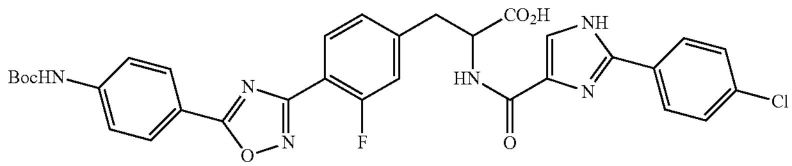 [SMILES: CC(C)(C)OC(=O)Nc1ccc(-c2nc(-c3ccc(CC(NC(=O)c4c[nH]c(-c5ccc(Cl)cc5)n4)C(=O)O)cc3F)no2)cc1] |
| 44 | 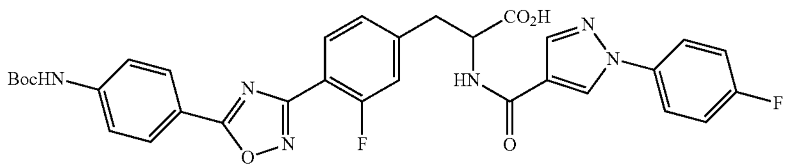 [SMILES: CC(C)(C)OC(=O)Nc1ccc(-c2nc(-c3ccc(CC(NC(=O)c4cnn(-c5ccc(F)cc5)c4)C(=O)O)cc3F)no2)cc1] |
| 45 | 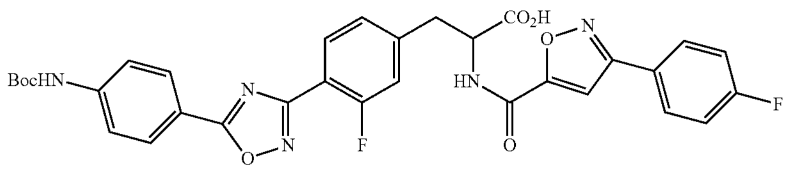 [SMILES: CC(C)(C)OC(=O)Nc1ccc(-c2nc(-c3ccc(CC(NC(=O)c4cc(-c5ccc(F)cc5)no4)C(=O)O)cc3F)no2)cc1] |
| 46 | 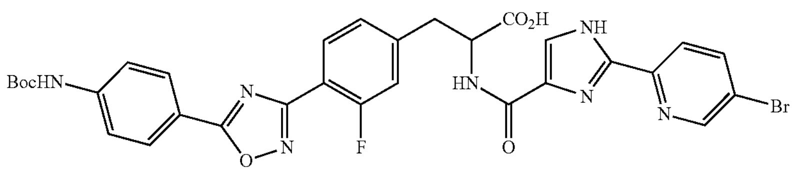 [SMILES: CC(C)(C)OC(=O)Nc1ccc(-c2nc(-c3ccc(CC(NC(=O)c4c[nH]c(-c5ccc(Br)cn5)n4)C(=O)O)cc3F)no2)cc1] |
| 47 | 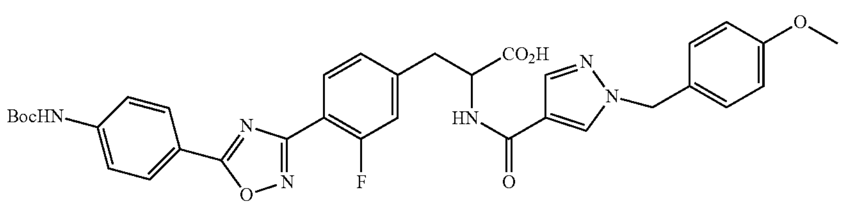 [SMILES: COc1ccc(Cn2cc(C(=O)NC(Cc3ccc(-c4noc(-c5ccc(NC(=O)OC(C)(C)C)cc5)n4)c(F)c3)C(=O)O)cn2)cc1] |
| 48 | 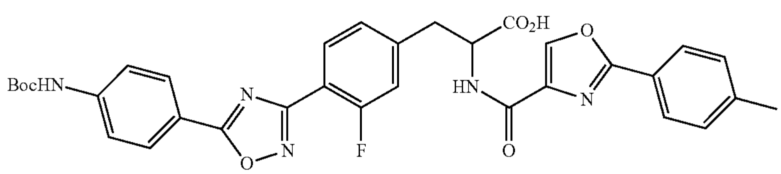 [SMILES: Cc1ccc(-c2nc(C(=O)NC(Cc3ccc(-c4noc(-c5ccc(NC(=O)OC(C)(C)C)cc5)n4)c(F)c3)C(=O)O)co2)cc1] |
| 49 | 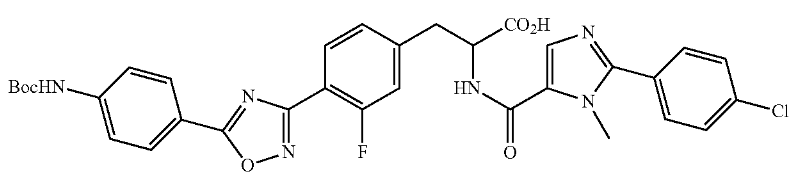 [SMILES: Cn1c(C(=O)NC(Cc2ccc(-c3noc(-c4ccc(NC(=O)OC(C)(C)C)cc4)n3)c(F)c2)C(=O)O)cnc1-c1ccc(Cl)cc1] |
| 50 | 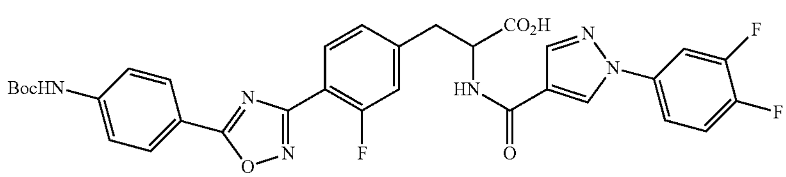 [SMILES: CC(C)(C)OC(=O)Nc1ccc(-c2nc(-c3ccc(CC(NC(=O)c4cnn(-c5ccc(F)c(F)c5)c4)C(=O)O)cc3F)no2)cc1] |
| 51 | 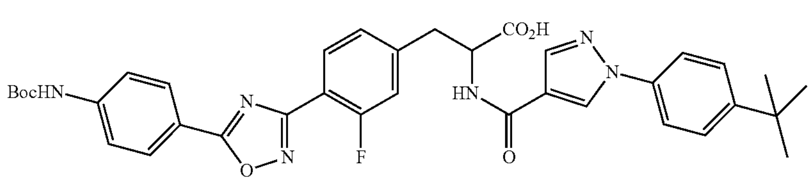 [SMILES: CC(C)(C)OC(=O)Nc1ccc(-c2nc(-c3ccc(CC(NC(=O)c4cnn(-c5ccc(C(C)(C)C)cc5)c4)C(=O)O)cc3F)no2)cc1] |

-continued

| Number | Structure |
|---|---|
| 52 | 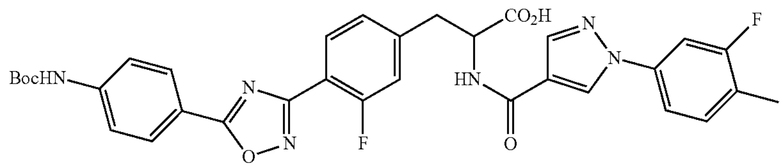 [SMILES: Cc1ccc(-n2cc(C(=O)NC(Cc3ccc(-c4noc(-c5ccc(NC(=O)OC(C)(C)C)cc5)n4)c(F)c3)C(=O)O)cn2)cc1F] |
| 53 | 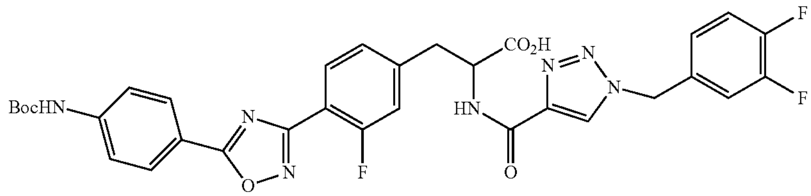 [SMILES: CC(C)(C)OC(=O)Nc1ccc(-c2nc(-c3ccc(CC(NC(=O)c4cn(Cc5ccc(F)c(F)c5)nn4)C(=O)O)cc3F)no2)cc1] |
| 54 | 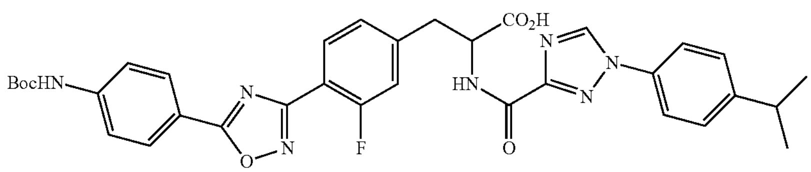 [SMILES: CC(C)c1ccc(-n2cnc(C(=O)NC(Cc3ccc(-c4noc(-c5ccc(NC(=O)OC(C)(C)C)cc5)n4)c(F)c3)C(=O)O)n2)cc1] |
| 55 | 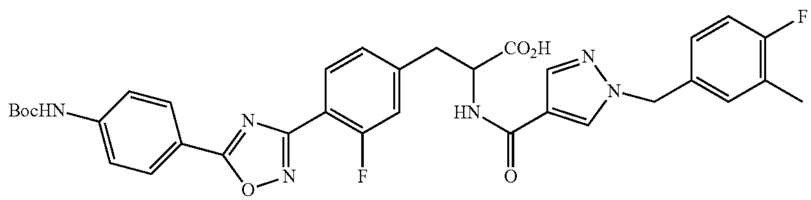 [SMILES: Cc1cc(Cn2cc(C(=O)NC(Cc3ccc(-c4noc(-c5ccc(NC(=O)OC(C)(C)C)cc5)n4)c(F)c3)C(=O)O)cn2)ccc1F] |
| 56 | 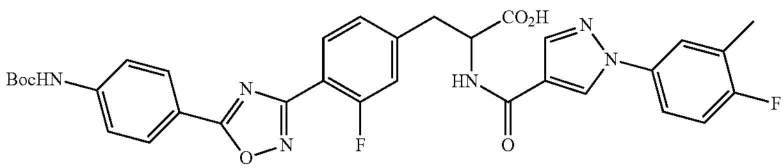 [SMILES: Cc1cc(-n2cc(C(=O)NC(Cc3ccc(-c4noc(-c5ccc(NC(=O)OC(C)(C)C)cc5)n4)c(F)c3)C(=O)O)cn2)ccc1F] |
| 57 | 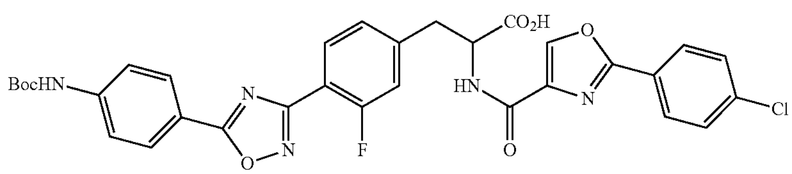 [SMILES: CC(C)(C)OC(=O)Nc1ccc(-c2nc(-c3ccc(CC(NC(=O)c4coc(-c5ccc(Cl)cc5)n4)C(=O)O)cc3F)no2)cc1] |
| 58 | 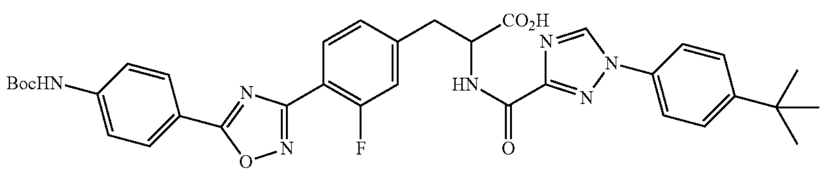 [SMILES: CC(C)(C)OC(=O)Nc1ccc(-c2nc(-c3ccc(CC(NC(=O)c4ncn(-c5ccc(C(C)(C)C)cc5)n4)C(=O)O)cc3F)no2)cc1] |
| 59 | 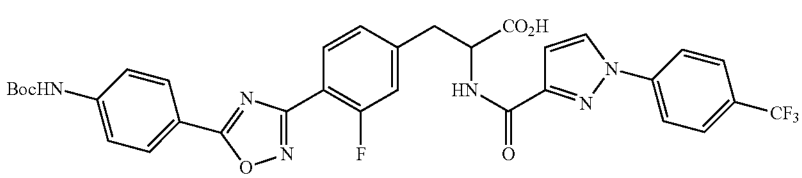 [SMILES: CC(C)(C)OC(=O)Nc1ccc(-c2nc(-c3ccc(CC(NC(=O)c4ccn(-c5ccc(C(F)(F)F)cc5)n4)C(=O)O)cc3F)no2)cc1] |

-continued
| Number | Structure |
|---|---|
| 60 | 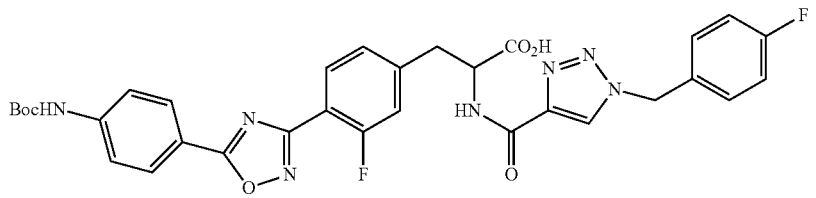 [SMILES: CC(C)(C)OC(=O)Nc1ccc(-c2nc(-c3ccc(CC(NC(=O)c4cn(Cc5ccc(F)cc5)nn4)C(=O)O)cc3F)no2)cc1] |
| 61 | 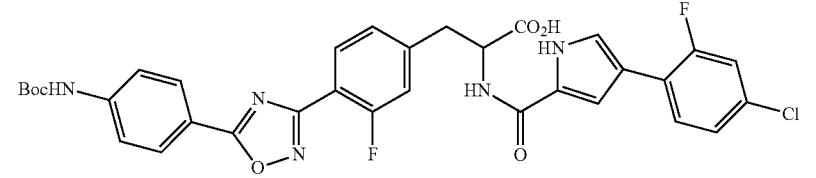 [SMILES: CC(C)(C)OC(=O)Nc1ccc(-c2nc(-c3ccc(CC(NC(=O)c4cc(-c5ccc(Cl)cc5F)c[nH]4)C(=O)O)cc3F)no2)cc1] |
| 62 | 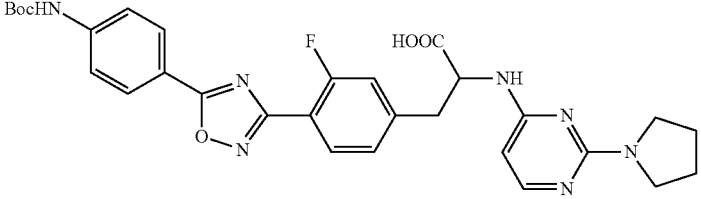 [SMILES: CC(C)(C)OC(=O)Nc1ccc(-c2nc(-c3ccc(CC(Nc4ccnc(N5CCCC5)n4)C(=O)O)cc3F)no2)cc1] |
| 63 | 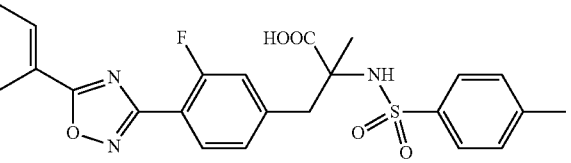 |
| 64 | 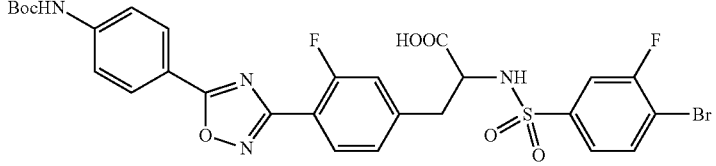 [SMILES: CC(C)(C)OC(=O)Nc1ccc(-c2nc(-c3ccc(CC(NS(=O)(=O)c4ccc(Br)c(F)c4)C(=O)O)cc3F)no2)cc1] |
| 65 | 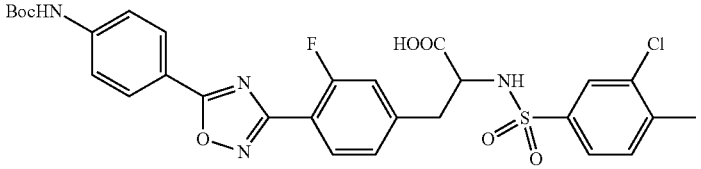 [SMILES: Cc1ccc(S(=O)(=O)NC(Cc2ccc(-c3noc(-c4ccc(NC(=O)OC(C)(C)C)cc4)n3)c(F)c2)C(=O)O)cc1Cl] |
| 66 | 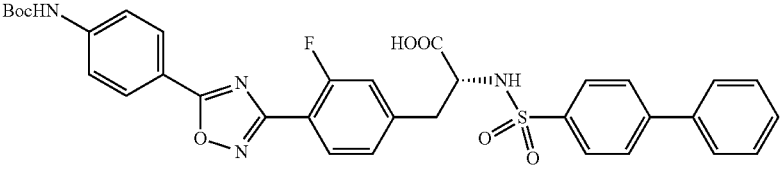 [SMILES: CC(C)(C)OC(=O)Nc1ccc(-c2nc(-c3ccc(C[C@@H](NS(=O)(=O)c4ccc(-c5ccccc5)cc4)C(=O)O)cc3F)no2)cc1] |
| 67 | 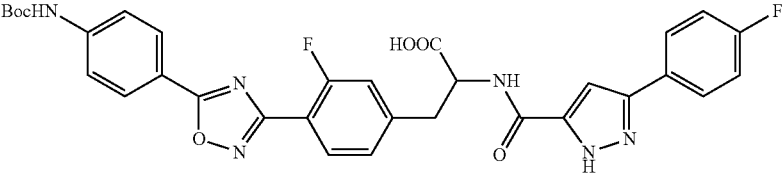 [SMILES: CC(C)(C)OC(=O)Nc1ccc(-c2nc(-c3ccc(CC(NC(=O)c4cc(-c5ccc(F)cc5)n[nH]4)C(=O)O)cc3F)no2)cc1] |

-continued

| Number | Structure |
|---|---|
| 68 | 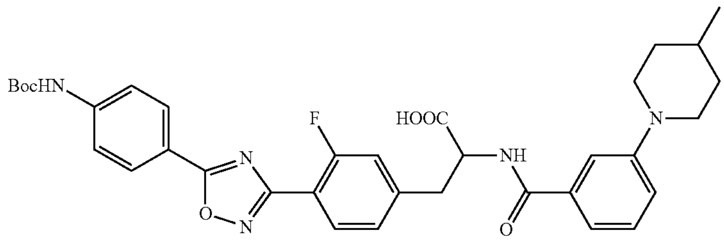 [SMILES: CC1CCN(c2cccc(C(=O)NC(Cc3ccc(-c4noc(-c5ccc(NC(=O)OC(C)(C)C)cc5)n4)c(F)c3)C(=O)O)c2)CC1] |
| 69 | 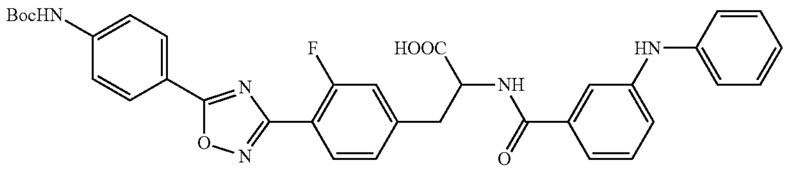 [SMILES: CC(C)(C)OC(=O)Nc1ccc(-c2nc(-c3ccc(CC(NC(=O)c4cccc(Nc5ccccc5)c4)C(=O)O)cc3F)no2)cc1] |
| 70 | 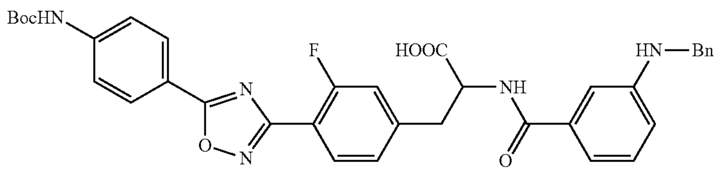 [SMILES: CC(C)(C)OC(=O)Nc1ccc(-c2nc(-c3ccc(CC(NC(=O)c4cccc(NCc5ccccc5)c4)C(=O)O)cc3F)no2)cc1] |
| 71 | 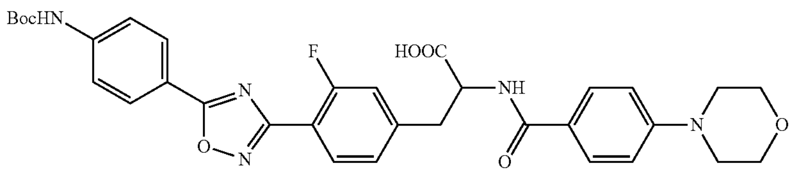 [SMILES: CC(C)(C)OC(=O)Nc1ccc(-c2nc(-c3ccc(CC(NC(=O)c4ccc(N5CCOCC5)cc4)C(=O)O)cc3F)no2)cc1] |
| 72 | 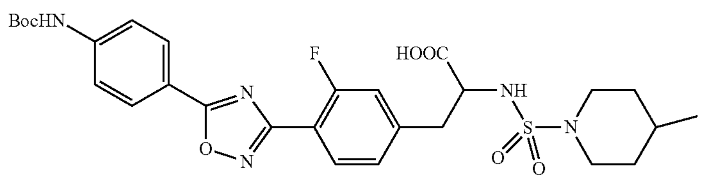 [SMILES: CC1CCN(S(=O)(=O)NC(Cc2ccc(-c3noc(-c4ccc(NC(=O)OC(C)(C)C)cc4)n3)c(F)c2)C(=O)O)CC1] |
| 73 | 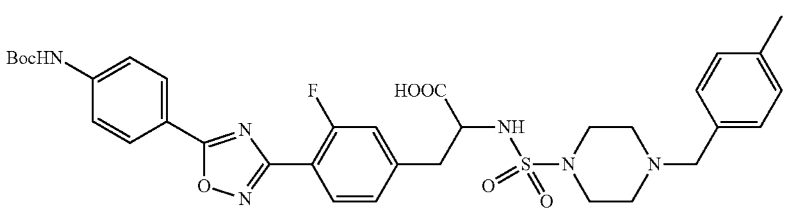 [SMILES: Cc1ccc(CN2CCN(S(=O)(=O)NC(Cc3ccc(-c4noc(-c5ccc(NC(=O)OC(C)(C)C)cc5)n4)c(F)c3)C(=O)O)CC2)cc1] |
| 74 | 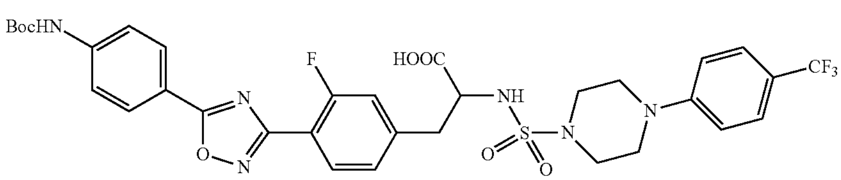 [SMILES: CC(C)(C)OC(=O)Nc1ccc(-c2nc(-c3ccc(CC(NS(=O)(=O)N4CCN(c5ccc(C(F)(F)F)cc5)CC4)C(=O)O)cc3F)no2)cc1] |
| 75 | 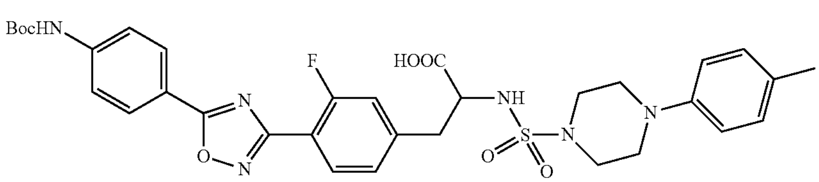 [SMILES: Cc1ccc(N2CCN(S(=O)(=O)NC(Cc3ccc(-c4noc(-c5ccc(NC(=O)OC(C)(C)C)cc5)n4)c(F)c3)C(=O)O)CC2)cc1] |

-continued
| Number | Structure |
|---|---|
| 76 | 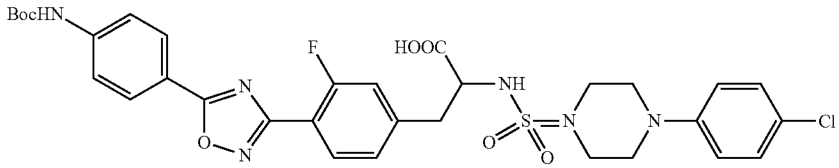 |
| 77 | 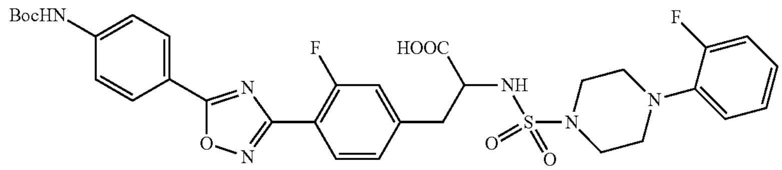 [SMILES: CC(C)(C)OC(=O)Nc1ccc(-c2nc(-c3ccc(CC(NS(=O)(=O)N4CCN(c5ccccc5F)CC4)C(=O)O)cc3F)no2)cc1] |
| 78 | 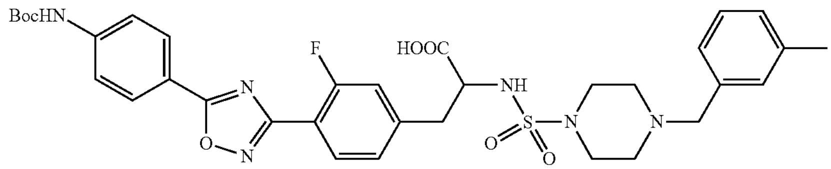 [SMILES: Cc1cccc(CN2CCN(S(=O)(=O)NC(Cc3ccc(-c4noc(-c5ccc(NC(=O)OC(C)(C)C)cc5)n4)c(F)c3)C(=O)O)CC2)c1] |
| 79 | 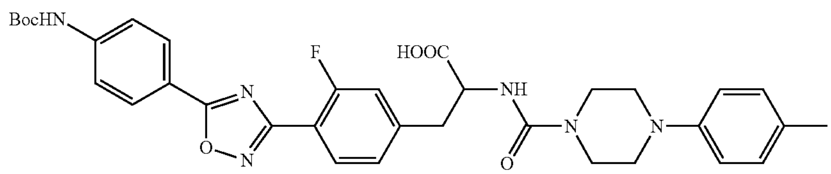 [SMILES: Cc1ccc(N2CCN(C(=O)NC(Cc3ccc(-c4noc(-c5ccc(NC(=O)OC(C)(C)C)cc5)n4)c(F)c3)C(=O)O)CC2)cc1] |
| 80 | 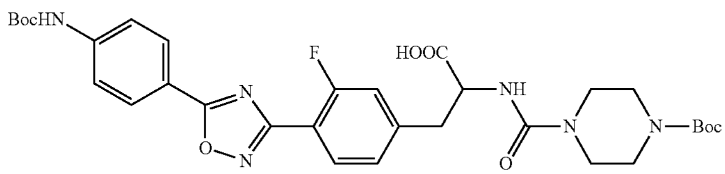 [SMILES: CC(C)(C)OC(=O)Nc1ccc(-c2nc(-c3ccc(CC(NC(=O)N4CCN(C(=O)OC(C)(C)C)CC4)C(=O)O)cc3F)no2)cc1] |
| 81 | 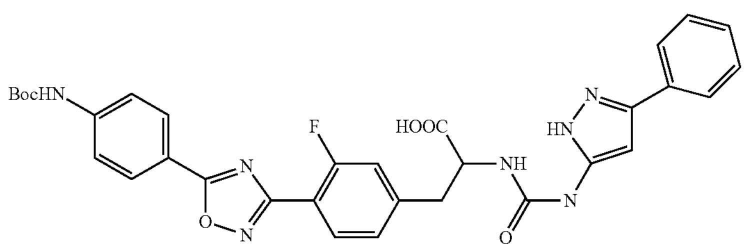 [SMILES: CC(C)(C)OC(=O)Nc1ccc(-c2nc(-c3ccc(CC(NC(=O)Nc4cc(-c5ccccc5)n[nH]4)C(=O)O)cc3F)no2)cc1] |
| 82 | 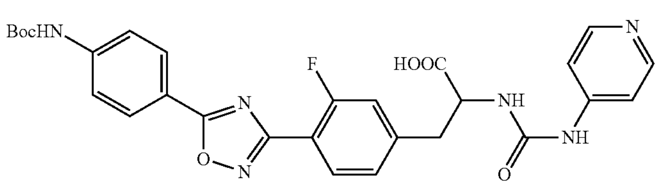 [SMILES: CC(C)(C)OC(=O)Nc1ccc(-c2nc(-c3ccc(CC(NC(=O)Nc4ccncc4)C(=O)O)cc3F)no2)cc1] |
| 83 | 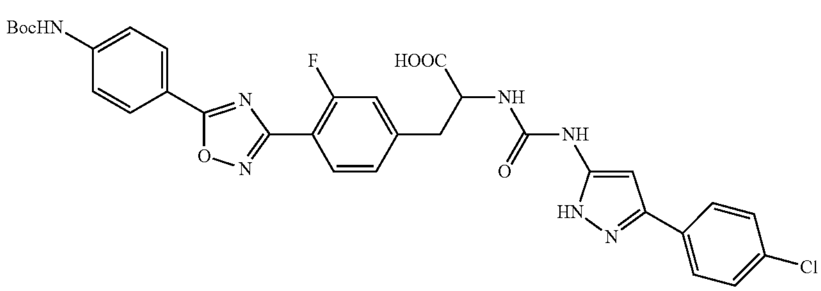 [SMILES: CC(C)(C)OC(=O)Nc1ccc(-c2nc(-c3ccc(CC(NC(=O)Nc4cc(-c5ccc(Cl)cc5)n[nH]4)C(=O)O)cc3F)no2)cc1] |
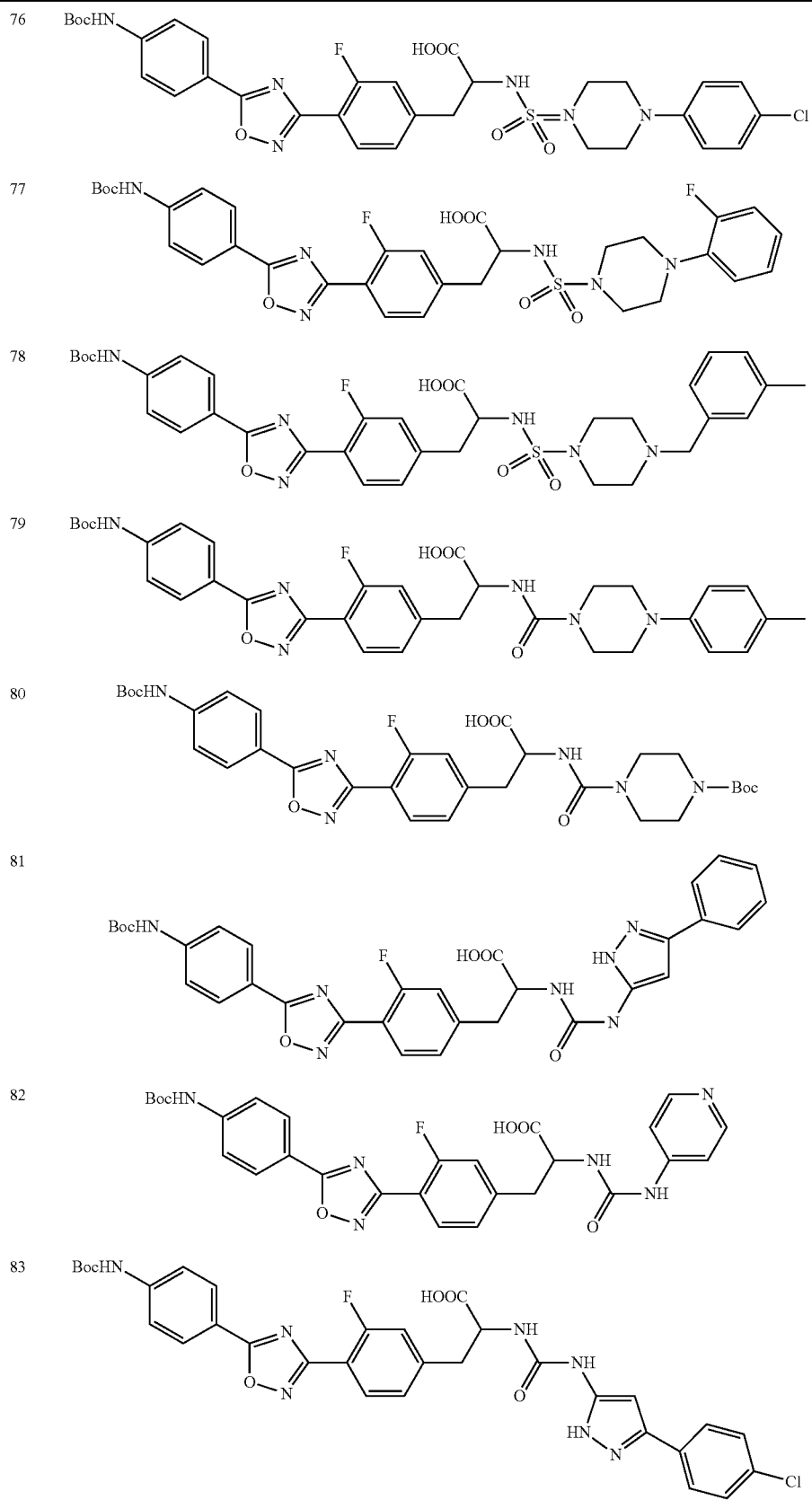

| Number | Structure |
|---|---|
| 84 | 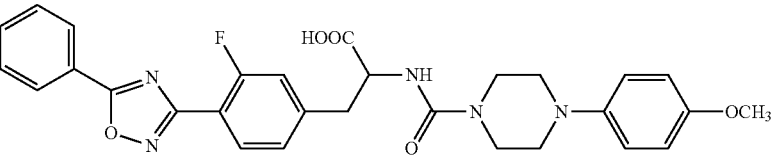 |
| 85 | 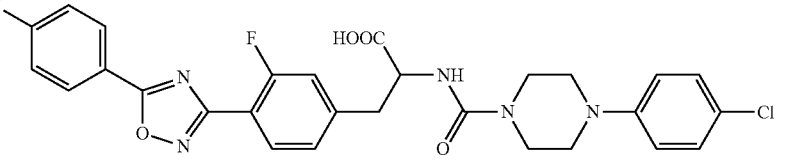 |
| 86 | 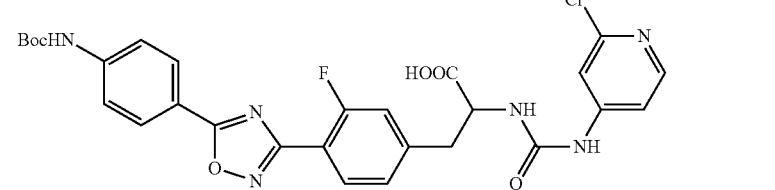 |
| 87 | 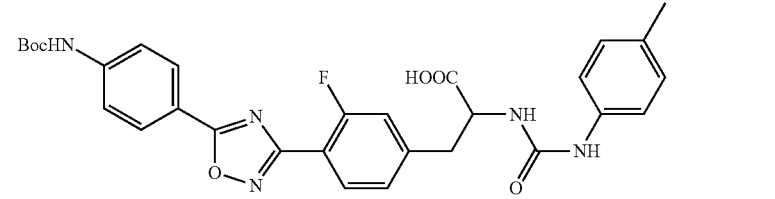 [SMILES: Cc1ccc(NC(=O)NC(Cc2ccc(-c3noc(-c4ccc(NC(=O)OC(C)(C)C)cc4)n3)c(F)c2)C(=O)O)cc1] |
| 88 | 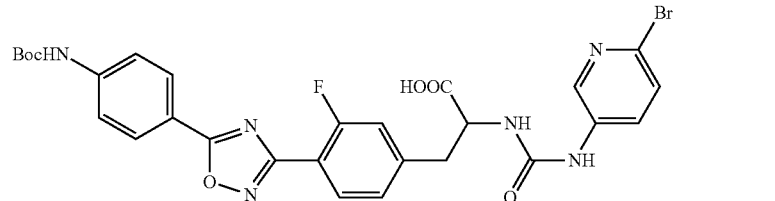 [SMILES: CC(C)(C)OC(=O)Nc1ccc(-c2nc(-c3ccc(CC(NC(=O)Nc4ccc(Br)nc4)C(=O)O)cc3F)no2)cc1] |
| 89 | 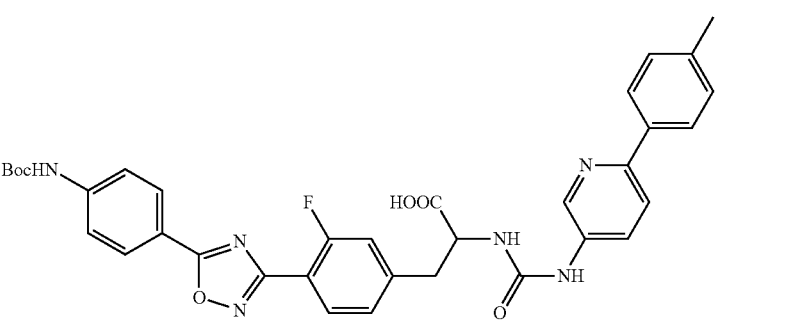 [SMILES: Cc1ccc(-c2ccc(NC(=O)NC(Cc3ccc(-c4noc(-c5ccc(NC(=O)OC(C)(C)C)cc5)n4)c(F)c3)C(=O)O)cn2)cc1] |
| 90 | 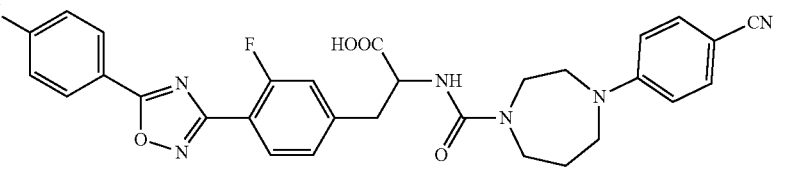 |

-continued
| Number | Structure |
|---|---|
| 91 | 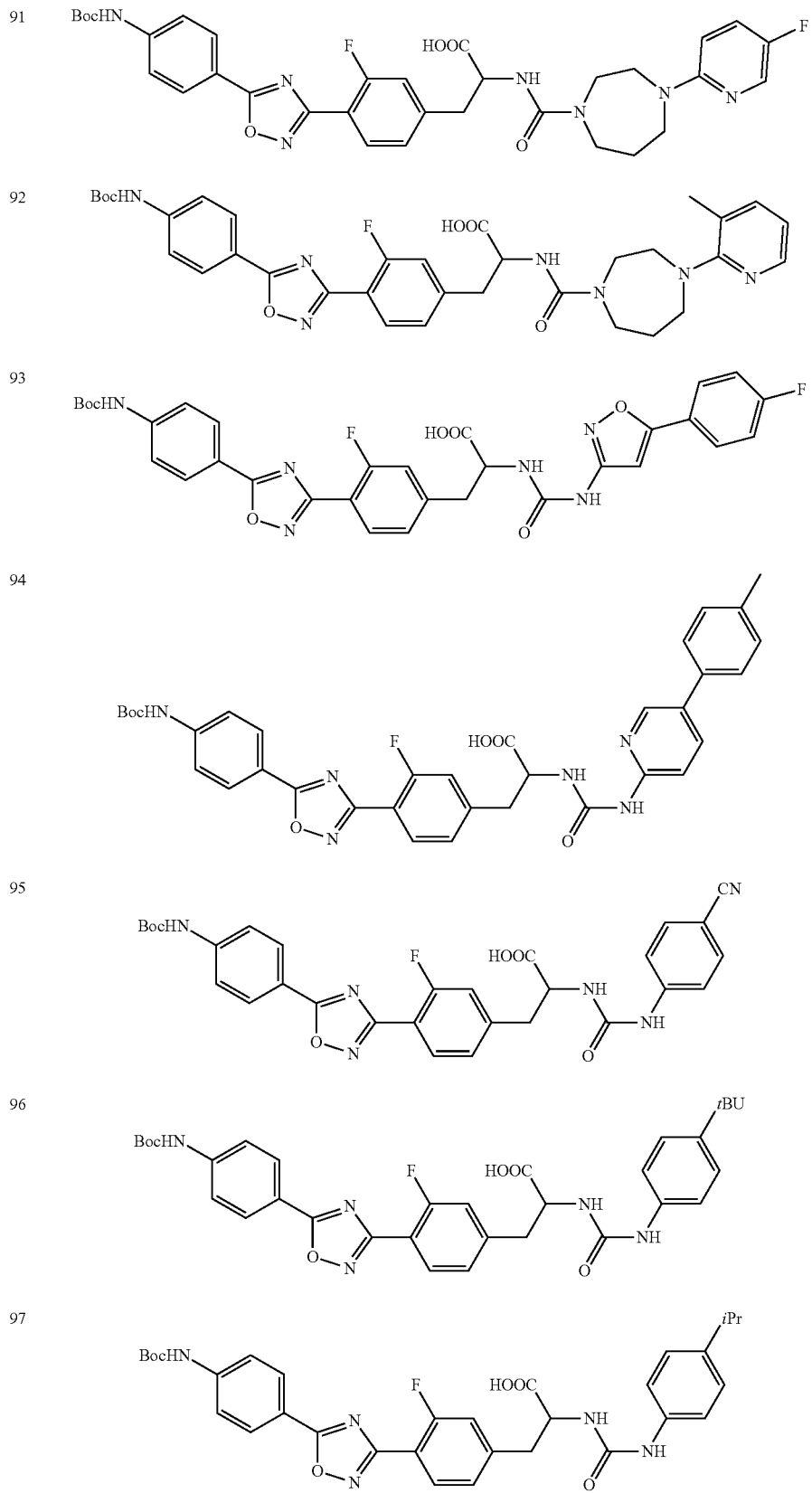 |
| 92 | 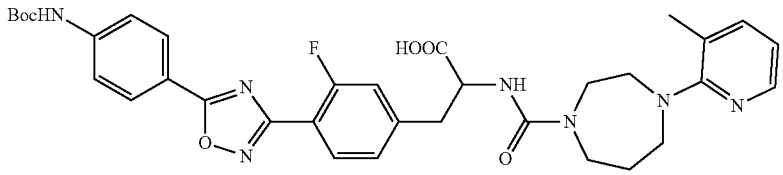 [SMILES: Cc1cccnc1N1CCCN(C(=O)NC(Cc2ccc(-c3noc(-c4ccc(NC(=O)OC(C)(C)C)cc4)n3)c(F)c2)C(=O)O)CC1] |
| 93 | 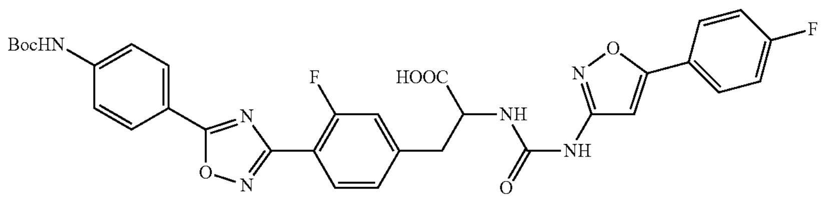 [SMILES: CC(C)(C)OC(=O)Nc1ccc(-c2nc(-c3ccc(CC(NC(=O)Nc4cc(-c5ccc(F)cc5)on4)C(=O)O)cc3F)no2)cc1] |
| 94 | 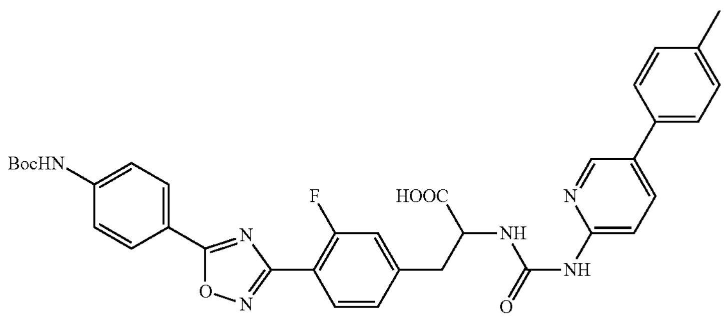 [SMILES: Cc1ccc(-c2ccc(NC(=O)NC(Cc3ccc(-c4noc(-c5ccc(NC(=O)OC(C)(C)C)cc5)n4)c(F)c3)C(=O)O)nc2)cc1] |
| 95 | 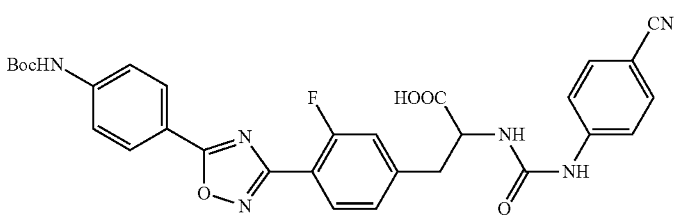 [SMILES: CC(C)(C)OC(=O)Nc1ccc(-c2nc(-c3ccc(CC(NC(=O)Nc4ccc(C#N)cc4)C(=O)O)cc3F)no2)cc1] |
| 96 | 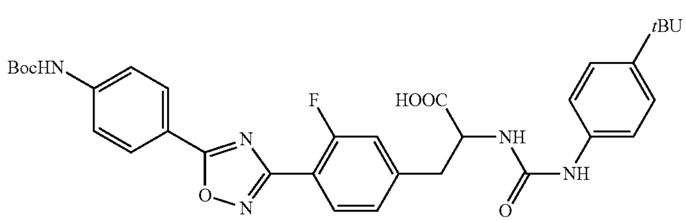 |
| 97 | 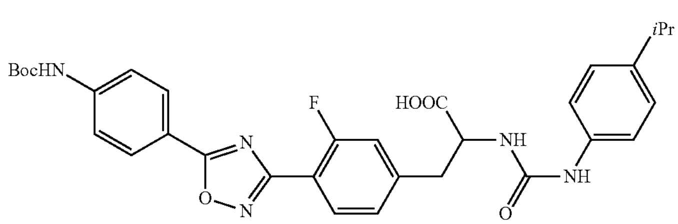 |

| Number | Structure |
|---|---|
| 98 | 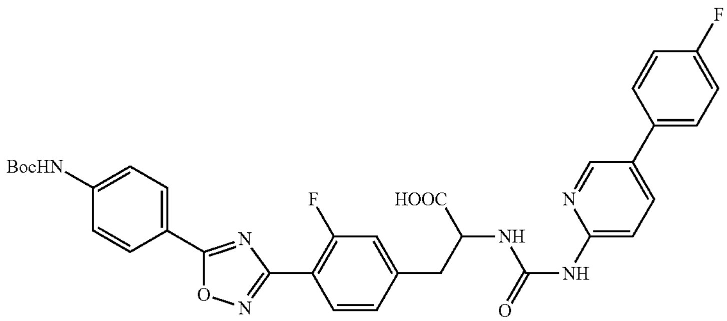 [SMILES: CC(C)(C)OC(=O)Nc1ccc(-c2nc(-c3ccc(CC(NC(=O)Nc4ccc(-c5ccc(F)cc5)cn4)C(=O)O)cc3F)no2)cc1] |
| 99 | 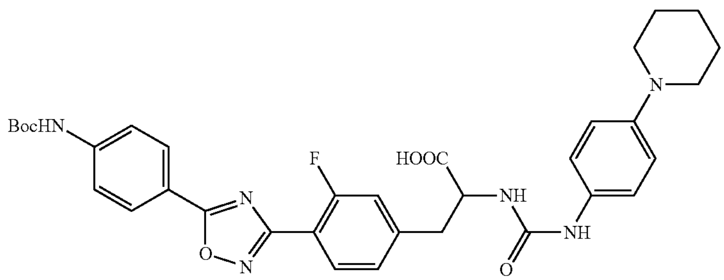 [SMILES: CC(C)(C)OC(=O)Nc1ccc(-c2nc(-c3ccc(CC(NC(=O)Nc4ccc(N5CCCCC5)cc4)C(=O)O)cc3F)no2)cc1] |
| 100 | 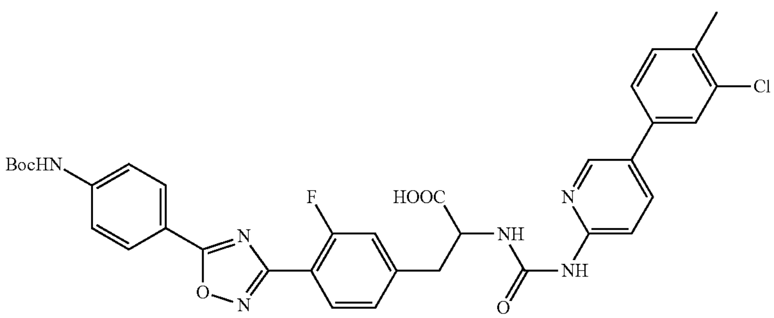 [SMILES: Cc1ccc(-c2ccc(NC(=O)NC(Cc3ccc(-c4noc(-c5ccc(NC(=O)OC(C)(C)C)cc5)n4)c(F)c3)C(=O)O)nc2)cc1Cl] |
| 101 | 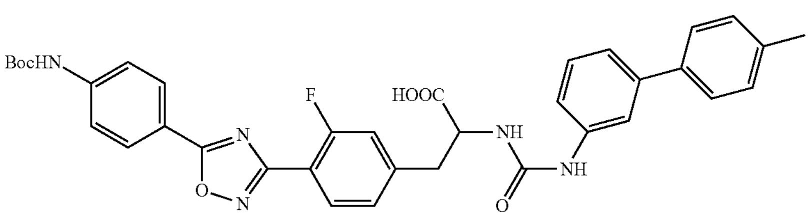 [SMILES: Cc1ccc(-c2cccc(NC(=O)NC(Cc3ccc(-c4noc(-c5ccc(NC(=O)OC(C)(C)C)cc5)n4)c(F)c3)C(=O)O)c2)cc1] |
| 102 | 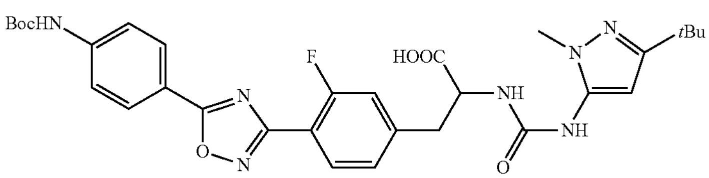 [SMILES: Cn1nc(C(C)(C)C)cc1NC(=O)NC(Cc1ccc(-c2noc(-c3ccc(NC(=O)OC(C)(C)C)cc3)n2)c(F)c1)C(=O)O] |
| 103 | 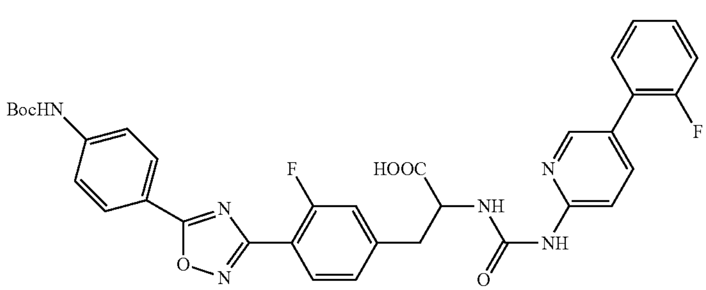 [SMILES: CC(C)(C)OC(=O)Nc1ccc(-c2nc(-c3ccc(CC(NC(=O)Nc4ccc(-c5ccccc5F)cn4)C(=O)O)cc3F)no2)cc1] |

-continued
| Number | Structure |
|---|---|
| 104 | 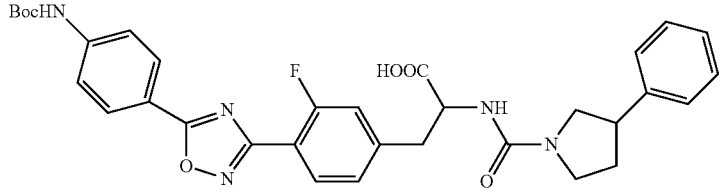 [SMILES: CC(C)(C)OC(=O)Nc1ccc(-c2nc(-c3ccc(CC(NC(=O)N4CCC(c5ccccc5)C4)C(=O)O)cc3F)no2)cc1] |
| 105 | 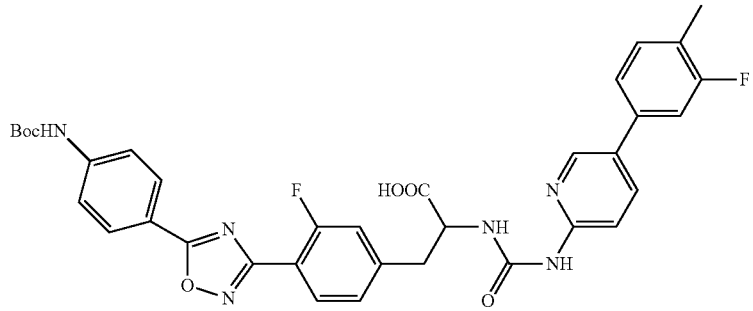 [SMILES: Cc1ccc(-c2ccc(NC(=O)NC(Cc3ccc(-c4noc(-c5ccc(NC(=O)OC(C)(C)C)cc5)n4)c(F)c3)C(=O)O)nc2)cc1F] |
| 106 | 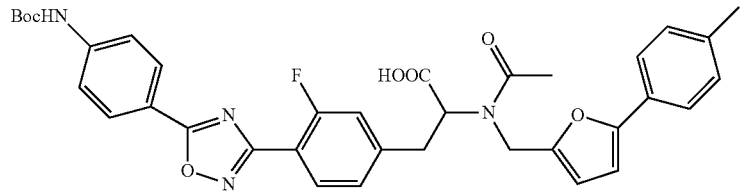 [SMILES: CC(=O)N(Cc1ccc(-c2ccc(C)cc2)o1)C(Cc1ccc(-c2noc(-c3ccc(NC(=O)OC(C)(C)C)cc3)n2)c(F)c1)C(=O)O] |
| 107 | 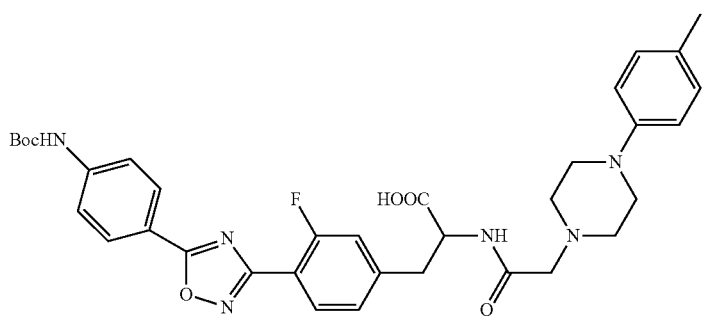 [SMILES: Cc1ccc(N2CCN(CC(=O)NC(Cc3ccc(-c4noc(-c5ccc(NC(=O)OC(C)(C)C)cc5)n4)c(F)c3)C(=O)O)CC2)cc1] |
| 108 | 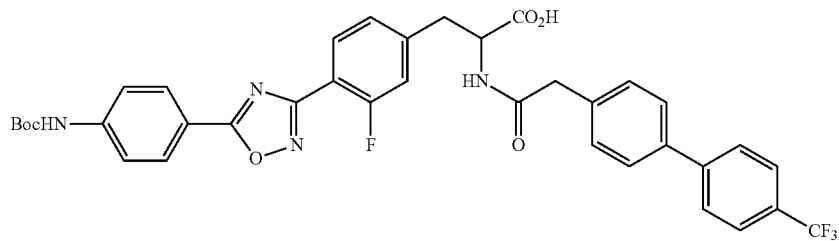 [SMILES: CC(C)(C)OC(=O)Nc1ccc(-c2nc(-c3ccc(CC(NC(=O)Cc4ccc(-c5ccc(C(F)(F)F)cc5)cc4)C(=O)O)cc3F)no2)cc1] |
| 109 | 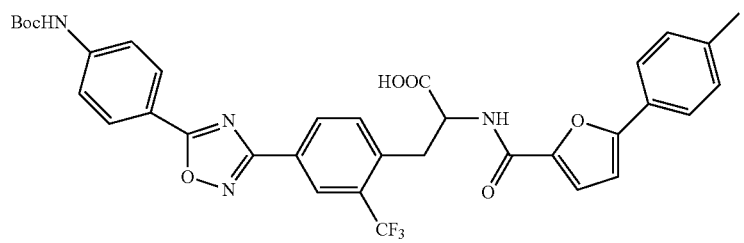 [SMILES: Cc1ccc(-c2ccc(C(=O)NC(Cc3ccc(-c4noc(-c5ccc(NC(=O)OC(C)(C)C)cc5)n4)cc3C(F)(F)F)C(=O)O)o2)cc1] |

-continued
| Number | Structure |
|---|---|
| 110 | 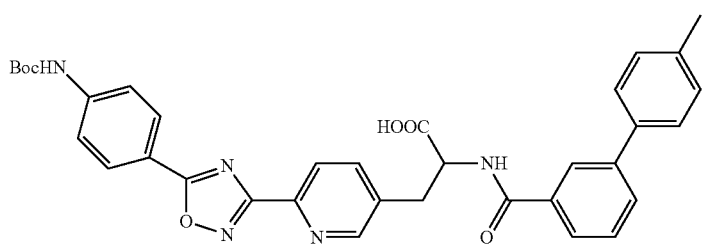 [SMILES: Cc1ccc(-c2cccc(C(=O)NC(Cc3ccc(-c4noc(-c5ccc(NC(=O)OC(C)(C)C)cc5)n4)nc3)C(=O)O)c2)cc1] |
| 111 | 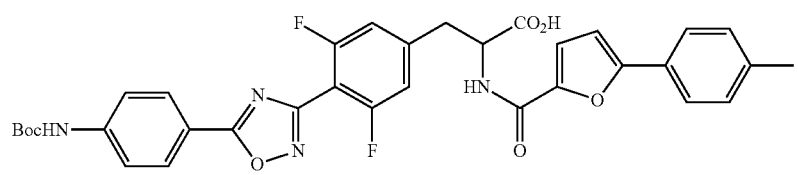 [SMILES: Cc1ccc(-c2ccc(C(=O)NC(Cc3cc(F)c(-c4noc(-c5ccc(NC(=O)OC(C)(C)C)cc5)n4)c(F)c3)C(=O)O)o2)cc1] |
| 112 | 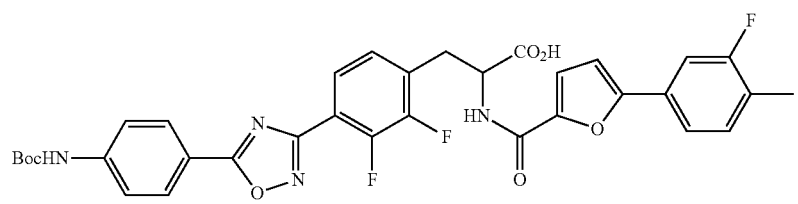 [SMILES: Cc1ccc(-c2ccc(C(=O)NC(Cc3ccc(-c4noc(-c5ccc(NC(=O)OC(C)(C)C)cc5)n4)c(F)c3F)C(=O)O)o2)cc1F] |
| 113 | 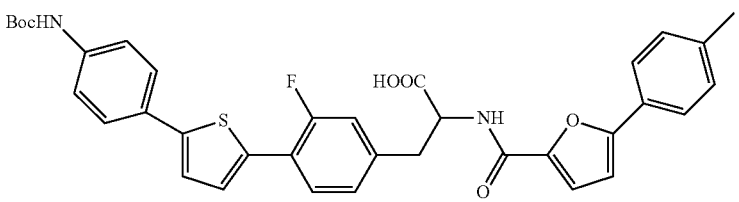 [SMILES: Cc1ccc(-c2ccc(C(=O)NC(Cc3ccc(-c4ccc(-c5ccc(NC(=O)OC(C)(C)C)cc5)s4)c(F)c3)C(=O)O)o2)cc1] |
| 114 | 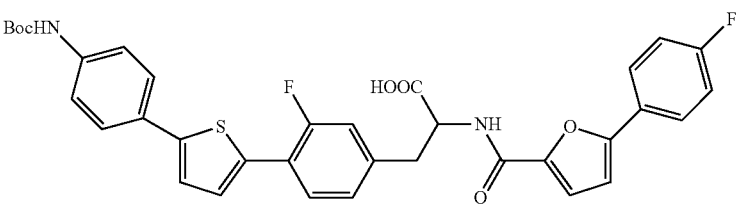 [SMILES: CC(C)(C)OC(=O)Nc1ccc(-c2ccc(-c3ccc(CC(NC(=O)c4ccc(-c5ccc(F)cc5)o4)C(=O)O)cc3F)s2)cc1] |
| 115 | 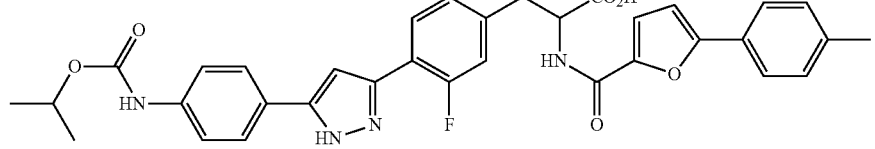 |
| 116 | 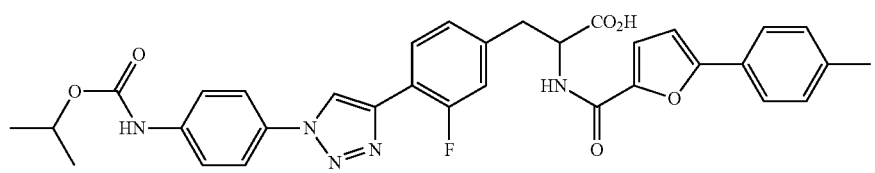 [SMILES: Cc1ccc(-c2ccc(C(=O)NC(Cc3ccc(-c4cn(-c5ccc(NC(=O)OC(C)C)cc5)nn4)c(F)c3)C(=O)O)o2)cc1] |
| 117 | 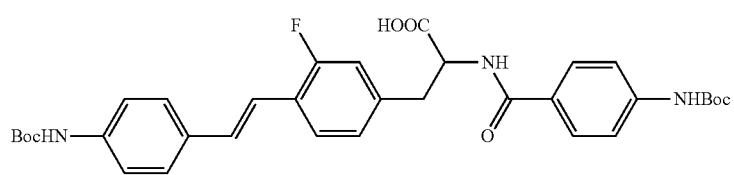 [SMILES: CC(C)(C)OC(=O)Nc1ccc(/C=C/c2ccc(CC(NC(=O)c3ccc(NC(=O)OC(C)(C)C)cc3)C(=O)O)cc2F)cc1] |

| Number | Structure |
|---|---|
| 119 | 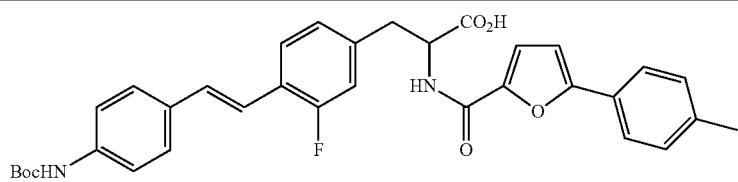 |
| 120 | 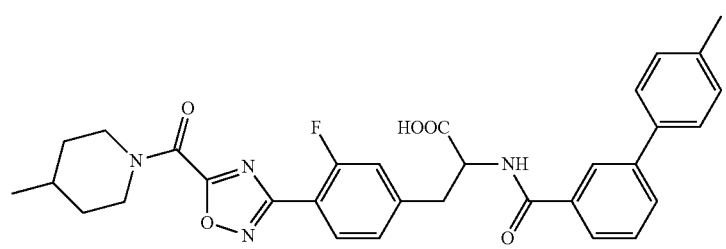 |
| 125 | 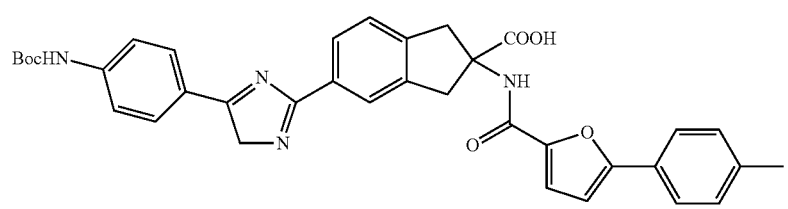 [SMILES: Cc1ccc(-c2ccc(C(=O)NC3(C(=O)O)Cc4ccc(C5=NCC(c6ccc(NC(=O)OC(C)(C)C)cc6)=N5)cc4C3)o2)cc1] |
| 126 | 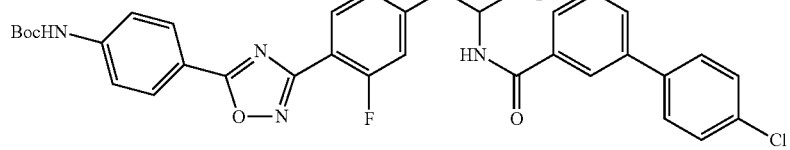 |
| 127 | 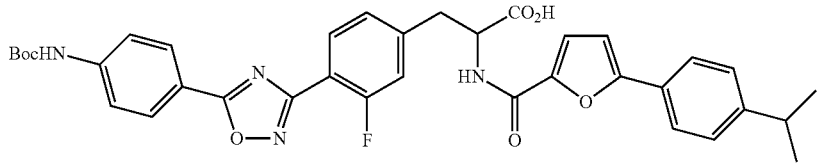 |
| 128 | 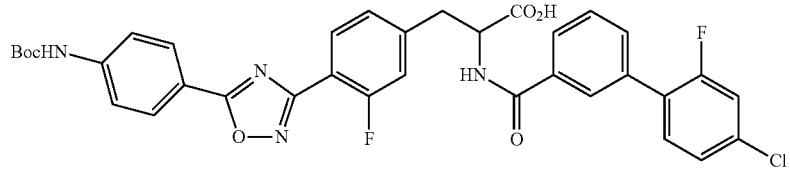 [SMILES: CC(C)(C)OC(=O)Nc1ccc(-c2nc(-c3ccc(CC(NC(=O)c4cccc(-c5ccc(Cl)cc5F)c4)C(=O)O)cc3F)no2)cc1] |
| 129 | 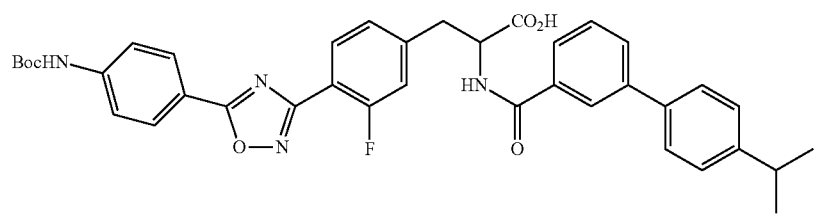 [SMILES: CC(C)c1ccc(-c2cccc(C(=O)NC(Cc3ccc(-c4noc(-c5ccc(NC(=O)OC(C)(C)C)cc5)n4)c(F)c3)C(=O)O)c2)cc1] |
| 130 | 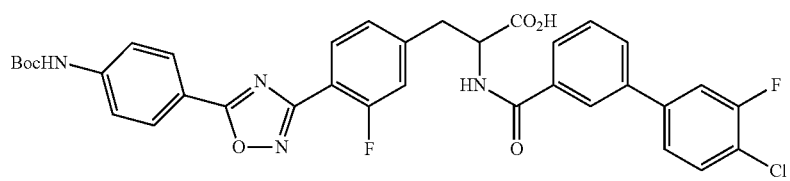 [SMILES: CC(C)(C)OC(=O)Nc1ccc(-c2nc(-c3ccc(CC(NC(=O)c4cccc(-c5ccc(Cl)c(F)c5)c4)C(=O)O)cc3F)no2)cc1] |

-continued

| Number | Structure |
|---|---|
| 131 | 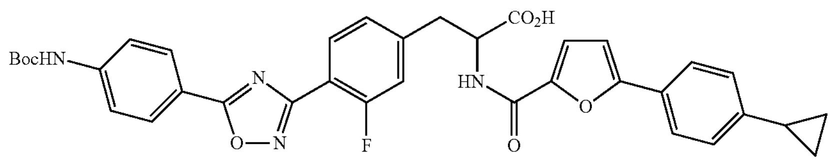 [SMILES: CC(C)(C)OC(=O)Nc1ccc(-c2nc(-c3ccc(CC(NC(=O)c4ccc(-c5ccc(C6CC6)cc5)o4)C(=O)O)cc3F)no2)cc1] |
| 132 | 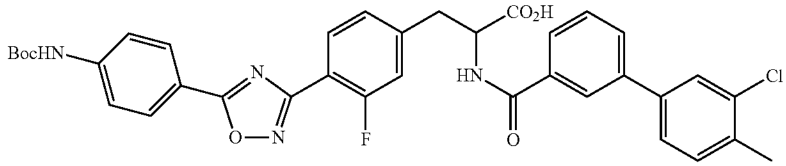 |
| 133 | 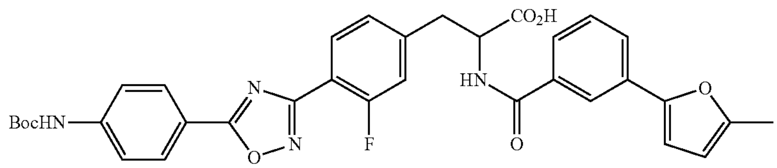 |
| 134 | 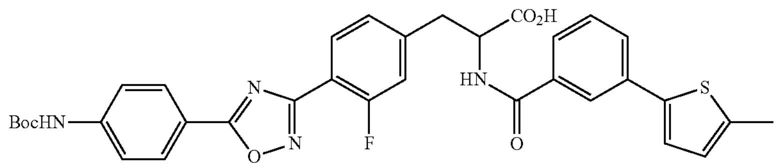 [SMILES: Cc1ccc(-c2cccc(C(=O)NC(Cc3ccc(-c4noc(-c5ccc(NC(=O)OC(C)(C)C)cc5)n4)c(F)c3)C(=O)O)c2)o1] |
| 135 | 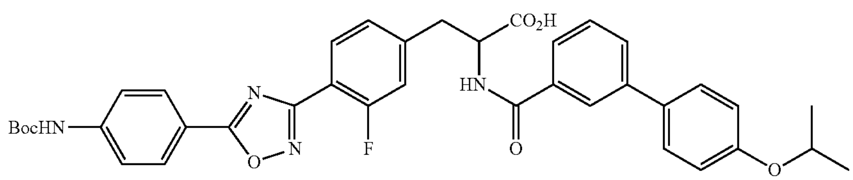 [SMILES: CC(C)Oc1ccc(-c2cccc(C(=O)NC(Cc3ccc(-c4noc(-c5ccc(NC(=O)OC(C)(C)C)cc5)n4)c(F)c3)C(=O)O)c2)cc1] |
| 136 | 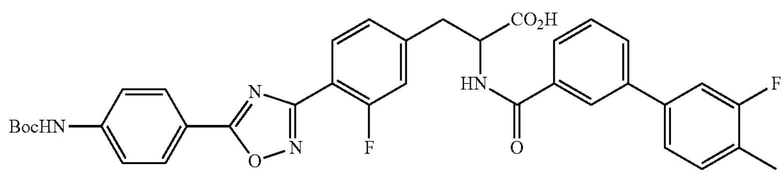 [SMILES: Cc1ccc(-c2cccc(C(=O)NC(Cc3ccc(-c4noc(-c5ccc(NC(=O)OC(C)(C)C)cc5)n4)c(F)c3)C(=O)O)c2)cc1F] |
| 137 | 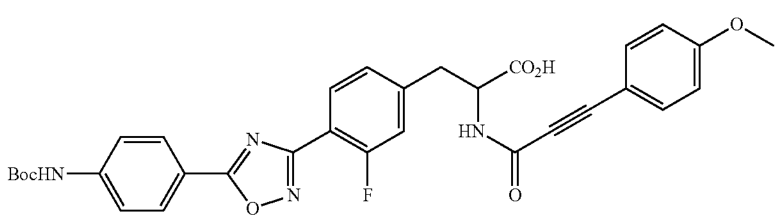 [SMILES: COc1ccc(C#CC(=O)NC(Cc2ccc(-c3noc(-c4ccc(NC(=O)OC(C)(C)C)cc4)n3)c(F)c2)C(=O)O)cc1] |
| 138 | 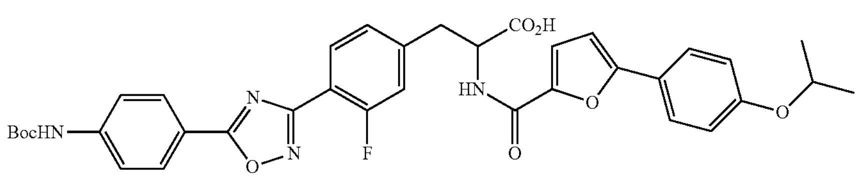 [SMILES: CC(C)Oc1ccc(-c2ccc(C(=O)NC(Cc3ccc(-c4noc(-c5ccc(NC(=O)OC(C)(C)C)cc5)n4)c(F)c3)C(=O)O)o2)cc1] |

| Number | Structure |
|---|---|
| 139 | 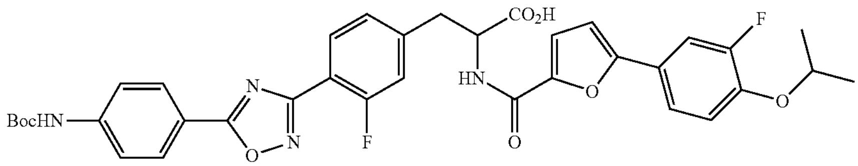 [SMILES: CC(C)Oc1ccc(-c2ccc(C(=O)NC(Cc3ccc(-c4noc(-c5ccc(NC(=O)OC(C)(C)C)cc5)n4)c(F)c3)C(=O)O)o2)cc1F] |
| 140 | 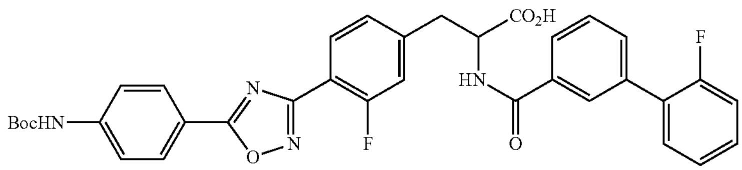 [SMILES: CC(C)(C)OC(=O)Nc1ccc(-c2nc(-c3ccc(CC(NC(=O)c4cccc(-c5ccccc5F)c4)C(=O)O)cc3F)no2)cc1] |
| 141 | 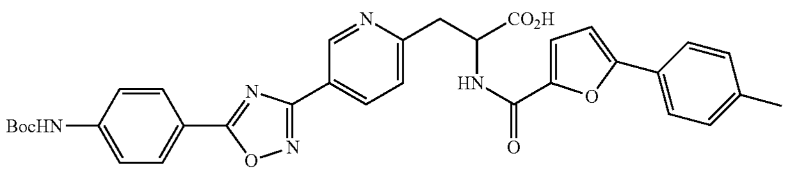 [SMILES: Cc1ccc(-c2ccc(C(=O)NC(Cc3ccc(-c4noc(-c5ccc(NC(=O)OC(C)(C)C)cc5)n4)cn3)C(=O)O)o2)cc1] |
| 142 | 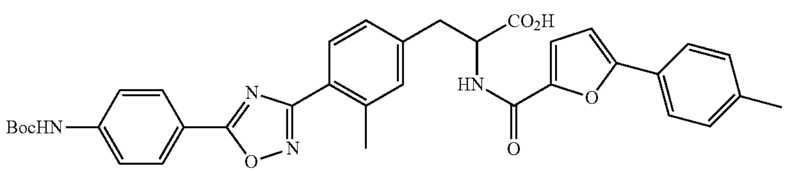 [SMILES: Cc1ccc(-c2ccc(C(=O)NC(Cc3ccc(-c4noc(-c5ccc(NC(=O)OC(C)(C)C)cc5)n4)c(C)c3)C(=O)O)o2)cc1] |
| 143 | 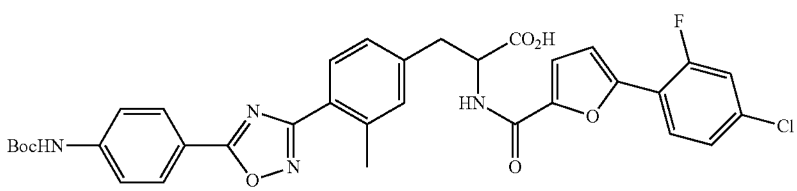 [SMILES: Cc1cc(CC(NC(=O)c2ccc(-c3ccc(Cl)cc3F)o2)C(=O)O)ccc1-c1noc(-c2ccc(NC(=O)OC(C)(C)C)cc2)n1] |
| 144 | 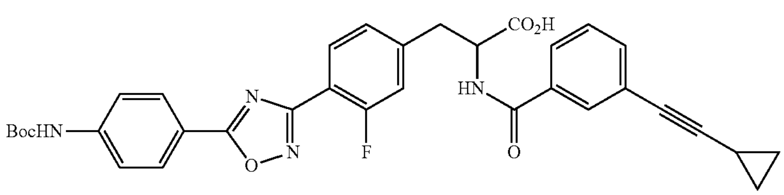 [SMILES: CC(C)(C)OC(=O)Nc1ccc(-c2nc(-c3ccc(CC(NC(=O)c4cccc(C#CC5CC5)c4)C(=O)O)cc3F)no2)cc1] |
| 145 | 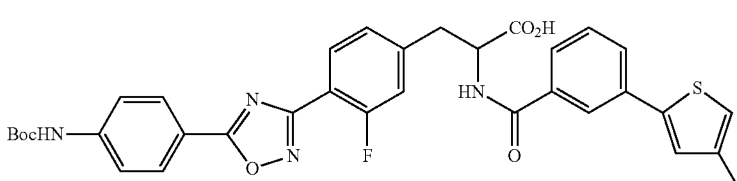 |
| 146 | 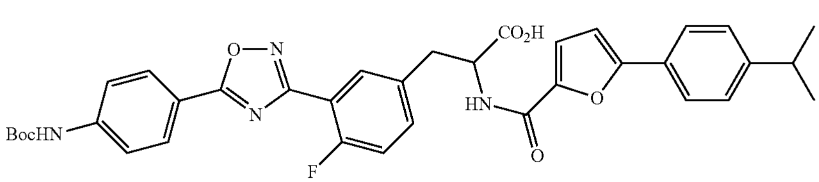 [SMILES: CC(C)c1ccc(-c2ccc(C(=O)NC(Cc3ccc(F)c(-c4noc(-c5ccc(NC(=O)OC(C)(C)C)cc5)n4)c3)C(=O)O)o2)cc1] |

| Number | Structure |
|---|---|
| 147 | 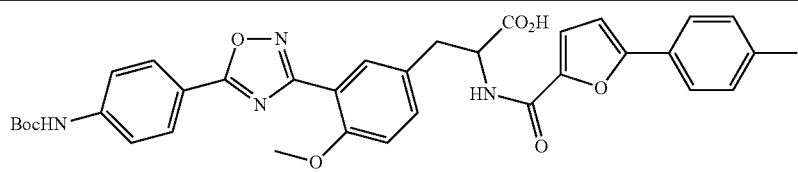 |
| 148 | 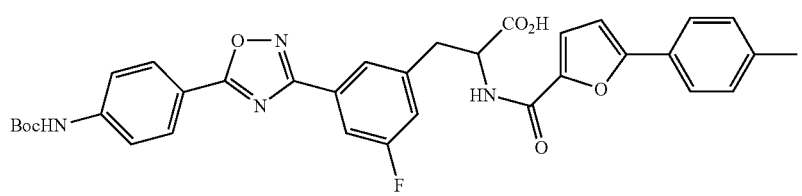 |
| 149 | 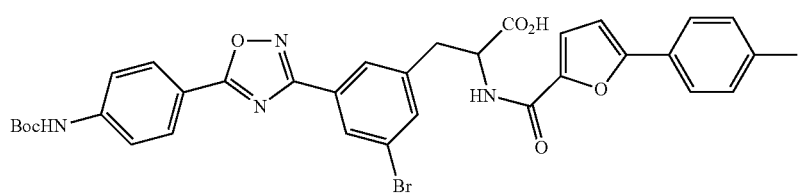 [SMILES: Cc1ccc(-c2ccc(C(=O)NC(Cc3cc(Br)cc(-c4noc(-c5ccc(NC(=O)OC(C)(C)C)cc5)n4)c3)C(=O)O)o2)cc1] |
| 150 | 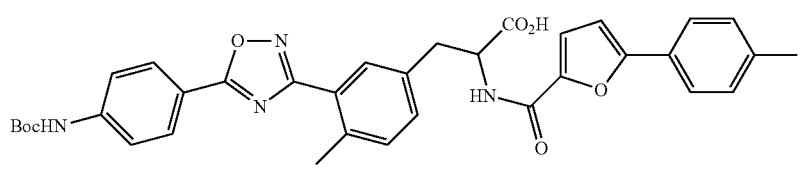 [SMILES: Cc1ccc(-c2ccc(C(=O)NC(Cc3ccc(C)c(-c4noc(-c5ccc(NC(=O)OC(C)(C)C)cc5)n4)c3)C(=O)O)o2)cc1] |
| 151 | 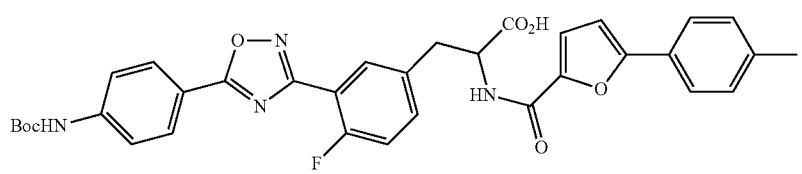 |
| 152 | 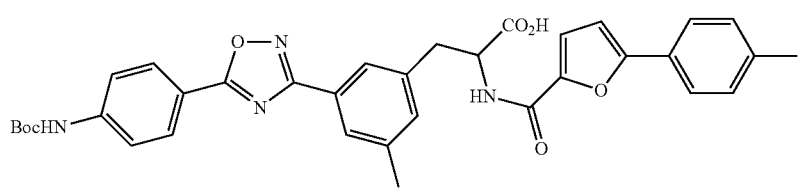 [SMILES: Cc1ccc(-c2ccc(C(=O)NC(Cc3cc(C)cc(-c4noc(-c5ccc(NC(=O)OC(C)(C)C)cc5)n4)c3)C(=O)O)o2)cc1] |
| 153 | 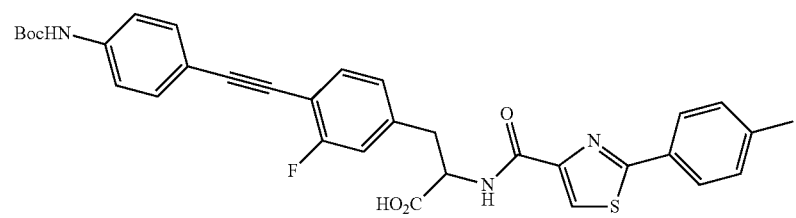 |
| 154 | 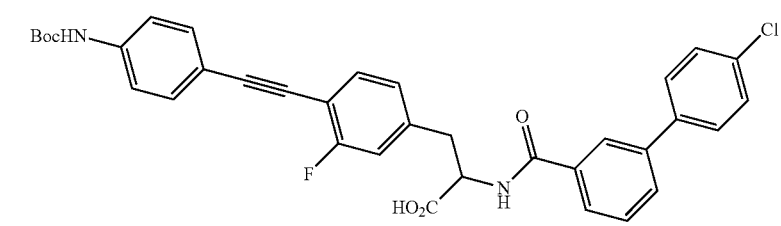 [SMILES: CC(C)(C)OC(=O)Nc1ccc(C#Cc2ccc(CC(NC(=O)c3cccc(-c4ccc(Cl)cc4)c3)C(=O)O)cc2F)cc1] |

-continued
| Number | Structure |
|---|---|
| 155 | 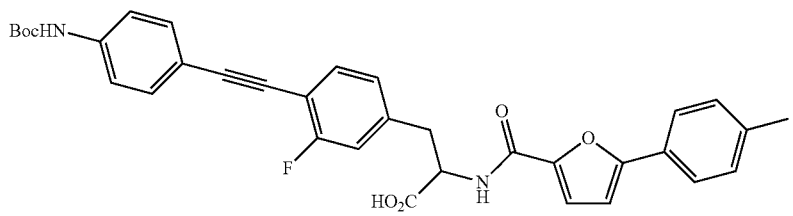 [SMILES: Cc1ccc(-c2ccc(C(=O)NC(Cc3ccc(C#Cc4ccc(NC(=O)OC(C)(C)C)cc4)c(F)c3)C(=O)O)o2)cc1] |
| 156 | 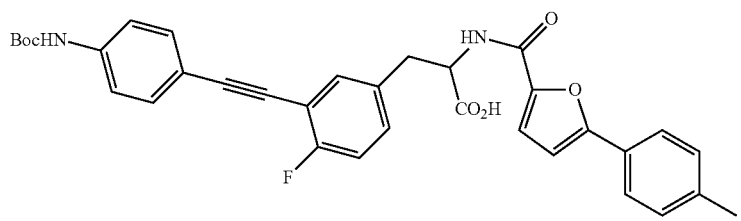 [SMILES: Cc1ccc(-c2ccc(C(=O)NC(Cc3ccc(F)c(C#Cc4ccc(NC(=O)OC(C)(C)C)cc4)c3)C(=O)O)o2)cc1] |
| 157 | 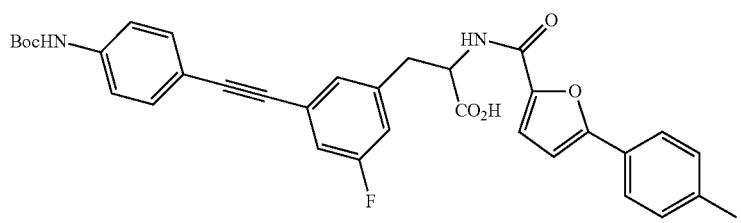 [SMILES: Cc1ccc(-c2ccc(C(=O)NC(Cc3cc(F)cc(C#Cc4ccc(NC(=O)OC(C)(C)C)cc4)c3)C(=O)O)o2)cc1] |
| 158 | 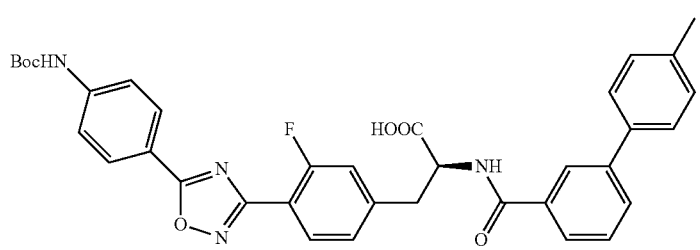 [SMILES: Cc1ccc(-c2cccc(C(=O)N[C@@H](Cc3ccc(-c4noc(-c5ccc(NC(=O)OC(C)(C)C)cc5)n4)c(F)c3)C(=O)O)c2)cc1] |
| 159 | 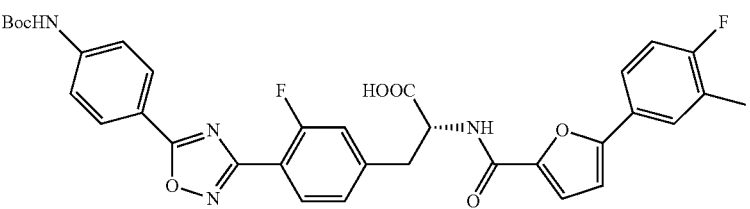 |
| 160 | 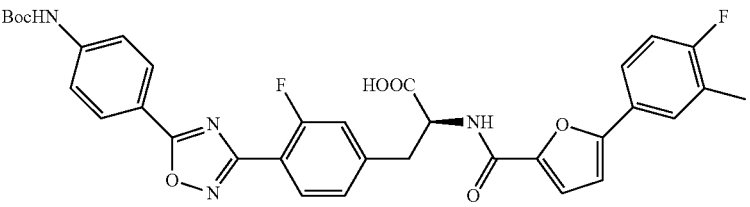 [SMILES: Cc1cc(-c2ccc(C(=O)N[C@@H](Cc3ccc(-c4noc(-c5ccc(NC(=O)OC(C)(C)C)cc5)n4)c(F)c3)C(=O)O)o2)ccc1F] |
| 161 | 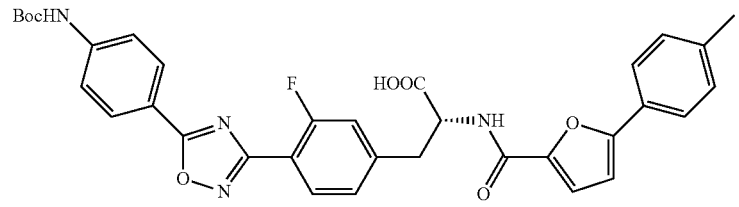 |

| Number | Structure |
|---|---|
| 162 | BocHN-[4-phenyl]-[1,2,4-oxadiazol-3-yl]-[3-fluoro-4-phenyl]-CH₂-CH(COOH)-NH-C(O)-[furan-2-yl]-[5-(4-methylphenyl)] |

41. A pharmaceutical composition comprising a compound of claim 1, and one or more pharmaceutically acceptable carriers.

42. The pharmaceutical composition of claim 41, further comprising an additional therapeutic agent.

43. A method of modulating the activity of glucagon-like peptide-1 (GLP-1) receptor comprising contacting an effective amount of a compound of claim 1 with a cell containing GLP-1 receptor.

44. A method of treating a condition or disease associated with GLP-1, or one or more symptoms thereof, in a subject comprising administering to the subject an effective amount of a compound of claim 1.

45. The method of claim 44, wherein the condition or disease is selected from the group consisting of a metabolic disorder, diabetes, obesity, hyperlipidemia, a cardiovascular disease, and a combination thereof.

46. A method for increasing insulin secretion in a subject comprising administering to the subject an effective amount of a compound of claim 1.

47. A method for reducing gastric motility in a subject comprising administering to the subject an effective amount of a compound of claim 1.

48. A method for delaying gastric emptying in a subject comprising administering to the subject an effective amount of a compound of claim 1.

49. A method for lowering plasma glucagon levels in a subject comprising administering to the subject an effective amount of a compound of claim 1.

50. A method for suppressing prandial glucagon secretion in a subject comprising administering to the subject an effective amount of a compound of claim 1.

51. A method for reducing food intake in a subject comprising administering to the subject an effective amount of a compound of claim 1.

52. A method for reducing appetite in a subject comprising administering to the subject an effective amount of a compound of claim 1.

53. The method of claim 44, wherein the compound of claim 1 is co-administered with an additional therapeutic agent.

54. A compound of Formula (I):

$$A-L^3-E \cdots \text{(structure with } U, V, W, X, Y \text{ ring, } R^1, R^2, R^3, R^4, L^1, L^2, (R^6)_m)$$ (I)

or a pharmaceutically acceptable salt or prodrug thereof; wherein:

A is $C_{3-8}$ carbocyclyl, $C_{6-14}$ aryl, $C_{7-15}$ aralkyl;

E is a bond, $C_{2-6}$ alkenylene, $C_{2-6}$ alkynylene, arylene, heteroarylene, carbocyclylene, heterocyclylene; with the proviso that E is not 4-oxo-imidazolidinylene;

$L^3$ is a bond, —C(O)—, —O—, —OC(O)O—, —OC(O)NR$^{1a}$—, —NR$^{1a}$C(O)O—, —OS(O)—, —S(O)O—, —OS(O)$_2$—, —S(O)$_2$O—, —OS(O)NR$^{1a}$—, —NR$^{1a}$S(O)O—, —OS(O)$_2$NR$^{1a}$—, —NR$^{1a}$S(O)$_2$O—, —NR$^{1a}$—, —NR$^{1a}$C(O)NR$^{1d}$—, —NR$^{1a}$S(O)NR$^{1d}$—, —NR$^{1a}$S(O)$_2$NR$^{1d}$—, —S—, —S(O)—, —S(O)$_2$—, —S(O)NR$^{1a}$—, —NR$^{1a}$S(O)—, —S(O)$_2$NR$^{1a}$—, or —NR$^{1a}$S(O)$_2$—; with the provisos that (a) E and $L^3$ are not both a bond at the same time; and (b) when $L^3$-E together is —O—, $R^6$ is not iodo or benzoxy;

m is an integer of 0, 1, 2, 3, or 4;

$L^1$ is a carboxylate bioisostere selected from the group consisting of —CH$_2$OH, —CONH$_2$, —CO$_2$H, —P(O)(OH)$_2$, —P(OH)$_2$, tetrazolyl, or 3-hydroxyisoxazolyl;

$L^2$ is —CH$_2$N(R$^5$)—, —N(R$^5$)CH$_2$—, —N(R$^5$)—, —O—, —S—, —C(O)NR$^5$—, —NR$^5$C(O)—, —CH$_2$C(O)NR$^5$—, —NR$^5$C(O)CH$_2$—, —CH=CH—C(O)NR$^5$—, —NR$^5$C(O)—CH=CH—, —C≡C—C(O)NR$^5$—, —NR$^5$C(O)—C≡C—, —S(O)NR$^5$—, —NR$^5$S(O)—, —S(O)$_2$NR$^5$—, —NR$^5$S(O)$_2$—, —NR$^5$C(O)NR$^{5a}$—, —NR$^5$S(O)$_2$NR$^{5a}$—, —CH$_2$NR$^5$S(O)$_2$NR$^{5a}$—, —NR$^5$S(O)$_2$NR$^{5a}$CH$_2$—, —NR$^5$C(O)-alkylene, —NR$^5$S(O)-alkylene, —NR$^5$S(O)$_2$-alkylene, —NR$^5$C(O)-alkenylene, —NR$^5$S(O)-alkenylene, or —NR$^5$S(O)$_2$-alkenylene; or alternatively; or alternatively, $L^2$ and V or W, together with other atoms to which they are attached, form 5- to 8-membered optionally substituted carbocyclyl or heterocyclyl; or alternatively, V or W and the carbon atom which is attached to $R^3$, $L^1$, and $L^2$, together with other atoms to which they are attached, form 5- to 8-membered optionally substituted carbocyclyl or heterocyclyl;

U, V, W, X, and Y are each independently C, CH, or N; and U, V, W, X, and Y, together with the carbon atom to which V and W are attached, form an aromatic 6-membered ring; with the proviso that at most 3 of U, V, W, X, and Y are N or NH;

$R^1$, $R^2$, and $R^3$ are selected from (i), (ii), (iii), and (iv):

(i) $R^1$, $R^2$, and $R^3$ are each independently (a) hydrogen, halo, or cyano; (b) $C_{1-6}$ alkyl, $C_{2-6}$ alkenyl, $C_{2-6}$ alkynyl, $C_{3-8}$ carbocyclyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

(ii) $R^1$ or $R^2$ forms a double bond with $R^3$; and the other of $R^1$ and $R^2$ is selected as in (i);

(iii) two of $R^1$, $R^2$, and $R^3$ are joined together to form $C_{3-8}$-carbocyclyl, or 3- to 8-membered heterocyclyl; and the third is selected as in (i); and (iv) $R^3$ and V or W, together with the other atoms to which are attached, form $C_{5-8}$ carbocyclyl, or 5- to 8-membered heterocyclyl; and $R^1$ and $R^2$ are selected as in (i);

$R^4$ is $C_{1-6}$ alkyl, $C_{2-6}$ alkenyl, $C_{2-6}$ alkynyl, $C_{3-7}$ carbocyclyl, $C_{6-14}$ aryl, $C_{7-15}$ aralkyl, heteroaryl, or heterocyclyl; or alternatively, $R^4$ and $R^5$ together with the N atom to which they are attached form heterocyclyl;

$R^5$ and $R^{5a}$ are each independently hydrogen, $C_{1-6}$ alkyl, —C(O)—$C_{1-6}$ alkyl; $C_{2-6}$ alkenyl, $C_{2-6}$ alkynyl, $C_{3-7}$ carbocyclyl, $C_{6-14}$ aryl, $C_{7-15}$ aralkyl, heteroaryl, or heterocyclyl; or alternatively, $R^4$ and $R^5$ are joined together to form heterocyclyl;

$R^6$ is cyano, halo, azido, nitro, $C_{1-6}$ alkyl, $C_{2-6}$ alkenyl, $C_{2-6}$ alkynyl, $C_{3-7}$ carbocyclyl, $C_{6-14}$ aryl, $C_{7-15}$ aralkyl, heteroaryl, heterocyclyl, —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

when U, V, W, X, and Y are each independently C or CH; $R^1$, $R^2$, and $R^3$ are hydrogen; $L^1$ is —CONH$_2$ or —CO$_2$H; $L^2$ is —N$R^5$C(O)—; and $R^4$ is -heteroarylaryl; then A-$L^3$-E- is cyano group;

each $R^{1a}$, $R^{1b}$, $R^{1c}$, and $R^{1d}$ is independently hydrogen, $C_{1-6}$ alkyl, $C_{2-6}$ alkenyl, $C_{2-6}$ alkynyl, $C_{3-7}$ carbocyclyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl;

wherein each alkyl, alkenyl, alkenylene, alkynyl, alkynylene, carbocyclyl, carbocyclylene, aryl, arylene, aralkyl, heteroaryl, heteroarylene, heterocyclyl, and heterocyclylene, in $R^1$, $R^2$, $R^3$, $R^4$, $R^5$, $R^{5a}$, $R^6$, $R^{1a}$, $R^{1b}$, $R^{1c}$, $R^{1d}$, A, and E is optionally substituted with one or more substituents Q, where each Q is independently selected from (a) cyano, halo, azido, and nitro;

(b) $C_{1-6}$ alkyl, $C_{2-6}$ alkenyl, $C_{2-6}$ alkynyl, $C_{3-7}$ carbocyclyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(=N$R^d$)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —S$R^a$, —S(O)$R^a$, —S(O)$_2R^a$, —S(O)N$R^bR^c$, and —S(O)$_2$N$R^bR^c$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-7}$ carbocyclyl, $C_{6-14}$ aryl, $C_{7-15}$ aralkyl, heteroaryl, or heterocyclyl, each optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$; and wherein each $Q^a$ is independently selected from the group consisting of (a) cyano, halo, and nitro; (b) $C_{1-6}$ alkyl, $C_{2-6}$ alkenyl, $C_{2-6}$ alkynyl, $C_{3-7}$ carbocyclyl, $C_{6-14}$ aryl, $C_{7-15}$ aralkyl, heteroaryl, and heterocyclyl; and (c) —C(O)$R^e$, —C(O)O$R^e$, —C(O)N$R^fR^g$, —C(N$R^e$)N$R^fR^g$, —O$R^e$, —OC(O)$R^e$, —OC(O)O$R^e$, —OC(O)N$R^fR^g$, —OC(=N$R^e$)N$R^fR^g$, —OS(O)$R^e$, —OS(O)$_2R^e$, —OS(O)N$R^fR^g$, —OS(O)$_2$N$R^fR^g$, —N$R^fR^g$, —N$R^e$C(O)$R^h$, —N$R^e$C(O)O$R^f$, —N$R^e$C(O)N$R^fR^g$, —N$R^e$C(=N$R^h$)N$R^fR^g$, —N$R^e$S(O)$R^h$, —N$R^e$S(O)$_2R^h$, —N$R^e$S(O)N$R^fR^g$, —N$R^e$S(O)$_2$N$R^fR^g$, —S$R^e$, —S(O)$R^e$, —S(O)$_2R^e$, —S(O)N$R^fR^g$, and —S(O)$_2$N$R^fR^g$; wherein each $R^e$, $R^f$, $R^g$, and $R^h$ is independently (i) hydrogen; (ii) $C_{1-6}$ alkyl, $C_{2-6}$ alkenyl, $C_{2-6}$ alkynyl, $C_{3-7}$ carbocyclyl, $C_{6-14}$ aryl, $C_{7-15}$ aralkyl, heteroaryl, or heterocyclyl; or (iii) $R^f$ and $R^g$ together with the N atom to which they are attached form heterocyclyl.

\* \* \* \* \*